United States Patent
Pool et al.

(10) Patent No.: US 7,862,502 B2
(45) Date of Patent: Jan. 4, 2011

(54) METHOD AND APPARATUS FOR ADJUSTING A GASTROINTESTINAL RESTRICTION DEVICE

(75) Inventors: Scott Pool, Laguna Hills, CA (US); Blair Walker, Mission Viejo, CA (US); Jay R. McCoy, Temecula, CA (US); Peter P. Tran, Irvine, CA (US); Richard L. Quick, Mission Viejo, CA (US); Shahram Moaddeb, Irvine, CA (US); Arvin Chang, West Covina, CA (US)

(73) Assignee: Ellipse Technologies, Inc., Irvine, CA (US)

( * ) Notice: Subject to any disclaimer, the term of this patent is extended or adjusted under 35 U.S.C. 154(b) by 621 days.

(21) Appl. No.: 11/760,482

(22) Filed: Jun. 8, 2007

(65) Prior Publication Data

US 2008/0097487 A1 Apr. 24, 2008

Related U.S. Application Data

(60) Provisional application No. 60/853,105, filed on Oct. 20, 2006, provisional application No. 60/854,574, filed on Oct. 25, 2006, provisional application No. 60/904,625, filed on Mar. 1, 2007.

(51) Int. Cl.
*A61B 17/00* (2006.01)
*A61B 17/12* (2006.01)
(52) U.S. Cl. ........................................ 600/37
(58) Field of Classification Search ............... 600/29, 600/30, 37
See application file for complete search history.

(56) References Cited

U.S. PATENT DOCUMENTS 3,111,945 A 11/1963 Solbrig (Continued)

FOREIGN PATENT DOCUMENTS

AU 20068468 B2 3/2001

(Continued)

OTHER PUBLICATIONS

Horbach, T. et al., "First Experiences with the Routine Use of the Rapid Port™ System with the Lap-Band®", Obesity Surgery, 2006, vol. 16, No. 4, p. 418, McGraw-Hill Medical Publishing Division, New York, U.S.A.

(Continued)

*Primary Examiner*—Charles A Marmor, II
*Assistant Examiner*—Catherine E. Burk
(74) *Attorney, Agent, or Firm*—Vista IP Law Group LLP

(57) ABSTRACT

A gastrointestinal implant system includes an adjustable restriction device having a contact surface configured for at least partially engaging a surface of a gastrointestinal tract of a mammal. The implant system further includes an implantable interface including a first driving element, the first driving element being moveable and operatively coupled to the adjustable restriction device by an actuator configured to change the dimension or configuration of the contact surface in response to movement of the first driving element. The system also includes an external adjustment device having a second driving element configured to non-invasively engage the first driving element of the implantable interface from a location external to the mammal. In the system, actuation of the second driving element of the external adjustment device produces movement in the first driving element of the implantable interface and results in a change in the dimension or configuration of the contact surface.

12 Claims, 110 Drawing Sheets

U.S. PATENT DOCUMENTS

| | | |
|---|---|---|
| 3,527,220 A | 9/1970 | Summers |
| 3,726,279 A | 4/1973 | Barefoot et al. |
| 3,749,098 A | 7/1973 | De Bennetot |
| 3,750,194 A | 8/1973 | Summers |
| 3,810,259 A | 5/1974 | Summers |
| 3,840,018 A | 10/1974 | Heifetz |
| 3,976,060 A | 8/1976 | Hildebrandt et al. |
| 4,010,758 A | 3/1977 | Rockland et al. |
| 4,118,805 A | 10/1978 | Reimels |
| 4,204,541 A | 5/1980 | Kapitanov |
| 4,222,374 A | 9/1980 | Sampson et al. |
| 4,235,246 A | 11/1980 | Weiss |
| 4,256,094 A | 3/1981 | Kapp et al. |
| 4,300,223 A * | 11/1981 | Maire .................. 368/85 |
| 4,357,946 A | 11/1982 | Dutcher et al. |
| 4,486,176 A | 12/1984 | Tardieu et al. |
| 4,550,279 A * | 10/1985 | Klein .................. 318/696 |
| 4,592,339 A | 6/1986 | Kuzmak et al. |
| 4,592,355 A | 6/1986 | Antebi |
| 4,595,007 A | 6/1986 | Mericle |
| 4,696,288 A | 9/1987 | Kuzmak et al. |
| 4,700,091 A * | 10/1987 | Wuthrich ............ 310/49.32 |
| 4,747,832 A | 5/1988 | Buffet |
| 4,760,837 A | 8/1988 | Petit |
| 5,074,868 A | 12/1991 | Kuzmak |
| 5,152,770 A | 10/1992 | Bengmark et al. |
| 5,226,429 A | 7/1993 | Kuzmak |
| 5,330,503 A | 7/1994 | Yoon |
| 5,356,424 A | 10/1994 | Buzerak et al. |
| 5,360,407 A | 11/1994 | Leonard |
| 5,433,721 A | 7/1995 | Hooven et al. |
| 5,437,266 A | 8/1995 | McPherson et al. |
| 5,449,368 A | 9/1995 | Kuzmak |
| 5,509,888 A | 4/1996 | Miller |
| 5,582,616 A | 12/1996 | Bolduc et al. |
| 5,626,613 A | 5/1997 | Schmieding |
| 5,662,683 A | 9/1997 | Kay |
| 5,704,893 A | 1/1998 | Timm |
| 5,704,939 A | 1/1998 | Justin |
| 5,720,746 A | 2/1998 | Soubeiran |
| 5,762,599 A | 6/1998 | Sohn |
| 5,771,903 A | 6/1998 | Jakobsson |
| 5,829,662 A | 11/1998 | Allen et al. |
| 5,830,221 A | 11/1998 | Stein et al. |
| 5,938,669 A | 8/1999 | Kaliber et al. |
| 5,961,553 A | 10/1999 | Coty et al. |
| 6,067,991 A | 5/2000 | Forsell |
| 6,074,341 A * | 6/2000 | Anderson et al. ............ 600/29 |
| 6,102,922 A | 8/2000 | Jakobsson et al. |
| 6,138,681 A | 10/2000 | Chen et al. |
| 6,210,347 B1 | 4/2001 | Forsell |
| 6,315,784 B1 | 11/2001 | Djurovic |
| 6,368,083 B1 | 4/2002 | Wampler |
| 6,400,980 B1 | 6/2002 | Lemelson |
| 6,417,750 B1 | 7/2002 | Sohn |
| 6,432,040 B1 | 8/2002 | Meah |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,494,879 B2 | 12/2002 | Lennox et al. |
| 6,499,907 B1 | 12/2002 | Baur |
| 6,500,110 B1 | 12/2002 | Davey et al. |
| 6,503,189 B1 | 1/2003 | Forsell |
| 6,511,490 B2 | 1/2003 | Robert |
| 6,527,701 B1 | 3/2003 | Sayet et al. |
| 6,527,702 B2 | 3/2003 | Whalen et al. |
| 6,547,801 B1 * | 4/2003 | Dargent et al. ............. 606/157 |
| 6,558,400 B2 | 5/2003 | Deem et al. |
| 6,587,719 B1 | 7/2003 | Barrett et al. |
| 6,609,025 B2 | 8/2003 | Barrett et al. |
| 6,626,917 B1 | 9/2003 | Craig |
| 6,627,206 B2 | 9/2003 | Lloyd |
| 6,656,194 B1 | 12/2003 | Gannoe et al. |
| 6,676,674 B1 | 1/2004 | Dudai |
| 6,709,385 B2 | 3/2004 | Forsell |
| 6,749,556 B2 | 6/2004 | Banik |
| 6,752,754 B1 | 6/2004 | Feng et al. |
| 6,765,330 B2 | 7/2004 | Baur |
| 6,789,442 B2 | 9/2004 | Forch |
| 6,796,984 B2 | 9/2004 | Soubeiran |
| 6,835,207 B2 | 12/2004 | Zacouto et al. |
| 6,849,076 B2 | 2/2005 | Blunn et al. |
| 6,915,165 B2 | 7/2005 | Forsell |
| 6,916,326 B2 | 7/2005 | Benchetrit |
| 6,923,951 B2 | 8/2005 | Contag et al. |
| 6,953,429 B2 | 10/2005 | Forsell |
| 6,997,952 B2 | 2/2006 | Furukawa et al. |
| 7,011,621 B2 | 3/2006 | Sayet et al. |
| 7,060,080 B2 | 6/2006 | Bachmann |
| 7,105,968 B2 | 9/2006 | Nissen |
| 7,128,750 B1 | 10/2006 | Stergiopulos |
| 7,160,312 B2 | 1/2007 | Saadat |
| 7,172,607 B2 | 2/2007 | Hofle et al. |
| 7,175,589 B2 | 2/2007 | Deem et al. |
| 7,191,007 B2 | 3/2007 | Desai et al. |
| 7,238,191 B2 | 7/2007 | Bachmann |
| 7,255,682 B1 | 8/2007 | Bartol, Jr. et al. |
| 7,601,162 B2 * | 10/2009 | Hassler et al. ............. 606/151 |
| 2001/0011543 A1 | 8/2001 | Forsell |
| 2003/0032857 A1 | 2/2003 | Forsell |
| 2003/0088148 A1 | 5/2003 | Forsell |
| 2003/0092962 A1 | 5/2003 | Forsell |
| 2003/0114731 A1 | 6/2003 | Cadeddu et al. |
| 2003/0208212 A1 | 11/2003 | Cigaina |
| 2004/0055610 A1 | 3/2004 | Forsell |
| 2004/0064030 A1 | 4/2004 | Forsell |
| 2004/0089313 A1 | 5/2004 | Utley et al. |
| 2004/0098121 A1 | 5/2004 | Opolski |
| 2004/0102677 A1 | 5/2004 | Frering |
| 2004/0116773 A1 | 6/2004 | Furness et al. |
| 2004/0133219 A1 | 7/2004 | Forsell |
| 2004/0138725 A1 | 7/2004 | Forsell |
| 2004/0147801 A1 | 7/2004 | Kugler et al. |
| 2004/0176797 A1 | 9/2004 | Opolski |
| 2004/0230137 A1 | 11/2004 | Mouton |
| 2004/0249453 A1 | 12/2004 | Cartledge et al. |
| 2004/0250820 A1 | 12/2004 | Forsell |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2005/0002984 A1 | 1/2005 | Byrum et al. |
| 2005/0049718 A1 | 3/2005 | Dann et al. |
| 2005/0055039 A1 | 3/2005 | Burnett et al. |
| 2005/0070937 A1 | 3/2005 | Jambor et al. |
| 2005/0104457 A1 | 5/2005 | Jordan et al. |
| 2005/0119672 A1 | 6/2005 | Benchetrit |
| 2005/0131352 A1 | 6/2005 | Conlon et al. |
| 2005/0143765 A1 | 6/2005 | Bachmann et al. |
| 2005/0143766 A1 * | 6/2005 | Bachmann et al. .......... 606/158 |
| 2005/0165440 A1 | 7/2005 | Cancel et al. |

| | | | |
|---|---|---|---|
| 2005/0165449 | A1 | 7/2005 | Cadeddu et al. |
| 2005/0192531 | A1* | 9/2005 | Birk .......................... 604/96.01 |
| 2005/0250979 | A1 | 11/2005 | Coe |
| 2005/0267406 | A1 | 12/2005 | Hassler, Jr. |
| 2005/0267500 | A1 | 12/2005 | Hassler, Jr. et al. |
| 2005/0272968 | A1 | 12/2005 | Byrum et al. |
| 2005/0277963 | A1 | 12/2005 | Fields |
| 2005/0277974 | A1 | 12/2005 | Hassler, Jr. et al. |
| 2005/0283118 | A1 | 12/2005 | Uth et al. |
| 2005/0283119 | A1 | 12/2005 | Uth et al. |
| 2006/0009767 | A1 | 1/2006 | Kiester |
| 2006/0047282 | A1 | 3/2006 | Gordon |
| 2006/0058792 | A1 | 3/2006 | Hynes |
| 2006/0074439 | A1* | 4/2006 | Garner et al. ................ 606/153 |
| 2006/0124140 | A1 | 6/2006 | Forsell |
| 2006/0155347 | A1 | 7/2006 | Forsell |
| 2006/0161186 | A1 | 7/2006 | Hassler, Jr. et al. |
| 2006/0190039 | A1 | 8/2006 | Birk et al. |
| 2006/0199997 | A1 | 9/2006 | Hassler, Jr. et al. |
| 2006/0211914 | A1 | 9/2006 | Hassler, Jr. et al. |
| 2006/0229696 | A1 | 10/2006 | Boustani et al. |
| 2006/0235299 | A1 | 10/2006 | Martinelli |
| 2006/0235445 | A1 | 10/2006 | Birk et al. |
| 2006/0235448 | A1 | 10/2006 | Roslin et al. |
| 2006/0252982 | A1 | 11/2006 | Hassler, Jr. et al. |
| 2006/0252983 | A1 | 11/2006 | Lembo et al. |
| 2006/0276812 | A1 | 12/2006 | Hill et al. |
| 2006/0293625 | A1 | 12/2006 | Hunt et al. |
| 2006/0293626 | A1 | 12/2006 | Byrum et al. |
| 2006/0293627 | A1 | 12/2006 | Byrum et al. |
| 2006/0293628 | A1 | 12/2006 | Hunt et al. |
| 2007/0010790 | A1 | 1/2007 | Byrum et al. |
| 2007/0015954 | A1 | 1/2007 | Dlugos |
| 2007/0015955 | A1 | 1/2007 | Tsonton |
| 2007/0015956 | A1 | 1/2007 | Crawford et al. |
| 2007/0016230 | A1 | 1/2007 | Jambor et al. |
| 2007/0025868 | A1 | 2/2007 | Swayze et al. |
| 2007/0027356 | A1 | 2/2007 | Ortiz |
| 2007/0149947 | A1 | 6/2007 | Byrum |
| 2007/0156013 | A1 | 7/2007 | Birk |
| 2007/0213751 | A1 | 9/2007 | Scirica et al. |
| 2007/0255088 | A1 | 11/2007 | Jacobson et al. |
| 2007/0276378 | A1 | 11/2007 | Harrison et al. |

FOREIGN PATENT DOCUMENTS

| | | |
|---|---|---|
| DE | 1541262 | 6/1969 |
| DE | 19626230 A1 | 1/1998 |
| DE | 19751733 A1 | 12/1998 |
| DE | 19745654 A1 | 4/1999 |
| EP | 0663184 A1 | 7/1995 |
| EP | 1547549 A2 | 6/2005 |
| EP | 1745765 A2 | 1/2007 |
| FR | 2802406 A1 | 6/2001 |
| FR | 2823663 A1 | 10/2002 |
| FR | 2827756 A1 | 1/2003 |
| GB | 1174814 | 12/1969 |
| WO | WO 86/04498 | 8/1986 |
| WO | WO 96/01597 | 1/1996 |
| WO | WO 99/51160 | 10/1999 |
| WO | WO 99/63907 | 12/1999 |
| WO | WO 01/24742 | 4/2001 |
| WO | WO 2005/072195 A2 | 8/2005 |
| WO | WO 2005/072664 A1 | 8/2005 |
| WO | WO 2005/105001 A2 | 11/2005 |
| WO | WO 2007/118179 A2 | 10/2007 |

OTHER PUBLICATIONS

Invis®/Lamello Catalog, 2006, Article No. 68906A001GB.

Korenkov, M. et al., "Port Function After Laparoscopic Adjustable Gastric Banding for Morbid Obesity", Surgical Endoscopy, 2003, vol. 17, No. 7, pp. 1068-1071, Springer-Verlag, New York, U.S.A.

Lechner, W. et al., "In Vivo Band Manometry: A New Method in Band Adjustment", Obesity Surgery, 2005, vol. 15, No. 7, p. 935, McGraw-Hill Medical Publishing Division, New York, U.S.A.

Lechner, W. et al., "In Vivo Band Manometry: A New Access to Band Adjustment", Obesity Surgery, 2005, vol. 15, No. 10, pp. 1432-1436, McGraw-Hill Medical Publishing Division, New York, U.S.A.

Lechner, W. et al., "Intra-Band Manometry for Band Adjustments: The Basics", Obesity Surgery, 2006, vol. 16, No. 4, pp. 417-418, McGraw-Hill Medical Publishing Division, New York, U.S.A.

Matthews, M. et al., "Magnetically Adjustable Intraocular Lens", Journal of Cataract and Refractive Surgery, 2003, vol. 29, No. 11, pp. 2211-2216, American Society of Cataract and Refractive Surgery, Fairfax, U.S.A.

Piorkowski, J. et al., "Preventing Port Site Inversion in Laparoscopic Adjustable Gastric Banding", Surgery for Obesity and Related Diseases, 2007, vol. 3, No. 2, pp. 159-162, Elsevier, New York, U.S.A.

Ren, C. et al., "Laparoscopic Adjustable Gastric Banding: Surgical Technique", Journal of Laparoendoscopic & Advanced Surgical Techniques, 2003, vol. 13, No. 4, pp. 257-263, Mary Ann Liebert, Inc, Larchmont, U.S.A.

Rode, V. et al., "A Simple Way to Adjust Bands Under Radiologic Control", Obesity Surgery, 2006, vol. 16, No. 4, p. 418, McGraw-Hill Medical Publishing Division, New York, U.S.A.

Scott, D. et al., "Transgastric, Transcolonic and Transvaginal Cholecystectomy Using Magnetically Anchored Instruments", Sages Annual Scientific Sessions, Poster Abstracts, Apr. 18-22, 2007, P511, p. 306.

Suter, M. et al., "A 10-year Experience with Laparoscopic Gastric Banding for Morbid Obesity: High Long-Term Complication and Failure Rates", Obesity Surgery, 2006, vol. 16, No. 7, pp. 829-835, McGraw-Hill Medical Publishing Division, New York, U.S.A.

Weiner, R. et al., "Initial Clinical Experience with Telemetrically Adjustable Gastric Banding", Surgical Technology International, 2006, vol. 15, pp. 63-69, Universal Medical Press, San Francisco, U.S.A.

Weiner, R. et al., "Early Results with a New Telemetrically Adjustable Gastric Banding", Obesity Surgery, 2007, vol. 17, No. 6, pp. 717-721, McGraw-Hill Medical Publishing, New York, U.S.A.

Yonnet, J. et al., "Passive Magnetic Bearings with Permanent Magnets", IEEE Transactions on Magnetics, 1978, vol. 14, No. 5, pp. 803-805, Institute of Electrical and Electronics Engineers, New York, U.S.A.

Yonnet, J., "A New Type of Permanent Magnet Coupling", IEEE Transactions on Magnetics, 1981, vol. 17, No. 6, pp. 2991-2993, Institute of Electrical and Electronics Engineers, New York, U.S.A.

Zheng, P. et al., "Force and Torque Characteristics for Magnetically Driven Blood Pump", Journal of Magnetism and Magnetic Materials, 2002, vol. 241, No. 2, pp. 292-302, Elsevier, New York, U.S.A.

PCT International Preliminary Report on Patentability for PCT/US2008/055039, Applicant: Ellipse Technologies, Inc. et al., Form PCT/IB/373, dated Nov. 26, 2009 (2 pages).

PCT Written Opinion of the International Searching Authority for PCT/US08/55039, Applicant: Ellipse Technologies, Inc., Form PCT/ISA/237, dated Jun. 3, 2009 (6 pages).

Gupta, A., Meswania, J., Pollock, R., Cannon, S., Briggs, T., Taylor, S., Blunn, G., "Non-Invasive Distal Femoral Expandable Endoprosthesis for Limb-Salvage Surgery in Paediatric Tumours", The Journal of Bone & Joint Surgery—British Volume, 2006, vol. 88-B, No. 5, pp. 649-654, British Editorial Society of Bone and Joint Surgery, London, England.

Sharke, P., "The Machinery of Life", Mechanical Engineering Magazine, Feb. 2004, Printed from Internet site Oct. 24, 2007 http://www.memagazine.org/contents/current/features/moflife/moflife.html.

Gebhart, M, Neel, M., Soubeiran, A., Dubousset, J., "Early Clinical Experience with a Custom Made Growing Endoprosthesis in Children with Malignant Bone Tumors of the Lower Extremity Actioned by an External Permanent Magnet: The Phenix M System", 14th International Symposium on Limb Salvage, Sep. 13, 2007, Hamburg, Germany.

Soubeiran, A., Gebhart, M, Miladi, L., Griffet, J., Neel, M., Dubousset, J., "The Phenix M System, a Fully Implanted Non-Invasive Lengthening Device Externally Controllable Through the Skin with a Palm Size Permanent Magnet. Applications in Limb Salvage", 14th International Symposium on Limb Salvage, Sep. 13, 2007, Hamburg, Germany.

Soubeiran, A., Gebhart, M, Miladi, L., Griffet, J., Neel, M., Dubousset, J., "The Phenix M System. A Mechanical Fully Implanted Lengthening Device Externally Controllable Through the Skin with a Palm Size Permanent Magnet; Applications to Pediatric Orthopaedics2", 14th International Symposium on Limb Salvage, Oct. 6, 2006, Toulouse, France.

International Search Report and Written Opinion of related patent application PCT/US08/55039 dated Jun. 3, 2008 (10 pages).

Angrisani, L. et al., "Lap-Band® Rapid Port™ System: Preliminary Results in 21 Patients", Obesity Surgery, 2005, vol. 15, No. 7, p. 936, McGraw-Hill Medical Publishing Division, New York, U.S.A.

Boudjemline, Y. et al., "Off-Label Use of an Adjustable Gastric Banding System for Pulmonary Artery Banding", The Journal of Thoracic and Cardiovascular Surgery, 2006, vol. 131, No. 5, pp. 1130-1135, C. B. Mosby, St. Louis, U.S.A.

Brown, S. et al., "Single Port Surgery and the Dundee Endocone", SAGES Annual Scientific Sessions, Poster Abstracts, Apr. 18-22, 2007, ETP007, pp. 323-324.

Chapman, A. et al., "Laparoscopic Adjustable Gastric Banding in the Treatment of Obesity: A Systematic Literature Review", Surgery, 2004, vol. 135, No. 3, pp. 326-351, Elsevier, New York, U.S.A.

Fabry, H. et al., "A Technique for Prevention of Port Complications After Laparoscopic Adjustable Silicone Gastric Banding", Obesity Surgery, 2002, vol. 12, No. 2, pp. 285-288, McGraw-Hill Medical Publishing Division, New York, U.S.A.

Fried, M. et al., "In Vivo Measurements of Different Gastric Band Pressures Towards the Gastric Wall at the Stoma Region", Obesity Surgery, 2004, vol. 14, No. 7, p. 914, McGraw-Hill Medical Publishing Division, New York, U.S.A.

Grunert, R., "The Development of a Totally Implantable Electronic Sphincter" (translated from the German "Die Entwicklung eines total implantierbaren elektronischen Sphincters"), Langenbecks Archiv für Chirurgie, 1969, vol. 325, pp. 1170-1174, Springer-Verlag, Berlin, Germany.

* cited by examiner

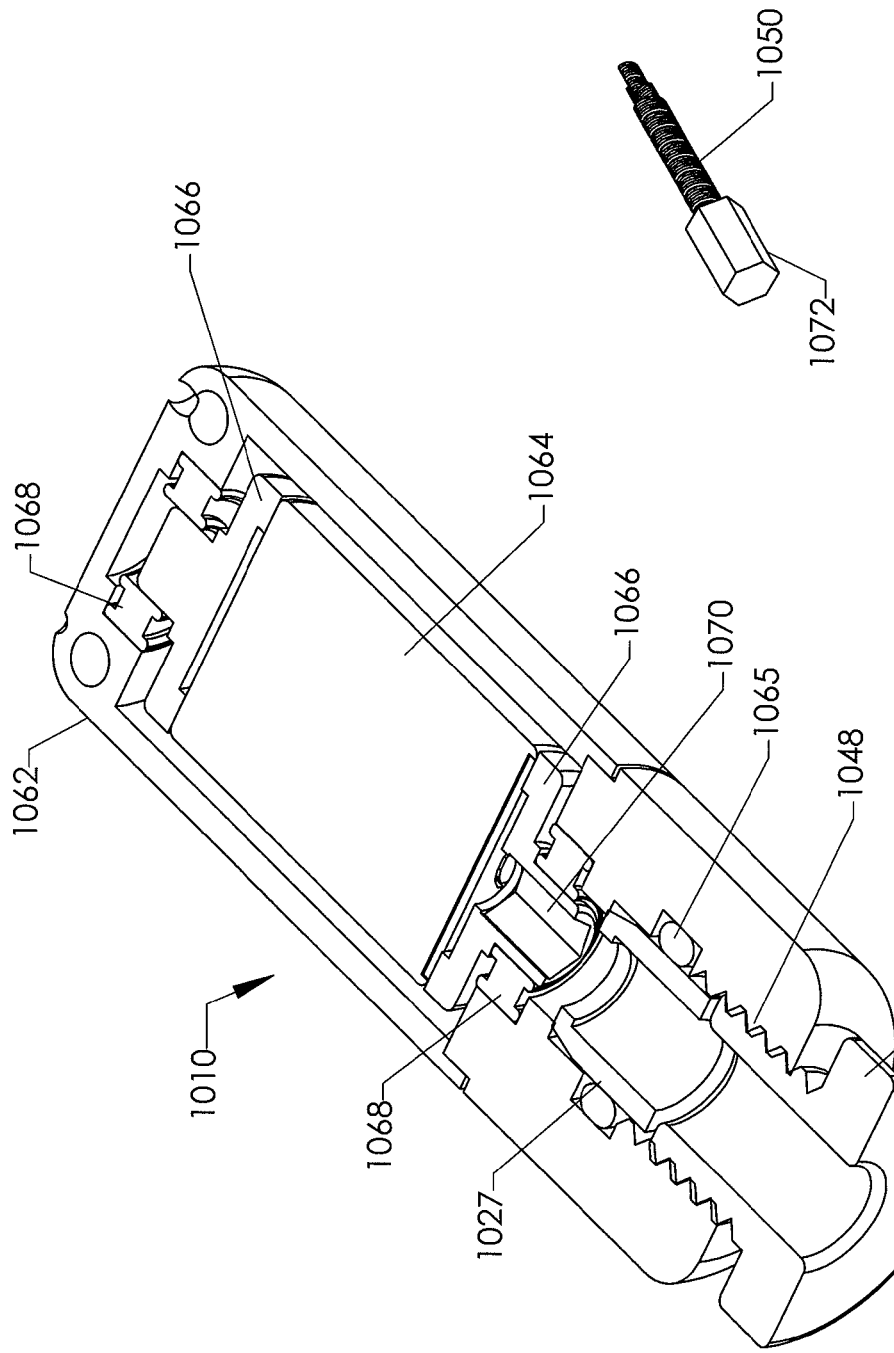

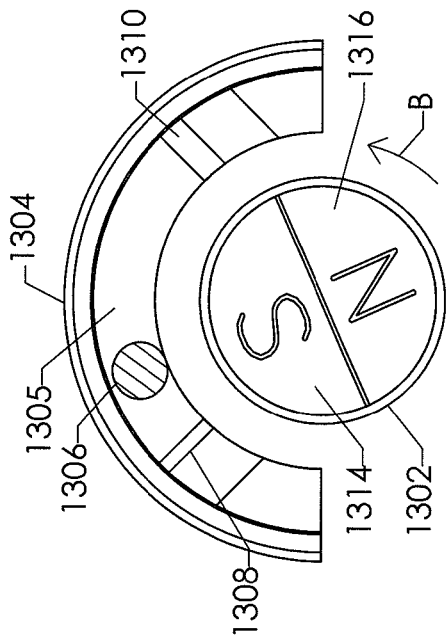
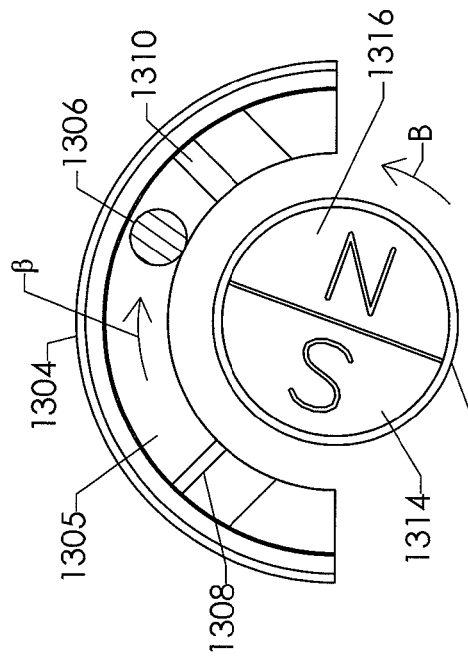
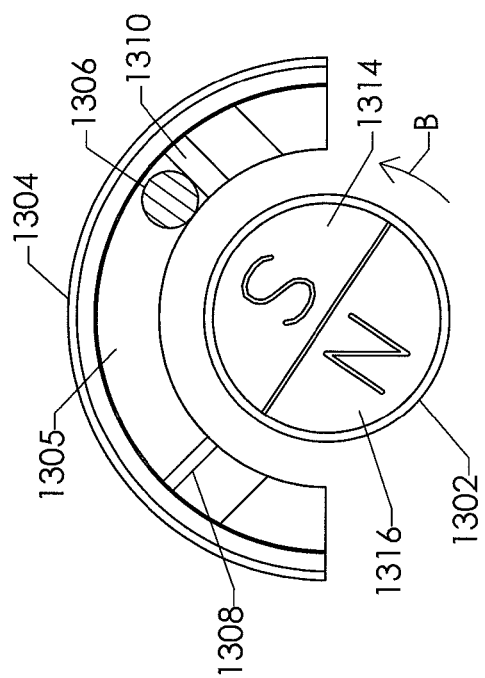
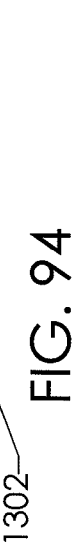

METHOD AND APPARATUS FOR ADJUSTING A GASTROINTESTINAL RESTRICTION DEVICE

RELATED APPLICATIONS

This Application claims priority to U.S. Provisional Patent Application Nos. 60/853,105 filed on Oct. 20, 2006, 60/854,574 filed on Oct. 25, 2006, and 60/904,625 filed on Mar. 1, 2007. Priority is claimed pursuant to 35 U.S.C. §§119, 120. The '105, '574, and '625 Provisional Patent Applications are incorporated by reference as if set forth fully herein.

FIELD OF THE INVENTION

The field of the invention generally relates to medical devices for accessing and controlling dimensions of body lumens and cavities along a mammalian alimentary canal, including methods and devices for treating obesity and gastroesophageal reflux disease (GERD).

BACKGROUND OF THE INVENTION

Obesity is a common disease of unknown etiology. It is a chronic, multifactorial disease that develops from an integration of genetic, environmental, social, behavioral, physiological, metabolic, neuron-endocrine and psychological elements. This disease is considered a cause or co-morbidity to such conditions as GERD, high blood pressure, elevated cholesterol, diabetes, sleep apnea, mobility and orthopedic deterioration, and other consequences, including those limiting social and self image and those affecting the ability to perform certain everyday tasks. Since traditional weight loss techniques, such as diet, drugs, exercise, etc., are frequently ineffective with many of these patients, surgery is often the only viable alternative.

Body Mass Index (BMI) is the most common method used to define the obese patient. This measurement is obtained by taking a persons weight in Kilograms (Kg) and dividing by the square of height in meters. Based on policies set forth by the United States National Institutes of Health (NIH), BMI is used to characterize the degree of excess weight. These categories are listed in Table 1 listed below. Presently, based on current NIH policy, only those people with a BMI of 35 or greater qualify for surgical intervention.

TABLE 1

Table 1 - Risk of Associated Disease According to BMI and Waist Size

| BMI | Weight Classification | Disease Risk Waist ≦ 40 in. (men) or 35 in. (women) | Disease Risk Waist > 40 in. (men) or 35 in. (women) |
| --- | --- | --- | --- |
| 18.5 or less | Underweight | — | N/A |
| 18.5-24.9 | Normal | — | N/A |
| 25.0-29.9 | Overweight | Increased | High |
| 30.0-34.9 | Obese Class 1 | High | Very High |
| 35.0-39.9 | Obese Class 2 | Very High | Very High |
| 40.0 to 49.9 | Morbidly Obese | Extremely High | Extremely High |
| >49.9 | Super Obese | Extremely High | Extremely High |

In the United States, more than 30% of the population is obese as defined in Table 1, including men, women, and children. There are more than 15 million Americans (5.5%) who are morbidly obese. The number of obese children is growing at an alarmingly fast rate. Surgical treatments for obesity continue to be a strong focus of research due to their high level of effectiveness although no treatment is considered ideal. It is well-established in the medical literature that obesity adversely affects general health, and can result in reduced quality of life and reduced lifespan. It is now well-accepted that obesity is associated with increased risk of cardiovascular disease, diabetes and other health issues. In contrast, animal studies show that longevity is increased in lean subjects (Weindruch, R. & Walford, R. L., 1988. The Retardation of Aging and Disease by Dietary Restriction, Thomas, Springfield, Ill.; Spindler, S. R., 2003, in Anti-Aging Therapy for Plastic Surgery, eds. Kinney, B. & Carraway, J., Quality Medical, St. Louis, Mo.). Much work continues to be needed before a widely acceptable solution can be expected.

Surgical weight loss (bariatric) procedures are designed to restrict weight gain by either limiting caloric intake by restricting effective stomach size or by malabsorption, which is reducing the intestine's ability to absorb nutrition. Many surgeons offer their patients a combined procedure that includes a restrictive and malabsorption material. These procedures are irreversible and rely on a surgeon's judgment to estimate the final size of the new restrictive stomach as well as the remaining small intestine length to provide adequate nutrition for optimal weight loss and management for the patient's lifetime.

Presently, bariatric procedures can be performed by open or laparoscopic surgery. Open surgery typically requires a ten day hospitalization and a prolonged recovery period with a commensurate loss of productivity. Laparoscopic procedures have reduced in-hospital stay to three days, followed by a three week at-home recovery. These procedures can even be performed as an outpatient procedure. Laparoscopic procedures have reduced cost considerably, making the minimally invasive laparoscopic procedure available to more patients. In 2000, there were 30,000 bariatric procedures performed, while in 2003, over 90,000 procedures were reported.

One common obesity surgery is the Roux-en-Y gastric bypass (often known only as a "gastric bypass"). During this type of operation, the surgeon permanently changes the shape of the stomach by surgically reducing (cutting or stapling) its size to create an egg-sized gastric pouch or "new stomach." The rest of the stomach is then divided and separated from this new stomach pouch, greatly reducing the amount of food that can be consumed after surgery. In addition to reducing the actual size of the stomach, a significant portion of the digestive tract is bypassed and the new stomach pouch is reconnected directly to the bypassed segment of small intestine. This operation, therefore, is both a restrictive and malabsorptive procedure, because it limits the amount of food that one can eat and the amount of calories and nutrition that are absorbed or digested by the body. Once completed, gastric bypass surgery is essentially irreversible. Some of the major risks associated with the Roux-en-Y Gastric Bypass procedure include bleeding, infection, pulmonary embolus, anastomotic stricture or leak, anemia, ulcer, hernia, gastric distention, bowel obstruction and death.

Another common obesity surgery is known as vertical banded gastroplasty ("VBG"), or "stomach stapling." In a gastroplasty procedure, the surgeon staples the upper stomach to create a small, thumb-sized stomach pouch, reducing the quantity of food that the stomach can hold to about 1-2 ounces. The outlet of this pouch is then restricted by a band that significantly slows the emptying of the pouch to the lower part of the stomach. Aside from the creation of a small stomach pouch, there is no other significant change made to the gastrointestinal tract. So while the amount of food the stomach can contain is reduced, the stomach continues to digest nutrients and calories in a normal way. This procedure is purely restrictive; there is no malabsorptive effect. Following this operation, many patients have reported feeling full but not satisfied after eating a small amount of food. As a result, some patients have attempted to get around this effect by eating more or by eating gradually all day long. These practices can result in vomiting, tearing of the staple line, or simply reduced weight loss. Major risks associated with VBG include: unsatisfactory weight loss or weight regain, vomiting, band erosion, band slippage, breakdown of staple line, anastomotic leak, and intestinal obstruction.

A third procedure, the Duodenal Switch, is less common. It is a modification of the biliopancreatic diversion or "Scopinaro procedure." While this procedure is considered by many to be the most powerful weight loss operation currently available, it is also accompanied by significant long-term nutritional deficiencies in some patients. Many surgeons have stopped performing this procedure due to the serious associated nutritional risks.

In the Duodenal Switch procedure, the surgeon removes about 80% of the stomach, leaving a very small new stomach pouch. The beginning portion of the small intestine is then removed, and the severed end portions of the small intestine are connected to one another near the end of the small intestine and the beginning of the large intestine or colon. Through this procedure a large portion of the intestinal tract is bypassed so that the digestive enzymes (bile and pancreatic juices) are diverted away from the food stream until very late in the passage through the intestine. The effect of this procedure is that only a small portion of the total calories that are consumed are actually digested or absorbed. This irreversible procedure, therefore, is both restrictive (the capacity of the stomach is greatly reduced) and malabsorptive (the digestive tract is shortened, severely limiting absorption of calories and nutrition). Because of the very significant malabsorptive material of this operation, patients must strictly adhere to dietary instructions including taking daily vitamin supplements, consuming sufficient protein and limiting fat intake. Some patients also experience frequent large bowel movements, which have a strong odor. The major risks associated with the Duodenal Switch are: bleeding, infection, pulmonary embolus, loss of too much weight, vitamin deficiency, protein malnutrition, anastomotic leak or stricture, bowel obstruction, hernia, nausea/vomiting, heartburn, food intolerances, kidney stone or gallstone formation, severe diarrhea and death.

One relatively new and less invasive form of bariatric surgery is Adjustable Gastric Banding. Through this procedure the surgeon places a band around an upper part of the stomach to divide the stomach into two parts, including a small pouch in the upper part of the stomach. The small upper stomach pouch can only hold a small amount of food. The remainder of the stomach lies below the band. The two parts are connected by means of a small opening called a stoma. Risks associated with Gastric Banding are significantly less than other forms of bariatric surgery, since this surgery does not involve opening of the gastric cavity. There is no cutting, stapling or bypassing.

It has been found that the volume of the small upper stomach pouch above the band increases in size up to ten times after operation. Therefore the pouch volume during surgery needs to be very small, approximately 7 ml. To enable the patient to feed the stomach with sufficient nutrition immediately after an operation considering such a small gastric pouch, the stoma initially needs to be relatively large and later needs to be substantially reduced, as the pouch volume increases. To be able to achieve a significant range of adjustment of the band, the cavity in the band has to be relatively large and is defined by a thin flexible wall, normally made of silicone material. Furthermore, the size of the stoma opening has to be gradually reduced during the first year after surgery as the gastric pouch increases in size. Reduction of the stoma opening is commonly achieved by adding liquid to the cavity of the band via an injection port to expand the band radially inwardly.

A great disadvantage of repeatedly injecting liquid via the injection port is the increased risk of the patient getting an infection in the body area surrounding the injection port. If such an infection occurs the injection port has to be surgically removed from the patient. Moreover, such an infection might be spread along the tube interconnecting the injection port and the band to the stomach, causing even more serious complications. Thus, the stomach might be infected where it is in contact with the band, which might result in the band migrating (eroding) through the wall of the stomach. Also, it is uncomfortable for the patient when the necessary, often many, post-operation adjustments of the stoma opening are carried out using a relatively large injection needle penetrating the skin of the patient into the injection port.

It may happen that the patient swallows pieces of food too large to pass through the restricted stoma opening. If that occurs the patient has to visit a doctor who can remove the food pieces, if the band design so permits, by withdrawing some liquid from the band to enlarge the stoma opening to allow the food pieces to pass the stoma. The doctor then has to add liquid to the band in order to regain the restricted stoma opening. Again, these measures require the use of an injection needle penetrating the skin of the patient, which is painful and uncomfortable for the patient, and can sometimes be the cause of infection, thus risking the long-term viability of the implant. The adjustment of the band can be inconsistent. For example, if some air is inadvertently injected with the liquid (sterile saline), it can cause some compressibility to the pressurization media and take away some of the "one-to-one" feel when pressurizing and depressurizing.

The LAP-BAND Adjustable Gastric Banding System (Inamed) is a product used in the Adjustable Gastric Banding procedure. The LAP-BAND system, includes a silicone band, which is essentially an annular-shaped balloon. The surgeon places the silicone band around the upper part of the stomach. The LAP-BAND system further includes a port that is placed under the skin, and tubing that provides fluid communication between the port and the band. A physician can inflate the band by injecting a fluid (such as saline) into the band through the port. As the band inflates, the size of the stoma shrinks, thus further limiting the rate at which food can pass from the upper stomach pouch to the lower part of the stomach. The physician can also deflate the band, and thereby increase the size of the stoma, by withdrawing the fluid from the band through the port. The physician inflates and deflates the band by piercing the port, through the skin, with a long, non-coring needle. There is often ambiguous feedback to the physician between the amount injected and the restriction the patient feels during the adjustment procedure, such as when swallowing a bolus of liquid to test the stoma. In addition, a change of as little as 0.5 ml or less can sometimes make a difference between too much restriction and the correct amount of restriction.

The lower esophageal sphincter (LES) is a ring of increased thickness in the circular, smooth muscle layer of the esophagus. At rest, the lower esophageal sphincter maintains a high-pressure zone between 15 and 30 millimeters (mm) Hg above intragastric pressures. The lower esophageal sphincter relaxes before the esophagus contracts, and allows food to pass through to the stomach. After food passes into the stomach, the sphincter constricts to prevent the contents from regurgitating into the esophagus. The resting tone of the LES is maintained by myogenic (muscular) and neurogenic (nerve) mechanisms. The release of acetylcholine by nerves maintains or increases lower esophageal sphincter tone. It is also affected by different reflex mechanisms, physiological alterations, and ingested substances. The release of nitric oxide by nerves relaxes the lower esophageal sphincter in response to swallowing, although transient lower esophageal sphincter relaxations may also manifest independently of swallowing. This relaxation is often associated with transient gastroesophageal reflux in normal people.

Gastroesophageal reflux disease, commonly known as GERD, results from incompetence of the lower esophageal sphincter, located just above the stomach in the lower part of the esophagus. Acidic stomach fluids may flow retrograde across the incompetent lower esophageal sphincter into the esophagus. The esophagus, unlike the stomach, is not capable of handling highly acidic contents so the condition results in the symptoms of heartburn, chest pain, cough, difficulty swallowing, or regurgitation. These episodes can ultimately lead to injury of the esophagus, oral cavity, the trachea, and other pulmonary structures.

Evidence indicates that up to 36% of otherwise healthy Americans suffer from heartburn at least once a month, and that 7% experience heartburn as often as once a day. It has been estimated that approximately 1-2% of the adult population suffers from GERD, based on objective measures such as endoscopic or histological examinations. The incidence of GERD increases markedly after the age of 40, and it is not uncommon for patients experiencing symptoms to wait years before seeking medical treatment, even though mild cases can be successfully treated with lifestyle modifications and pharmaceutical therapy. For patients, who are resistant, or refractory, to pharmaceutical therapy or lifestyle changes, surgical repair of the lower esophageal sphincter is an option.

The most common surgical repair, called fundoplication surgery, generally involves manipulating the diaphragm, wrapping the upper portion of the stomach, the fundus, around the lower esophageal sphincter, thus tightening the sphincter, and reducing the circumference of the sphincter so as to eliminate the incompetence. The hiatus, or opening in the diaphragm is reduced in size and secured with 2 to 3 sutures to prevent the fundoplication from migrating into the chest cavity. The repair can be attempted through open surgery, laparoscopic surgery, or an endoscopic, or endoluminal, approach by way of the throat and the esophagus. The open surgical repair procedure, most commonly a Nissen fundoplication, is effective but entails a substantial insult to the abdominal tissues, a risk of anesthesia-related iatrogenic injury, a 7 to 10 day hospital stay, and a 6 to 12 week recovery time, at home. The open surgical procedure is performed through a large incision in the middle of the abdomen, extending from just below the ribs to the umbilicus (belly button).

Endoscopic techniques for the treatment of GERD have been developed. Laparoscopic repair of GERD has the promise of a high success rate, currently 90% or greater, and a relatively short recovery period due to minimal tissue trauma. Laparoscopic Nissen fundoplication procedures have reduced the hospital stay to an average of 3 days with a 3-week recovery period at home.

Another type of laparoscopic procedure involves the application of radio-frequency waves to the lower part of the esophagus just above the sphincter. The waves cause damage to the tissue beneath the esophageal lining and a scar (fibrosis) forms. The scar shrinks and pulls on the surrounding tissue, thereby tightening the sphincter and the area above it. These radio-frequency waves can also be used to create a controlled neurogenic defect, which may negate inappropriate relaxation of the LES.

A third type of endoscopic treatment involves the injection of material or devices into the esophageal wall in the area of the lower esophageal sphincter. This increases the pressure in the lower esophageal sphincter and prevents reflux.

One laparoscopic technique that appears to show promise for GERD therapy involves approaching the esophageal sphincter from the outside, using laparoscopic surgical techniques, and performing a circumference reducing tightening of the sphincter by placement of an adjustable band such that it surrounds the sphincter. However, this procedure still requires surgery, which is more invasive than if an endogastric transluminal procedure were performed through the lumen of the esophagus or stomach, such as via the mouth. Furthermore, the necessity to provide for future adjustment in the band also requires some surgical access and this adjustment would be more easily made via a transluminal approach.

For both treatment of obesity and GERD, gastric banding has proven to be a desirable treatment option. However, despite the advantages provided by gastric banding methods, they nonetheless suffer from drawbacks that limit the realization of the full potential of this therapeutic approach. For example, slippage may occur if a gastric band is adjusted too tight, or too loose, depending on the situation and the type of slippage. Slippage can also occur in response to vomiting, as occurs when a patient eats more food that can be comfortably accommodated in the upper pouch. During slippage, the size of the upper pouch may grow, causing the patient to be able to consume a larger amount of food before feeling full, thus lowering the effectiveness of the gastric band. On the other hand, erosion may occur if the gastric band is adjusted or secured too tightly. In either case detecting slippage or reducing the risk of erosion may be accomplished by adjusting the device to provide a proper flow rate.

Furthermore, current methods of adjusting gastric bands and restriction devices require invasive procedures. For example, one method requires penetration of the abdomen with a needle in order to withdraw or inject a solution from a subcutaneous access port that is connected to a tube that in turn regulates the inflation of the gastric band. Infection and patient discomfort and pain are related to the use of the needle required to fill the gastric band with saline. As a result, non-invasively adjustable gastric bands have been proposed, some of which seek to provide a correct reading of the inner diameter of the gastric band at all times. However, because the wall thickness of the stomach is not uniform from patient to patient, the actual inner diameter of the stomach at the stoma opening will be unknown. Thus the size of the opening of the band is at best an approximation of the stomal opening that connects the smaller upper pouch and the remainder of the stomach.

As a result, in order to properly adjust a gastric band some method of measuring flow through the device or otherwise related the luminal aperture of the alimentary canal at the side of the band is needed. Current methods typically make use of radiological procedures such as X-ray fluoroscopy of barium sulfate suspensions. However, the use of X-ray procedures in a significant number of patients is highly undesirable. The majority of gastric banding patients undergoing therapy to treat obesity are women of child-bearing age. The first few weeks of pregnancy, when a mother may be unaware she is pregnant, is an especially critical time of fetal development, and exposure to X-rays is to be avoided if at all possible. In addition, while fluoroscopy can monitor flow of a radio-opaque material such as barium sulfate, it is not particularly well suited to provide accurate information about the size of the band aperture, the size of the lumen in the alimentary canal where the band is placed, or whether the band is causing secondary problems such as erosion of the gastric wall. Thus it would be desirable to have a gastric banding system that included a non-invasive means of adjusting and monitoring band function in the patient that improves on the prior art methods.

SUMMARY OF THE INVENTION

In a first embodiment of the invention, a gastrointestinal implant system includes an adjustable restriction device having a contact surface configured for at least partially engaging a surface of a gastrointestinal tract of a mammal. The implant system further includes an implantable interface including a first driving element, the first driving element being moveable and operatively coupled to the adjustable restriction device by an actuator configured to change the dimension or configuration of the contact surface in response to movement of the first driving element. The system also includes an external adjustment device having a second driving element configured to non-invasively engage the first driving element of the implantable interface from a location external to the mammal. In the system, actuation of the second driving element of the external adjustment device produces movement in the first driving element of the implantable interface and results in a change in the dimension or configuration of the contact surface.

In another embodiment of the invention, a gastrointestinal implant system includes an adjustable restriction device having a contact surface configured for at least partially engaging a surface of a gastrointestinal tract of a mammal. The system includes an implantable interface including a driving element, the driving element being moveable and operatively coupled to the adjustable restriction device by an actuator configured to change the dimension or configuration of the contact surface in response to movement of the driving element. Movement of the driving element is effectuated by application of a moving magnetic field originating external to the mammal.

In another embodiment of the invention, a gastrointestinal implant includes an adjustable restriction device having a contact surface configured for at least partially engaging a surface of a gastrointestinal tract of a mammal. The implant includes an actuator configured to change the dimension or configuration of the contact surface in response to rotational movement of an implantable interface operatively coupled to the actuator via a drive transmission. The drive transmission includes a rotatable lead screw having mounted thereon a nut affixed to an end of the actuator. In this embodiment, an external adjustment device is configured to non-invasively couple to the implantable interface from a location external to the mammal. Rotational movement of the implantable interface results in a change in the dimension or configuration of the contact surface.

In still another embodiment, a gastrointestinal implant system includes an adjustable restriction device having a contact surface configured for at least partially engaging a surface of a gastrointestinal tract of a mammal. The system includes an implantable interface including a moveable magnetic element, the moveable magnetic element being operatively coupled to the adjustable restriction device by an actuator configured to change the dimension or configuration of the contact surface in response to movement of the moveable magnetic element of the implantable interface. The system further includes an external adjustment device having at least one moveable magnetic element configured to magnetically engage the moveable magnetic element of the implantable interface from a location external to the mammal. When the at least one moveable magnetic element of the external adjustment device is magnetically engaged with the moveable magnetic element of the implantable interface, movement of the at least one moveable magnetic element of the external adjustment device produces corresponding movement in the moveable magnetic element of the implantable interface and results in a change in the dimension or configuration of the contact surface.

In yet another embodiment, a gastrointestinal implant system that is configured to be implanted within a mammal includes an external drive assembly including at least one external magnet, the external drive assembly having a plurality of alternating magnetic poles rotationally arranged about an axis of rotation. The system further includes an internal drive assembly including at least one internal magnet, the internal drive assembly having a plurality of alternating magnetic poles rotationally arranged about an axis of rotation. The at least one external magnet and the at least one internal magnet are adapted for magnetic coupling and wherein rotation of the at least one external magnet in a first direction results in a corresponding rotation of the at least one internal magnet in a second direction.

In another embodiment, a gastrointestinal implant system includes a restrictive band configured to at least partially engage a surface of a gastrointestinal tract of a mammal, the restrictive band having a first configuration and a second configuration, wherein the second configuration constricts the gastrointestinal tract more than does the first configuration. The system further includes an actuation element at least partially disposed on or in the restrictive band, wherein actuation of the actuation element results in movement of the restrictive band from the first configuration to the second configuration. The system further includes an implantable interface containing a first magnetic assembly coupled to the actuation element, the implantable interface being configured for implantation within the mammal. An external adjustment device containing a second magnetic assembly is part of the functioning system, wherein movement of the second magnetic assembly causes movement of the first magnetic assembly and actuation of the actuation element.

In still another aspect of the invention, a gastrointestinal implant device includes an adjustable restriction device having a flexible adjustable body including a contact surface configured for at least partially engaging a surface of a gastrointestinal tract of a mammal, the flexible adjustable body including a moveable actuator anchored at a distal end to the flexible adjustable body, the moveable actuator being disposed within the flexible adjustable body about a plurality of ribs.

In yet another aspect of the invention, a method of treating obesity in a mammal includes providing an adjustable restriction device configured for at least partially engaging a surface of a gastrointestinal tract of a mammal, the adjustable restriction device including an implantable interface comprising a first moveable driving element, the first moveable driving element being operatively coupled to the adjustable restriction device by an actuator configured to change the dimension or configuration of the adjustable restriction device in response to movement of the first moveable driving element. An external adjustment device external to an abdominal region of the mammal is provided, the external adjustment device having a second moveable driving element configured to non-invasively engage the first moveable driving element of the implantable interface from a location external to the mammal. The first moveable driving element of the implantable interface is moved by moving the second moveable driving element of the external adjustment device.

In another embodiment of the invention, a method of treating obesity in a mammal includes providing an adjustable restriction device configured for at least partially engaging a surface of a gastrointestinal tract of a mammal, the adjustable restriction device including an implantable interface including a moveable magnetic element, the moveable magnetic element being operatively coupled to the adjustable restriction device by an actuator configured to change the dimension or configuration of the adjustable restriction device in response to movement of the moveable magnetic element of the implantable interface. An external adjustment device external to an abdominal region of the mammal is provided, the external adjustment device having at least one moveable magnetic element configured to magnetically engage the moveable magnetic element of the implantable interface from a location external to the mammal. The moveable magnetic element of the implantable interface is moved by moving the at least one moveable magnetic element of the external adjustment device.

The at least one magnetic element of the external adjustment device may be magnetically coupled to the at least one magnetic element of the implantable interface via various faces of the two magnetic elements. These may include, for instance, facing axial or end surfaces (e.g., ends of a cylinder or sector-shaped element) as well as radial surfaces (e.g., circumferential surface of a cylindrical-shaped element).

BRIEF DESCRIPTION OF THE DRAWINGS

FIG. 38 thus represents the relative location between the implantable interface and the external device after the implantable interface has been implanted in a patient.

FIG. 68 illustrates a cross-sectional view of the implantable interface according to another embodiment.

FIG. 69 illustrates a perspective view of a distal end of a drive cable according to one embodiment.

FIG. 75A illustrates the permanent magnet of the implantable interface in the 0° position.

FIG. 75B illustrates the permanent magnet of the imglantable interface in the 90° position.

FIG. 75C illustrates the permanent magnet of the implantable interface in the 180° position.

FIG. 75D illustrates the permanent magnet of the implantable interface in the 270° position.

FIGS. 91-98 illustrate cross-sectional views of the driven magnet along with the acoustic or sonic indicator housing illustrating the rotational orientation of the magnet and the magnetic ball. Various states are illustrated as the magnet rotates in the counter-clockwise direction.

DETAILED DESCRIPTION OF THE ILLUSTRATED EMBODIMENTS

Figure 1:
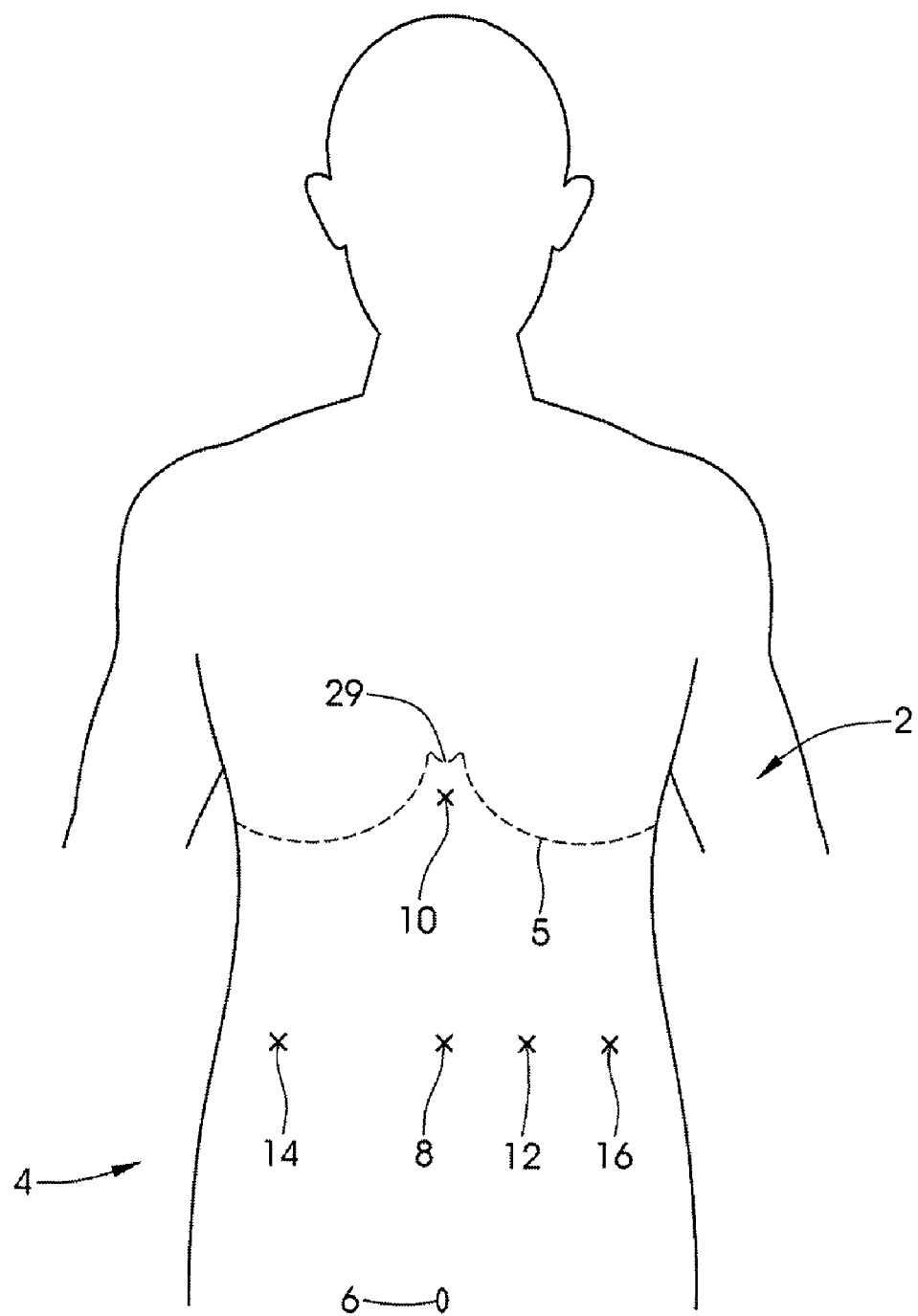
FIG. 1 illustrates a patient's torso showing the locations for placement of trocars and various other tools during a laparoscopic procedure for implantation of an obesity control system.
Figure 2:
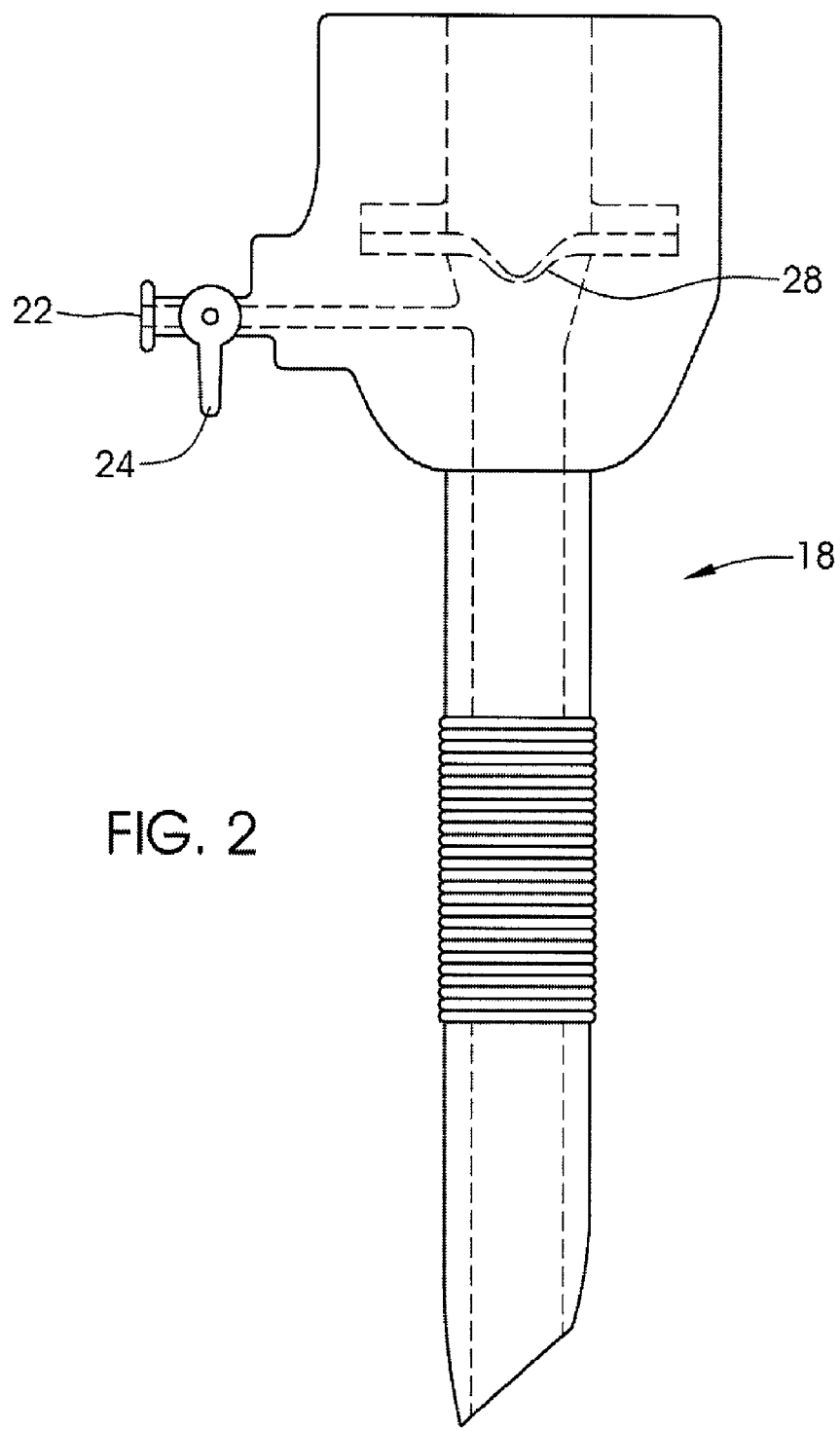
FIG. 2 illustrates a side view of a trocar with an obturator removed.
Figure 3:
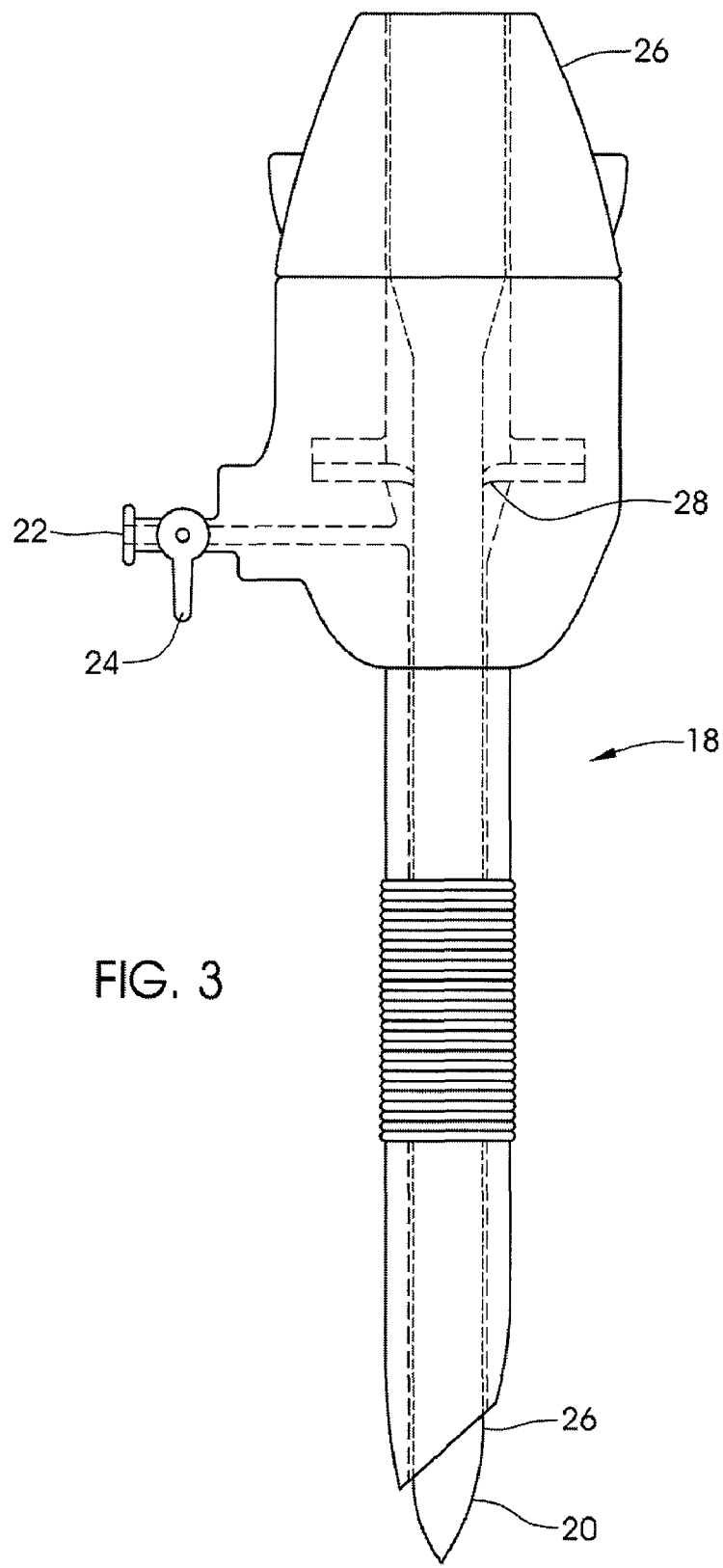
FIG. 3 illustrates a side view of a trocar with an obturator in place.

FIG. 1 illustrates the abdomen 4 of a patient 2. The navel 6 and the ribline 5 are shown for reference. In typical laparoscopic surgeries for placement of gastric restriction systems, a 12 mm trocar (or a larger trocar) is placed at first site 8. FIGS. 2 and 3 illustrate a trocar 18 of this type. This trocar 18 is placed prior to insufflation (inflation of the abdominal cavity by pressurized gas, such as carbon dioxide), so for safety purposes, often a trocar with an optically clear tip 20 is used. A scope (such as a 5 mm laparoscope) is inserted inside the tip 20 and can view the separation of tissue layers and the safe entrance into the abdominal cavity. Alternatively, instead of using the trocar tip 20 to separate the tissue, an incision can first be made in the skin followed by finger dissection into the abdominal cavity. The trocar 18 is then placed through the tract made by the finger dissection. After insertion of the trocar 18, pressurized $CO_2$ is injected into the abdominal cavity by attaching the pressure line to a luer 22 on the trocar 18. The pressure is maintained whether the trocar 18 has an obturator 26 in place, as in FIG. 3, or has no obturator 26, as in FIG. 2, by the use of a trocar valve 28. The pressure inside the abdominal cavity can be maintained even after detaching the pressure line by closing a luer valve 24.

Once insufflation is achieved, for example at a pressure of 10 to 20 mm Hg, other trocars can be placed at additional sites 10, 12, 14, 16. The trocars placed at sites 10, 14 and 16 are typically 5 mm trocars. Site 10 is located just below xiphoid process 29 of the sternum. The 5 mm trocar placed at site 10 is removed and replaced with a liver retractor, which allows easier access and visualization of the upper portion of the stomach, and easier dissection of the surrounding features. Sites 12, 14 and 16 are used for the variety of laparoscopic grasping, cutting, electrosurgical, and manipulating instruments, which are usually placed through the trocars, with the obturators removed. Sites 8 and 12 are often used for placement of laparoscopes through the respective trocars, for example 10 mm or 5 mm laparoscopes. A 5 mm, 10 mm, or 12 mm trocar, for example can be used in site 12, depending on the size of laparoscope desired. Many variations of this trocar placement are commonly used. This description is only relates to one particular method.

Figure 4:
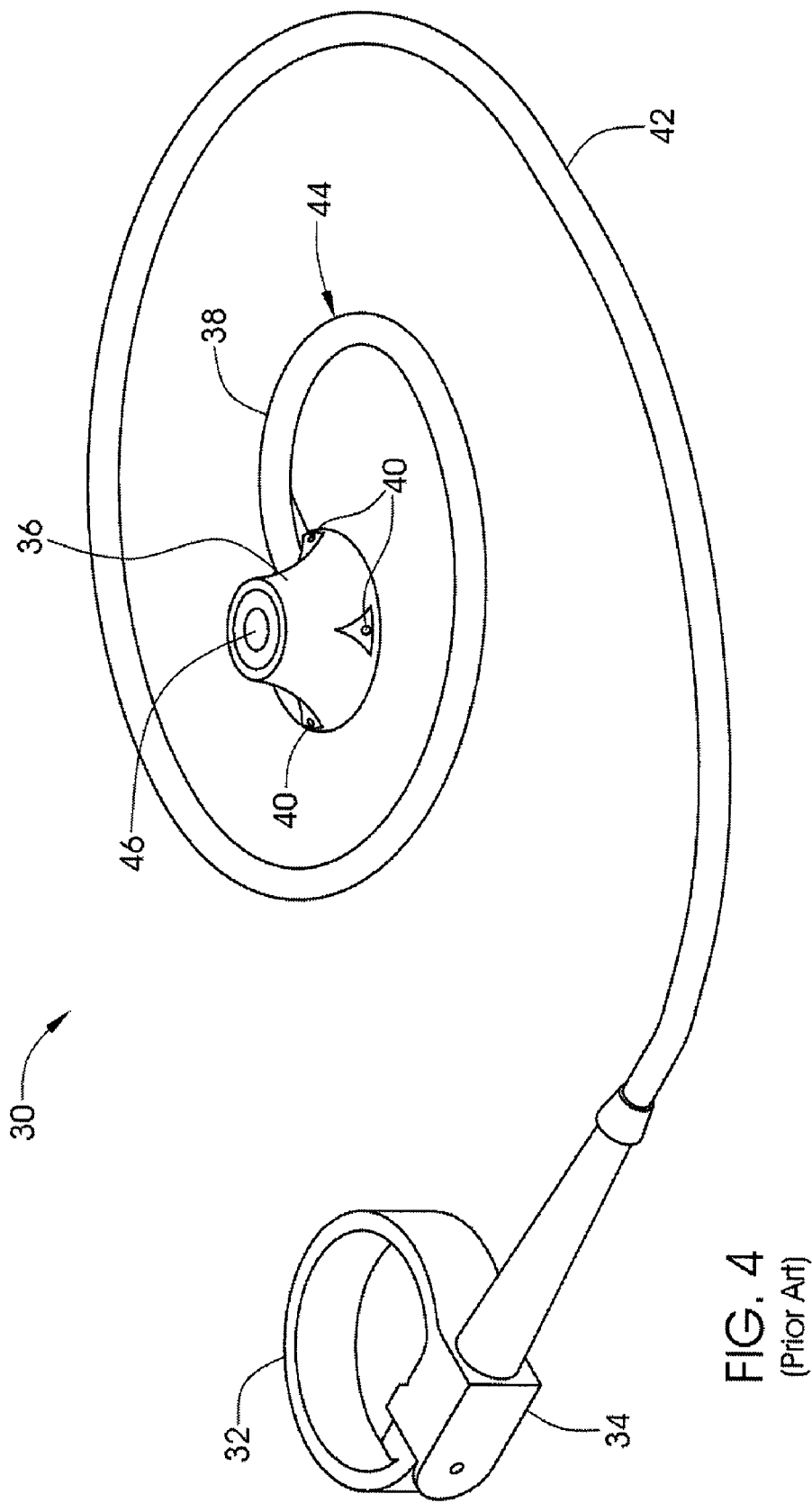
FIG. 4 illustrates an inflatable laparoscopic obesity control system according to the prior art.
Figure 5:
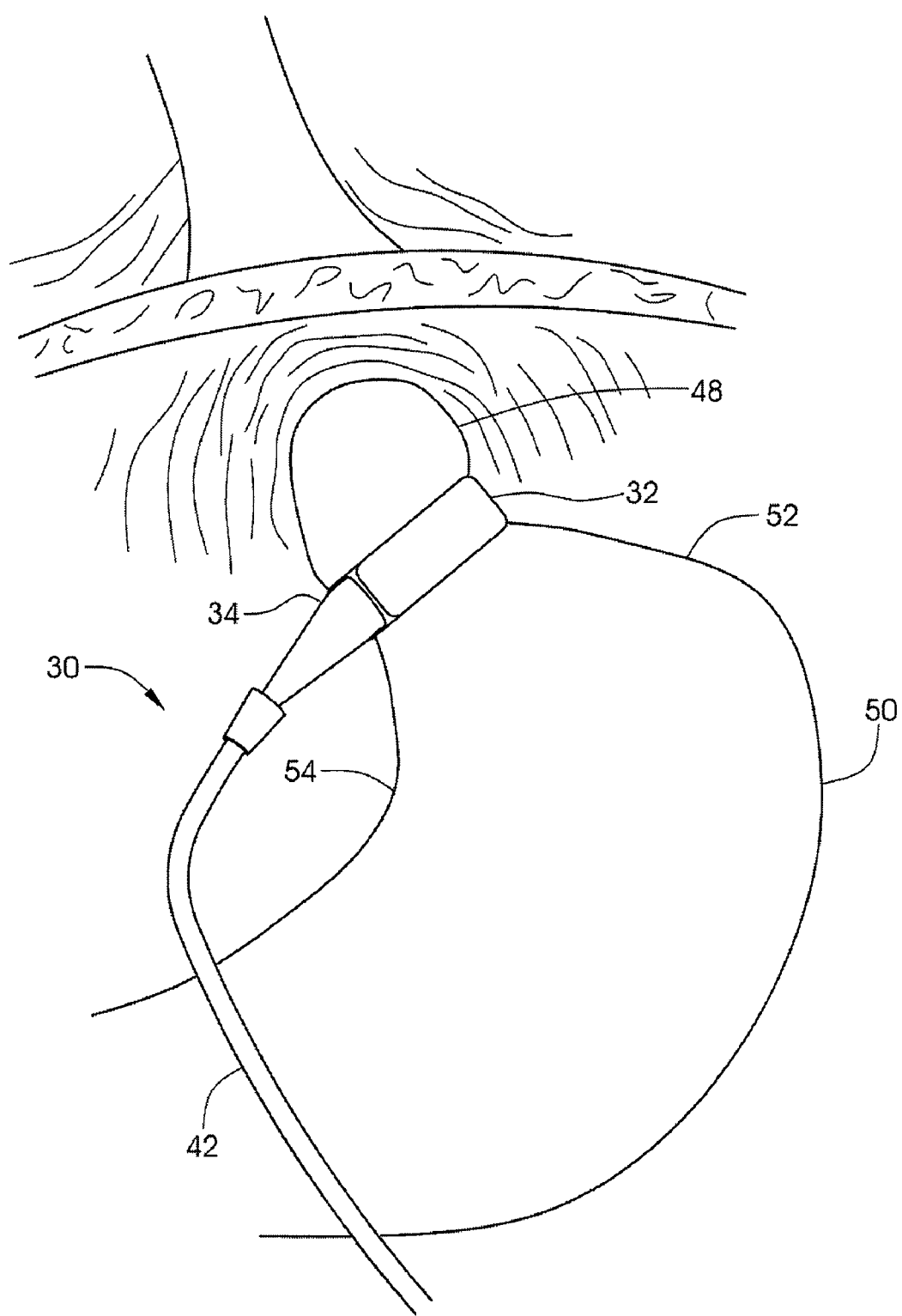
FIG. 5 illustrates a prior art laparoscopic obesity control system after being locked around the stomach.
Figure 6:
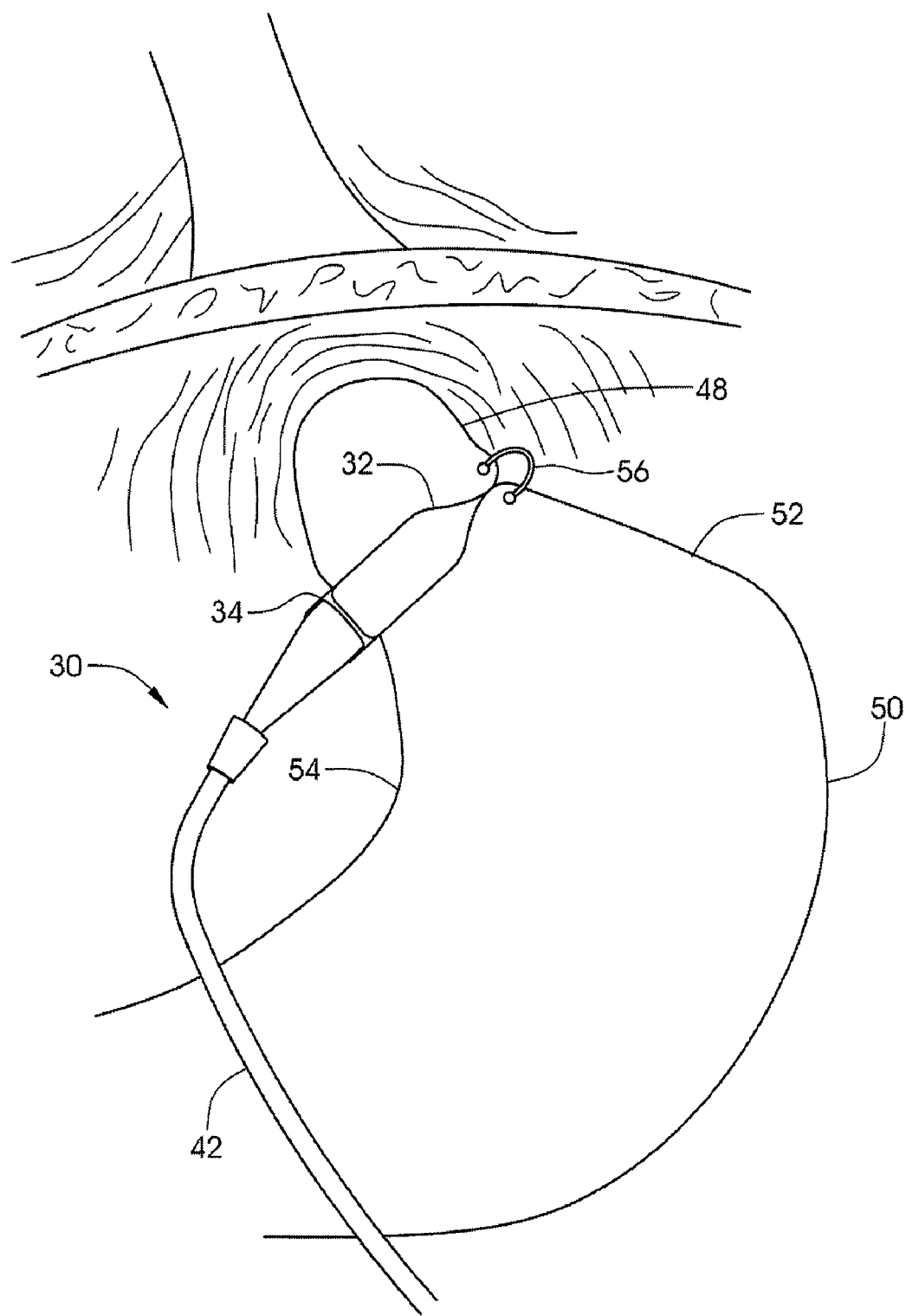
FIG. 6 illustrates a prior art laparoscopic obesity control system after being secured by suturing the stomach around a portion of the inflatable ring.

FIG. 4 illustrates a prior art inflatable obesity control system 30. Inflatable ring 32 is closed around the upper portion of the stomach, using general techniques described in, for example, Ren et al., *Laparoscopic Adjustable Gastric Banding: Surgical Technique*, Journal of Laparoendoscopic & Advanced Surgical Techniques, Vol. 13, No. 4, 2003, which is incorporated by reference as if set forth fully herein. The most common current technique is known as the pars flaccida technique, which is described in the above-noted publication. The inflatable ring 32 is attached to itself around the stomach using a locking mechanism 34. The orientation of the inflatable band after attachment is illustrated in FIG. 5. The stomach 50 includes a fundus 52 and a lesser curvature 54. The attached inflatable ring 32 forms a small upper pouch 48 in the stomach 50, separated by a smaller diameter stoma (not visible) underneath the attached inflatable ring 32. As shown in FIG. 6, a portion of the wall of the upper pouch is sutured to the wall of the remainder of the stomach 50 with suture 56.

Returning to FIG. 4, port 36 is implanted at a subcutaneous site and sutured to fascia (the sheath of tissue covering muscle) by the use of suture holes 40. The port 36 is attached to the inflatable ring 32 by an inflation tube 42. The inflation tube 42 provides a communication means between the port 36 and the inflatable ring 32 of the gastric restriction device. The proximal end 44 of the inflation tube 42 is forced over a metal barb (not shown) which is integral with an extension 38 of the port 36. This can be a difficult and time consuming portion of the procedure. Subsequent to the implantation surgery, the inflatable ring 32 can be inflated or deflated by the injection of sterile saline through the port 36 by use of a syringe attached to a non-coring needle. The needle punctures the skin and subcutaneous fat and is guided through the septum 46 of the port 36.

Figure 7:
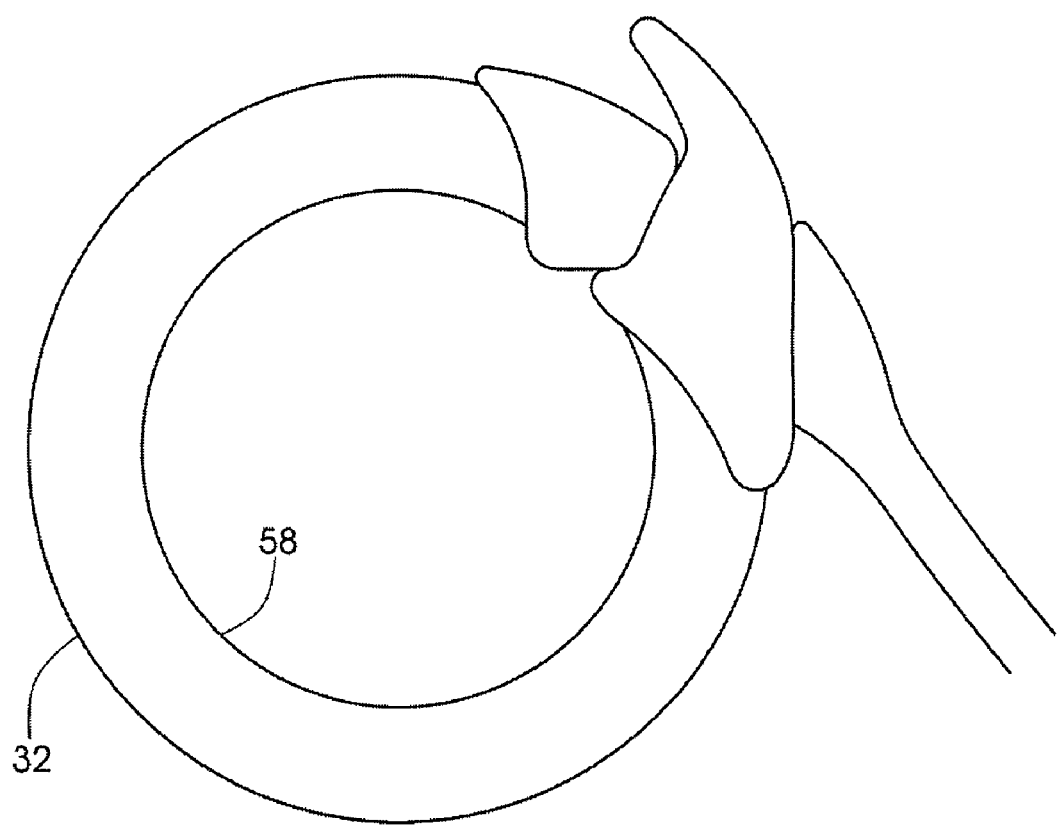
FIG. 7 illustrates the inflatable ring of a prior art inflatable obesity control system in a non-pressurized state.
Figure 8:
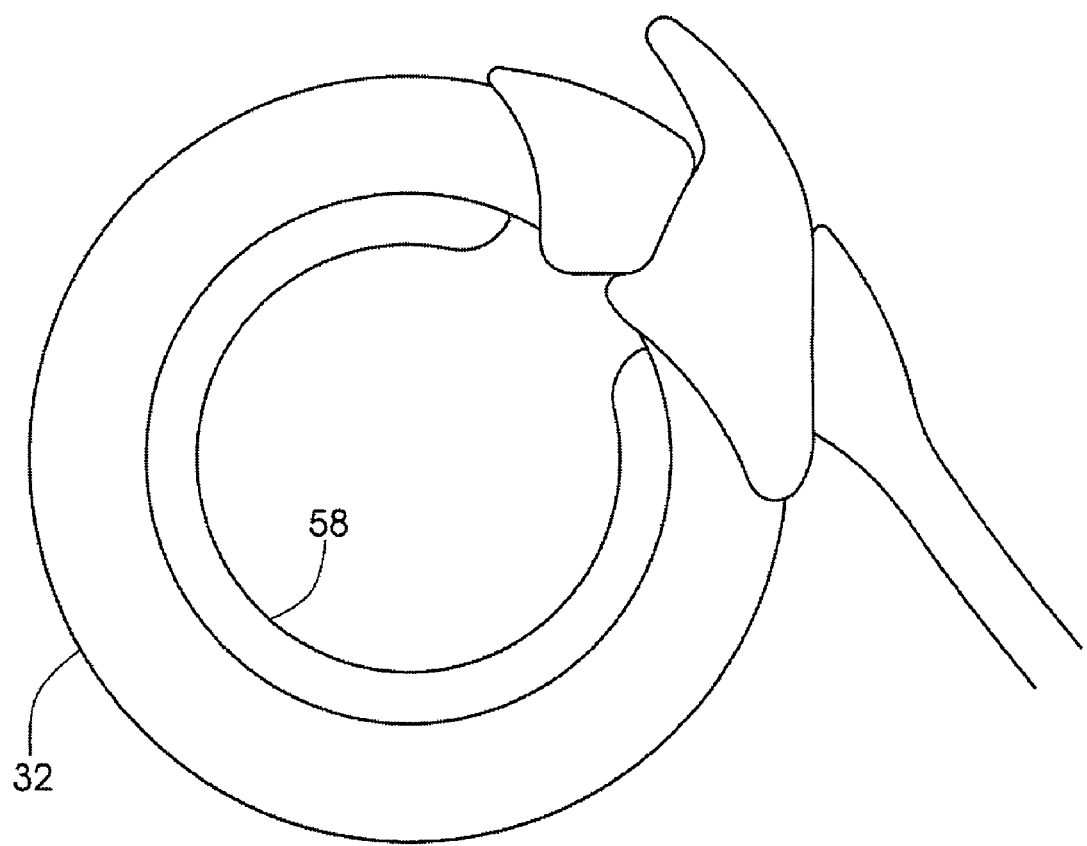
FIG. 8 illustrates the inflatable ring of a prior art inflatable obesity control system with an additional 2 ml injected.
Figure 9:
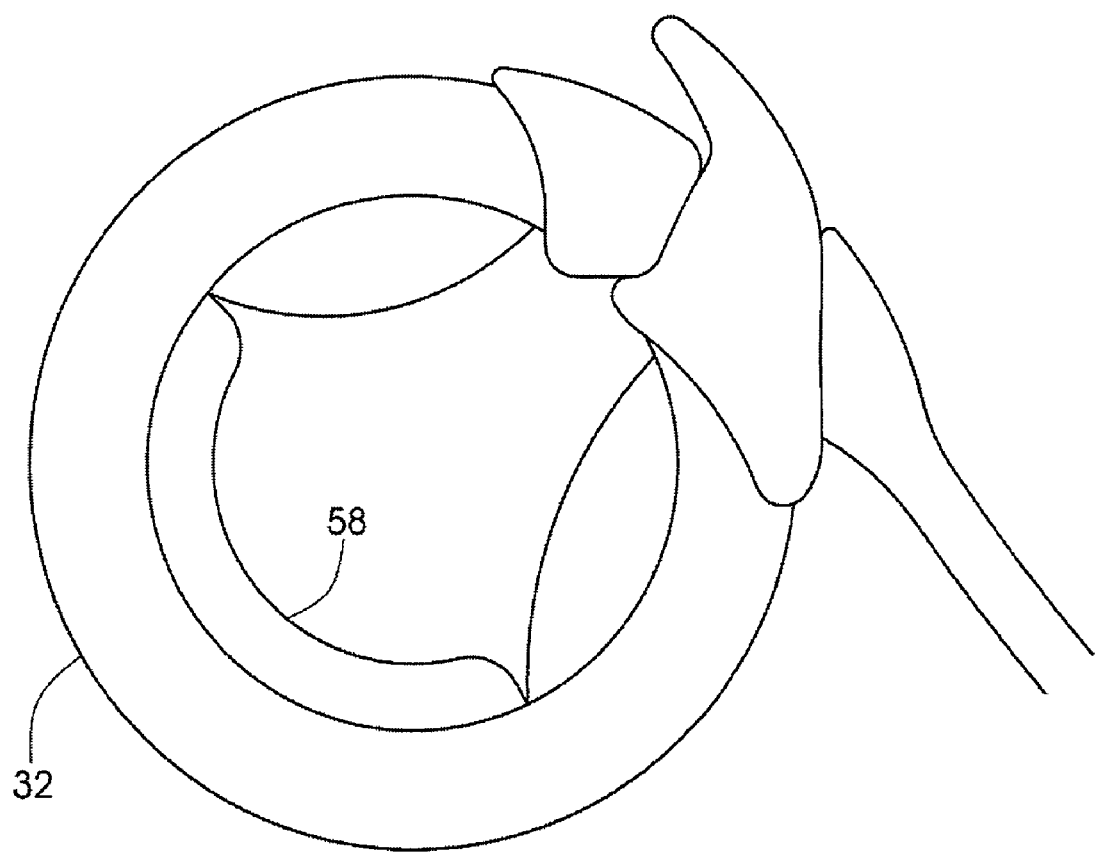
FIG. 9 illustrates the inflatable ring of a prior art inflatable obesity control system with an additional 4 ml injected.

Depending on the amount of restriction of the stomach desired, the inflatable ring 32 can be adjusted so that the patient feels full after eating a small amount of food. FIG. 7 illustrates the inflatable ring 32 in its non-pressurized state. Typically during the implantation procedure, the inflatable obesity control system 30 is primed with enough saline to fill its dead space volume while removing the air. It is left at ambient pressure (and not pressurized) usually for the first several weeks while the patient heals and the body forms a fibrous capsule over portions where the implanted device interfaces with the stomach. After this healing period, the inflatable obesity control system 30 is filled with saline as described, causing balloon 58 to distend inward radially, creating a smaller diameter stoma. FIG. 8 illustrates the inflatable obesity control system 30 inflated with an additional 2 ml of saline (beyond the initial priming volume). FIG. 9 illustrates the inflatable obesity control system 30 inflated with an additional 4 ml of saline (beyond the initial priming volume).

Figure 10:
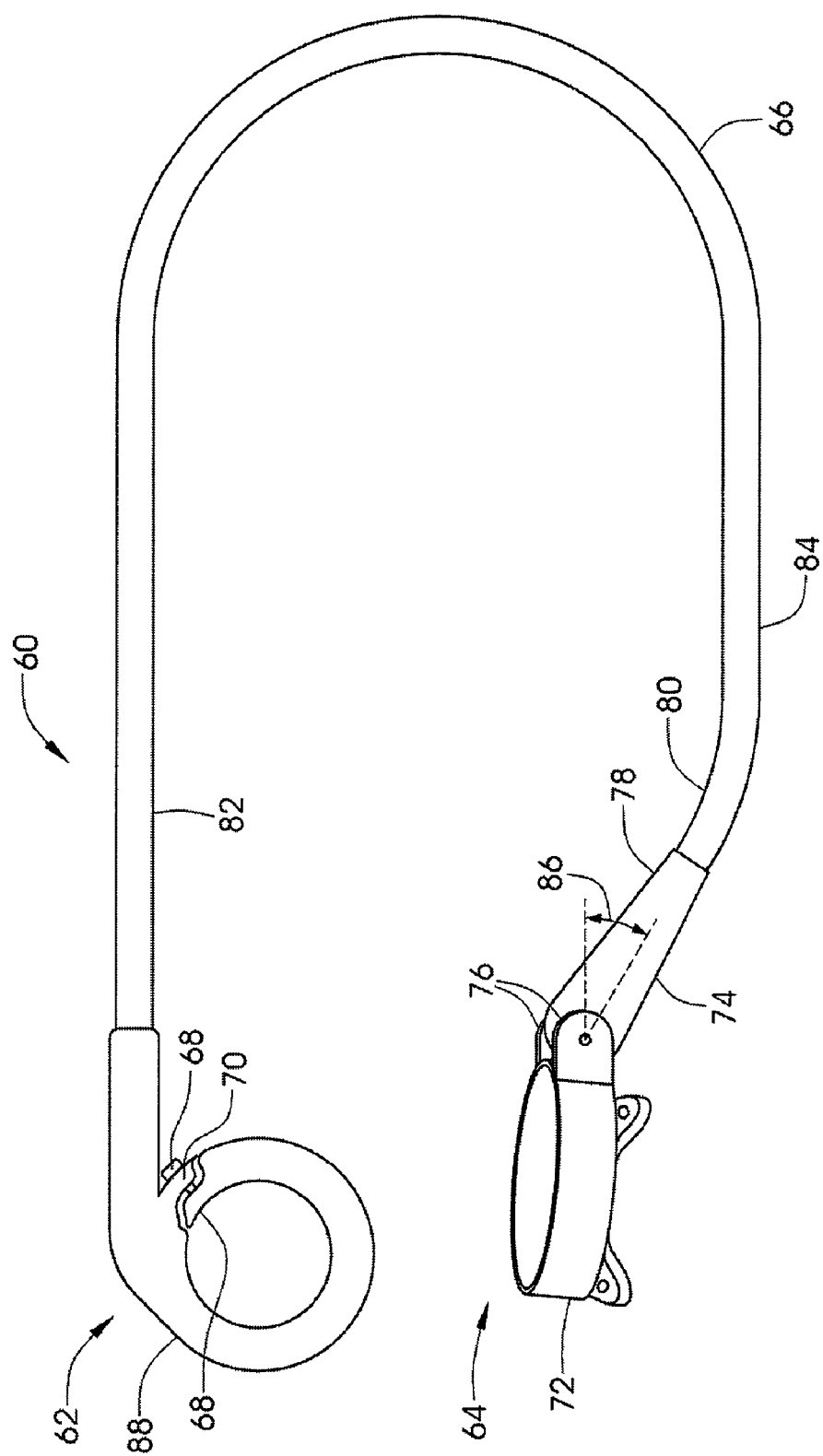
FIG. 10 illustrates an implantable obesity control system in accordance with one embodiment.
Figure 11:
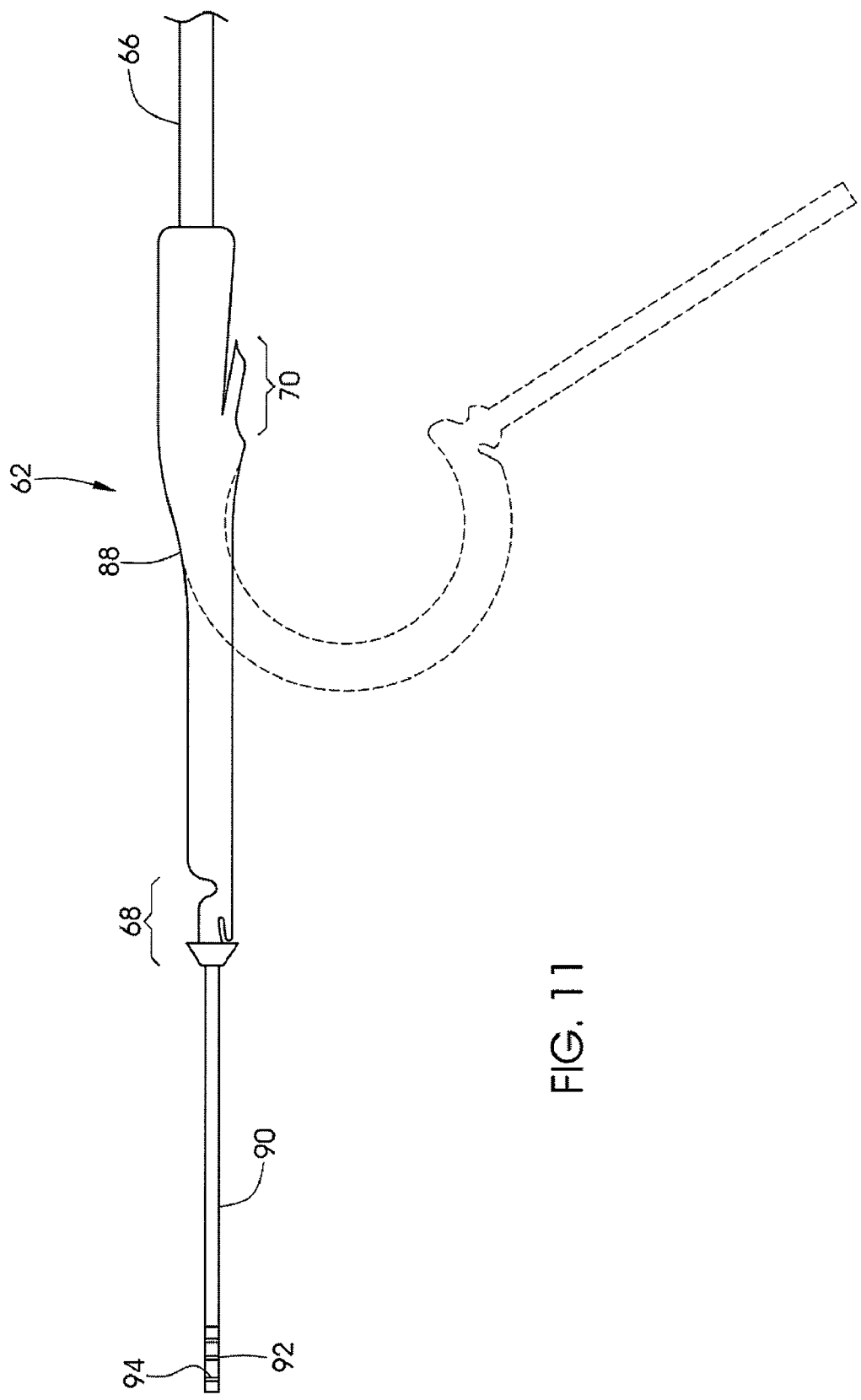
FIG. 11 illustrates a distal section of the obesity control system in a straightened configuration (solid lines), for example, for placement into the abdominal cavity.

FIG. 10 illustrates an implantable obesity control system 60 comprising a restriction device 62, an implantable interface 64 and a drive transmission 66. During an initial surgical procedure, the restriction device 62 is implanted in the patient so that it creates a stoma opening and controllably restricts the size of this opening between an upper pouch and the remainder of the stomach. The restriction device 62 comprises a body portion 88, a first attachment portion 68 and a second attachment portion 70. The implantable interface 64 comprises a main body 72 and an extension 74 which are coupled to each other by an articulation 76. The articulation 76 allows adjustment of an angle 86 between the main body 72 and the extension 74, for optimized implantation within the patient's anatomy. An exemplary angle is 45°. The drive transmission 66 has a distal end 82 and a proximal end 84. The implantable interface 64 can be attached, detached and reattached to the drive transmission 66 by coupling or decoupling an implantable interface attachment portion 78 and a drive shaft attachment portion 80. Referring now to FIG. 11, when the first attachment portion 68 and the second attachment portion 70 of the restriction device 62 are not attached to each other, the body portion 88 can be oriented in a linear or substantially linear shape that may be placed into the abdominal cavity through the inner lumen of the trocar 18, or any other type of cannula, for example, a 12 mm or 15 mm trocar 18.

Alternatively, the restriction device 62 may be placed through the tract made after a trocar, cannula, sheath, dilator, needle or other puncturing device, cutting, spreading or dissecting device is placed, then removed. For example, a 10 mm or 12 mm trocar 18. The restriction device 62 may also be placed through a direct incision. For example, an incision is made through the skin, and then finger dissection is used to create the tract through fat, fascia, muscle and other connective tissue. A leash 90 is adjacent the first attachment portion 68 of the restriction device 62 and can be used to aid the insertion of the restriction device 62. For example, forceps or graspers are used to grip the restriction device 62 and insert it through the trocar 18 or the tract, for example, at first site 8. For example, 5 mm laparoscopic graspers or Rochester-Pean forceps. The first attachment portion 68, may be chosen as the grasping point. Alternatively, the leash 90 may be chosen as the grasping point. For example, the leash 90 may be grasped at a flattened portion 92, which conforms to the jaws of the grasper or forceps. The flattened portion 92 has ribs 94 which resist slipping of the grasping instrument.

Figure 12:
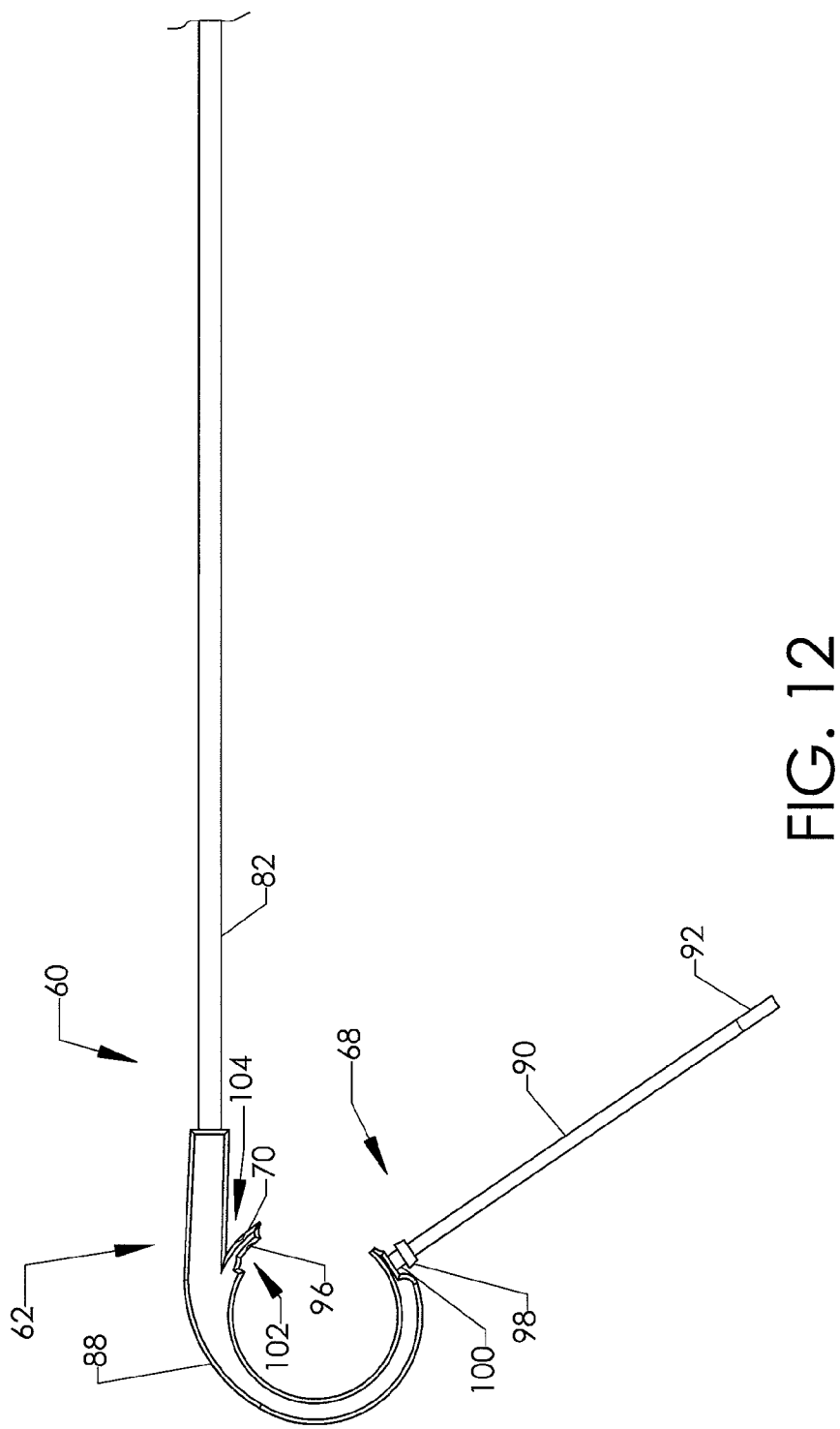
FIG. 12 illustrates a restriction device of the obesity control system just prior to being attached.
Figure 13:
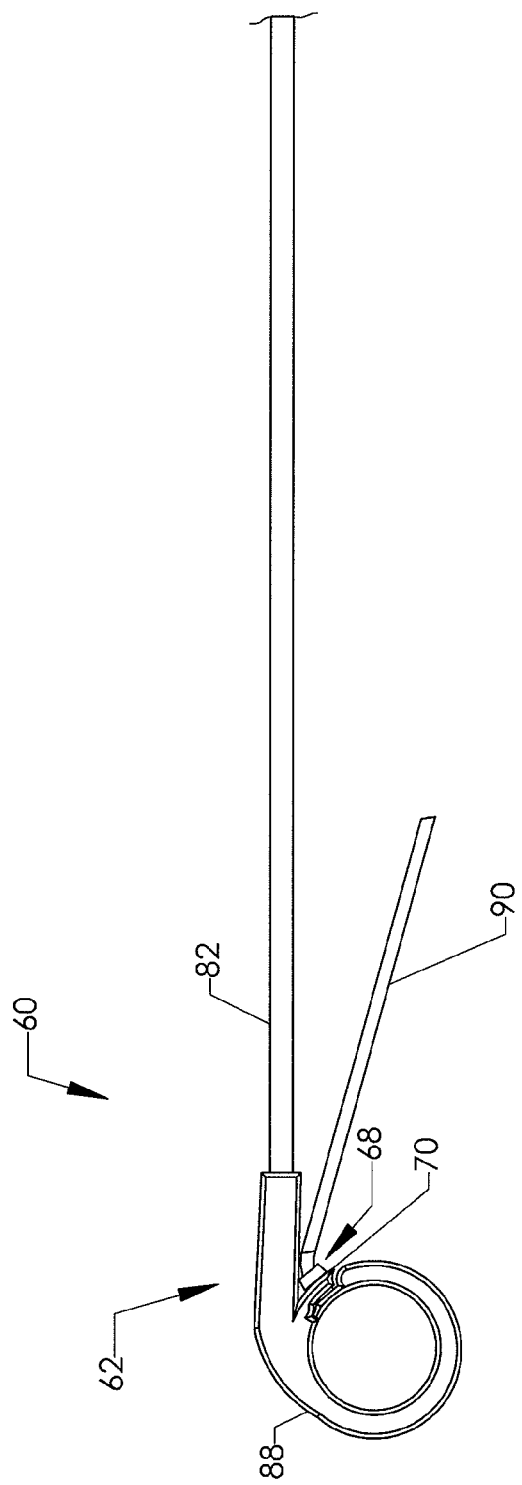
FIG. 13 illustrates the restriction device after being attached.
Figure 14:
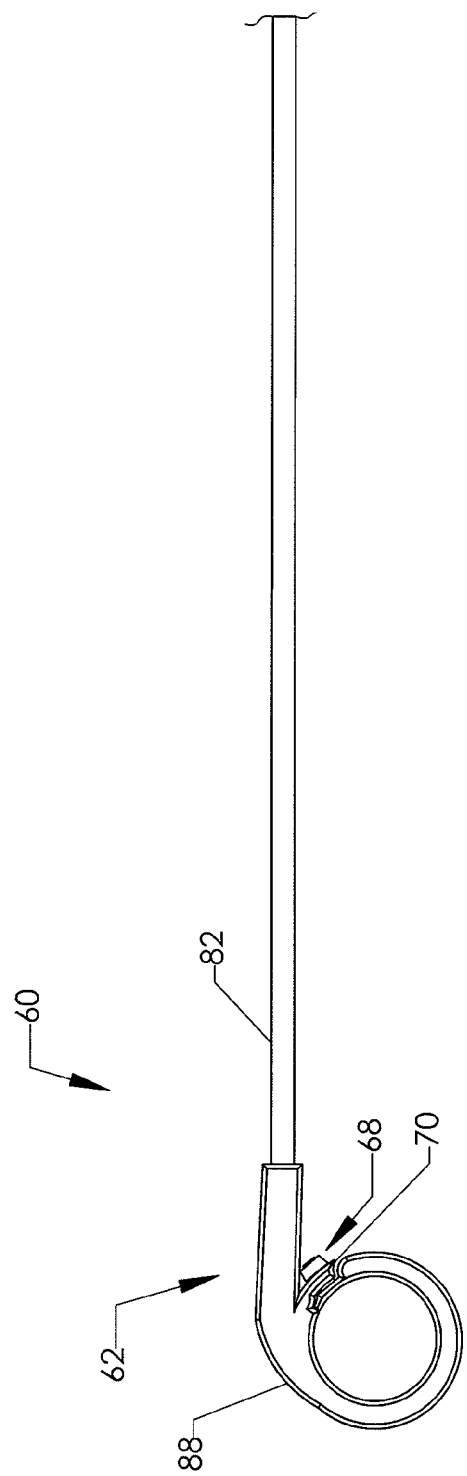
FIG. 14 illustrates the restriction device after being trimmed of its attachment leash.

After the restriction device 62 is placed into the abdominal cavity, the leash 90 is grasped. The restriction device 62 is then attached, as shown in FIGS. 12, 13 and 14. FIG. 12 illustrates the restriction device 62 prior to attachment around the stomach. Leash 90 is inserted through a hole 96, from the internal diameter side 102 towards the external diameter side 104. Leash 90 includes a tapered barb 98 which is larger in diameter than the hole 96 and a spaced portion 100. After being inserted through hole, and removing slack, leash 90 is pulled, for example with a laparoscopic grasper, while traction is applied to second attachment portion 70, until barb 98 is forced through hole 96. Because an elastomeric material is used to construct leash 90 and second attachment portion 70, temporary deformation occurs, allowing the parts to lock together, and forming the restriction device 62 into a closed configuration, as can be seen in FIG. 13.

Laparoscopic cutters are now used to trim off leash 90, close to barb 98. FIG. 14 illustrates the restriction device 62 after the trimming of leash 90. It can be seen that in the prior art obesity control system shown in FIG. 4, the entire length of the inflation tube 42 must be inserted into the abdominal cavity because the proximal end 44 of the inflation tube 42 needs to be located laparoscopically and then inserted through an opening in the locking mechanism 34 in order to lock the inflatable ring 32. In the inventive embodiment, the drive transmission 66 need not be inserted completely, because the first attachment portion 68 and second attachment portion 70 are all that need be manipulated in order to lock the restriction device 62 together. Likewise, the drive transmission proximal end 84 does not need to be located within the abdominal cavity prior to the locking step.

Figure 15:
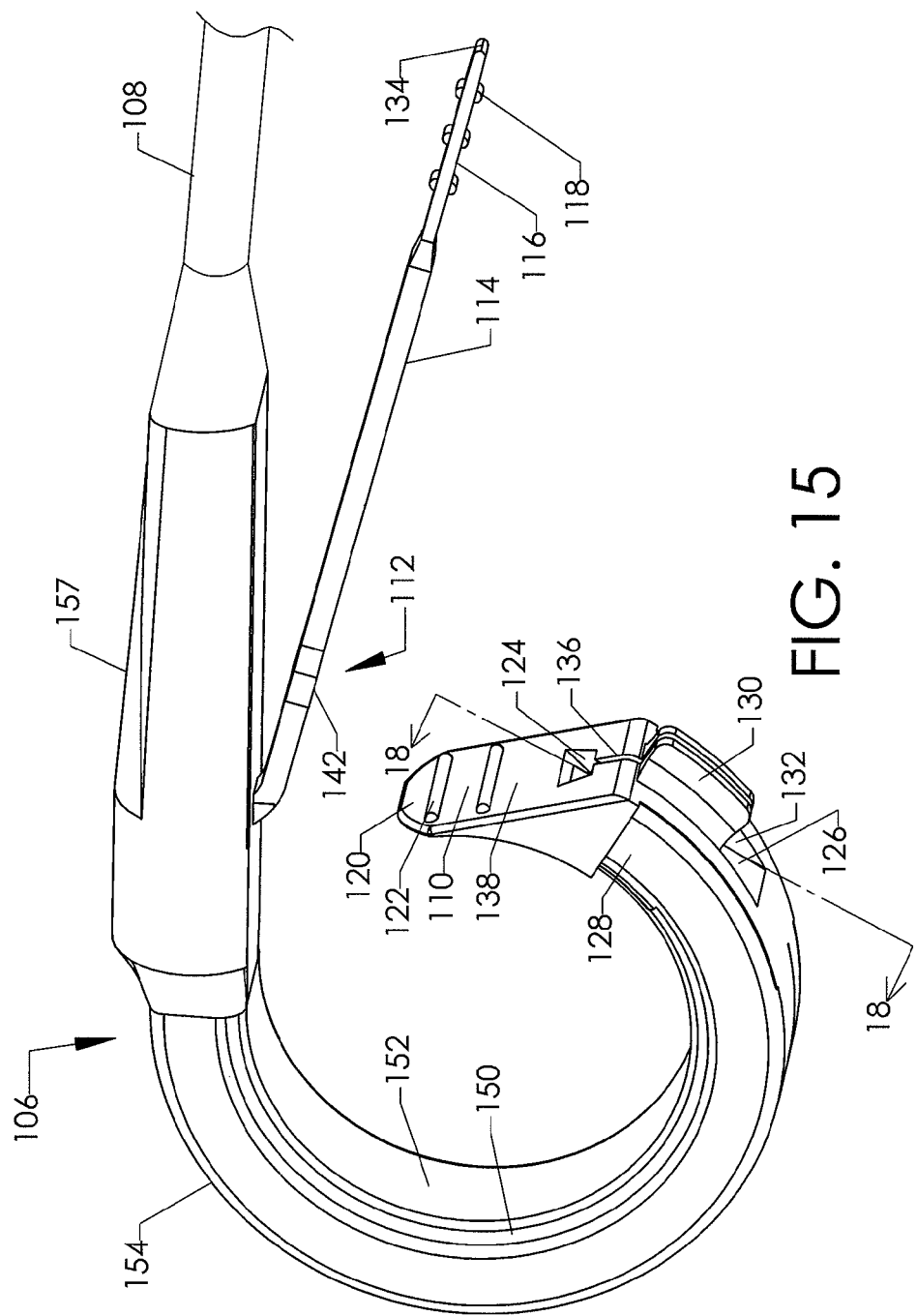
FIG. 15 illustrates an alternative embodiment of a restriction device.
Figure 16:
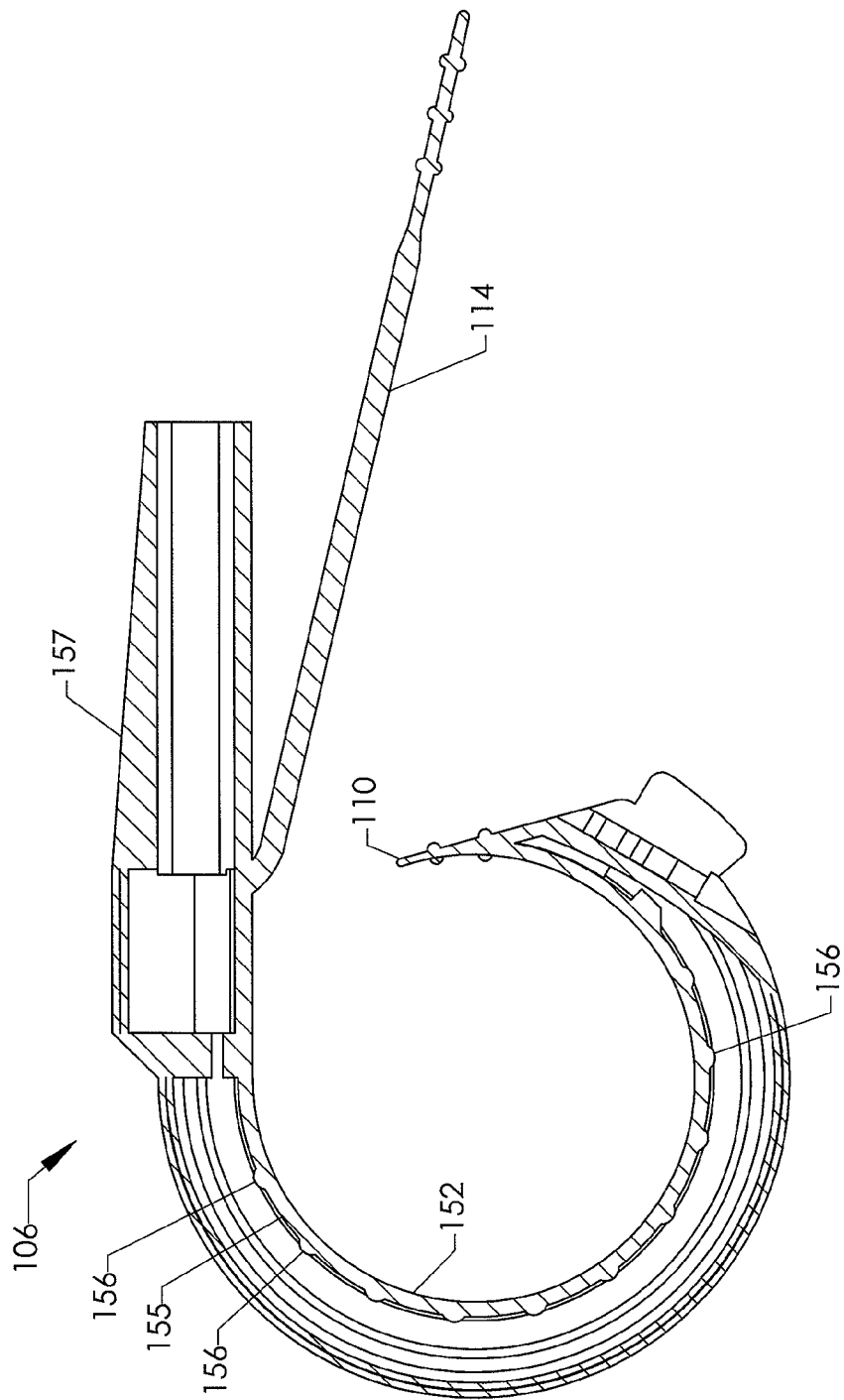
FIG. 16 illustrates a cross-sectional view of the outer shell or housing of the restriction device of FIG. 15.

FIG. 15 illustrates a restriction device 106 having an external perimeter 154 and a dynamic surface 152, which is allowed to constrict via a circumferential bellows 150. In FIG. 16, a better view of the dynamic surface 152 is visible in the cross-section. Interspersed between the thin walled portion 155 are ribs 156 that extend the majority of the width. The ribs 156 serve to reduce the contact area of a belt or band that is tightened to restrict the dynamic surface 152 to a smaller diameter, and thus to lower the tensile requirement to constrict the restriction device 106. The ribs 156 are made from the same material as the thin walled portion 155. The material can be a foam, for example, a polyurethane foam, which allows for compression, and also allows the inner diameter of the restriction device 106 to expand sufficiently, in the case of high stress, for example the high stress due to vomiting. Alternatively, the ribs 156 are made of a rigid metallic or polymeric material that is attached or embedded to the thin walled portion 155. In this manner, the diameter of the dynamic surface 152 can be compressed by using only a flexible rod that is pulled in tension. As the rod tightens, it creates a radial force on the ribs 156, causing a wider diameter portion to restrict. This is especially advantageous because now the extension portion 157 can be of smaller dimensions, because it only need accommodate a rod and not a wide belt.

Figure 17:
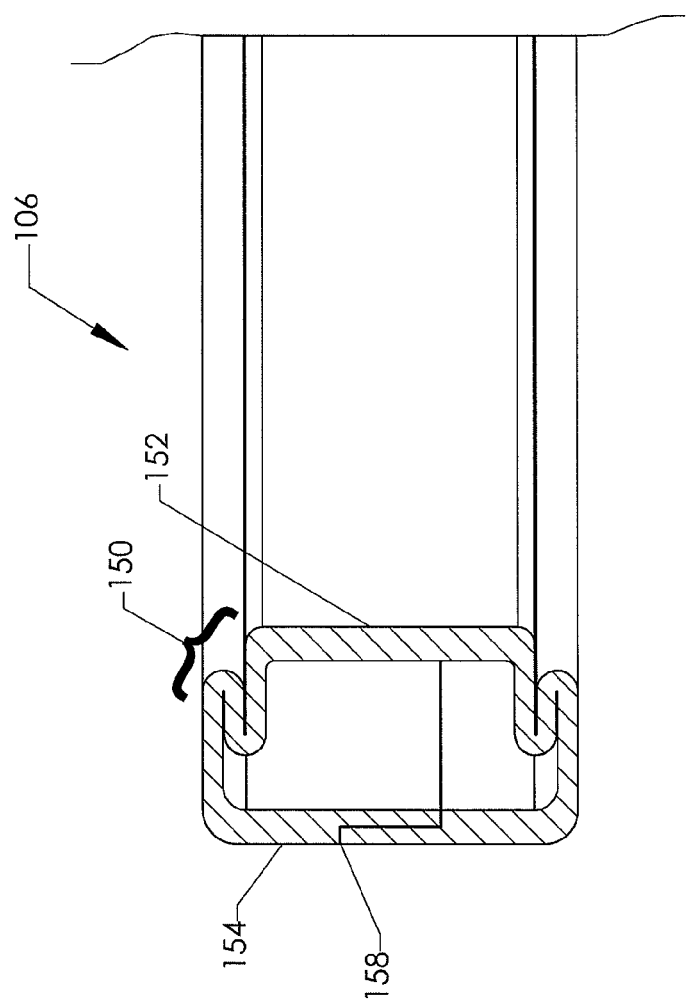
FIG. 17 illustrates another cross-sectional view of the outer shell or housing of the restriction device of FIG. 15.

A cross-section of the restriction device 106 showing more detail of the circumferential bellows 150 is illustrated in FIG. 17. It can be seen that a bias force in the form of tension from a belt or a rod will act on the dynamic surface 152 causing it to compress the diameter. The extra wall contained in the bellows 150 allows this to occur without requiring the material to have to substantially stretch, and therefore, allows this restriction to take place with a lower tension or torque requirement. Also shown in FIG. 17 is seam 158, which can aid in the manufacturing process. The outer shell of the restriction device 106 is molded with this seam open, and then during manufacture, the internal workings, such as the belt, are placed inside. Finally, an outer layer, such as a silicone dip, is covered around the assembly.

Returning to FIG. 15, a drive transmission 108 couples the restriction device 106 with an implantable interface. The restriction device 106 has a first attachment portion 110 and a second attachment portion 112 which can be connected together, for example, around a body lumen such as the stomach. The first attachment portion 110 and the second attachment portion 112 may also be disconnected from each other and reconnected to each other. During the implantation surgery, it is a benefit to be able to easily disconnect the first attachment portion 110 and the second attachment portion 112, for example, in the case of mis-positioning. It is also desirable to be able to easily disconnect the first attachment portion 110 and the second attachment portion 112 at a later period of time, for example in the case of a restriction device that requires emergent removal, for example, due to slippage, erosion or other reasons. The reversible attachment mechanism comprises a leash 114 having a flattened portion 116 which can be easily gripped by laparoscopic instruments, such as a grasper. Ribs 118 aid in engaging a grasper jaw that has teeth.

Figure 18:
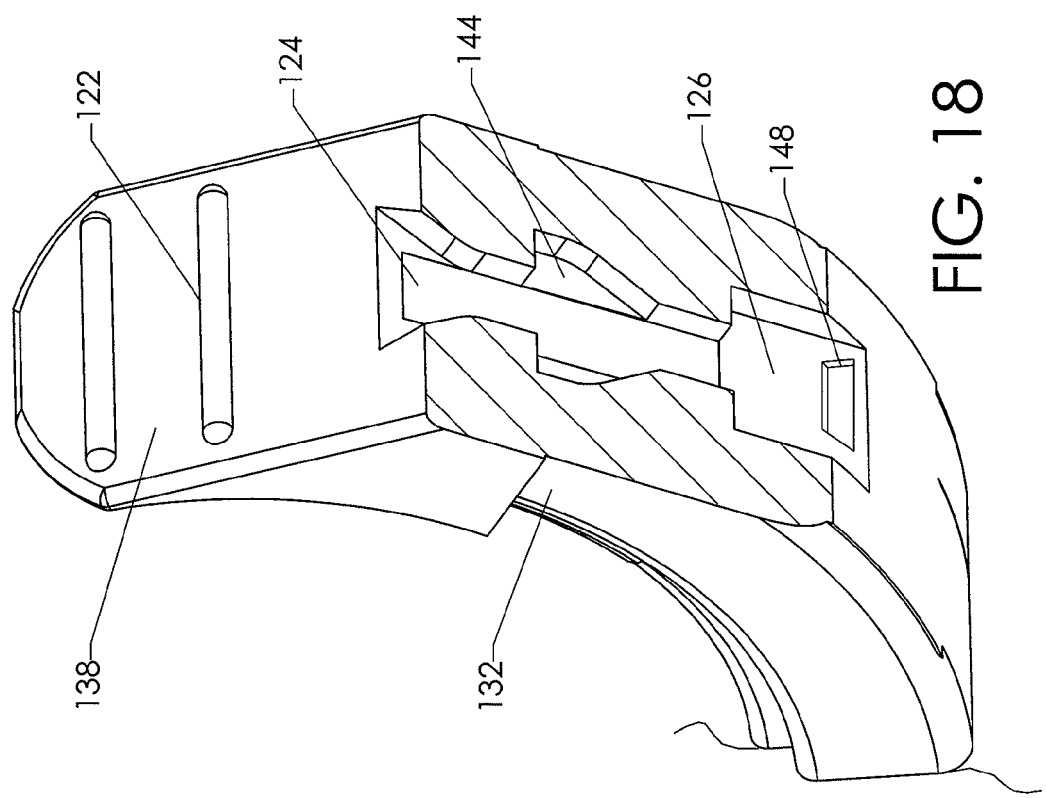
FIG. 18 illustrates a cross-sectional view of the restriction device taken through line 18-18' of FIG. 15.
Figure 19:
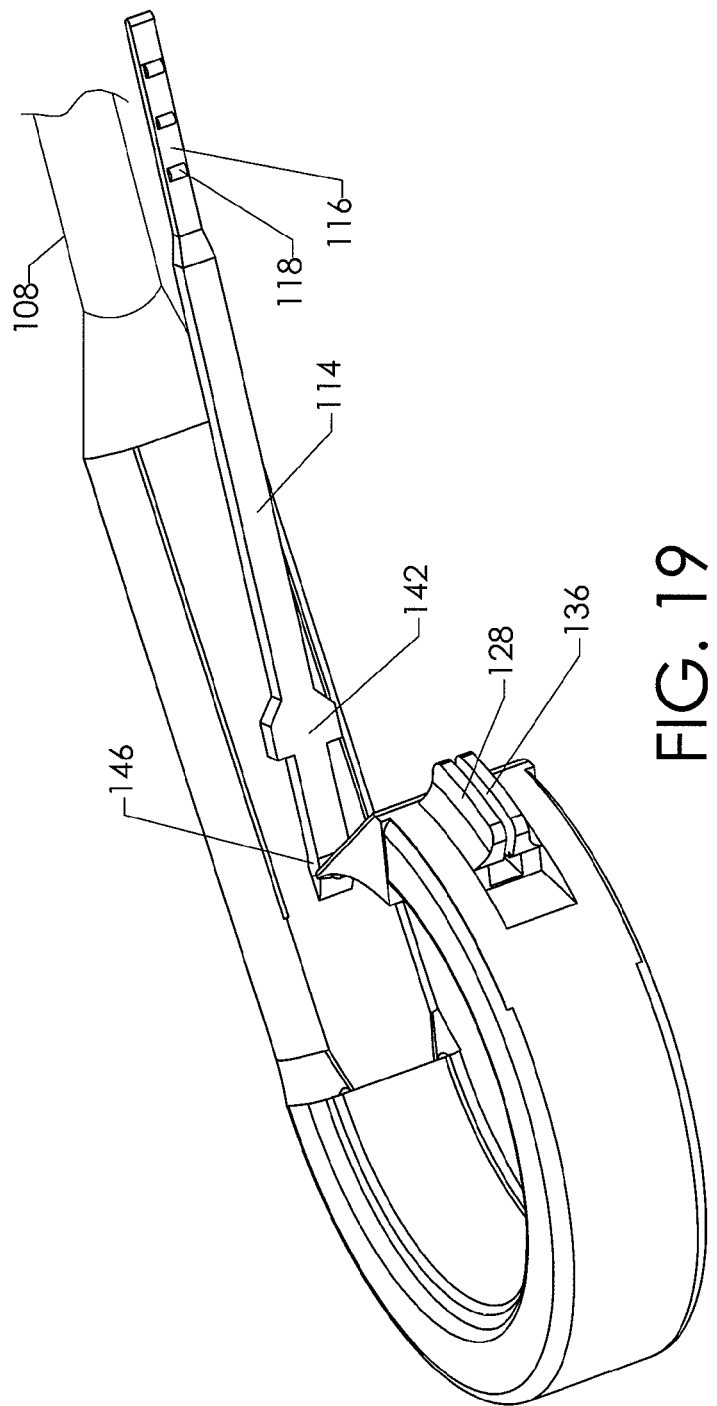
FIG. 19 illustrates a detailed perspective view of the restriction device of FIG. 15.

Following the pars flaccida technique described in the Ren et al. publication, a grasper is placed through the tunnel. The grasper is used to grasp gripping surface 120 which may also include ribs 122 for tooth engagement. The first attachment portion 110 is then pulled through the tunnel by the grasper, allowing the restriction device 106 to encircle the stomach or the area at the junction of the esophagus and stomach. The grasper is now used to stabilize the first attachment portion, by means of either an external gripping surface 128 (both sides of the restriction device 106), an extended gripping surface 130, or an indented gripping surface 132. While stabilizing the restriction device 106 using one of these gripping methods, another grasper is used to grasp the leash 114, for example at the flattened portion 116. The tip 134 of the leash 114 is inserted through an entry hole 124 until the tip 134 exits through an exit hole 126. As can be seen in FIG. 18 and FIG. 19, the leash 114 comprises a male snap 142, which is configured to lock into a female snap 144 inside the first attachment portion 110. The grasper that was used to insert the leash 114 through the first attachment portion 110 is now used to pull the leash 114 out the exit hole 126, and pull it taut until internally, and the male snap 142 is forced into the female snap 144. A base portion 146 of the leash 114 is able to elastomerically stretch to allow this locking to take place, but also to assure that a first face 138 presses up tightly against a second face 140.

It should be noted that the elastomeric property of the base portion 146, also allows a certain amount of compliance to the restriction device 106, which, for example, allows the restricted diameter of the restriction device 106 to temporarily open up during high stress events, such as vomiting, thus protecting the stomach from slippage or erosion. If the position of the restriction device 106 is considered acceptable, the tip 134 of the leash 114 is inserted by the grasper into a slack insertion hole 148, so that the slack of the leash is stored out of the way. If it is desired for any reason to disconnect the first attachment portion 110 from the second attachment portion 112, the grasper is used to grasp the leash 114 at the exit hole 126, where it remains accessible. By pulling to the side with the grasper, the leash 114 can be decoupled from the first attachment portion 110 by pulling it our of a split region 136. Split region 136 can be inherent, or it can alternatively be peel-away. Because the relevant portions of the first attachment portion 110 are desirably made from elastomeric materials, there is sufficient compliance to allow multiple disconnections and reconnections. Alternative to the method of connecting the restriction device and placing the slack of the leash 114 into the slack insertion hole 148, instead, laparoscopic cutters can be used to cut the slack portion of the leash 114. For example, by cutting the leash 114 at the exit hole 126 and removing the excess portion with laparoscopic graspers.

Figure 20:
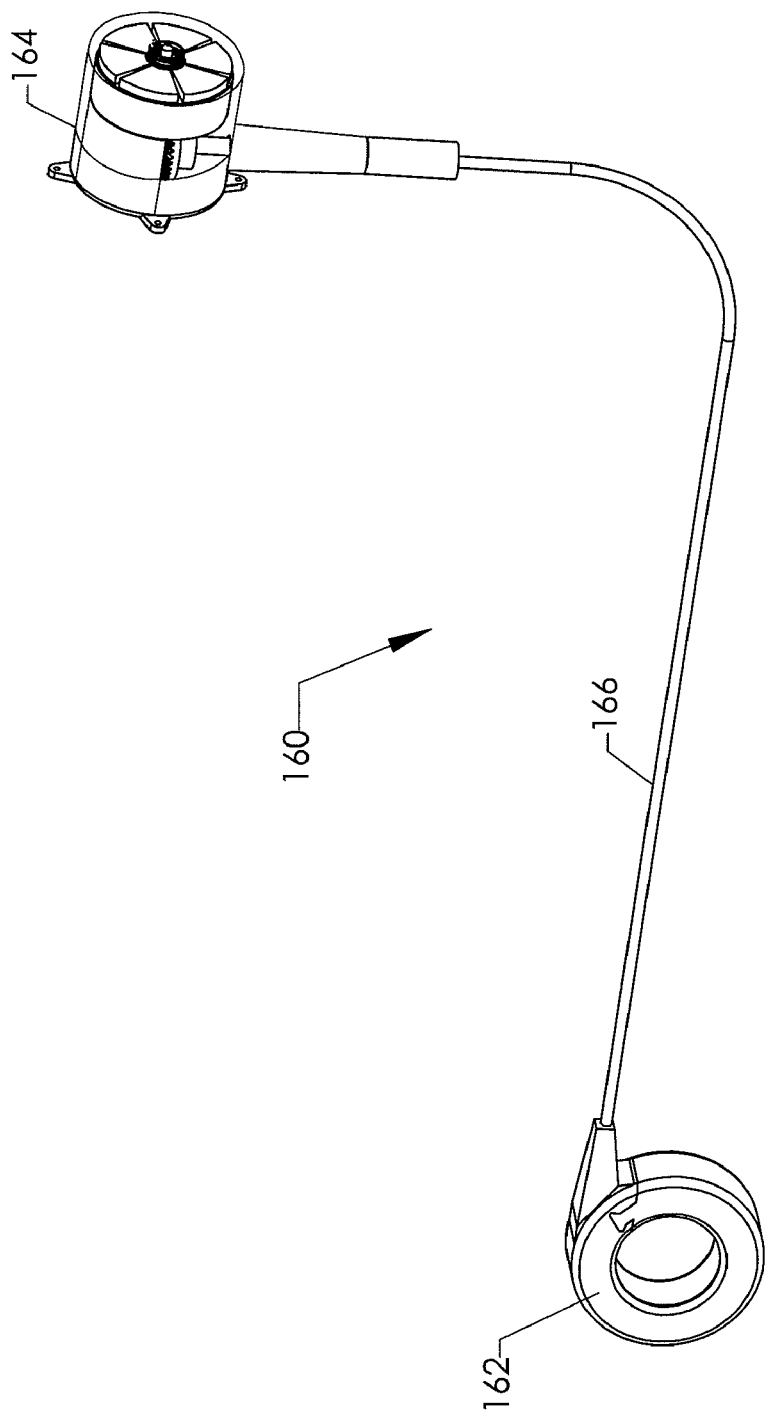
FIG. 20 illustrates a perspective view of an implantable obesity control system according to one embodiment.

FIG. 20 illustrates an implantable obesity control system 160 in accordance with an embodiment of the present invention. The implantable obesity control system 160 comprises a restriction device 162, an implantable interface 164 and a drive transmission 166. During an initial surgical procedure, the restriction device 162 is implanted in the patient so that it creates a stoma and controllably restricts the size of an opening between the stoma and the remainder of the stomach. For example, the restriction device 162 is laparoscopically placed into the abdominal cavity and configured in a position surrounding the stomach. The restriction device 162 is placed through a trocar, or alternatively is placed though the opening created after a trocar is inserted and then removed. The restriction device 162 may be implanted in a patient such that a contact surface of the restriction device 162 at least partially engages a surface of the gastrointestinal tract, such as the stomach and/or the esophagus of the patient. For example, the restriction device 162 may contact, touch, attach to, affix to, fasten to, access, penetrate (partially or completely) or otherwise engage the surface of the stomach and/or the esophagus.

During this initial procedure, the implantable interface 164 is placed subcutaneously at a site that may be subsequently accessed using an external device (168 in FIG. 21) but that does not interfere with the patient's mobility. Some example sites that may be used include below the collar bone, above the navel, and below the ribs.

Figure 21:
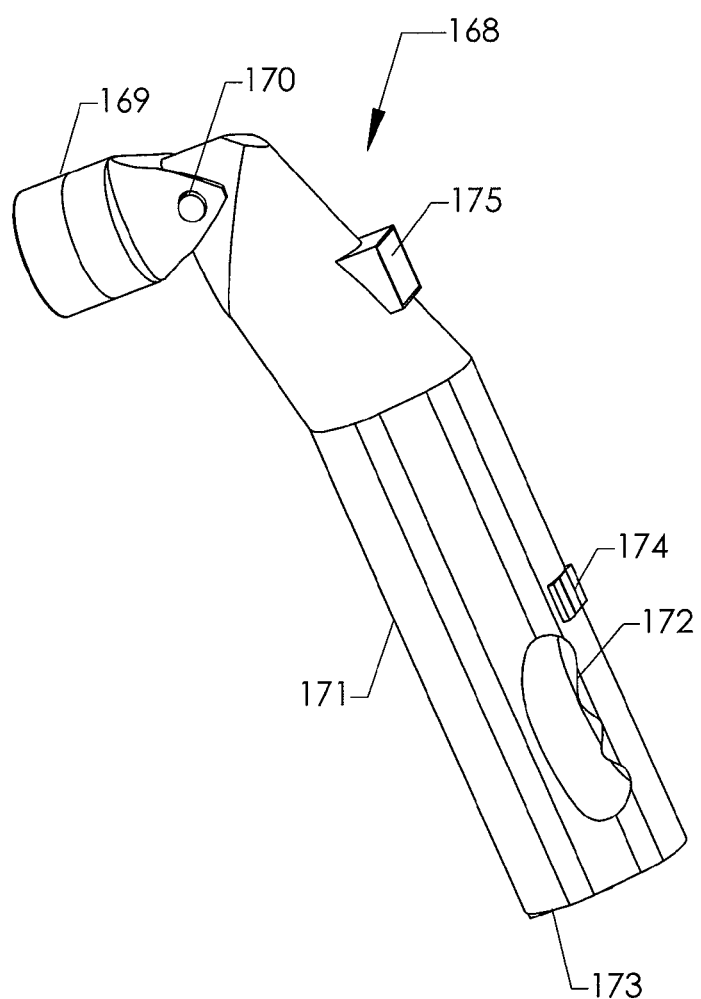
FIG. 21 illustrates a perspective view of an external device for use with the implantable obesity control system of the type illustrated in FIG. 20 according to another embodiment.
Figure 22:
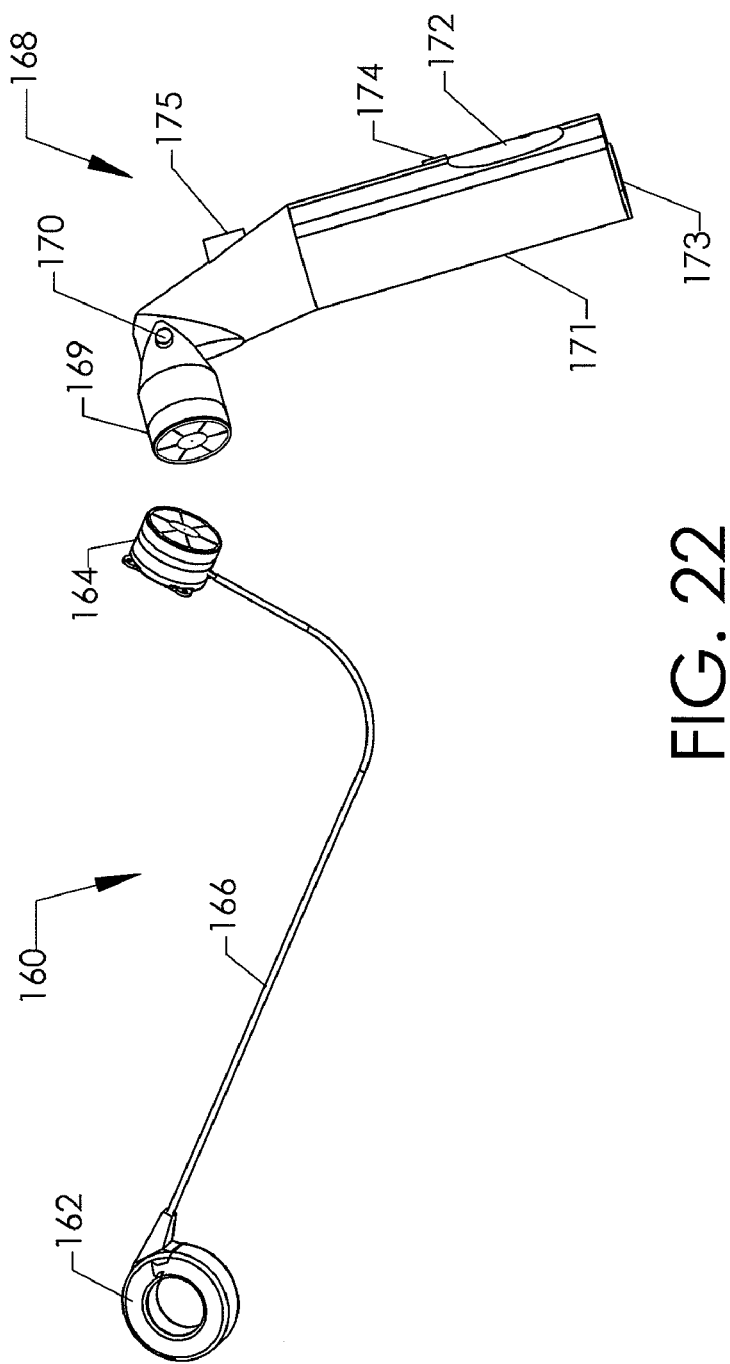
FIG. 22 illustrates a perspective view of the external device of FIG. 21 together with the implantable obesity control system of FIG. 20.

FIGS. 21 and 22 illustrate an external device 168 for use with the implantable obesity control system 160 of FIG. 20 in accordance with an embodiment of the present invention.

During a follow-up procedure, the restriction device 162 may be adjusted using the external device 168 without the need for penetrating the skin or entering any of the body's natural orifices. The external device interface 169 of the external device 168 is first placed adjacent the implantable interface 164, and the restriction device 162 may then be adjusted via the interaction of the external device interface 169 with the implantable interface 164 to its desired size or configuration (e.g., FIG. 22). In certain embodiments, the external device interface 169 may be manipulated by rotation about an axis using a motor device. In certain embodiments, the external device interface 169 may be manually rotated about an axis in order to adjust the size or configuration of the restriction device 162. Although in certain embodiments the restriction device 162 may be used to restrict the esophagus or stomach for the treatment of obesity, in other embodiments the device 162 can be used for other restriction applications, such as gastro-esophageal reflux disease (GERD), artificial sphincters (e.g. anus or urethra), annuloplasty, and full or partial occlusion of blood vessels, such as the pulmonary artery, or blood vessels supplying a cancerous area.

The external device 168 comprises the aforementioned external device interface 169 which in certain embodiments has one plane of free movement via a pivot 170. In addition, the external device 168 may comprise a base 171 having a handle 172. In certain embodiments, the external device 168 may be battery operated, as illustrated in FIG. 21, while in certain embodiments the external device 168 may be powered from external electricity and may include a power cord. In certain embodiments, the external device 168 may be configured to use batteries that may be rechargeable. The batteries may reside within the base 171 of the external device 168 and may be held in place by the battery cover 173. Buttons 174 near the handle 172 are thumb operated and include generic symbols for "off," "clockwise rotation" and "counter-clockwise rotation," or "off," "tighten," and "loosen." A display 175 allows the physician or health professional performing the adjustment procedure to visualize the current size or configuration of the restriction device 162. For example, the diameter, circumference, setting number (e.g. "1" through "10") or cross-sectional area of the restriction device 162 may be visualized. In addition, the display may also show patient information, such as procedure dates, the patient's name, or other statistics.

Figure 23:
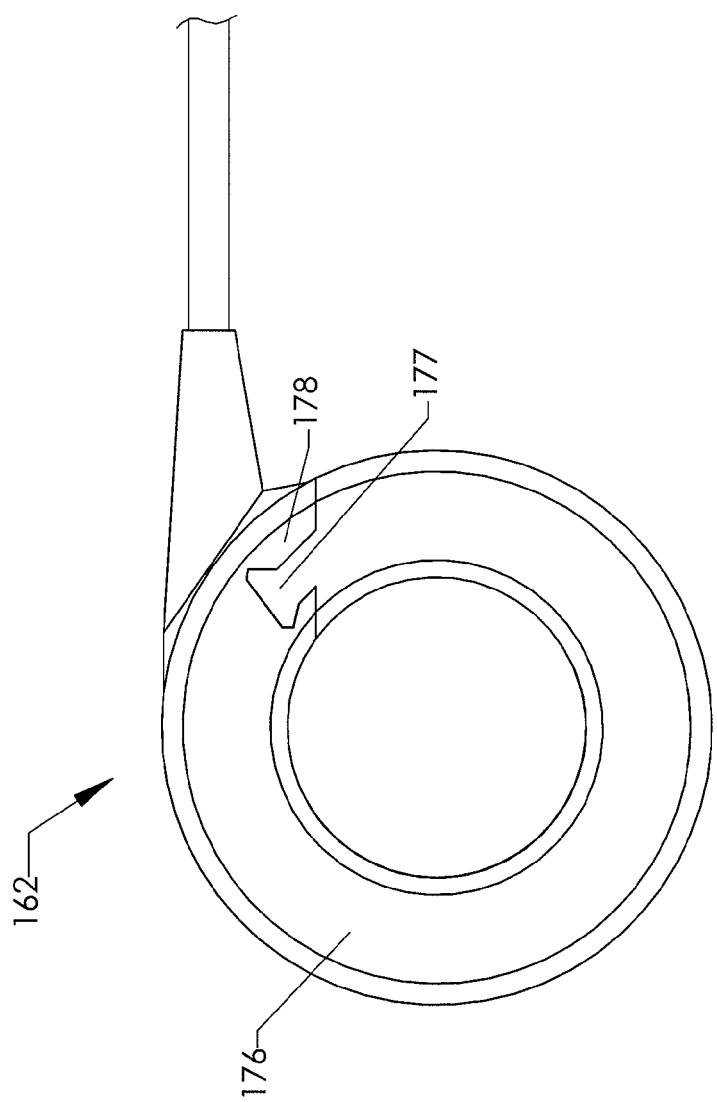
FIG. 23 illustrates a plan view of the restriction device portion of the implantable obesity control system of the type illustrated FIG. 20.

FIG. 23 illustrates the restriction device portion of the implantable obesity control system of FIG. 20 in accordance with an embodiment of the present invention. The body portion 176 of the restriction device 162 comprises two attachment portions 177 and 178. When the attachment portions 177 and 178 are not attached to each other, the body portion 176 may conform to a linear shape that may be placed into the abdominal cavity though the inner lumen of a cannula. For example, the restriction device 162 is configured so that it will dimensionally fit through the internal diameter of a 15 mm or 12 mm trocar 18. It is also configured so that it will dimensionally fit through the tract made by insertion and removal of a 10 mm or 12 mm trocar 18. The restriction device 162 may be placed through a tract made after a trocar, cannula, sheath, dilator, needle or other puncturing device is placed and then removed. The restriction device 162 may also be placed through a direct incision. When the body portion 176 is oriented around the stomach or esophagus, the attachment portions 177 and 178 are joined, creating a substantially encircling configuration. Although the body forms a substantially circular shape when joined using both attachment portions 177 and 178, in other embodiments the body may form a shape that is substantially oval, square, triangular or another shape when both attachment portions 177 and 178 are joined.

In certain embodiments, the body portion 176 may comprise a biocompatible material such as silicone or polyurethane. In certain embodiments, the external surface of the biocompatible material can be further altered in order to increase biocompatibility. In certain embodiments, a biocompatible material may be used to completely encapsulate a material that is not known to be biocompatible. The body portion 176 may also have holes (not illustrated) configured for the attachment of sutures, so that the restriction device 162 may be secured to the body. For example, the restriction device 162 may be attached to the stomach using sutures. Alternatively, in certain embodiments, the restriction device 162 may have grooves or hooks configured for the securing of suture material. This allows the restriction device 162 to be easily secured to the stomach wall in order to prevent slippage of the device or prolapse of the stomach.

In certain embodiments, the attachment portions 177 and 178 may be made from the same material as the body portion 176. The attachment portions 177 and 178 may be made from various polymeric or metallic materials. The attachment portions 177 and 178 may be laparoscopically detached, or a section of material adjacent to the attachment portions 177 and 178 may be laparoscopically severed if removal of the restriction device 162 is ever necessitated.

Figure 24:
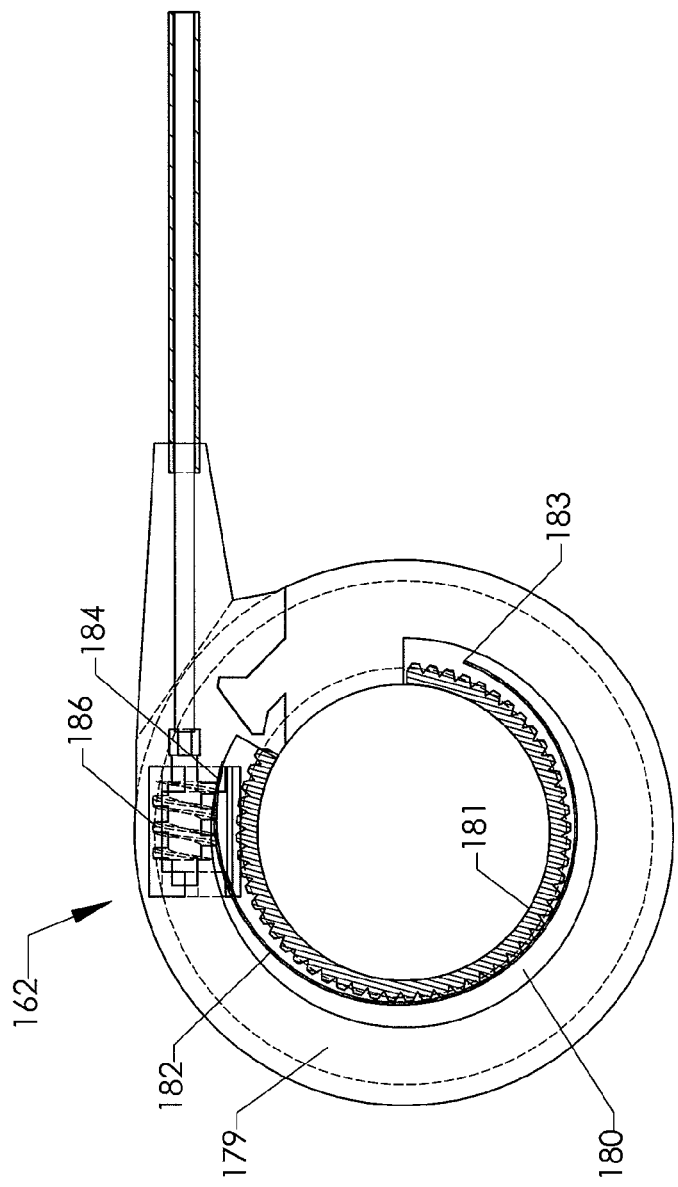
FIG. 24 illustrates a cross-sectional view of the restriction device portion of the implantable obesity control system illustrated in FIG. 23.

FIG. 24 illustrates a cross section of the restriction device portion 162 of the implantable obesity control system 160 of FIG. 20 in accordance with an embodiment of the present invention. The body portion 176 comprises an outer housing 179, a central cavity 180 and an inner distensible member 181. A dynamically adjustable band 182 resides between the housing 179 and the inner distensible member 181. The dynamically adjustable band 182 comprises a secured end 183 and a movable end 184. The secured end 183 may be coupled to the body portion 176 using any fastening method, including insert molding, overmolding, adhesive bonding, thermal bonding, or mechanical attachment. The movable end 184 is capable of moving to either increase or decrease the operative contact length of the dynamically adjustable band 182. This change in the operative contact length serves to act upon the inner distensible member 181, causing it to increase or decrease its effective perimeter, which allows for the dynamic adjustment of the size or shape of the opening between the stoma and the stomach.

The inner distensible member 181 is configured to cushion the wall of the stomach from any high stress concentrations imposed by the dynamically adjustable band 182, as well as minimize any pinching or folding of the stomach wall by the movement of the dynamically adjustable band 182. Alternatively, the central cavity 180 may be pre-inflated with an incompressible material, such as silicone oil, in order to create further cushioning. If pre-inflated, this also creates the desirable situation that if there were to be break in any structure, the restriction device 162 would not draw in a large amount of body fluid.

Figure 25:
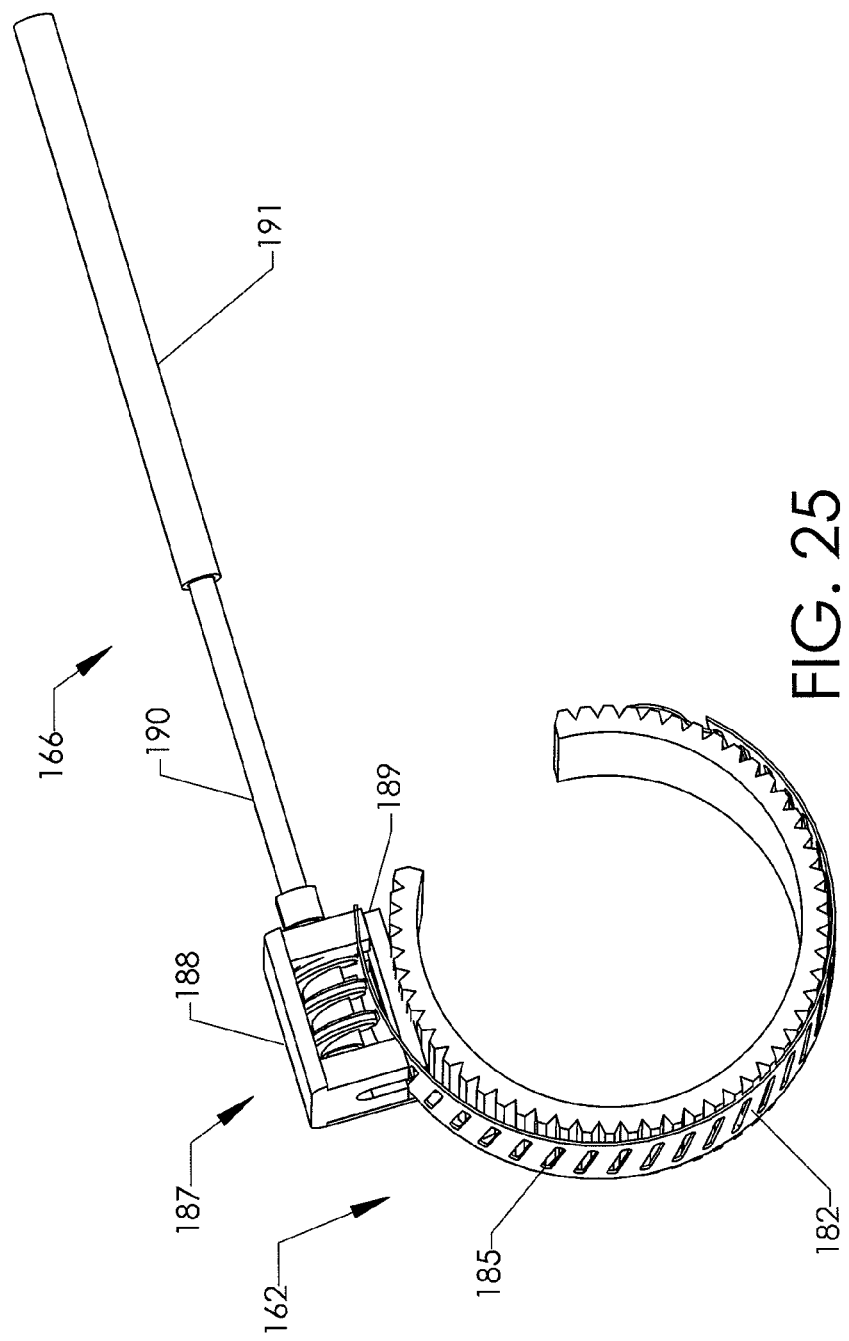
FIG. 25 illustrates a perspective view of an inner section of the restriction device portion of the implantable obesity control system of FIG. 20 according to one embodiment.

FIG. 25 illustrates an inner section of the restriction device portion of the implantable obesity control system of FIG. 20 in accordance with an embodiment of the present invention. The dynamically adjustable band 182 can comprise a variety of materials such as stainless steel, ELGILOY, superelastic NITINOL, polyester and Nylon (for example Nylon 6/6) that allow a small thickness with high tensile strength. It can alternatively be made from a metallic or high-strength KEVLAR mesh material encapsulated in a polymeric material. The dynamically adjustable band 182 is configured with grooves 185 that allow engagement by a worm gear (186 in FIG. 24). The worm gear 186 is housed within a gear housing 187 comprising an upper housing 188 and a lower housing 189.

The drive transmission 166 is configured to turn the worm gear 186 in either rotational direction. For example, the drive transmission 166 may turn the worm gear 186 in the clockwise direction to tighten the band 182 and in the counter-clockwise direction to loosen the band 182. The drive transmission 166 comprises a drive shaft 190 which turns inside a sheath 191.

In certain embodiments, the drive transmission 166 may be permanently attached to the restriction device 162 and the implantable interface 164, or it may be configured attach to and detach from the restriction device 162, the implantable interface 164, or both the restriction device 162 and the implantable interface 164. For example, although the drive transmission 166 may be permanently attached to the restriction device 162, the drive transmission 166 may be temporarily attachable to and detachable from the implantable interface 164. In the case of a malfunctioning implantable interface 164, the implantable interface 164 may be replaced, while leaving the restriction device 162 and the drive transmission 166 in place. The new implantable interface 164 can then be attached to the drive transmission 166. The implantable interface 164 may thus be replaced without the need for placement of laparoscopic trocars.

In certain other embodiments, the drive transmission 166 may be attachable to and detachable from both the restriction device 162 and the implantable interface 164. The implantable obesity control system 160 may thus use two or more drive transmissions 166 of differing lengths. The appropriate length drive transmission 166 may be chosen based on what best fits the anatomy of the patient in addition to the chosen surgical configuration. Additionally, if a drive transmission 166 fails while the implantable obesity control system 160 is in use, then a replacement drive transmission 166 may be attached laparoscopically to the restriction device 162 and the broken drive transmission may be removed.

Figure 26:
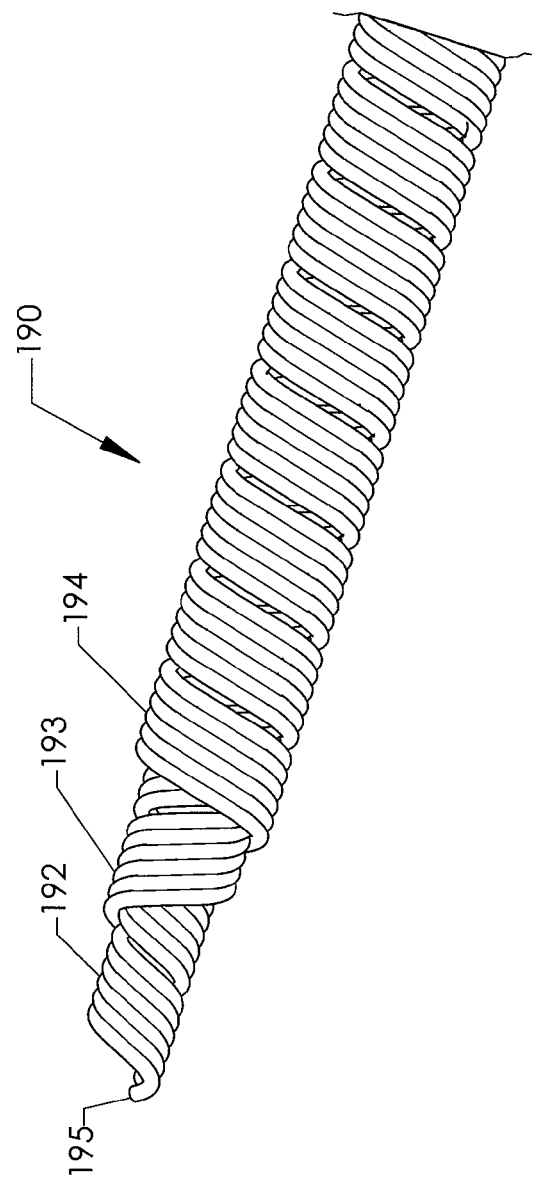
FIG. 26 illustrates a perspective view of the drive shaft portion of the implantable obesity control system of FIG. 20. Portions of the exterior or outer windings making up the complete drive shaft have been removed for clarity purposes.

FIG. 26 illustrates the drive shaft 190 portion of the implantable obesity control system 160 of FIG. 20 in accordance with an embodiment of the present invention. The drive shaft 190 comprises an inner coil 192, a middle coil 193, and an outer coil 194. In certain embodiments, all three of the coils 192, 193, 194 are wound with multi-filars of wire 195. The direction of winding for the outer coil 194 and the inner coil 192 are the same, while the middle coil 193 is wound in the opposite direction. This three layer configuration allows for torque transmission in either direction. For example, when the drive shaft 190 is turned in one direction, the outer coil 194 compresses and the middle coil 193 expands, causing them to support one another. When the drive shaft 190 is turned in the opposite direction, the middle coil 193 compresses and the inner coil 192 expands, causing them to support each other.

In certain embodiments, the wires 195 are made from spring tempered 304V stainless steel of diameters ranging from 0.003" to 0.015," but can also be made from a variety of materials, including ELGILOY, NITINOL and other metals. By making the drive shaft 190 from NITINOL or other super-eleastic materials, the drive shaft can be made resistant to kinking, which may occur during the implantation procedure. In certain embodiments, the wires 195 have a diameter of, for example, 0.008." The three coils may be connected to each other at the ends using any conventional joining technique, such as welding, brazing, soldering, adhesive, or epoxy. In certain other embodiments, the drive shaft 190 can be made from a braid reinforced polymeric tube or rod. In yet further embodiments, the drive shaft 190 can be made from a multilink transmission shaft. In other embodiments, the drive shaft 190 may be made from a metallic tube that has been laser machined in a way that creates a mechanically linked pseudo-spiral pattern. In another embodiment, the drive shaft 190 may simply be made from a single wire, for example a super-elastic or NITINOL wire.

Figure 27:
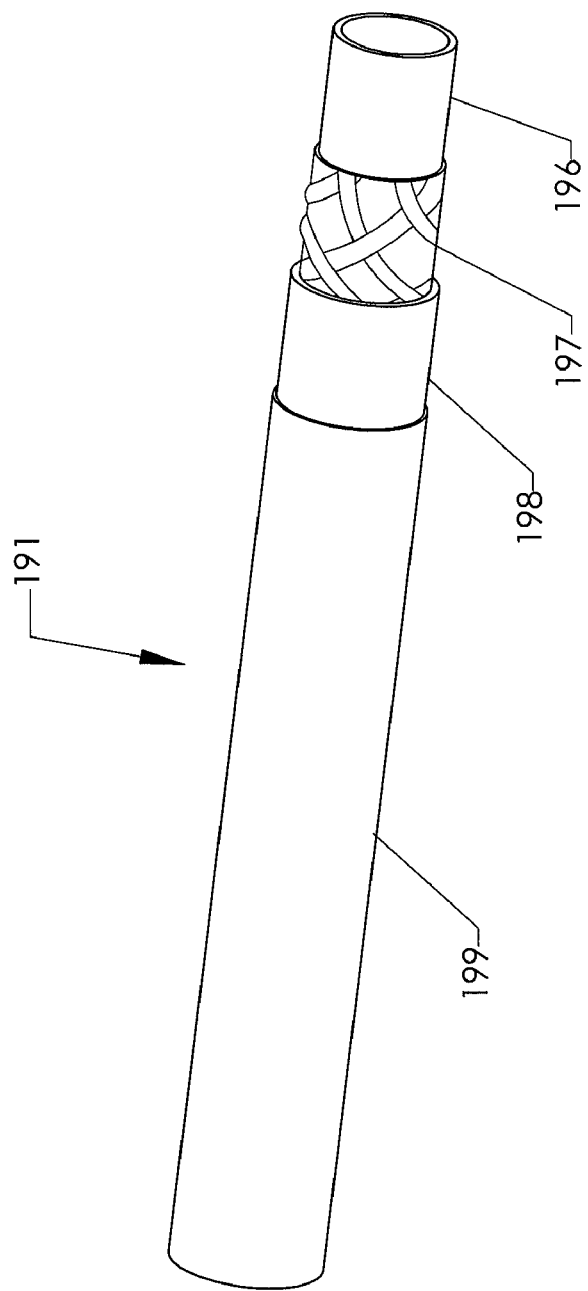
FIG. 27 illustrates a perspective view of a sheath portion of the implantable obesity control system of FIG. 20.

FIG. 27 illustrates the sheath 191 portion of the implantable obesity control system 160 of FIG. 20 in accordance with an embodiment of the present invention. The sheath 191, which houses the drive shaft 190, may comprise a composite configuration, including an inner layer 196, braiding 197, an intermediate layer 198 and an outer layer 199. The inner layer 196 comprises a material with high lubricity, such as a fluoropolymer. Sample fluoropolymers include polytetrafluoroethylene (PTFE) and ethylene tetrafluroethylene (ETFE). The use of high lubricity materials may reduce friction between the stationary sheath 191 and the turning drive shaft 190.

The braiding 197 supplies mechanical strength though tension, compression and/or torsion and maintains the sheath 191 in a round cross-section as the sheath 191 is placed in a flexed configuration. The braiding material may comprise 304 stainless steel, ELGILOY, MP35N, L-605 or a high strength polymeric material such as KEVLAR. Alternatively, the braiding 197 can be replaced by a metallic coil made from any of the aforementioned materials. For example, a NITINOL coil which serves to resist kinking of the sheath.

The intermediate layer 198 comprises a material that encapsulates the braiding 197 and gives mechanical characteristics to the sheath 191, such as stiffness or torsional rigidity. For example, the intermediate layer 198 may be of a low enough rigidity that the sheath 191 is able to curve and comfortably fit within the patient, but of a high enough rigidity that the sheath 191 is not able to bend into a small bend radius that would cause failure of the drive shaft 190. The intermediate layer 198 may also comprise a material that allows adherence between the inner layer 196 and the outer layer 199. The outer layer 199 comprises a biocompatible material such as silicone, polyurethane or ETFE.

Figure 28:
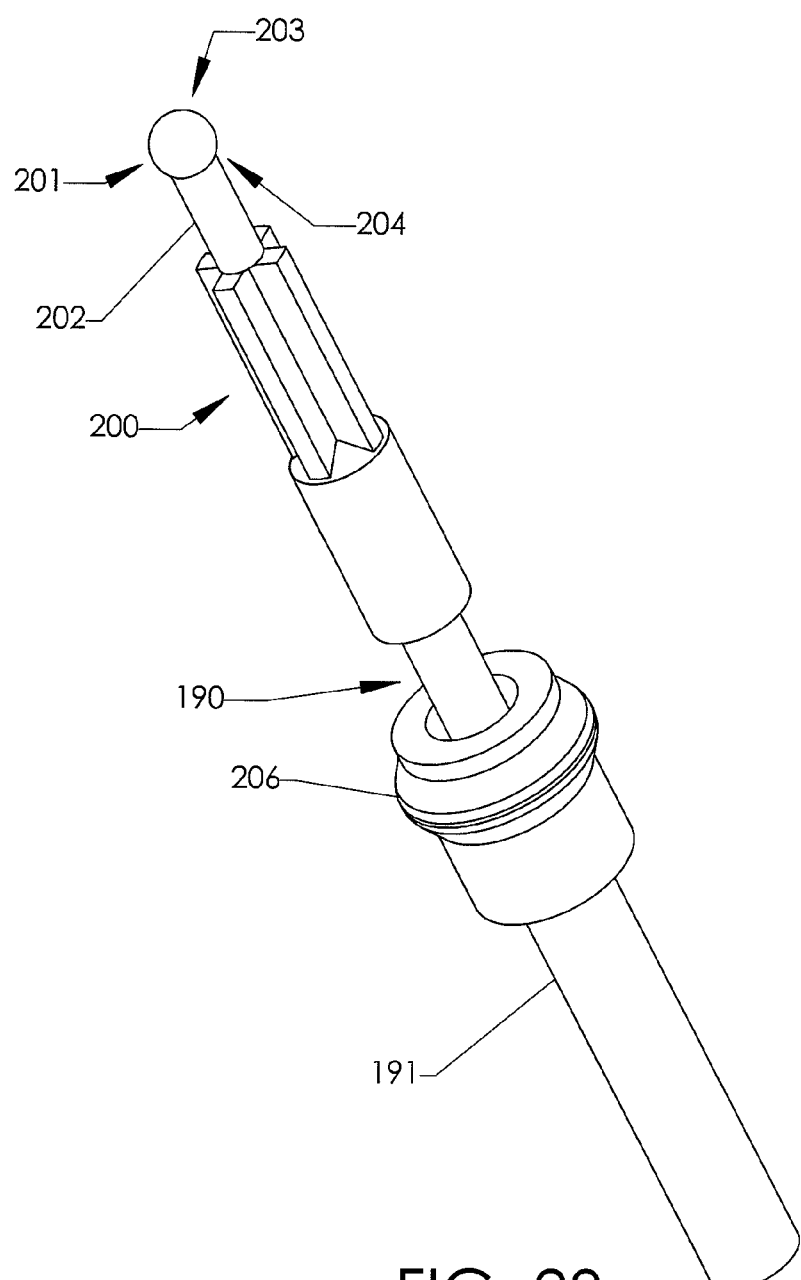
FIG. 28 illustrates a perspective view of the drive shaft portion which connects to the implantable interface of the implantable obesity control system of FIG. 20 according to one embodiment.
Figure 29:
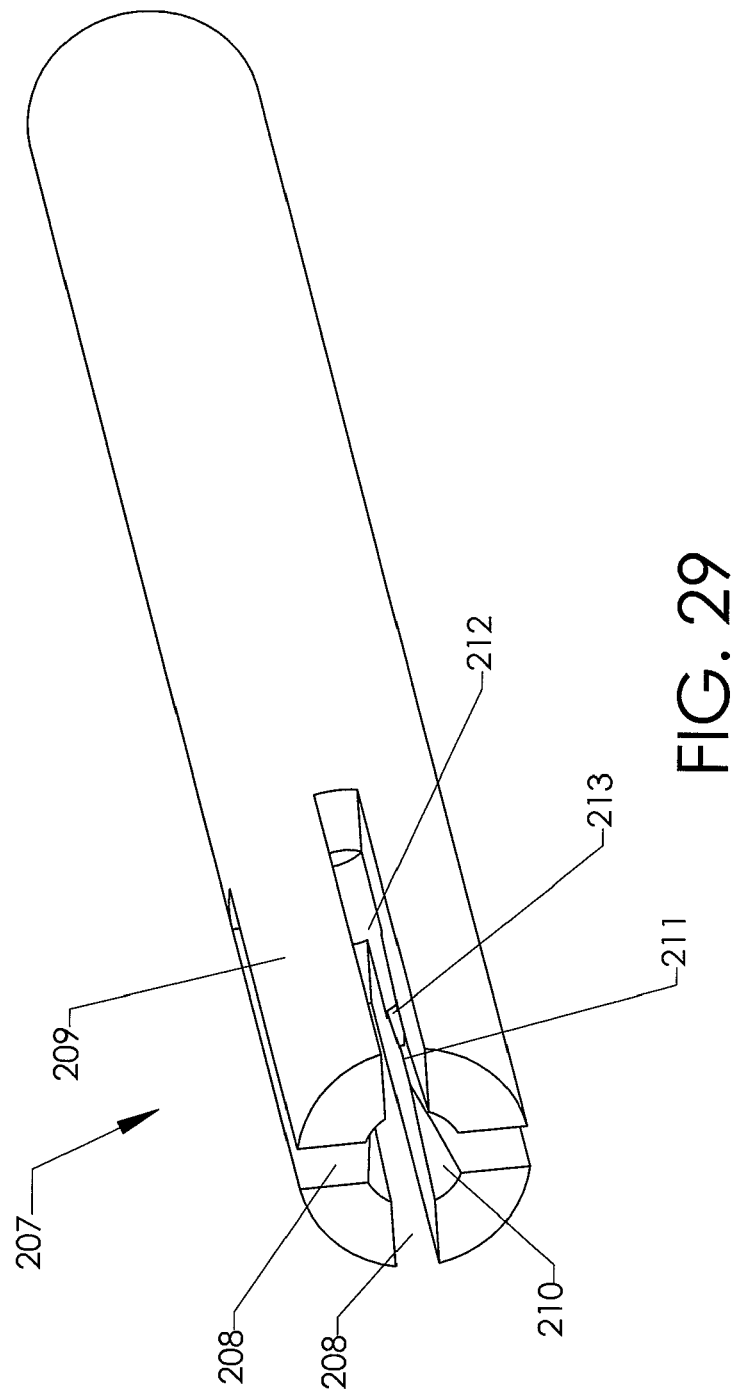
FIG. 29 illustrates a perspective view of the attachment portion of the implantable interface of the implantable obesity control system of FIG. 20 according to one embodiment.

FIG. 28 illustrates the drive shaft 190 portion which connects to the attachment portion (209 in FIG. 29) of the implantable interface 164 of the implantable obesity control system 160 of FIG. 20 in accordance with an embodiment of the present invention. FIG. 29 illustrates the attachment portion 207 of the implantable interface 164 of the implantable obesity control system 160 of FIG. 20 in accordance with an embodiment of the present invention.

In embodiments of the system 160 with an attachable/detachable implantable interface 164 configuration, the end of the drive shaft 190 includes a keyed element 200 including a raised portion 201 and an undercut portion 202. The keyed element 200 may also include a first lead in 203 and a second lead in 204. The end of the sheath 191 includes a barb 206. The attachment portion 207 of the implantable interface 164 as shown in FIG. 29 comprises a keyhole 208 and a dynamic snap 209. The dynamic snap 209 has an interior ramp 210, a mechanical detent 211 and relieved area 212 having a reverse ramp 213. The implantable interface 164 may also contain an elastic orifice (214 in FIG. 30).

During attachment, the first lead in 203 is guided through the interior ramp 210 and the raised portion 201 is forced through the dynamic snap 209, flexing it outward until the raised portion 201 reaches the relieved area 212. Also during attachment the keyed element 200 engages in the keyhole 208. This attachment allows for axial securement and rotational communication between the implantable interface and the drive shaft. Similarly, during attachment, the barb 206 engages with the internal diameter of the elastic orifice 214 to create a hermetic seal to protect the inner workings of the connection from the body fluids. During detachment, the keyed element 200 is removed from the keyhole 208, as the second lead in 204 of the raised portion 201 is guided through the reverse ramp 213 and the interior ramp 210. The elastic orifice 214 is also pulled off of the barb 206 during this detachment process. In certain embodiments, the attachment and detachment can both be performed using laparoscopic grasping and manipulating tools because of the attachable/detachable configuration between the drive transmission 166 and the restriction device 162. In certain embodiments, either the second lead in 204 or the reverse ramp 213 (or both) may be eliminated from the design if a permanent attachment is desired.

Figure 30:
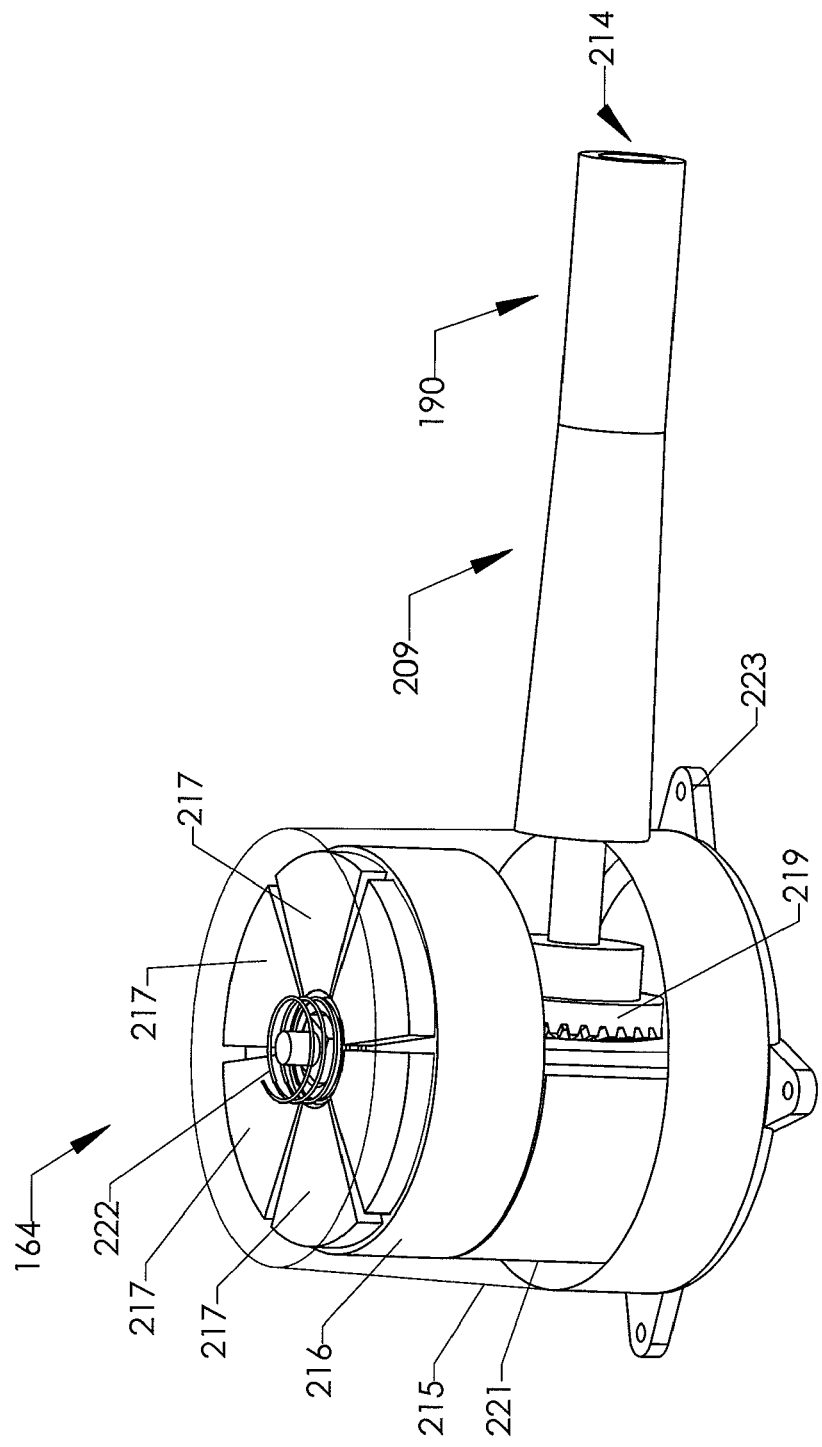
FIG. 30 illustrates a perspective top view of the implantable interface portion of the implantable obesity control system of FIG. 20.

FIG. 30 illustrates a front view of the implantable interface 164 portion of the implantable obesity control system 160 of FIG. 20 in accordance with an embodiment of the present invention. The implantable interface 164 comprises an interface housing 215 and a rotatable frame 216. The interface housing 215 includes suture tabs 223 for securing the implantable interface 164 to a patient. For example, the suture tabs 223 may be used to secure the implantable interface 164 to fascia covering muscular layers beneath the skin and fat of a patient.

The rotatable frame 216 contains several permanent magnets 217. The permanent magnets 217 are configured to magnetically engage a complimentary configuration on the external device interface 169 of the external device 168 of FIGS. 21 and 22 above. The permanent magnets 217 of the implantable interface 164 and the external device 168 are configured to create the maximum attraction to each other while also inhibiting the rotational slippage between the rotating portions of each component. This is achieved by using permanent magnets 217 which are shaped as wedges or sectors, and are oriented so that each consecutive permanent magnet 217 faces an opposite direction. For example, in one embodiment, the magnets 217 may be arranged in a north-south-north-south alternating configuration. The sector shape makes the best use of a minimum amount of space in the assembly. The rotatable frame 216 holds the permanent magnets 217 securely, even though many strong attractive and repulsive forces exist between each of the permanent magnets 217 of a single assembly. In certain embodiments, the magnet material comprises rare earth magnet materials, such as Neodymium-Iron-Boron (Nd—Fe—B), which have exceptionally high coercive strengths. In certain embodiments, the individual Nd—Fe—B magnets are enclosed within a stainless steel casing or various layers of nickel, gold or copper plating to protect the corrosive Nd—Fe—B material from the environment inside the body. In certain embodiments, other magnetic materials may be used, including SmCo5 (Samarium Cobalt) or AlNiCo (Aluminum Nickel Cobalt). In certain embodiments, Iron Platinum (Fe—Pt) may be used. Iron platinum magnets achieve a high level of magnetism without the risk of corrosion, and may possibly preclude the need to encapsulate. In certain embodiments, the permanent magnets 217 on the implantable interface may be replaced by magnetically responsive materials such as Vanadium Permendur (also known as Hiperco).

In certain embodiments, the rotatable frame 216 of the implantable interface 164 is caused to rotate via the rotation of the magnets on the external device interface 169 of the external device 168. In certain embodiments, the magnets on the external device are on a rotatable frame with the magnets themselves having a higher magnetism than those on the implantable interface 164. For example, the magnets on the external device 168 may also be permanent magnets of the same sector shape as the implantable interface 164, but may be of a much larger thickness or diameter. In other embodiments, the external device 168 may incorporate one or more electromagnets instead of permanent magnets. It can be appreciated that the implantable device has relatively few components and does not include a motor or electronics, thus creating a simpler, less costly, more reliable device with a higher likelihood of functioning many years after implantation.

Figure 31:
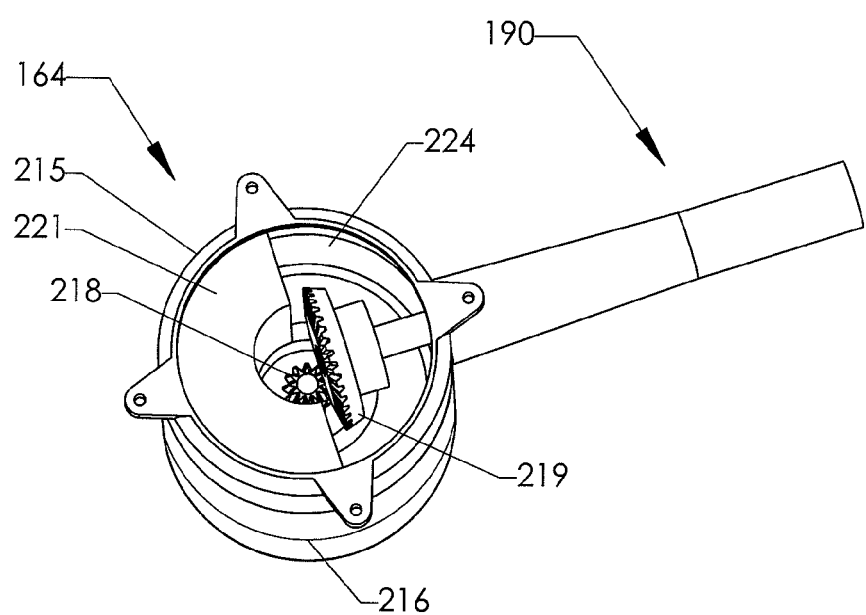
FIG. 31 illustrates a perspective bottom view of the implantable interface portion of the implantable obesity control system of FIG. 20.

FIG. 31 illustrates a rear view of the implantable interface portion 164 of the implantable obesity control system 160 of FIG. 20 in accordance with an embodiment of the present invention. The rotatable frame 216 of the implantable interface 164 is coupled to a first bevel gear 218 which then causes the rotation of a second bevel gear 219. The second bevel gear 219 is coupled to the drive shaft 190 (either permanently or by the attachable/detachable method described earlier). A gear ratio of less than 1:1 may be used (e.g. 1:3) in order to slow the rotation of the drive shaft 190, and to increase the torque delivery to the worm gear 186 of the restriction device 162. In order to ensure that the restriction device 162 is only adjusted when desired, the rotatable frame 216 is forced against a clutch 221 by a spring (222 in FIG. 30). The clutch 221 frictionally holds the rotatable frame 216 so that no rotational movement can occur, for example, during patient movement or exercise. The magnetic engagement between the magnets of the external device interface 169 of the external device 168 and the permanent magnets 217 of the implantable interface 164 forces the rotatable frame 216 to move axially towards the external device 168, compressing the spring 222 and releasing a clutch interface 224 of the rotatable frame 216 from the clutch 221.

Figure 32:
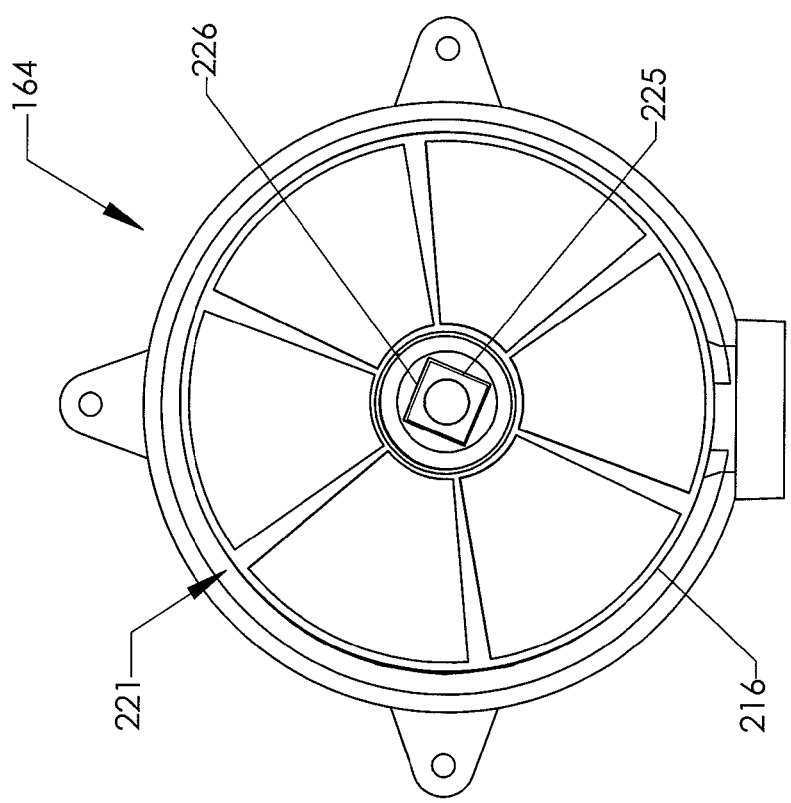
FIG. 32 illustrates a top down plan view of the implantable interface portion of FIGS. 30 and 31.

FIG. 32 illustrates a direct front view of the implantable interface 164 portion of the implantable obesity control system 160 of FIG. 20 in accordance with an embodiment of the present invention. The rotatable frame 216 has a square orifice 226 which is able to slide axially over a square cross-section hub 225, without allowing rotation between the two parts. Thus, when the external device 168 is in place, i.e., with the external device interface 169 adjacent the implantable interface 164, the rotatable frame 216 is magnetically pulled off of the clutch 221 and thus there is free rotation of the rotatable frame 216 caused by the rotation of the corresponding mechanism of the external device 168. The clutch 221 and the clutch interface 224 can be of several possible configurations so that they may engage each other, concave/convex, plate, cone, toothed, etc.

Figure 33:
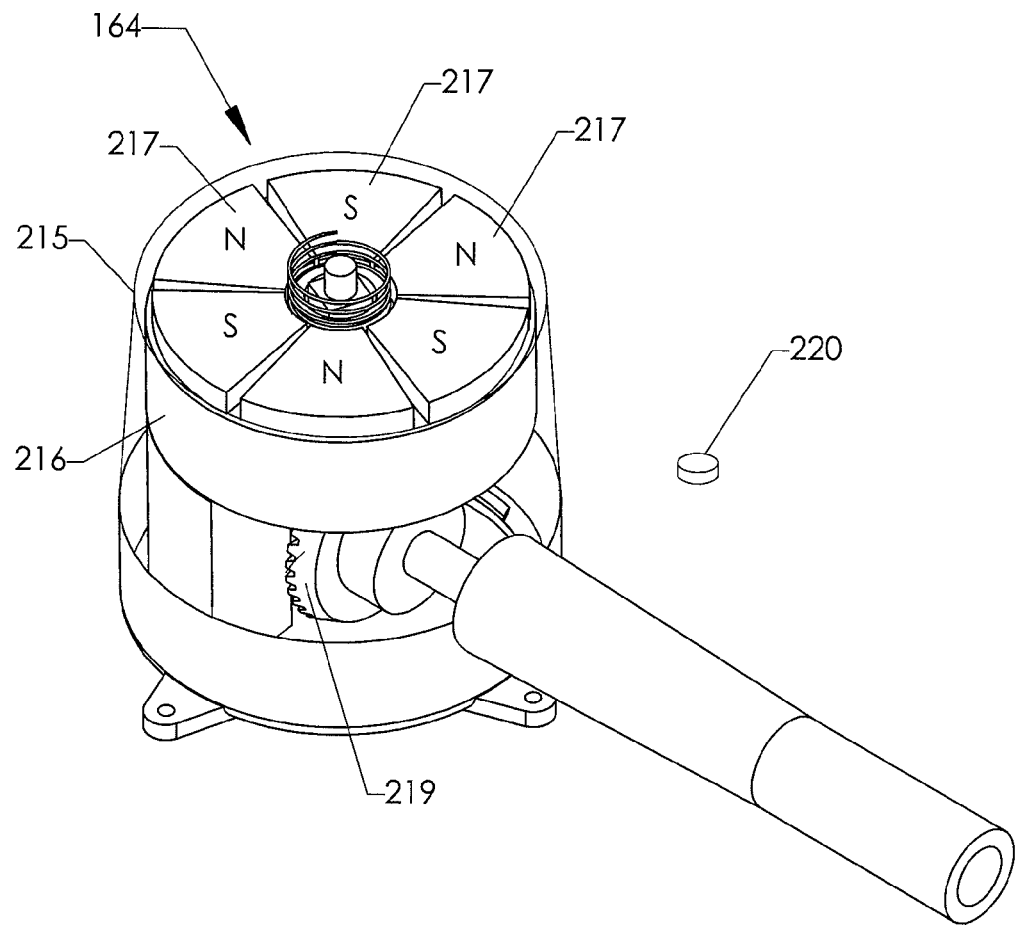
FIG. 33 illustrates a perspective view of a RFID chip disposed near or adjacent to an implantable interface portion of an implantable obesity control system of the type illustrated in FIG. 20.

FIG. 33 illustrates a radio frequency identification (RFID) chip 220 near the implantable interface portion 164 of the implantable obesity control system 160 of FIG. 20 in accordance with an embodiment of the present invention. An RFID (radio frequency identification) chip 220 may be implanted in a patient during the implantation of the implantable obesity control system 160. In certain embodiments, the RFID chip 220 may be implanted subcutaneously in a known location, such as a location near the implantable interface 164. In other embodiments, the RFID chip 220 may be located within the implantable interface 164. Upon the implantation of the restriction device 162, the external device 168 stores patient information on the RFID chip 220, including the current size of the restriction device 162, the amount adjusted, the serial number of the restriction device 162, the date of the procedure, patient name, flow rate of a test fluid through the stoma, and identification. With respect to flow rate measurements and various sensors, reference is made to U.S. Provisional Patent Application No. 60/880,080 filed on Jan. 11, 2007 which is incorporated by reference as if set forth fully herein. This application includes fully external sensors for detecting flow through the gastrointestinal lumen as well as sensors integral or incorporated with the gastric band for detecting flow through the gastrointestinal lumen, and other characteristics.

During subsequent adjustment procedures, the external device 168 may read the RFID chip 220 to determine information related to the patient, such as the current size of the restriction device 162. At the end of the adjustment procedure, the external device 168 may store updated patient information, including the size of the restriction device 162, to the RFID chip 220. An RFID antenna (not shown) in the external device 168 may be used to power the RFID chip in order facilitate the read and write functions.

Several techniques may be used to determine the current size of the restriction device 162. In certain embodiments, the size may be determined indirectly by the number of rotations of the rotatable assembly of the external device 168. In certain embodiments, the size may be determined by the number of rotations of the rotatable frame 216 of the implantable interface 164, by the number of rotations of any one of the gears or shafts of the implantable interface 164, or by the number of rotations of the restriction device 162 itself. In certain embodiments, a feedback mechanism, such as a Hall effect device (two additional magnets that move axially in relation to each other as drive shaft rotates and therefore as the restriction device constricts or loosens), may be used to determine the current size of the restriction device 162. In certain embodiments, an optical encoder feedback mechanism may be used by placing an optical encoder in the gear box of either the external device 168, the restriction device 162 or the implantable interface 164. A through-the-skin optical encoder is even envisioned that shines a light through the skin and fat and counts successive passes of a one or more reflective stripes on the rotatable frame 216 or magnets 217. In certain embodiments, the external device may include an audio sensor to determine the current size of the restriction device 162. For example, the sensor may listen to the cycling sound of gearing, thus giving feedback information on the amount of total adjustment.

Any of the materials of the restriction device 162, the implantable interface 164, the drive transmission 166 or even the external device interface 169 of the external device 168 can be made from radiopaque materials, so that the position, condition or alignment of the components may be seen during the initial surgical procedure, or during the subsequent adjustment procedures. For example, portions of the dynamically adjustable band 182 may be made radiopaque to allow the use of fluoroscopy to determine the dimension of the restrictive device 162. Alternatively, two components on the drive transmission (one that is stationary and one that moves axially with rotation) may each be radiopaque so that the measurement of the distance between the two components on a scaled x-ray will give the current size of the restriction device.

In the initial surgical implantation of some embodiments, one or more trocars are placed into the abdomen of the patient. The abdominal cavity is insufflated, such as by using $CO_2$, thus creating a space within which to perform the procedure. Laparoscopic dissecting tools are placed through trocars and under the visualization of a laparoscope tissue is dissected near the junction of the stomach and the esophagus. The restrictive device 162 is placed into the abdominal cavity. In certain embodiments, the restrictive device 162 is placed into the abdominal cavity through one of the trocars, while in certain embodiments the restrictive device 162 is placed into the abdominal cavity through a tract made by inserting and removing a trocar. The restrictive device 162 is laparoscopically placed around the desired section of the stomach and/or esophagus and secured. The implantable interface 164 may be attached subcutaneously by suturing the interface 164 to the fascia.

In the adjustment procedure, the external device 168 is placed against the outer surface of the skin, with the external device interface 169 placed adjacent the implantable interface 164. The external device 168 is operated so as to magnetically adjust the restrictive device 162 via the implantable interface 164.

Figure 34:
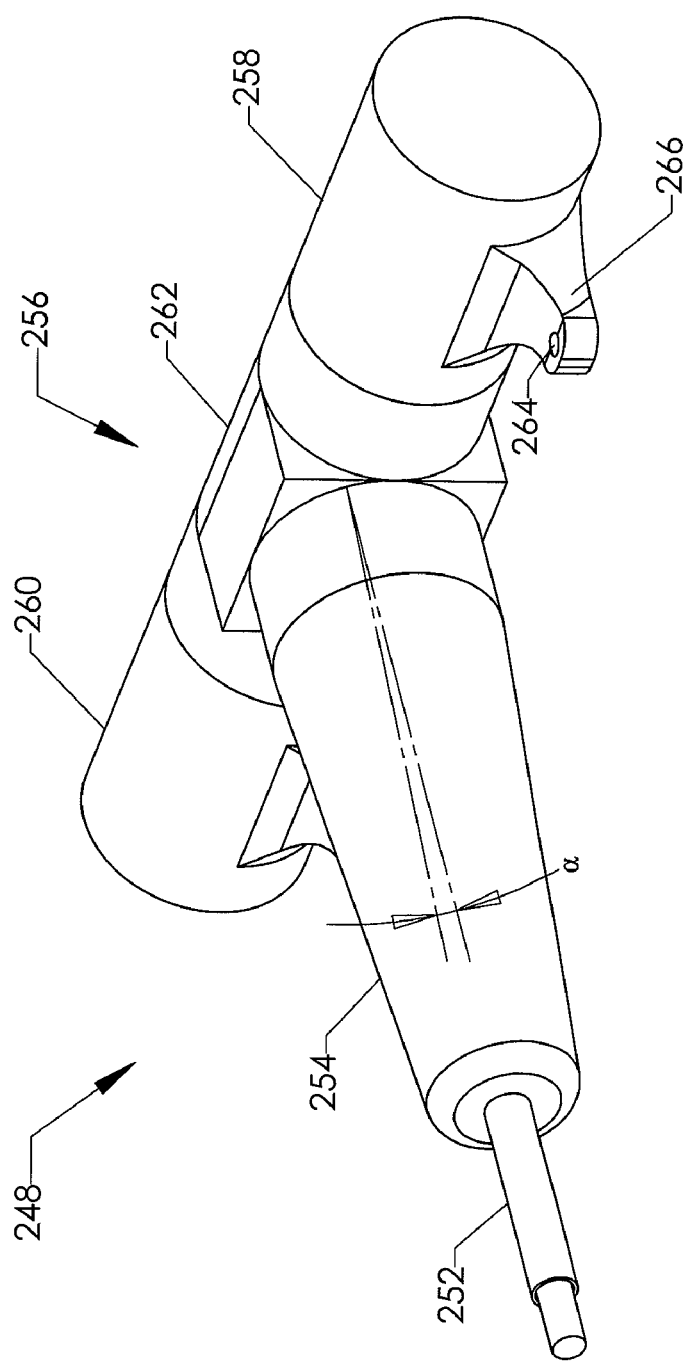
FIG. 34 illustrates an implantable interface according to one embodiment which utilizes cylindrical magnets.
Figure 35:
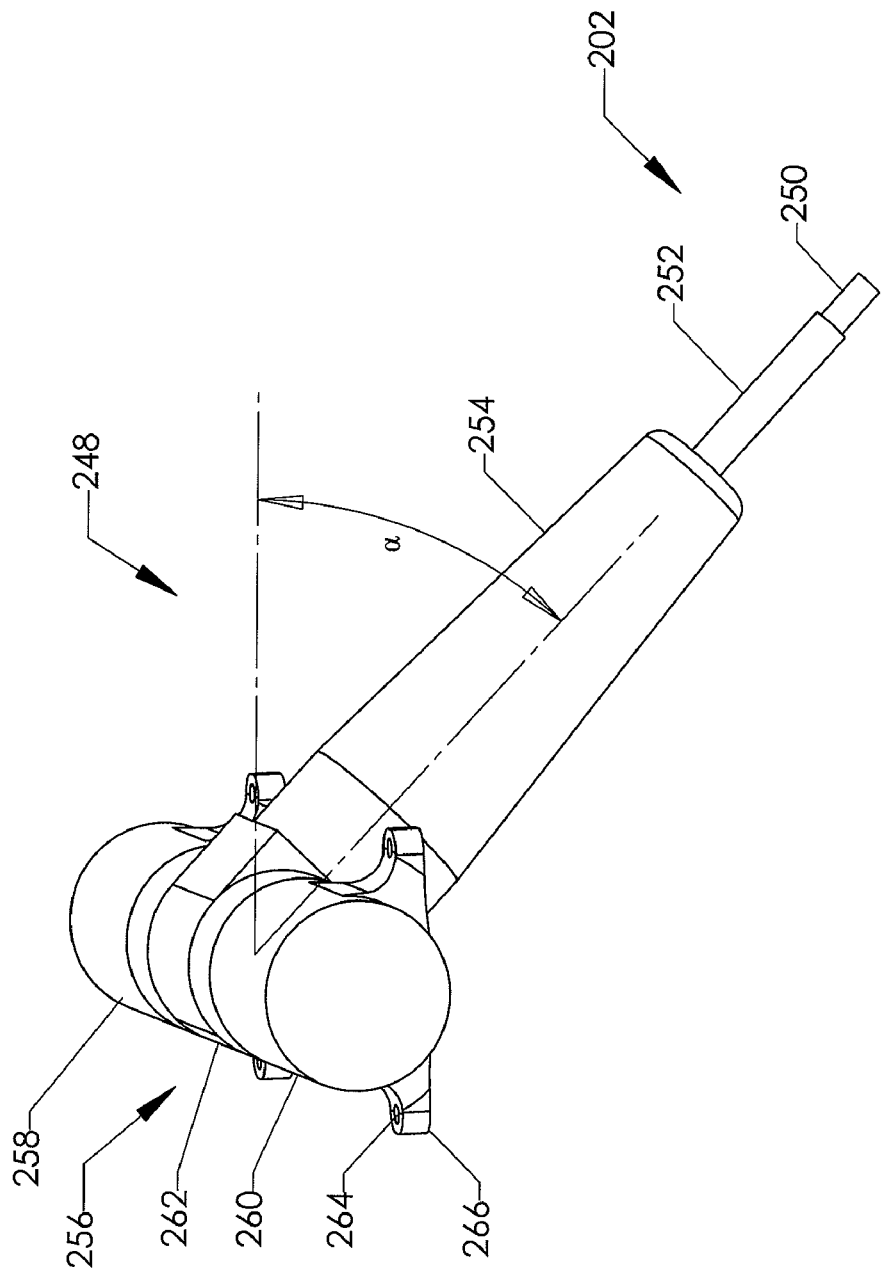
FIG. 35 illustrates the implantable interface of FIG. 34 after having been rotationally adjusted for custom fit in the patient.

FIG. 34 and FIG. 35 illustrate an implantable interface 248 which is configured to allow non-invasive adjustment of the restriction device. Externally, the implantable interface 248 comprises a housing 256 and a strain relief 254. The housing 256 is preferably made from rigid, implant-grade biocompatible materials such as PEEK, titanium or polysulfone. The strain relief is preferably made from elastomeric, implant-grade materials such as silicone, polyurethane or a silicone-urethane copolymer, such as Elast-eon™. The housing 256 may also be coated with an elastomeric material such as silicone, polyurethane or a silicone-urethane copolymer. The implantable interface 248 is coupled to the drive transmission 202 of the restriction device (e.g., restriction device 230 of FIG. 42). The drive transmission 202 comprises a drive shaft 250 and a sheath 252. The housing 256 comprises a first magnet cover 258, a second magnet cover 260 and an articulation 262. The strain relief 254 is coupled to the articulation 262, allowing the adjustment of an angle (α) for placement and securement to a patient. FIG. 35 shows the angle (α) adjusted to about 45° while FIG. 34 shows the angle (α) adjusted to close to 0°. Other angles may be desired, for example 180°. In addition, the housing 256 comprises a plurality of suture tabs 266 having suture holes 264, aiding in suturing the implantable interface 248 to the fascia.

Figure 36:
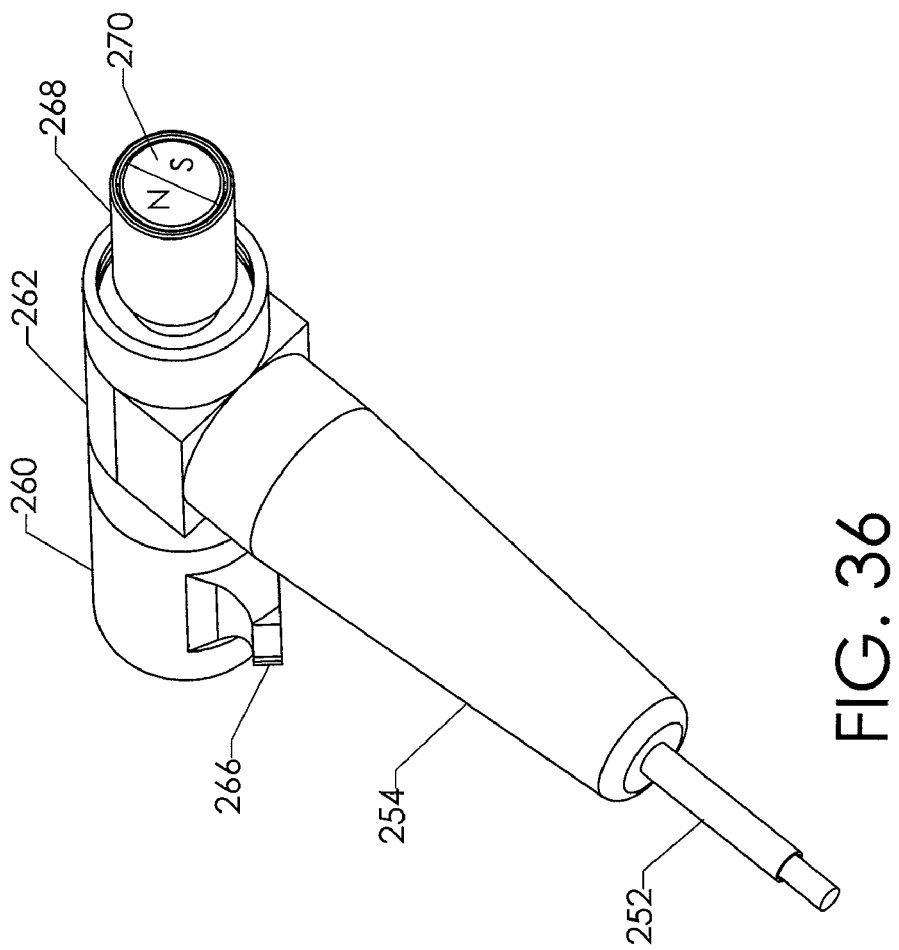
FIG. 36 illustrates the implantable interface of FIGS. 34 and 35 with a portion removed in order to show the orientation of the poles on one of the cylindrical-shaped magnets.

The implantable interface 248 is attachable to and detachable from the drive transmission 202, allowing the restriction device 230 and the drive transmission 202 to be inserted together into the abdomen, for example through a trocar-made hole in the abdominal wall. FIG. 36 illustrates the implantable interface 248 with the first magnet cover 258 removed. A cylindrical magnet 270 is secured within a turret 268 which is capable of rotation. The cylindrical magnet 270 is poled north-south across its diameter, as shown. Note, though two 180° sectors are shown, alternative poling, such as four 90° sectors, alternating north-south-north-south are conceived, for example by incorporating more than one magnet, as are other variations of sector angle and sector number.

Figure 37A:
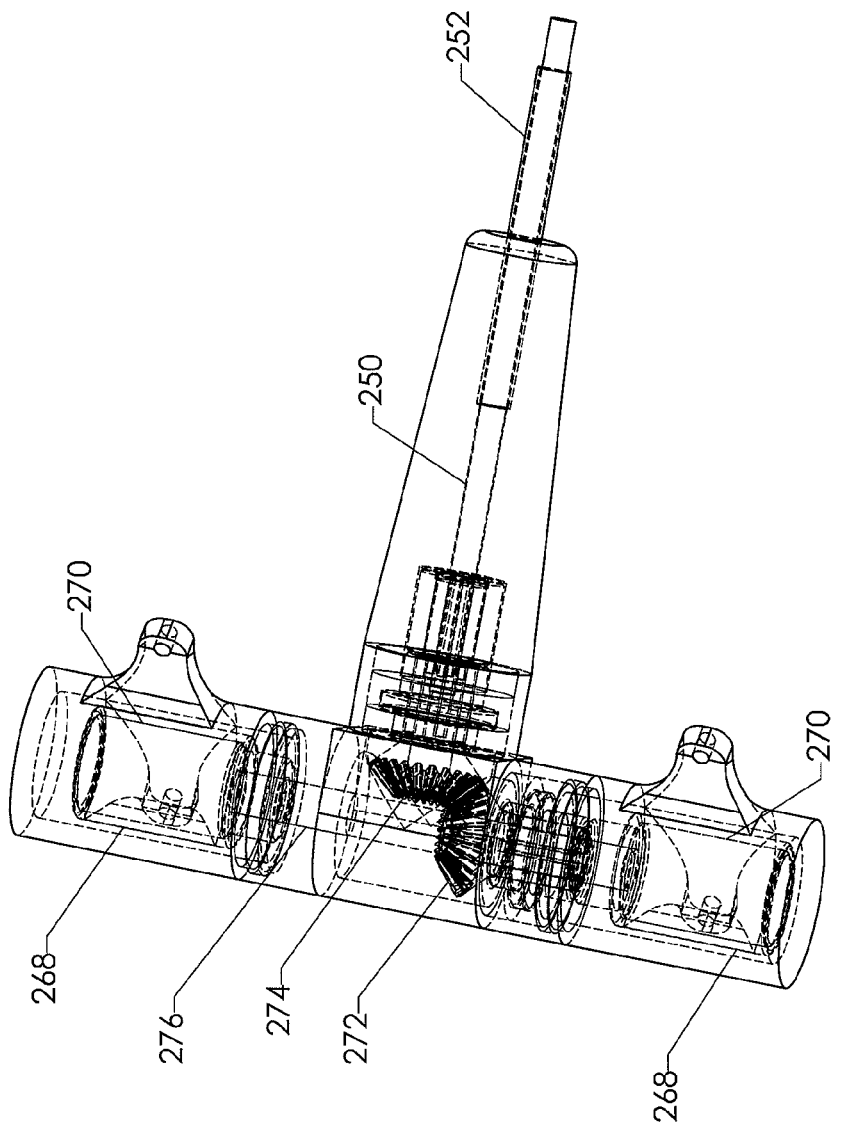
FIG. 37A illustrates the internal drive mechanism of the implantable interface of FIGS. 34-36.

Turning to FIG. 37A, rotation is imparted to the drive shaft 250 by means of a gearing arrangement. First miter gear 272 is coupled to a shaft 276. Both cylindrical magnets 270 are coupled to the same shaft 276. When both cylindrical magnets 270 are rotated by an external device 278, external to the patient, it causes shaft 276 and first miter gear 272 to turn. First miter gear 272 is rotatably engaged with second miter gear 274, which therefore is forced to turn when first miter gear 272 turns in response to rotation of cylindrical magnets 270. Second miter gear 274 is coupled to drive shaft 250, and so the forced rotation of the second miter gear 274 causes the rotation of the drive shaft 250. If bevel gears are used in place of the miter gears, for example, wherein the second (or follower) gear has a larger number of teeth than the first gear, then less torque is required to rotate the shaft 276, and drive shaft 250 rotates at a slower rate.

The drive shaft 250 is capable of delivering torque. It can be made, for example, from a triple coil configuration, wherein the inner and outer coils are would in one direction and the middle coil is wound in the opposite direction. The wires are made from 304 stainless steel or ELGILOY or NITINOL or other metallic or polymeric materials. Alternatively, the drive shaft 250 can be made from a braided tubing (polymeric tubing with embedded braiding). This braiding can be 304 stainless steel, ELGILOY, NITINOL, KEVLAR or other metallic or polymeric materials. The triple coil type drive shaft and the braided tube type drive shaft can both also be made with a core wire or rod in the center, for increased strength properties. If the designs allows for low enough torque of the drive shaft, the drive shaft 250 can be made of a single wire, for example a 0.010" to 0.030" NITINOL wire. Using NITINOL in any of the drive shaft configurations, especially in its superelastic state, makes for a more kink resistant drive shaft.

Figure 37B:
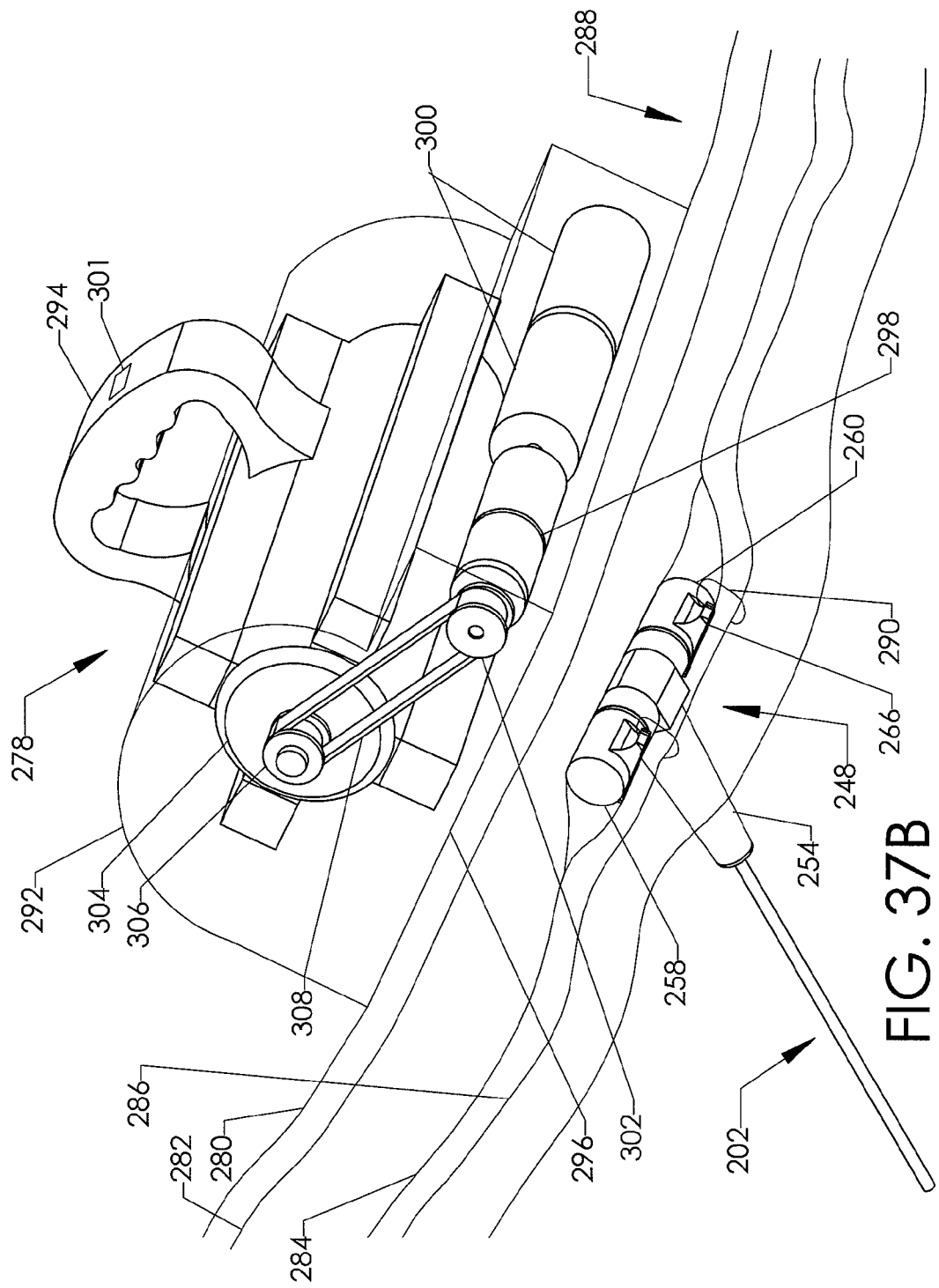
FIG. 37B illustrates the implantable interface implanted within a patient while being adjusted by an external device.

FIG. 37B illustrates the implantable interface 248 implanted within the abdominal wall 288 of a patient. The implantable interface 248 is implanted beneath the skin 280 and the subcutaneous fat 282 and is secured to the fascia 284 covering the muscle 286 by suture 290 or other means. Within a number of weeks after implantation of the implantable interface 248, the body forms a fibrous capsule around the implantable interface 248. The implantable interface 248 is shown in FIG. 37B in a preferred configuration, with the strain relief 254 extending through the fascia 284 and muscle 286. In order to non-invasively adjust the constriction amount of the restriction device 230, an external device 278 is placed on the skin surface opposite the implantable interface 248. The external device comprises an external device housing 292 having a flattened surface 296 for placement on the skin 280.

Figure 38:
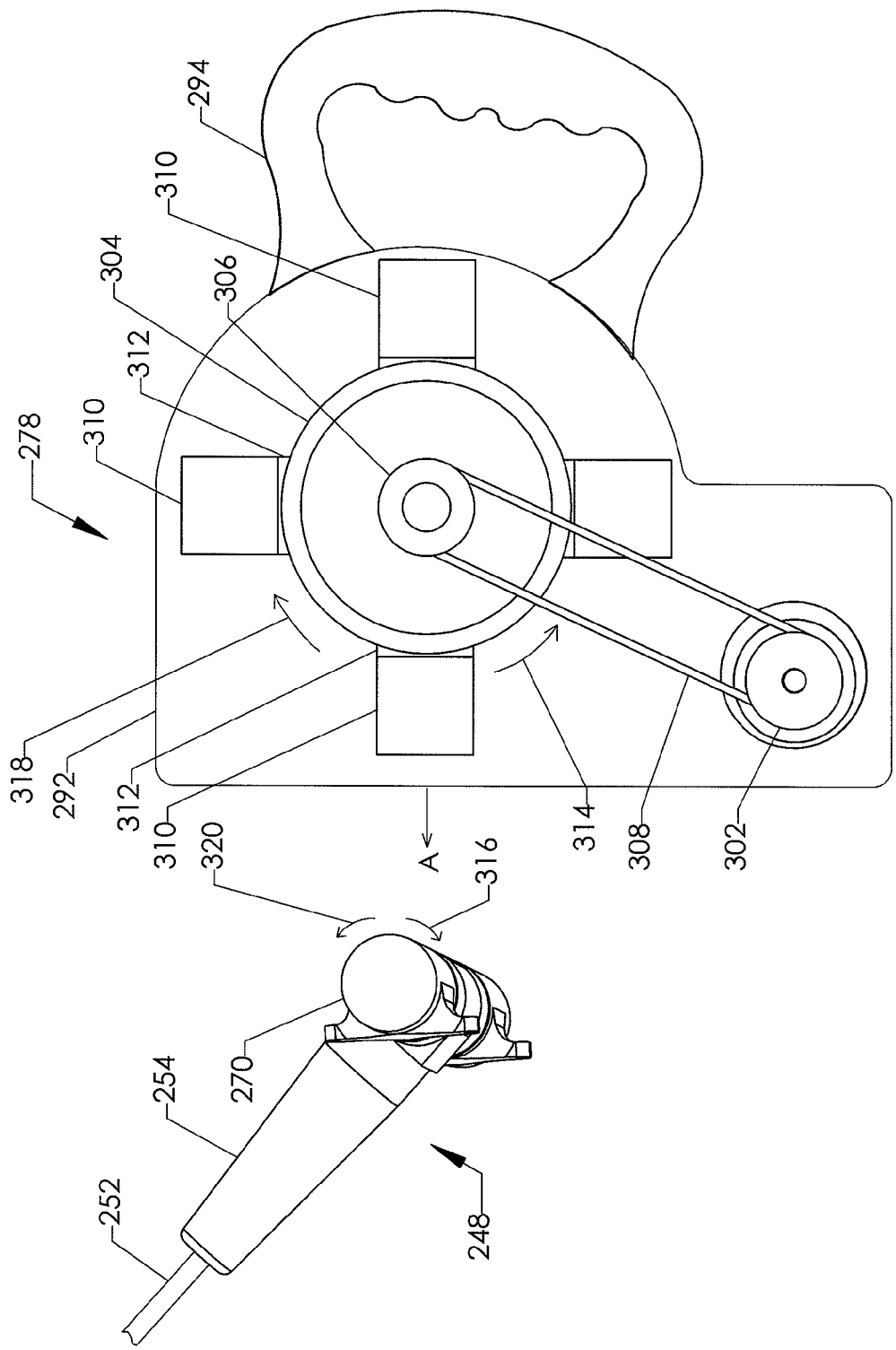
FIG. 38 illustrates the implantable interface situated adjacent or near an external device.

Alternatively, the surface for placement on the skin 280 can be contoured to match that of the abdomen. The external device 278 is held in place using a handle 294. Alternatively, the external device is clamped to the patient or held in place by means other than the attending operator's hands. Batteries 300 power a motor 298 which is operated via a switch 301. For example, the switch 301 has three settings: an off setting, an operation of the motor in one rotational direction and an operation of the motor in the opposite rotational direction. The motor 298 rotates a motor pulley 302, which then drives a cylinder 304 by means of a belt 308 and a cylinder pulley 306. It is conceived that other means of operation are all within the scope of causing rotation of the cylinder 304. Attached to the cylinder are four drive magnets 310, shown in FIG. 38. The drive magnets are poled as shown (through their thickness) so that alternating north-south faces are seen as the cylinder rotates.

Beneath each drive magnet 310 is a back iron 312. In certain embodiments, the drive magnets are made from rare earth magnetic materials, such as Neodymium-Iron-Boron (Nd—Fe—B), which have exceptionally high coercive strengths. In certain embodiments, the Nd—Fe—B magnets are enclosed within a stainless steel casing or a plating to protect the corrosive Nd—Fe—B material from the environment inside the body. In certain embodiments, other magnetic materials may be used, including SmCo5 (Samarium Cobalt) or AlNiCo (Aluminum Nickel Cobalt). In certain embodiments, Iron Platinum (Fe—Pt) may be used. Iron platinum magnets achieve a high level of magnetism without the risk of corrosion, and may possibly preclude the need to encapsulate. In certain embodiments, the permanent magnets used on the implantable interface may be replaced by magnetically responsive materials such as iron-cobalt-vanadium alloy (also known as HIPERCO).

The back iron 312 is preferably made from steel (AISI 1018) and may be coated, for example with Parylene, but the back iron 312 can also be made of stainless-steel. The back iron 312 preferably measures about half the thickness of the drive magnet. The back iron serves to force most of the magnetic field in direction A, creating improved coupling with the cylindrical magnets 270 of the implantable interface 248. When the switch 301 is operated to turn the cylinder 304, and thus drive magnets 310 and back irons 312 in a first rotational direction 314, magnetic coupling causes the cylindrical magnets 270 of the implantable interface 248 to turn in a second rotational direction 316. When the switch 301 is operated to turn the cylinder 304, and thus drive magnets 310 and back irons 312 in a third rotational direction 318, the cylindrical magnets 270 of the implantable interface 248 are forced to turn in a fourth rotational direction 320. It can be seen that the components in this embodiment behave like magnetic gearing, with the drive and driven "gears" engaged by magnetic attraction and repulsion.

Figure 39:
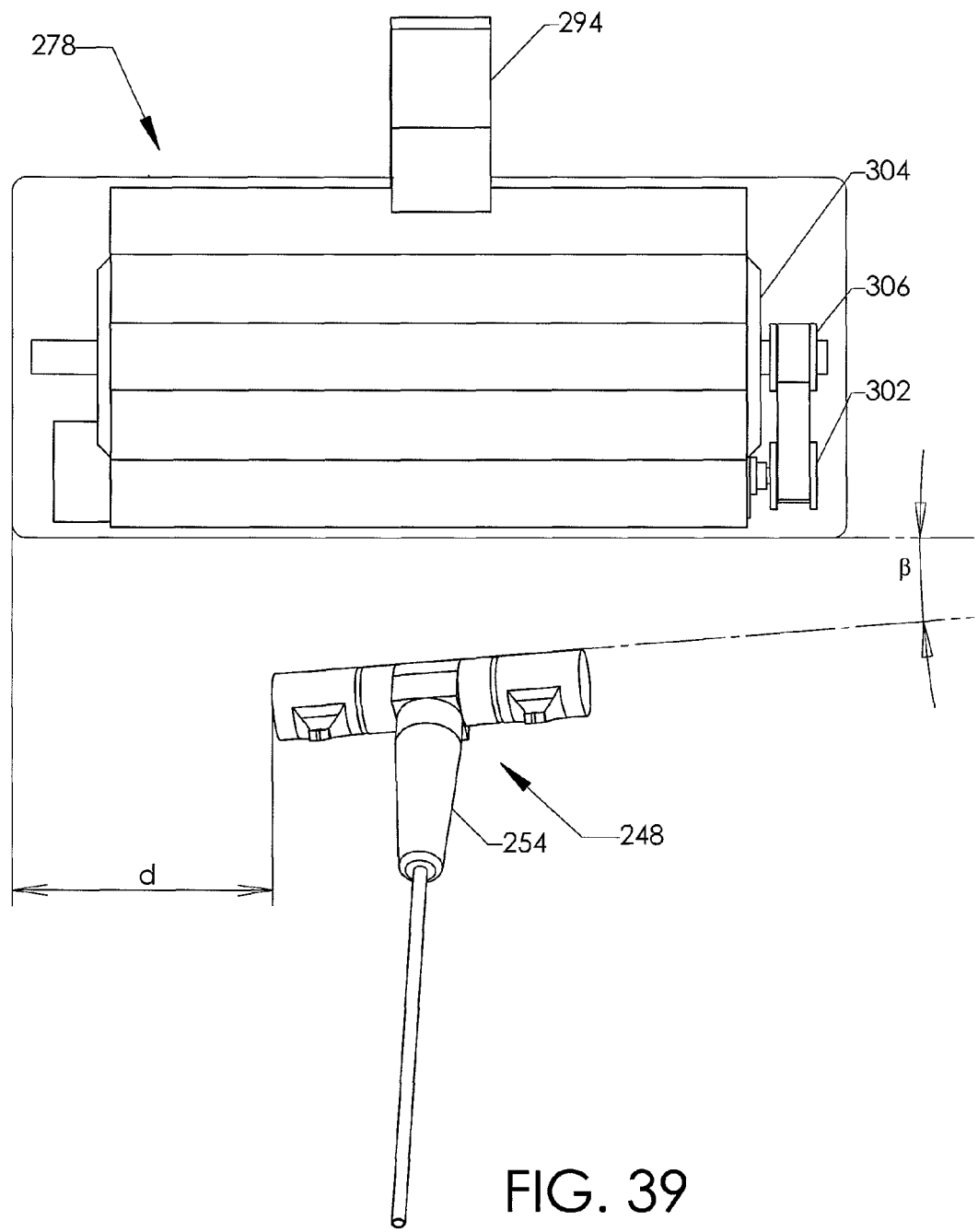
FIG. 39 illustrates a detail view of the cylinder/magnet assembly of the external device and the implantable interface. The external device is shown oriented at an angle with respect to the implantable interface.

The combination of the relatively large width of the drive magnets 310, and the effectiveness of back irons 312 to selectively shape the magnetic fields improves the coupling with the cylindrical magnets 270 of the implantable interface 248 so that even a non-ideal orientation of the implantable interface 248 in relation to the flattened surface 296 of the external device 278, as shown by angle β in FIG. 39, can still allow for acceptable coupling, and thus adjustment of the restriction device 230. Likewise, length d from the end of the external device 278 to the end of the implantable interface 248 can vary quite a bit while still allowing for good coupling. This is important, because the contours of the human body to not always allow for perfect parallel alignment, and because the implantable interface 248 cannot be seen through the skin 280 and fat 282, and thus the true optimum alignment cannot always be surmised.

Figure 40:
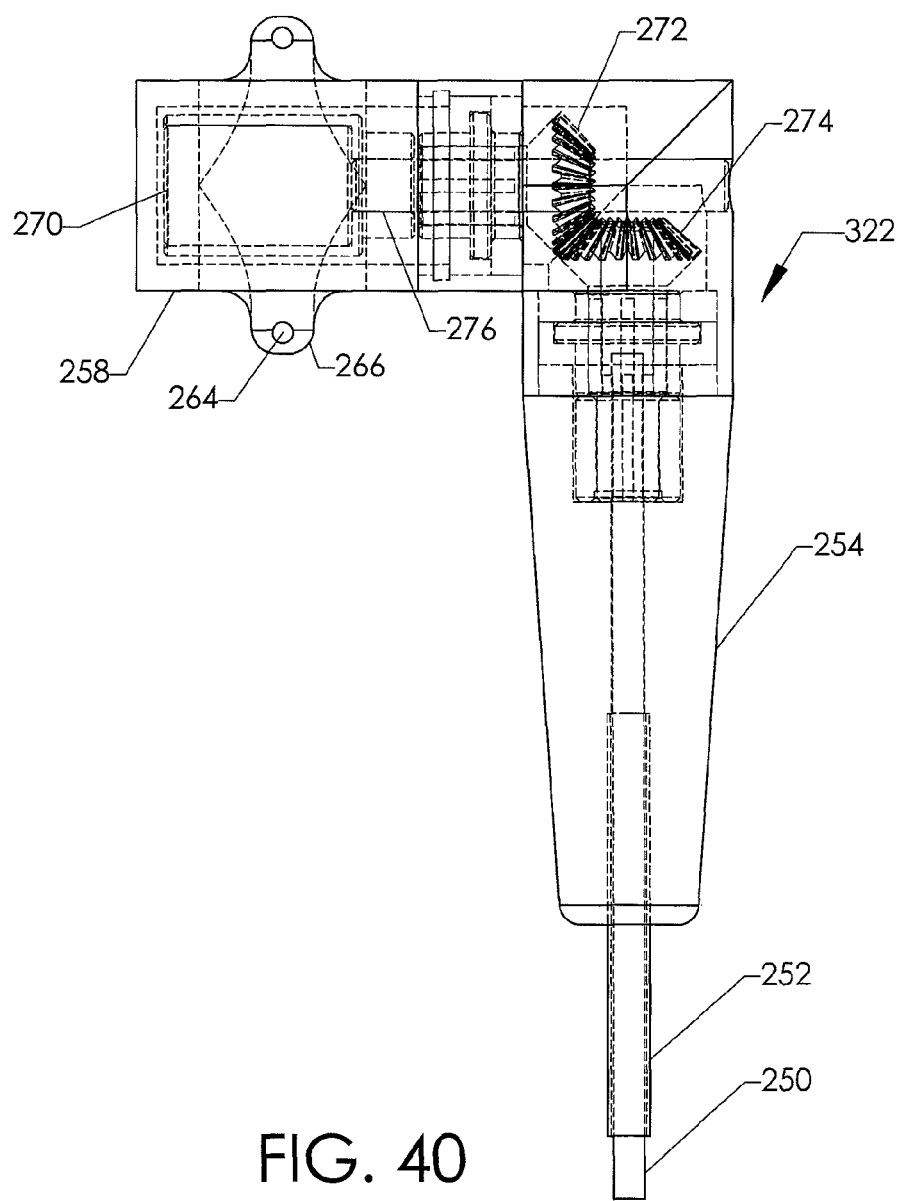
FIG. 40 illustrates an alternative embodiment of the implantable interface utilizing only one cylindrical magnet.
Figure 41:
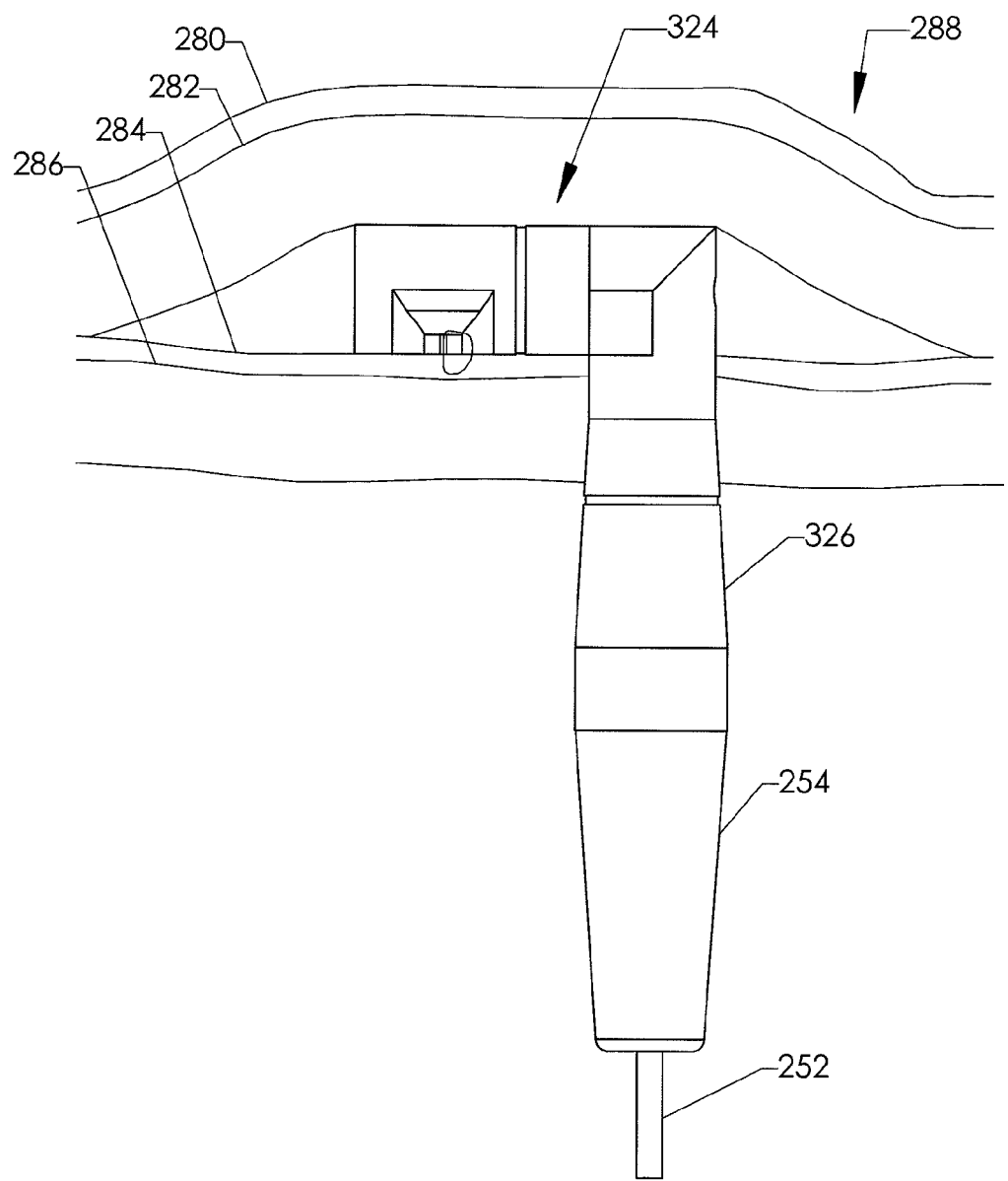
FIG. 41 illustrates an implantable interface secured to the fascia of a patient.

An alternative embodiment is shown in FIG. 40. In this single magnet implantable interface 322, there is only one cylindrical magnet 270, giving the implantable interface 322 an "L" shape instead of a "T" shape. The benefit is that this configuration can be secured within the abdominal wall of the patient with a smaller "footprint", and thus with less bother to the patient, either cosmetic or comfort related. FIG. 41 demonstrates this configuration. An alternative single magnet implantable interface 324 is illustrated in FIG. 41 in place within the abdominal wall 288. An additional feature of this alternative embodiment is a planetary gearbox 326, which can change the gear ratio to lessen the torque requirement and/or lower the rotational speed, without addition diameter to the housing.

The sheath 252 of the drive transmission 202 is preferably made with a coil reinforced configuration. For example, the inner layer is polyethylene, polypropylene, nylon, polyurethane, PTFE, FEP, PFA, ETFE or other relatively low friction polymers. The coil is made from stainless steel, ELGILOY, NITINOL, MP35N and serves to maintain a round inner diameter, and keep sheath 252 from kinking. This is important because the drive shaft 250 should in turn be free to rotate inside the sheath, even as sheath takes a curved configuration in the body over the life of the implant, due to patient movement. The entire outer surface of the restriction device 230, drive transmission 202 and implantable interface 248 are preferably made from implantable biocompatible materials, such as silicone, polyurethane or a silicone-urethane copolymer, such as Elast-eon™. The outer surface may be made more lubricious via the embedding of Parylene.

The external device may also include a torque meter that measures the torque during adjustment in order to determine whether the magnets are engaged, and thus is able to count rotations, and thus, the degree of adjustment of the restriction. The external device may also use electromagnets in order to generate the magnetic fields which will couple with the implantable interface magnets. Alternatively, the magnets of the implantable interface 248 may also have back irons in order to tailor the magnetic fields. The back iron may be steel (AISI1018) with Parylene coating, nickel and gold coating or other coating to assure biocompatibility.

Figure 42:
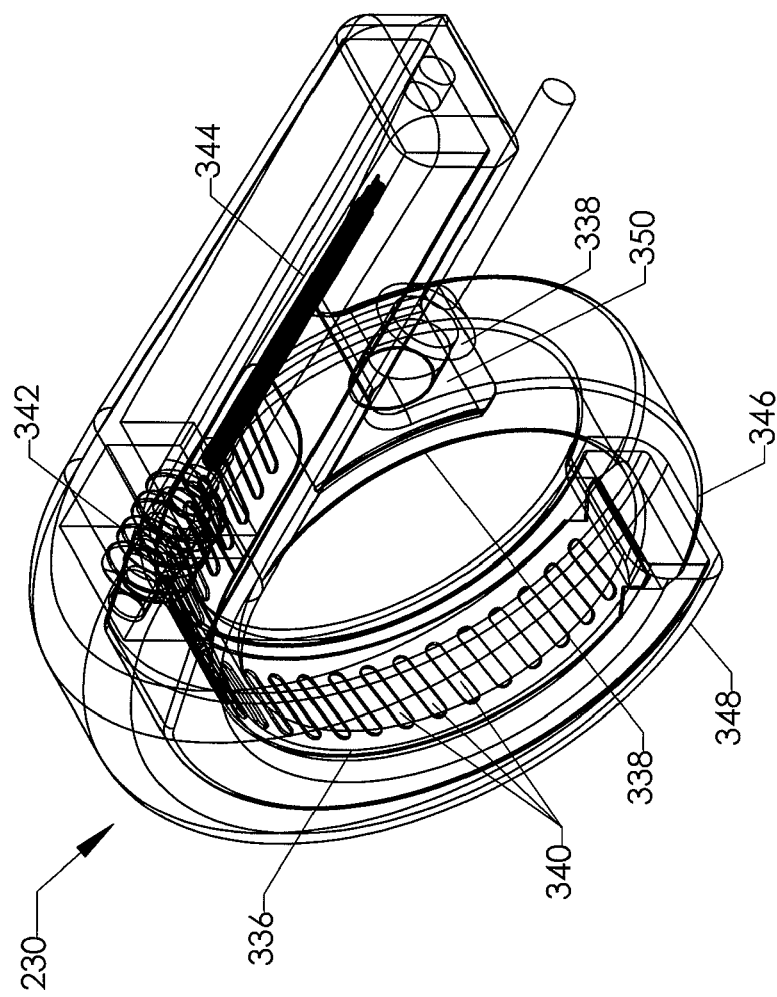
FIG. 42 illustrates an alternative embodiment of the restriction device having a sliding portion.

FIG. 42 illustrates an alternative embodiment of the restriction device 230 having a sliding section. A belt 336 is attached permanently at the first attachment portion 338. The belt 336 has grooves 340 which are engaged by a worm 342 which is turned by a drive shaft 344, for example, a magnetically driven drive shaft. At the worm 342 turns, the grooves 340 of the belt 336 are engaged by the threads of the worm 342, causing the perimeter of the belt 336 to either increase or decrease. This causes a female section 348 to slide over a male section 346 to either increase or decrease the inner diameter of the restriction device 230. An advantage of this configuration is that the restriction device 230 does not need to be made of compressible materials, such as foam. In this type of design, the emergent relief of stress, for example due to violent vomiting, can be controlled by a semi-compliant relationship between the attachment between the first attachment portion 338 and a second attachment portion 350.

Figure 43:
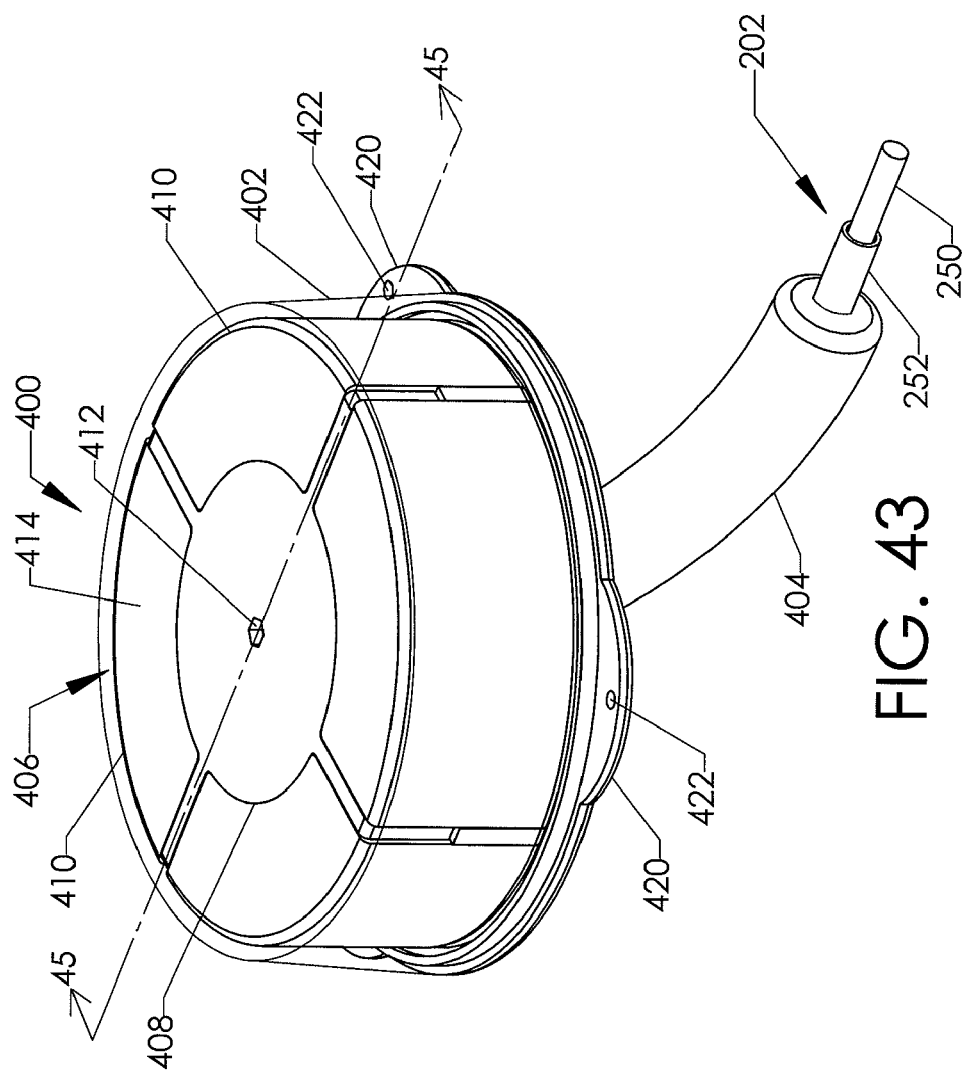
FIG. 43 illustrates an alternative embodiment of an implantable interface for magnetic coupling.

FIG. 43 illustrates an alternative embodiment of an implantable interface 400. A drive transmission 202, comprising a drive shaft 250 and a sheath 252 is coupleable to the implantable interface 400. The implantable interface 400 comprises a housing 402 a flexible strain relief 404 and a magnetically driven rotational assembly 406. The magnetically driven rotational assembly 406 comprises a turret 408 and four magnets 410. The turret 408 includes a keyed orifice 412, for example in the shape of a hexagon, which can be engaged by a corresponding male shape, for example a hex 418 at the end of the drive shaft 250 (see FIG. 44). The turret 408 also serves to hold the magnets 410 in their preferred configuration. Note that other numbers of magnets may be used, for example six instead of four. In the configuration illustrated, the magnets a poled through their thickness and oriented in an alternating manner (north-south-north-south) so that they are presented at the top face 414 to couple with a driving magnet or magnetic array in an external device (not pictured).

Figure 44:
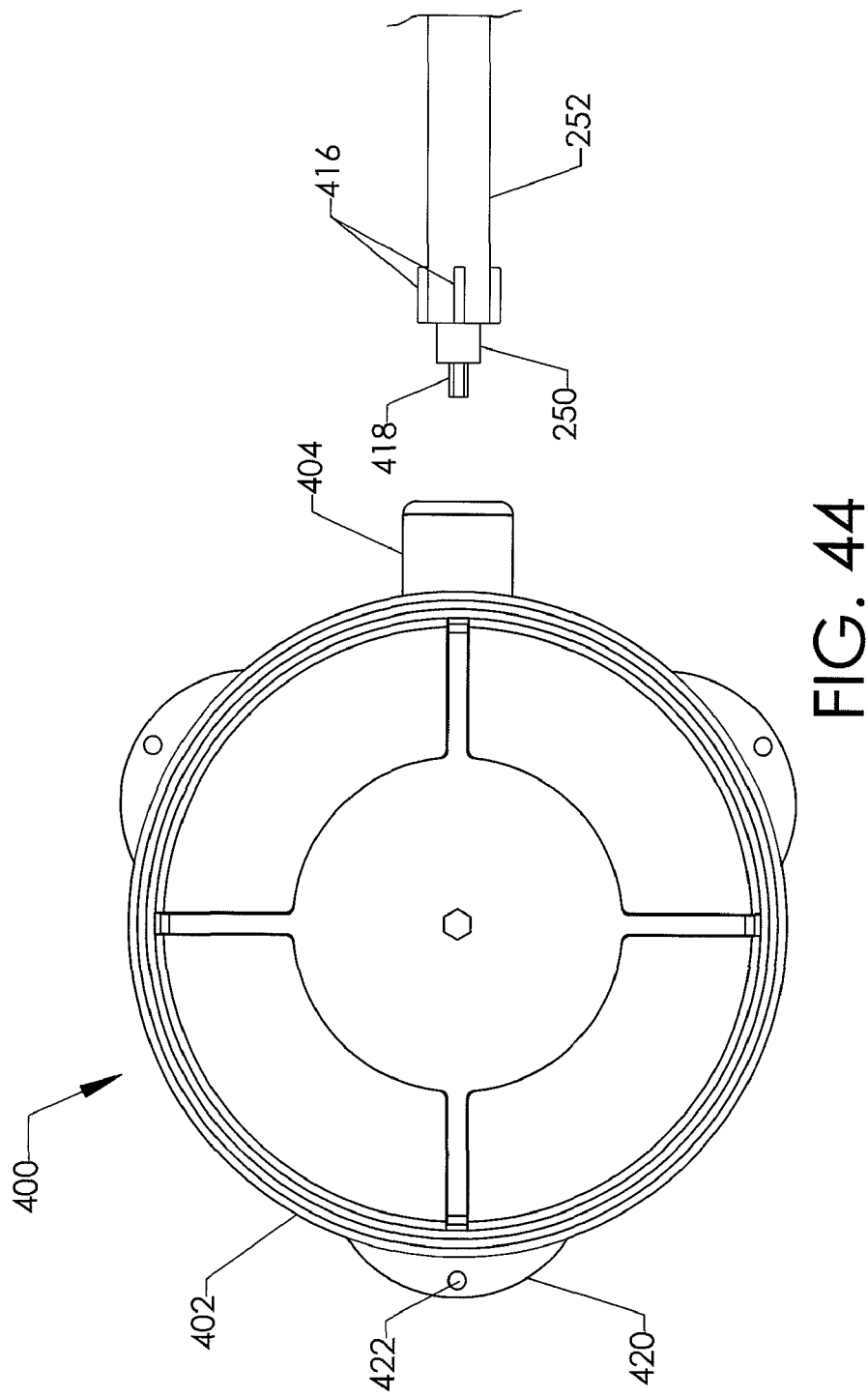
FIG. 44 illustrates a top view of the implantable interface of FIG. 43.
Figure 45:
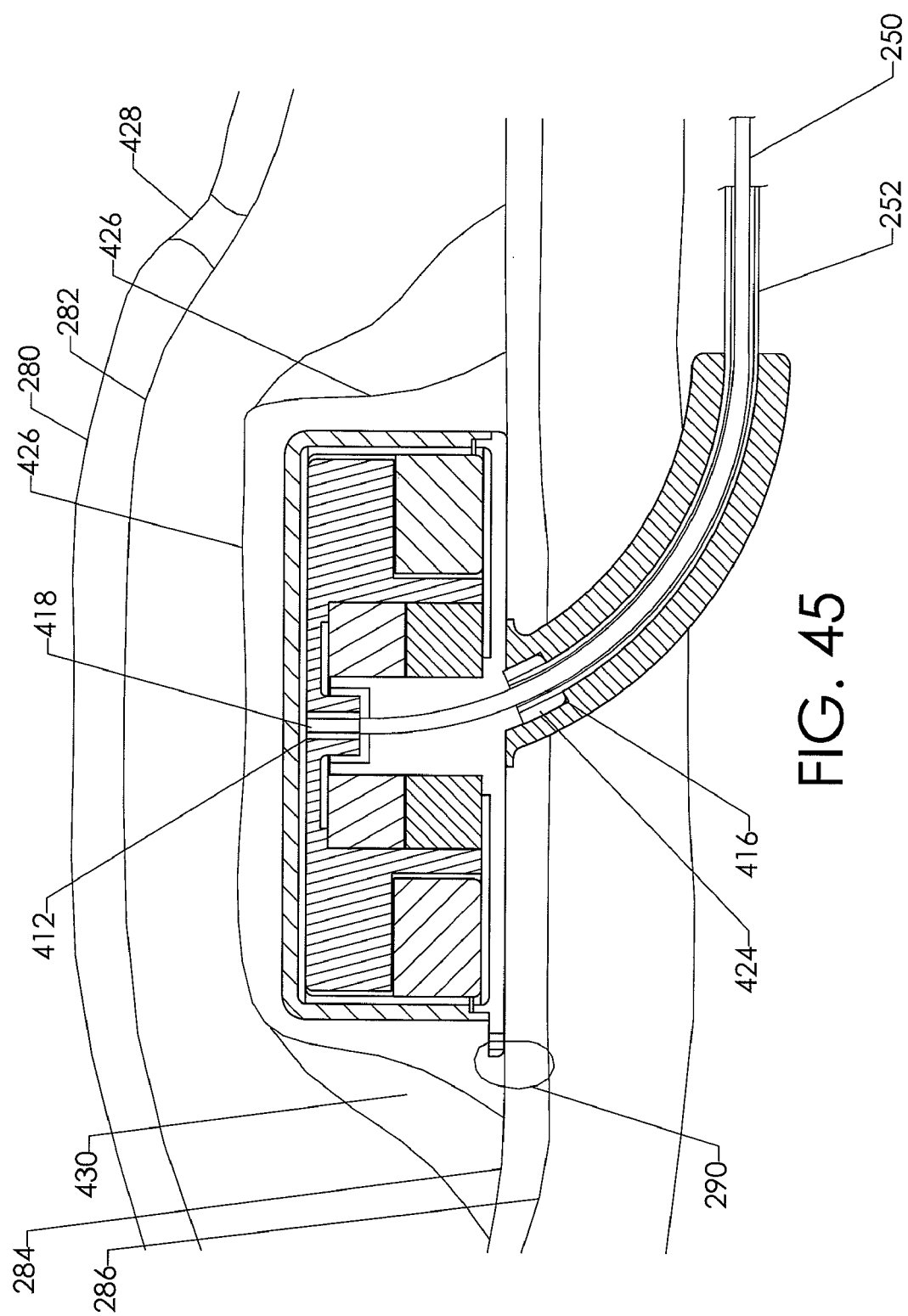
FIG. 45 illustrates a cross-sectional view of FIG. 43 taken along line 45-45', with the implantable interface sutured to the fascia and after several weeks of implantation.

The external device couples with the magnets 410, causing the turret 408 to turn, and in turn causing the drive shaft 250 to turn, thus allowing for adjustment of the restriction device. FIG. 44 illustrates the drive shaft 250 and the sheath 252 prior to being coupled to the turret 408 of the implantable interface 400. The sheath 252 has wings 416 which are inserted into the flexible strain relief 404 and locked into the wing lock 424 (see FIG. 45), while the hex 418 is inserted into the keyed orifice 412. The shape does not have to be a hexagon, and can be any keyable or friction engageable shape. FIG. 45 illustrates a cross-section of the implantable interface 400 after it has been sutured into a patient and after several weeks have passed, wherein the body has grown a fibrous capsule 426 around the implantable interface 400. The implantable interface 400 has been secured to the fascia 284 covering the muscle 286 by use of suture 290. The implantable interface 400 was originally inserted through an incision 428 and into a tunnel 430 between the skin 280 and fat 282 and the fascia 284 and muscle 286. The suturing is done through suture holes 422 in suture tabs 420. If necessary, the implantable interface 400 may be subsequently removed from the drive transmission 202 and replaced by another implantable interface of the same design or of a different design.

Figure 46:
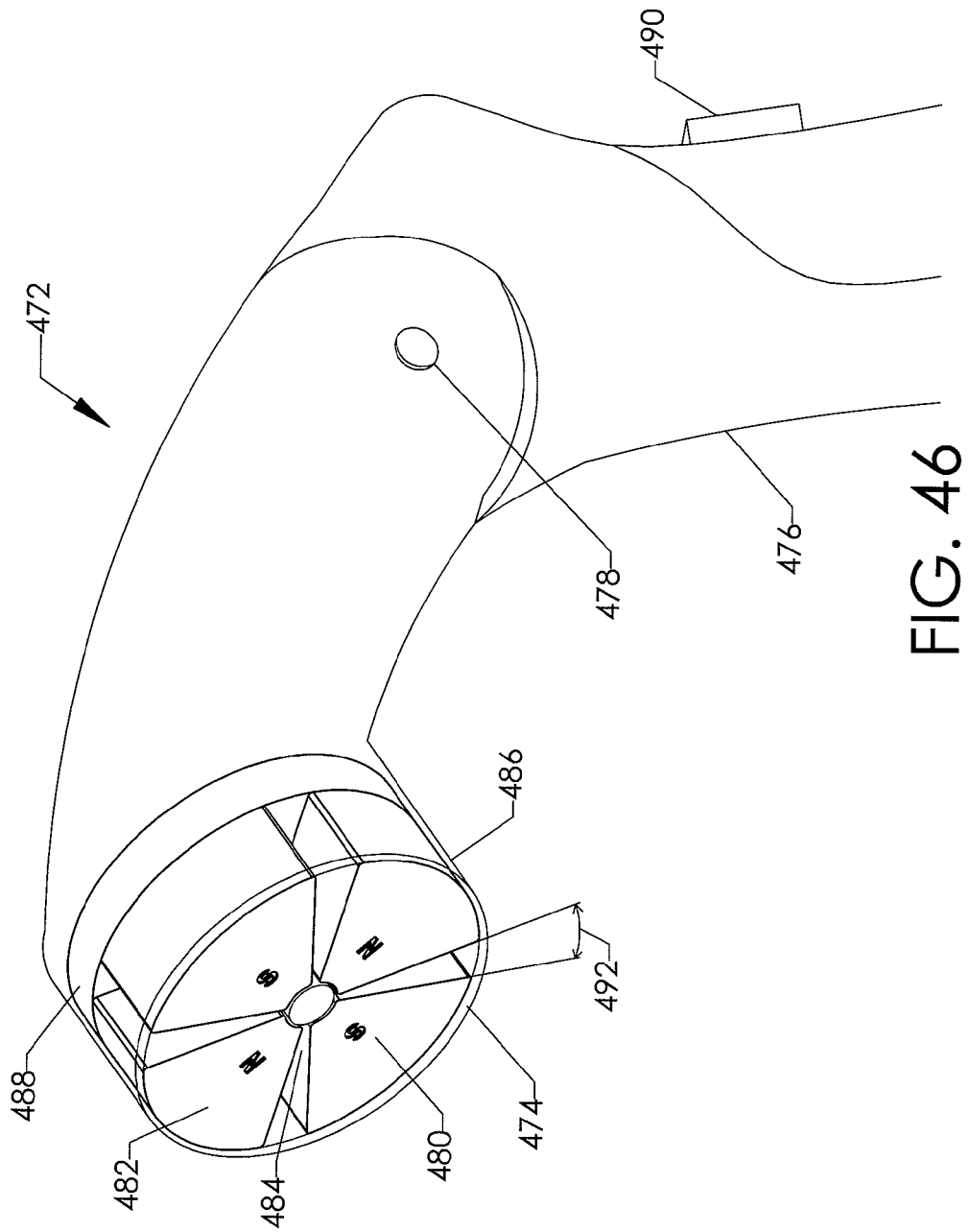
FIG. 46 illustrates a perspective view of an external driver according to one embodiment.
Figure 47:
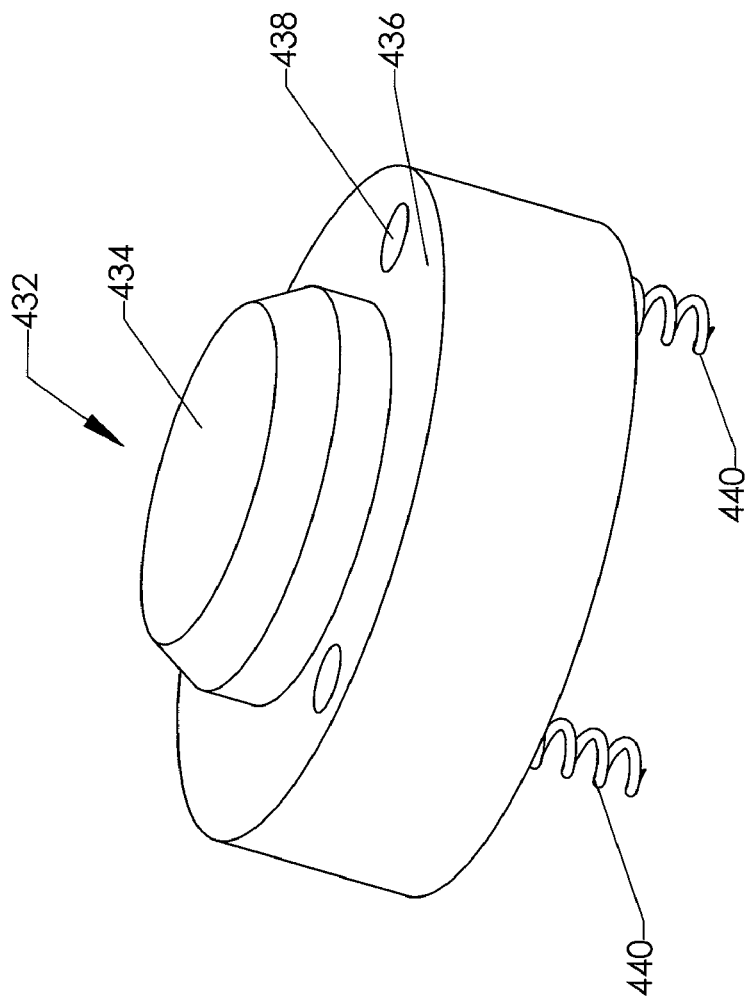
FIG. 47 illustrates one alternative embodiment of an implantable interface.
Figure 48:
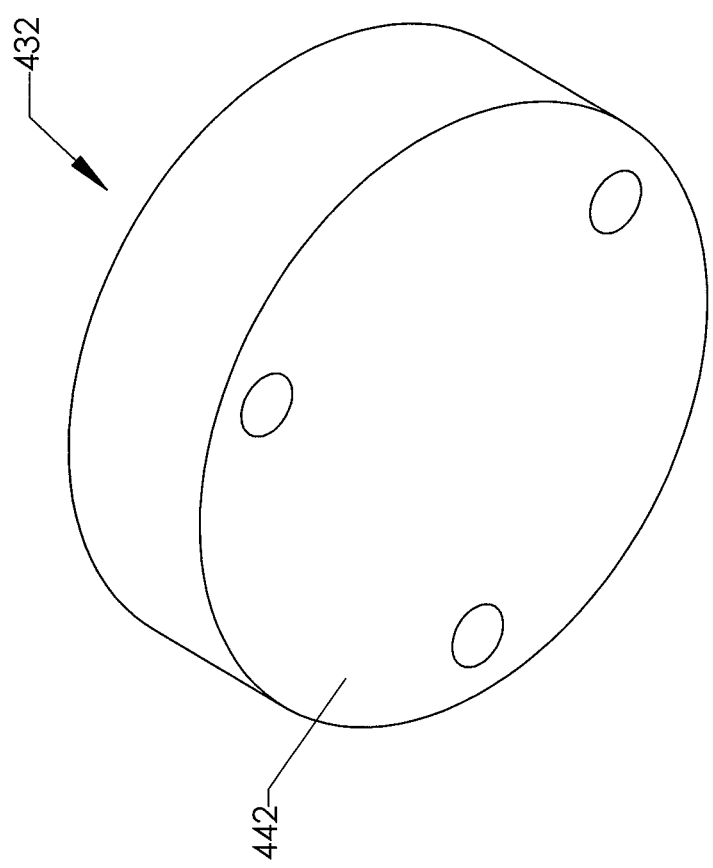
FIG. 48 illustrates the implantable interface of FIG. 47 prior to engagement or deployment of the rotatable coils.
Figure 49:
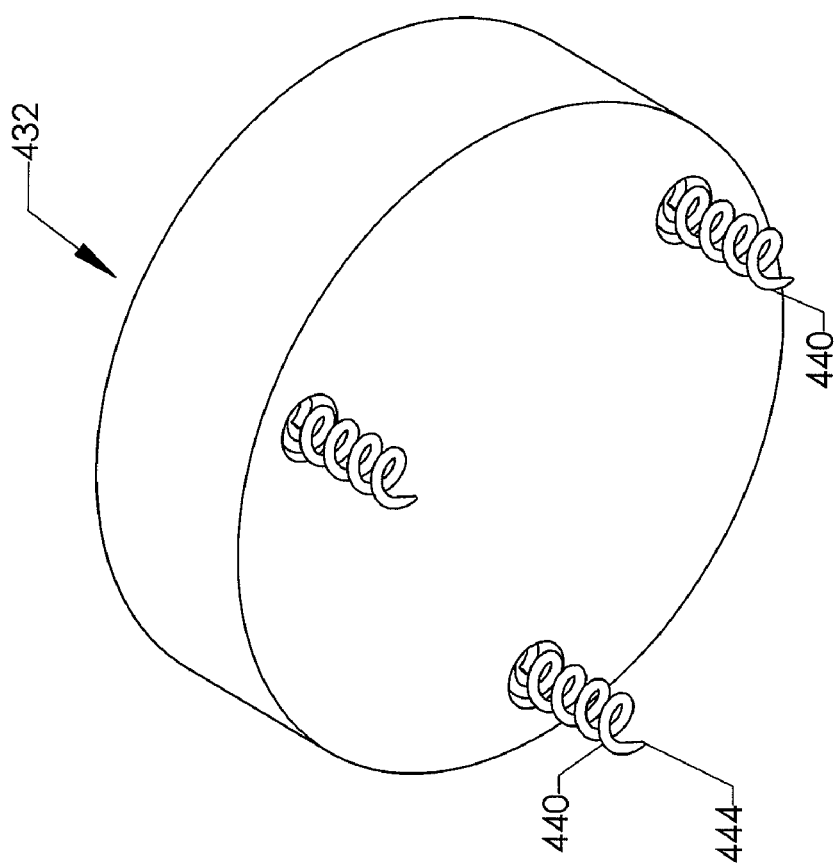
FIG. 49 illustrates an alternative embodiment of an implantable interface after engagement of the rotatable coils.

FIG. 46 illustrates an external device 472 for driving the implantable interface 400 of FIGS. 43-45. External device 472 comprises a head 474, a handle 476 and an articulation 478 that allows adjustment of the angle of the head 474 in relation to the handle 476. In use, front face 480 is placed against skin 280, opposite implantable interface 400. Four driving magnets 482 are arrayed on turret 484 in staggered (north-south-north-south) orientation. The turret 484 can be rotated within a housing 486 of head 474. Back iron 488 is approximately 50% of the thickness of each of the driving magnets 482. Back iron is a flat ring disk made from steel 1018, with an inner diameter matching the inner arc and an outer diameter matching the outer arc of each of the sector shaped driving magnets 482. Switch 490 is a three position switch controlling the operation of a motor which is either off, rotating clockwise or rotating counter-clockwise. The motor controls the rotation of the turret 484. The back iron 488 serves to orient the magnetic fields so that they are optimized in the direction of the implantable interface 400, and thus maximize magnetic coupling. The outer diameter of the magnet/back iron assembly is approximately 150% that of the diameter of the magnetically driven rotational assembly 406 of the implantable interface 400. The larger diameter of the magnet/back iron assembly in relation to the magnetically driven rotational assembly 406 allows for sufficient magnetic coupling, even if the external device 472 is not perfectly centered and angularly oriented in relation to the implantable interface 400. The spacing 492 between the driving magnets 482, also minimizes attraction between each of the adjacent magnets which may be antagonistic to the extent of coupling between the external device 472 and the implantable interface 400. An exemplary spacing is 5° to 15°. It should be noted that at maximum torque transfer, the poles of the driving magnets 482 are not perfectly aligned with the opposite poles of the magnets 410, but rather there is a nominal angular offset An alternative securing mechanism for an implantable interface 432 is illustrated in FIGS. 47-49. Currently, securing implantable couplers, for example injection ports for hydraulic gastric bands, using suture inserted through suture holes, can be time consuming and can sometimes lead to a port that is not evenly sutured at every suture location. This can lead to flippage of the port. An improvement for securement of both ports for hydraulic gastric bands, ports for other purposes or for the implantable interfaces described within the scope of this invention is illustrated in FIG. 47. The implantable interface 432 comprises a central portion 434, which may include a diaphragm (in the case of an injection port) or a magnetic assembly (in the case of a magnetically driven interface). The implantable interface 432 also comprises an outer portion 436 which includes keyholes 438 and rotatable coils 440. The rotatable coils 440 are rotated by placing a driver into one of the keyholes 438 and turning it. The rotatable coils 440 are connected to a driven head, for example a hex head, and the driver can be a matching hex head. For attachment to the fascia, the interface surface 442 is placed on top of the fascia and a slight force is placed on the implantable interface 432. A driver is placed into one of the keyholes 438 and into the hex head which is attached to one of the rotatable coils 440. The tip 444 of the rotatable coils 440 is sharp, so that it easily imbeds in the fascia. As the rotatable coil 440 is turned clockwise, the tip 444 embeds deeper and deeper into the fascia. All rotatable coils 440 can be secured into the fascia separately, or a gearing system, such as a planetary gearing system, can be used so that only one keyhole 438 is necessary, and allows the tightening of all rotatable coils 440 in unison. FIG. 48 illustrates the implantable interface 432 with the coils 440 retracted and FIG. 49 illustrates the implantable interface 432 with the rotatable coils 440 tightened. The rotatable coils 440 may be axially free within the keyholes, so that only the circumferential engagement into the fascia causes them to advance axially (like a wood screw). Alternatively, the rotatable coils 440 may be within a tapped structure within the keyholes 438 so that the turning of the rotatable coils 440 by the driver causes a specific axial engagement with each turn (as the tip 444 moves circumferentially it is also forced axially at a specific rate). If it is desired to remove the implantable interface 432, the rotatable coils 440, can be turned counter-clockwise to remove them from the fascia.

Alternative improvements include the following. It may be desired that after securement, the rotatable coils 440 be contactable by an electrosurgical device, in order to heat the tissue surrounding the rotatable coils 440, in order to promote local scarring and better hold the rotatable coils 440 in place. Because the securement of the rotatable coils is most important in the first several weeks (for example two weeks to six weeks), and in various applications is less important after this period (when the fibrous capsule has formed over the implantable interface 432), it is conceived that the rotatable coils 440 may be detachable, for example in the cases wherein easy removal of the implantable interface 432 is desired. Another way of achieving this is by making the rotatable coils 440 from a material that is biodegradable or bioabsorbable and will disappear in a time period after the important several weeks. An example of such material is magnesium.

Figure 50:
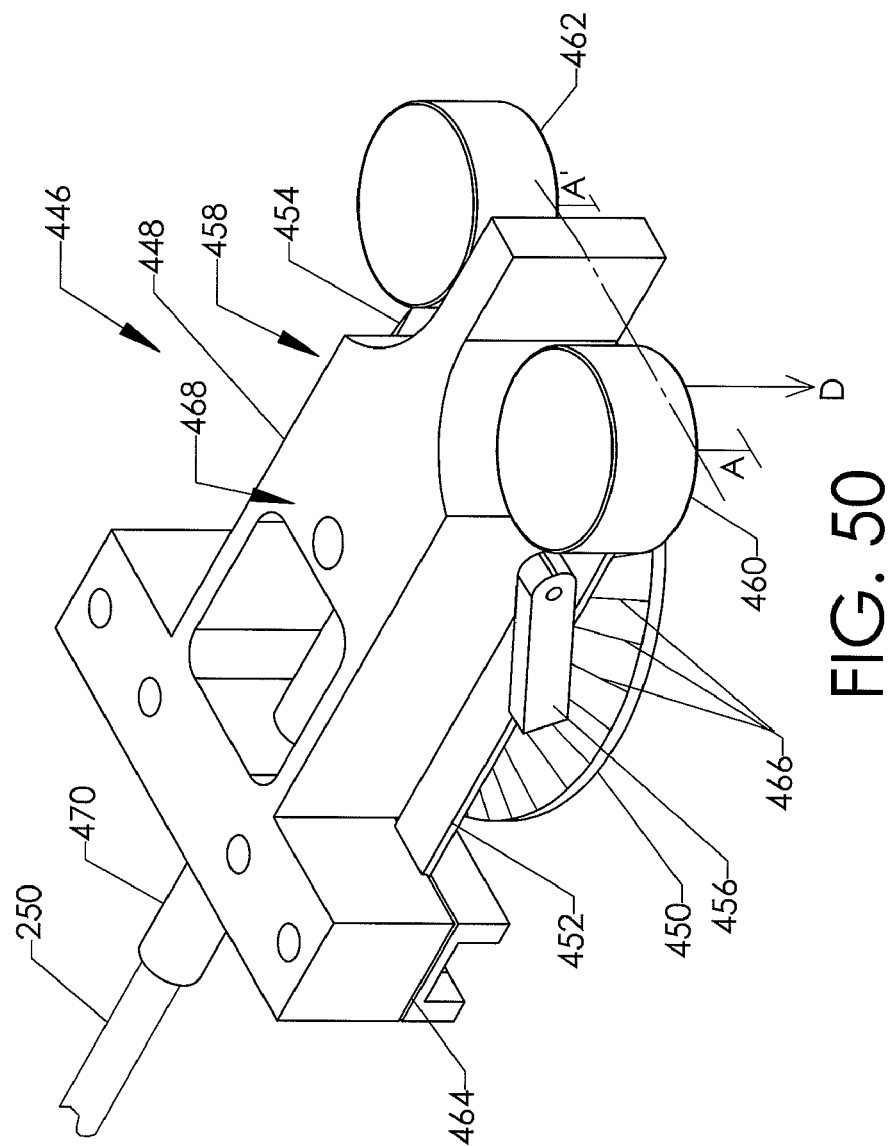
FIG. 50 illustrates various internal parts (without the housing) of an alternative embodiment of an implantable interface which uses resonance to turn or rotate a drive shaft.

FIG. 50 illustrates an alternative embodiment to the implantable interface using a resonance method to make the drive cable 250 rotate. In FIG. 50, an outer housing is not shown, in order to better display the detail of the internal workings. The resonance mechanism 446 comprises a frame 448, a circular ratchet plate 450, a first resonance beam 452, a second resonance beam 454, a first pawl 456, a second pawl 458, a first magnet 460 and a second magnet 462. The first magnet 460 and the second magnet 462 are attached respectively to the first resonance beam 452 and the second resonance beam 454. The two resonance beams are attached to the frame 448 at one end by use of a clamp 464. An external device having a rotating magnet or a pistoning magnet is operated using a specific repeating frequency that is identical to the resonating frequency of the first resonance beam 452. For example, the external device, consisting of a rotating magnet, is rotated at a frequency of 100 Hz, the resonance frequency of the first resonance beam 452. At this frequency, the repetitive attraction and repulsion of the first magnet 460 causes the first resonance beam 452 to oscillate in direction (D) at an amplitude (A). If this frequency of the rotating magnet is increased or decreased, the first resonance beam 452 will not oscillate at its resonant frequency, and therefore will resist the development of sufficient amplitude (A).

Likewise, because second resonance beam 454 has a resonance frequency of 180 Hz, it will not sufficiently oscillate when the external magnet is rotated at 100 Hz. As the first resonance beam 452 oscillates at 100 Hz and amplitude (A), a first pawl 456 attached to the first resonance beam 452 engages and moves ratchets 466 of the circular ratchet plate 450, causing the plate to turn, for example 0.010" tangentially with each cycle. For example, if the pawl is at a diametrical location of the circular ratchet plate 450 that is 1", then the disk will turn (100/sec)(0.010")/3.14" or about one turn every three seconds. The resonance activated rotation of the circular ratchet plate 450 causes gearing 468 to engage and thus turns shaft 470 to which is attached drive shaft 250. If this first direction of rotation corresponds to the compression of the restriction device, then the relaxation of the restriction device can be achieved by operating the external device so that the magnet rotates at 180 Hz, which is the resonant frequency of the second resonance beam 454. Now the second resonance beam 454 will oscillate at 180 Hz at an amplitude of A', causing a second pawl 458 to engage and move circular ratchet plate 450 in the opposite direction, thus causing the drive shaft 250 to turn in the opposite direction, and to relax the restriction device.

Alternatively, a single resonance beam structure, centered on the frame, can be used that allows the single beam to pivot to one side or the other of the circular ratchet plate (depending on the direction of rotation of the external magnet). Thus, when the external magnet is rotated in a first direction, the beam pivots to one side of the circular ratchet plate and causes the ratchet plate to turn in a second direction. When the external magnet is rotated in a third direction, opposite of the first direction, the beam pivots to the opposite side of the circular ratchet plate and causes the ratchet plate to turn in a fourth direction, opposite of the second direction.

It should be noted that on all of the magnetically-aided resonance beam designs, the oscillation of the beam is very insensitive to the location of the external magnet, making it easy for the attending physician or medical personnel to perform the adjustment of the restriction device, without too much concern for finding the correct placement of the external device.

Instead of using implanted magnets, the implantable interface using the resonance mechanism (but no magnets) can be implanted so that it touches a bone structure so that an external vibrator placed close to the bone (for example the rib) will cause the resonance of the beams at the selected frequencies.

Figure 51:
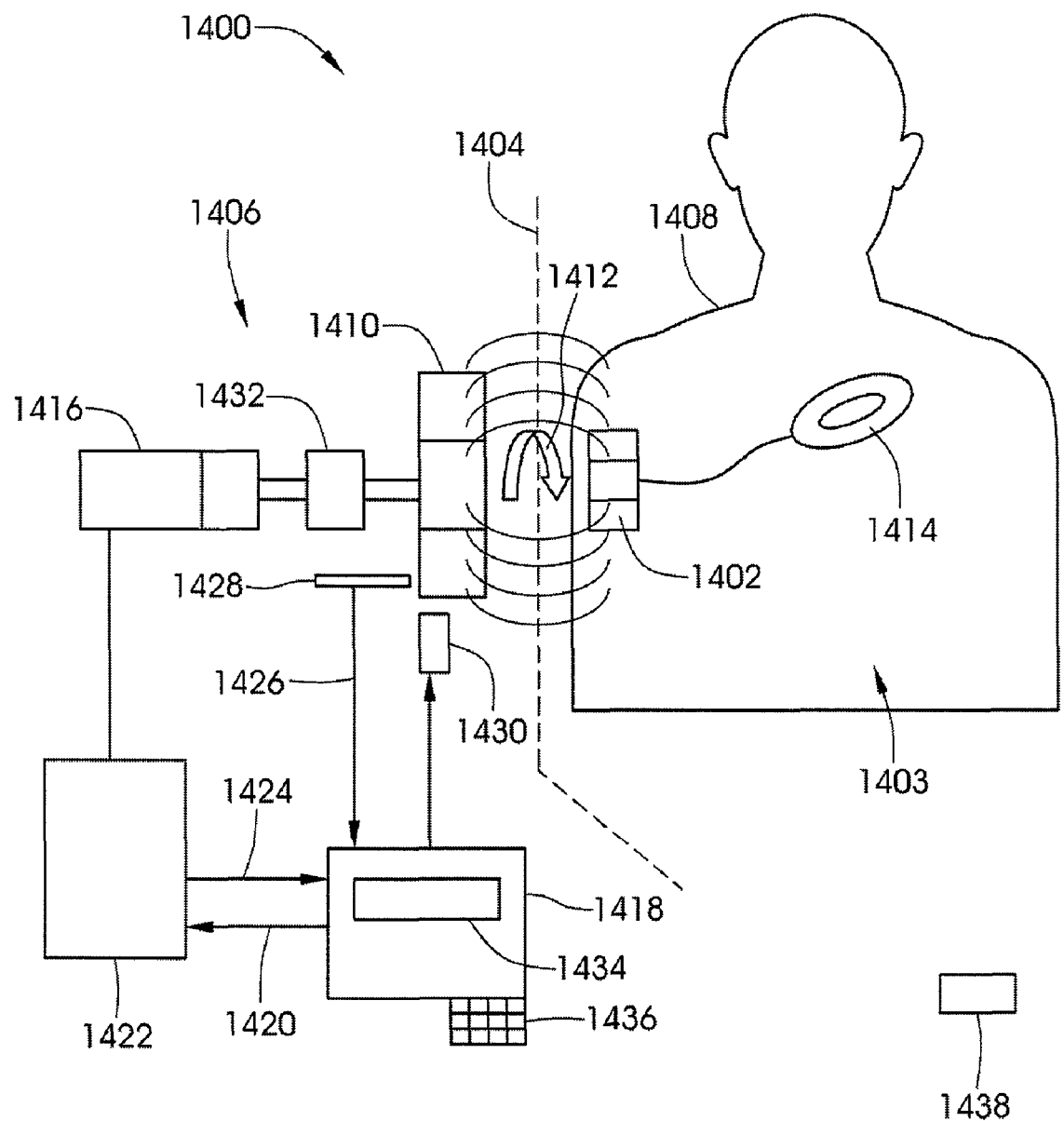
FIG. 51 illustrates a system for driving an internally located driven magnet via an external device using a feedback mechanism.

FIG. 51 illustrates a system 1400 for driving an internally located driven magnet 1402 of an implanted device 1403 via an external device 1406 using a feedback mechanism. One or more implanted driven magnets 1402 are coupled magnetically through the skin 1404 of a patient 1408 to one or more external drive magnets 1410. A rotation or movement of the external drive magnets 1410 causes an equal rotation of the driven magnets 1402. Turning the driven magnets 1402 in one direction 1412 causes a restriction device 1414 to close while turning the driven magnets 1402 in the opposite direction causes the restriction device 1414 to open. Changes to the restriction device 1414 diameter are directly proportional to the number of turns by the one or more drive magnets 1410.

The drive magnets 1410 are rotated by the external device 1406, which has an electric gear motor 1416 which is controlled by a programmable logic controller (PLC) 1418. The PLC 1418 outputs an analog signal 1420 to a motor drive circuit 1422 which is proportional to the motor speed desired. The PLC 1418 receives an analog signal 1424 from the motor drive circuit 1422 that is proportional to the current draw of the motor. The gear motor's 1416 current consumption is proportional to its output torque. An electronic torque sensor may be used for this purpose.

The PLC 1418 receives a pulsed input signal 1426 from an encoder 1428 that indicates the angular position of the drive magnets 1410. The PLC 1418 controls a spring loaded braking system 1430 that automatically stops the drive magnet 1410 if there is a loss of electrical power or other emergency.

A slip clutch 1432 is included between the gear motor 1416 and the drive magnet 1410 to prevent the gear motor 1416 from over torqueing the driven magnet 1402 and potentially damaging the implanted device 1403.

The PLC 1418 has a built in screen 1434 to display messages and a keypad 1436 for entering data. External push button switches and indicator lights may be incorporated for user comfort and ease of use.

The motor current (output torque) is monitored continuously whenever the device is turning. If the motor current exceeds the maximum allowable current (based on safety requirements of the device components and/or patient tissue) the gear motor 1416 is stopped and the brake 1430 is applied. This can be done both in software and hardware. The mechanical slip clutch 1432 also prevents over torqueing of the device. An exemplary threshold torque is 3.0 ounce-inches.

Each patient will have a number that corresponds to the diameter of their restriction. A fully open device will have a number such as 2.80 cm for its internal diameter and a fully closed device will have a number such as 1.50 cm.

This number can be stored on an electronic memory card 1438 that the patient 1408 carries. The PLC 1418 can read the current number from the memory card 1438 and update the number after adjustment. The patient's number can be recorded manually in the patient's chart and kept at the physician's office or printed on an information card that the patient carries. Alternatively, the information can be stored on and read from an RFID chip implanted in the patient.

The patient's number is first entered into the PLC 1418 so it knows the patient's starting point. If the patient's records are completely lost, the system can always fully open the restriction device 1414 (a known starting point). The number of turns to fully open the restriction device 1414 can be counted and the device can then be returned to the same restriction position.

A physician may adjust the restriction device 1414 several ways. An absolute move to a new restriction diameter may be entered directly. For example, a patient 1408 currently at 2.00 cm diameter may need to be adjusted to 1.80 cm diameter. The physician simply enters the new diameter and presses a 'GO' button. The physician may prefer a relative (incremental) move from the current diameter. Each press of a button will cause the device to open or close a fixed amount, say 0.20 cm of restriction diameter, or 0.02 cm. Finally, there may be provided open and close buttons which open/close the restriction device 1414 as long as the button is held.

Once the external device 1406 is commanded to move, the PLC 1418 slowly ramps up the speed of the gear motor 1416 while monitoring the motor current (torque). A known minimum drive torque must be present for verification that the magnetic coupling to the restriction device is locked and not slipping. The minimum torque value can be a curve that is stored in the PLC 1418 that is based on the current restriction device 1414 diameter, the direction of movement (opening/closing), even the model number or serial number of the restriction device.

Also, if a sudden torque reversal is detected by the PLC 1418, a slip has occurred. As the like magnet poles (North-North & South-South) which are repelling slip past each other, they are attracted to the adjacent opposite poles (North-South & South-North). This causes a momentary reversal of drive torque. This torque reversal can be detected by the PLC 1418. If a slip occurs, the PLC 1418 can subtract the appropriate amount from the move. If too many consecutive slips occur, the PLC 1418 can stop and display a message.

As the drive magnet 1410 rotates, revolutions and fractions of revolutions are counted by the PLC 1418 and converted to changes in the restriction. Once the move is complete, the PLC 1418 stops the gear motor 1416 and applies the brake 1430.

The feedback mechanism mentioned in the prior paragraphs is applicable to the external device 472 of FIG. 46, and any other type of magnetic drive, for example an external device that drives the implantable interface using a rotating turret containing electromagnets (instead of the permanent magnets presented previously).

Any of the compatible configurations of a) restriction device, b) drive transmission c) implantable interface and d) external device are conceived to be combinable as alternative embodiments to those presented. In addition, the compression of the restriction device can be achieved by any of the designs and methods by using a rotating drive shaft, or by a tension/compression member. In other words, rotation can be done only to proximal assemblies or assemblies within the implantable interface, which then, through gearing, cause longitudinal shortening or lengthening of a wire or cable, which pulls tension on a belt or rod to cause the restriction device to compress or expand (decrease or increase in inner diameter).

Figure 52:
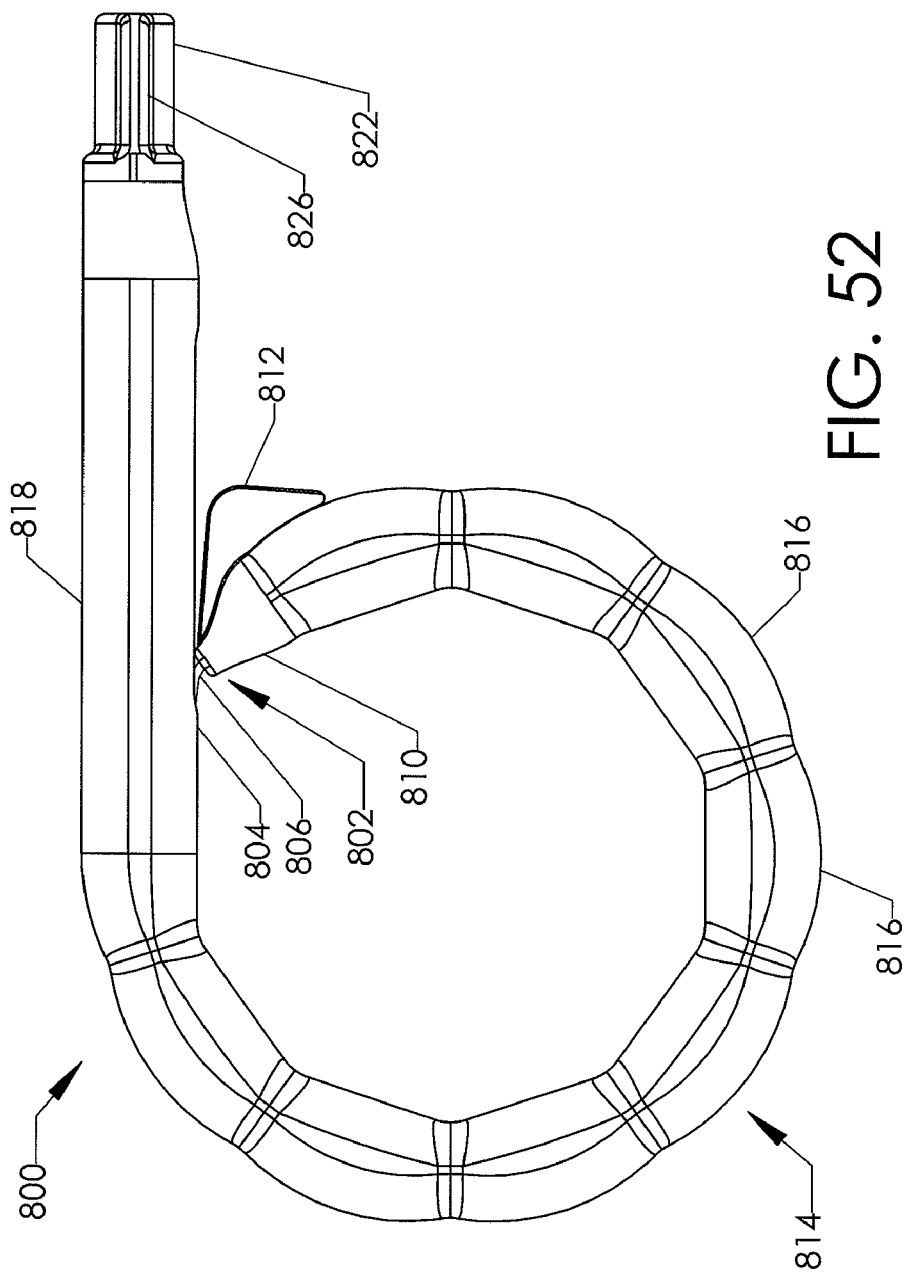
FIG. 52 illustrates a plan view of an alternative embodiment of a gastric restriction device.
Figure 53:
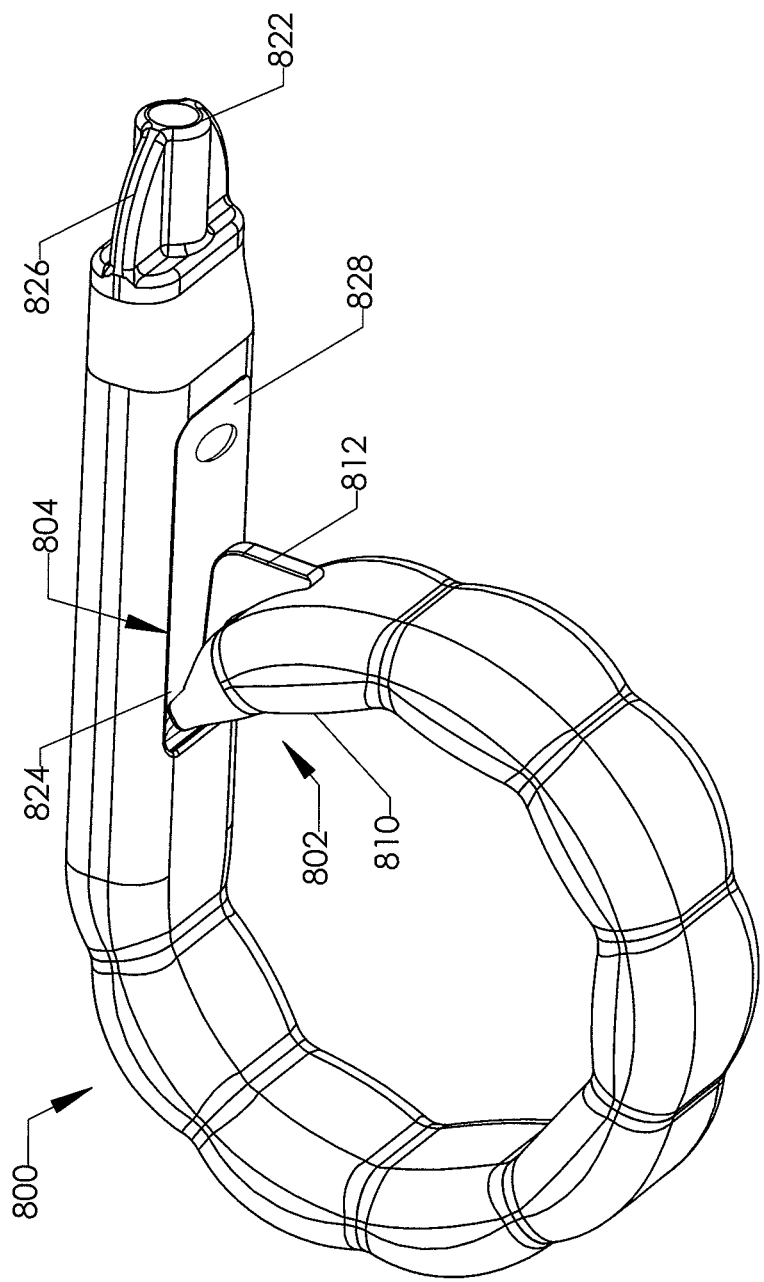
FIG. 53 illustrates a perspective view of an alternative embodiment of a gastric restriction device illustrated in FIG. 52.
Figure 54:
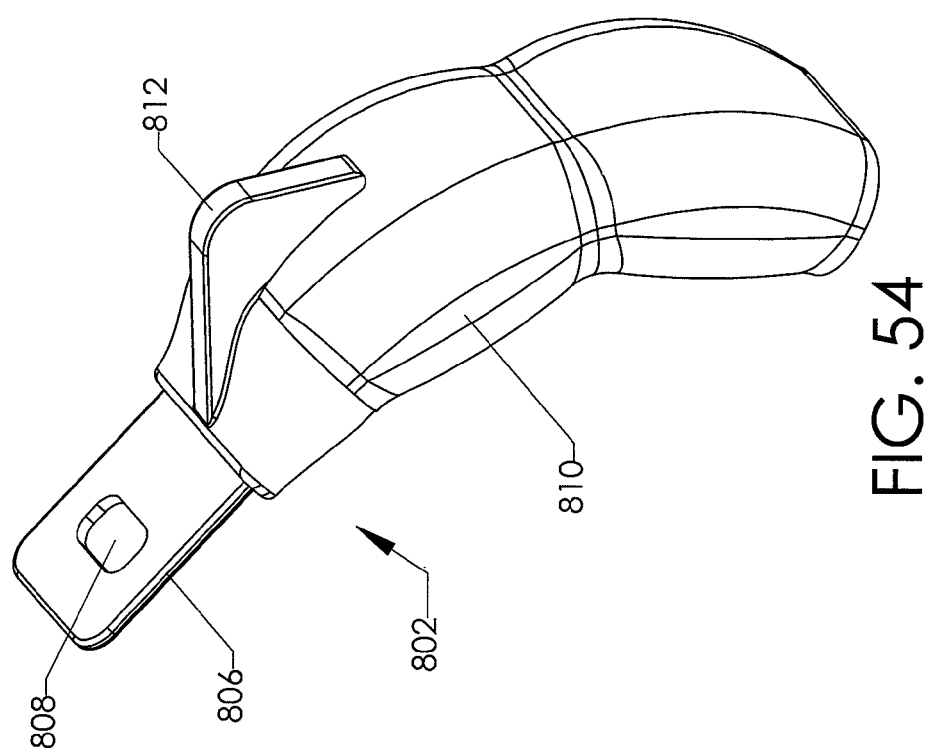
FIG. 54 illustrates a perspective view of one end of an unlatched gastric restriction device.

FIGS. 52, 53, and 54 illustrate an alternative embodiment of a restriction device 800 having a first attachment portion 802 and a second attachment portion 804. First attachment portion 802 comprises a tab 806 having an indentation 808 and a molded end piece 810 having a end grasping fin 812. The restriction device 800 also comprises a constrictable section 814 made up of deformable segments. The restriction device 800 also comprises a drive extension 818 which houses the actuating mechanism 820, seen in FIGS. 56-58. In FIGS. 52 and 53, the drive transmission is not shown, but extends from end 822 of drive extension 818. End 822 of drive extension 818 comprises drive grasping fins 826. Second attachment portion 804 comprises latching mechanism 824, which is described in more detail in FIGS. 58-62.

A grasper is placed through the tunnel made in the pars flaccida approach and the first attachment portion 802 is grasped by tab 806, as the first attachment portion 802 of the restriction device 800 is pulled through the tunnel. Alternatively, the laparoscopic grasper pulls by grasping the end grasping fin 812. Alternatively, the laparoscopic grasper pulls by grasping the entire thickness of the restriction device 800 at the first attachment portion 802. Once the restriction device 800 is straddling the tunnel, the first attachment portion 802 is grasped on the end grasping fin 812 by the grasper (or on the entire thickness of the restriction device 800), and the restriction device 800 is stabilized, for example by grasping the drive extension 818 by a second grasper. In this procedure, each of the laparoscopic graspers may be placed through its own 5 mm trocar. The tab 806 is then inserted into the latching mechanism 824 of the second attachment portion 804, and the first attachment portion 802 and the second attachment portion 804 are latched together. In addition, the process can be reversed in a similar manner to unlatch.

Figure 55:
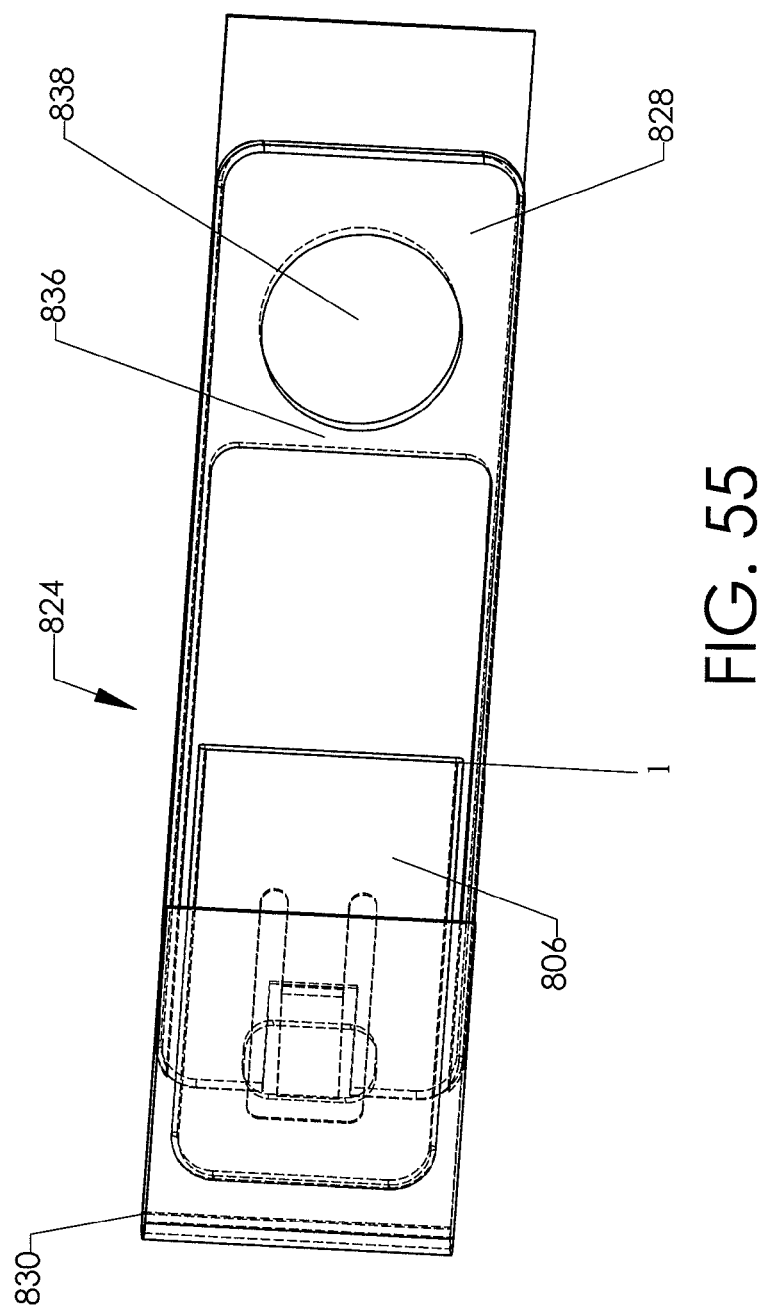
FIG. 55 illustrates a detailed perspective view of a latching mechanism used for a gastric restriction device according to one embodiment.

The latching and unlatching procedure is described in reference to FIG. 55 as well as FIGS. 58-62. In order to clearly show the latching mechanism 824, the molded end piece 810 and the rest of the first attachment portion 802 are not shown, and are visually cut from the tab 806 at line (l). Latching mechanism 824 comprises the tab 806, a slide 828, a retention member 830 and a spring lock 832. To latch the first attachment portion 802 to the second attachment portion 804, the tab 806 is inserted into the retention member 830 until the indentation 808 slides over the spring lock 832. FIG. 55 shows the first attachment portion 802 and the second attachment portion 804 latched together in this manner.

Figure 58:
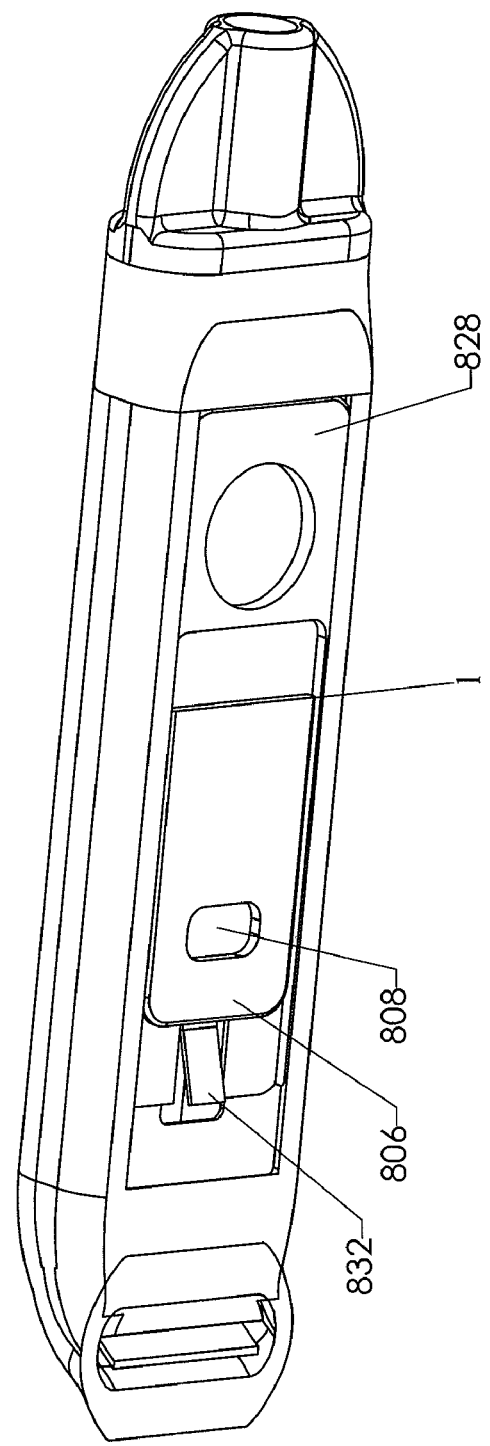
FIG. 58 illustrates a perspective view of a latching mechanism for the gastric restriction device according to one embodiment.
Figure 59:
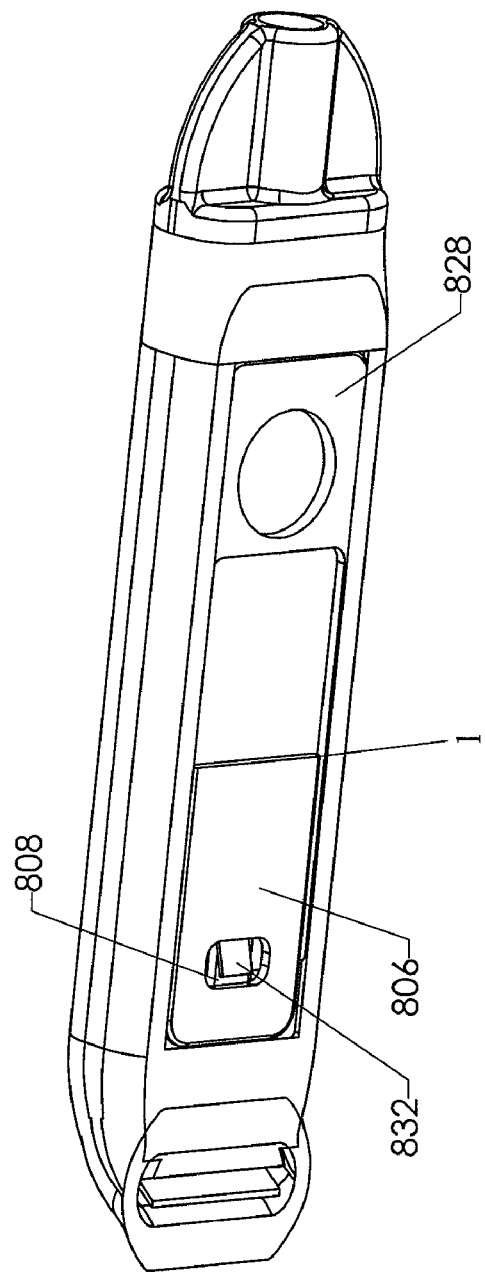
FIG. 59 illustrates another perspective view of the latching mechanism of FIG. 58.
Figure 60:
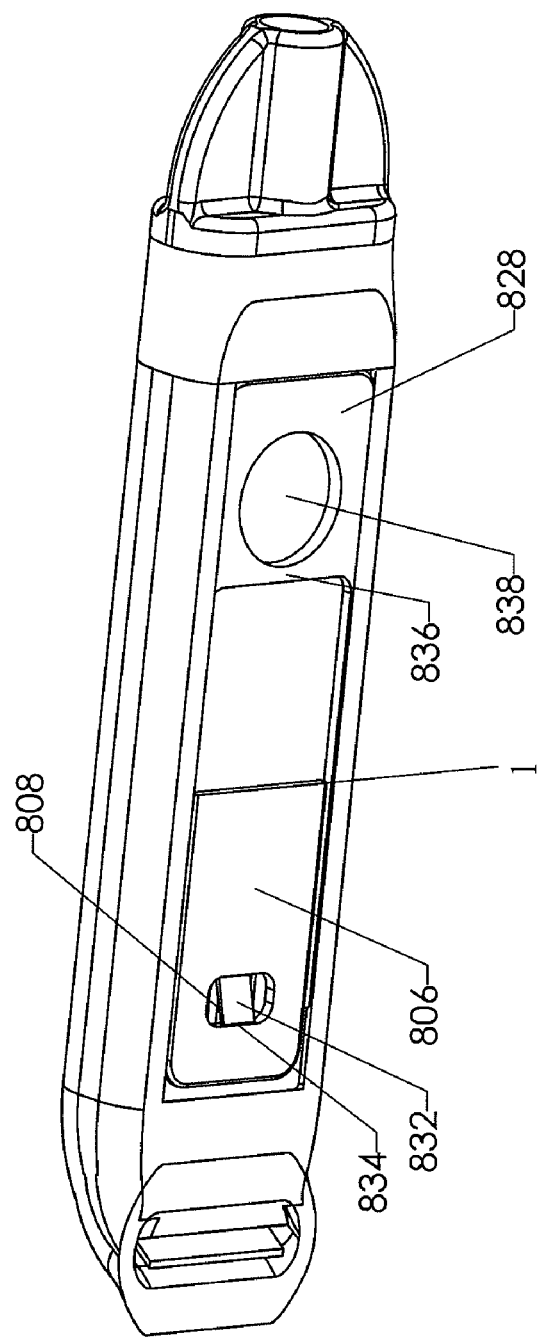
FIG. 60 illustrates another perspective view of the latching mechanism of FIG. 58.
Figure 61:
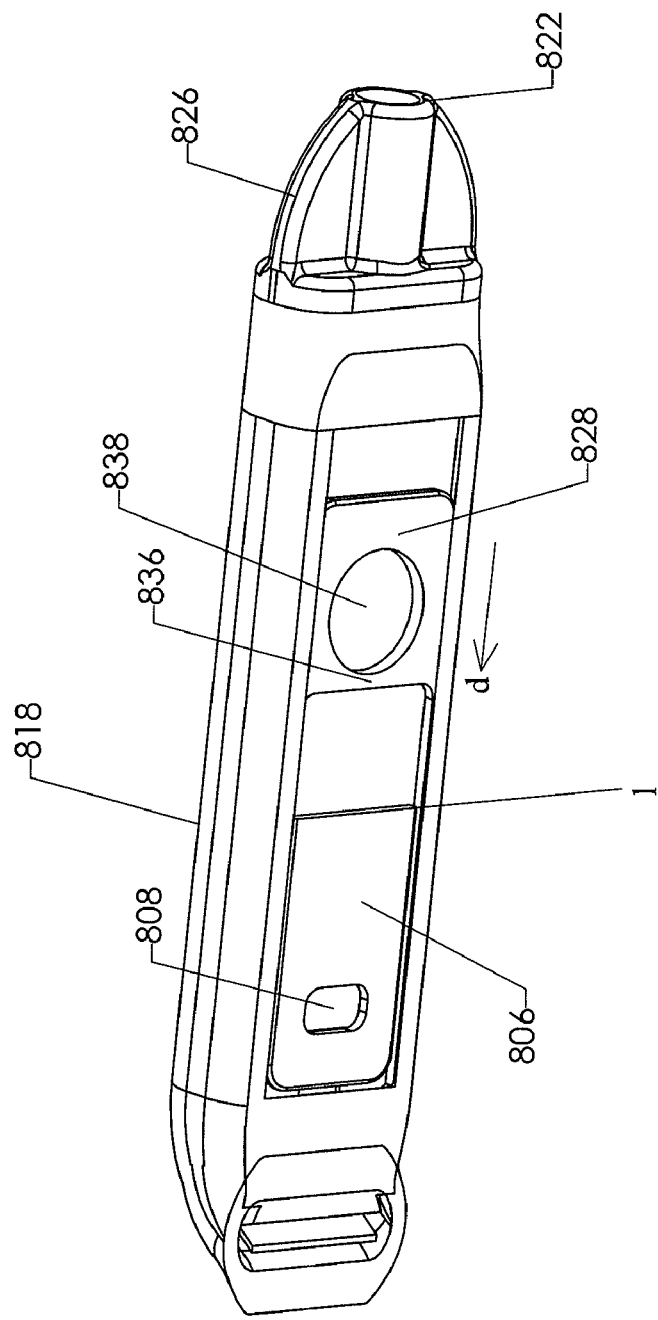
FIG. 61 illustrates another perspective view of the latching mechanism of FIG. 58.
Figure 62:
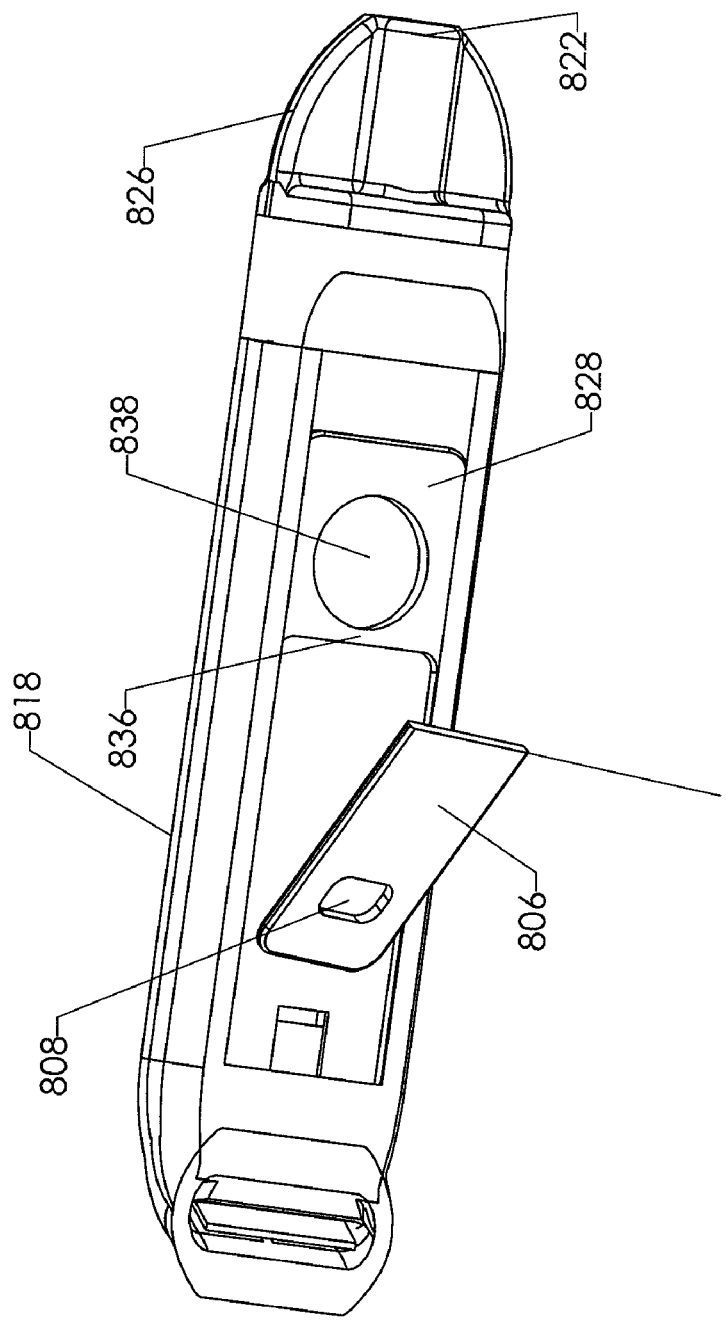
FIG. 62 illustrates another perspective view of the latching mechanism of FIG. 58.

FIGS. 58-62 illustrate the various steps of latching and unlatching, and are shown with the retention member 830 removed, for purposes of clarity. FIG. 58 shows the tab 806 as it is being inserted. FIG. 59 shows the tab 806 after it has been slid past the spring lock 832. The spring lock 832 is angled so that it easily flexes while the tab 806 is slid by it during latching. However, the spring lock 832 will not allow the tab 806 to be unlatched as shown in FIG. 60. The extreme edge of the spring lock 832 catches the edge inside the indentation 808 of the tab 806 at retention point 834. Retention member 830 (not shown in FIG. 56) assures that the tab 806 is forced against the spring lock 832. In order to unlatch, the slide 828 is grasped at wall 836 between depression 838 and the rest of slide 828, and is forced in direction (d), as shown in FIG. 61. Or the tip of a grasper or other surgical tool can be placed into the depression 838 to move the slide 828. This causes slide 828 to move over spring lock 832, forcing it down and covering it. This also releases the spring lock 832, from its locking arrangement with the tab 806. Tab 806 is now free and the first attachment portion 802 is unlatched from second attachment portion 804. Instead of a depression 838, alternatively, the slide 828 may have a fin or gripping surface.

Figure 56:
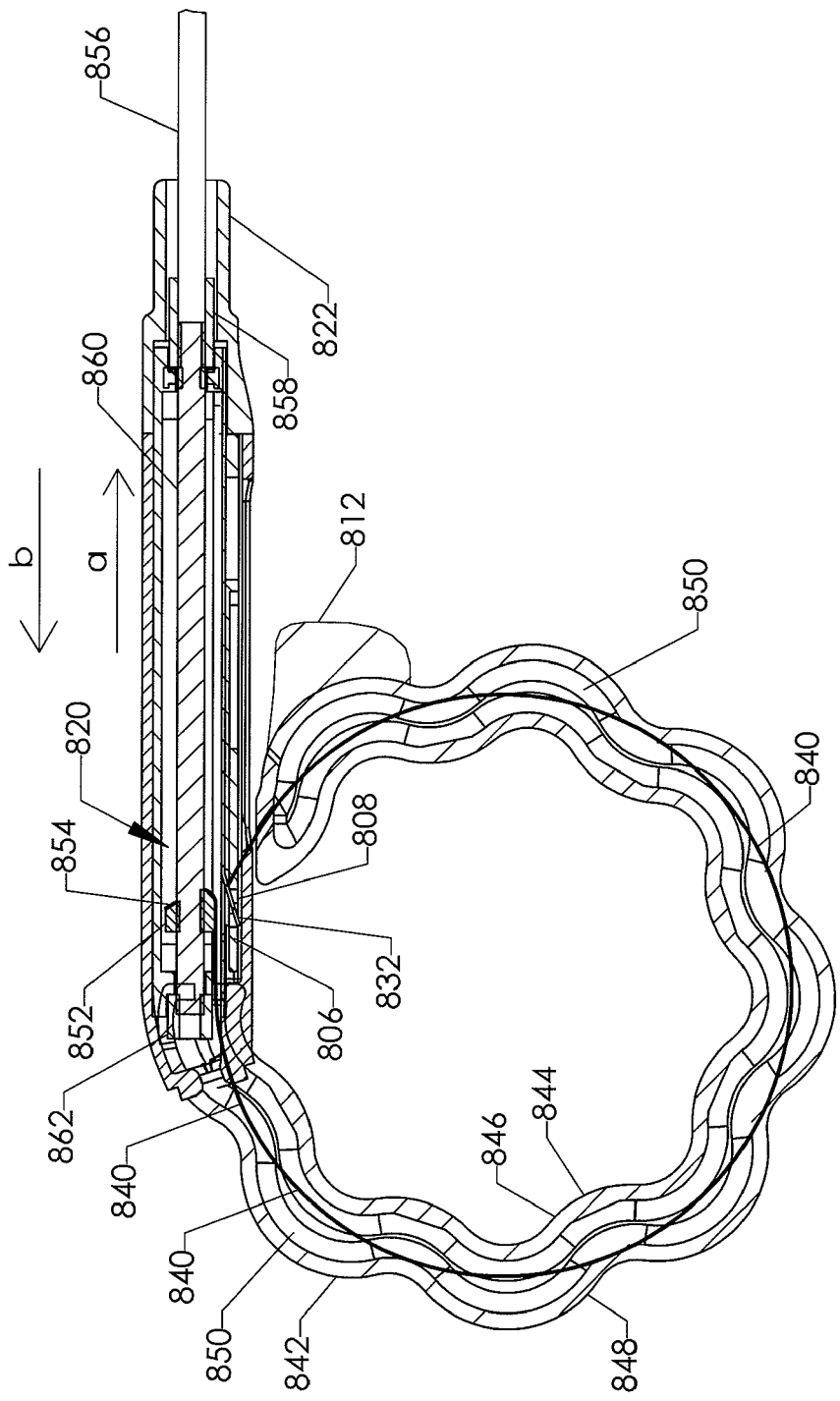
FIG. 56 illustrates a cross-sectional view of a gastric restriction device according to one embodiment.
Figure 57:
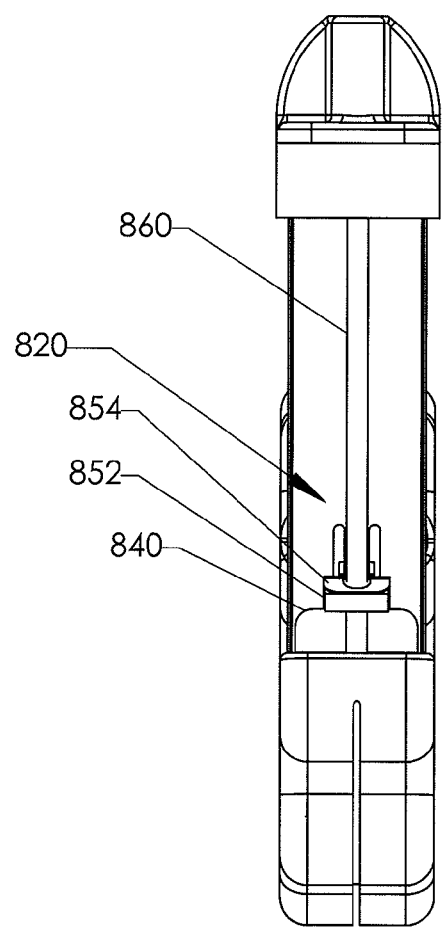
FIG. 57 illustrates a gastric restriction device with a portion removed to show detail of the actuating elements.

The actuation of the restriction device 800 is shown in sectional view in FIG. 56 and in FIG. 57 (with drive extension 818 removed for clarity). Restriction device 800 comprises a housing 842 having an outer wall 848, an inner surface 844 and an inner wall 846. A belt 840 resides within an internal cavity 850. The belt 840 may include the tab 806 at the first attachment portion 802, or the tab 806 may be a separate entity. The belt 840 is coupled to a nut 852, for example, by means of a curved retaining portion 854 at the extreme end of the belt 840. Rotation of drive shaft 856 turns coupling 858 which then turns screw 860. Screw 860 can be made from a number of materials, including stainless steel, titanium, NITINOL, nylon or other metallic or polymeric materials. An exemplary size for the screw is 0-80 UNF, though the screw 860 may be larger or smaller. The nut 852 has a matching female thread and is preferably a different material than the screw 860, to reduce static or dynamic friction. For example, nut 852 is made from bronze, acetal (Delrin), nylon, PEEK, stainless steel or other metallic or polymeric materials.

As the screw 860 turns, the nut 852 moves axially. For example, when the drive shaft 856 is turned clockwise (for example via magnetic coupling between an external device and an implantable interface), the nut 852 moves in direction (a), as shown in FIG. 56. This tightens the belt 840, and thus constricts the restriction device 800. A counter-clockwise rotation of the drive shaft 856, causes the nut to move in direction (b), thus loosening the belt 840, and lessening the constriction of the restriction device 800. The screw 860 is held in tension by coupling 858 and bearing 862. Bearing 862 may be, for example, a ball bearing constructed of ceramic, glass or sapphire. The use of the fine threaded screw 860 and nut 852 assembly to controllably apply the tension on the belt 840 greatly reduces the amount of torque required to turn the drive shaft 856, and thus, in a magnetically driven system, minimizes the required size of the implanted magnet.

As in the ball bearing constructed of ceramic, glass, or sapphire, the other elements of the actuating mechanism 820 can be made of MRI safe materials, such as many of those mentioned. This eliminates the possibility of movement of the restriction device 800 in the patient during an MRI scan, or heating of the restriction device 800, or interference or artifact on the image being created in a body area near the restriction device 800. The belt 840 may be made of metallic materials or polymeric materials. For example, PET with a thickness of 0.005" to 0.015". NITINOL, with a thickness of 0.003" to 0.007". Nylon, with a thickness of 0.010" to 0.20". PVC, with a thickness of 0.012" to 0.24". The belt 840 may also be made of stainless steel. Returning now to FIG. 52 and FIG. 53, the multiple deformable segments 816 allow for a controlled constriction of the interior of the restriction device 800 as the device is constricted.

Figure 63:
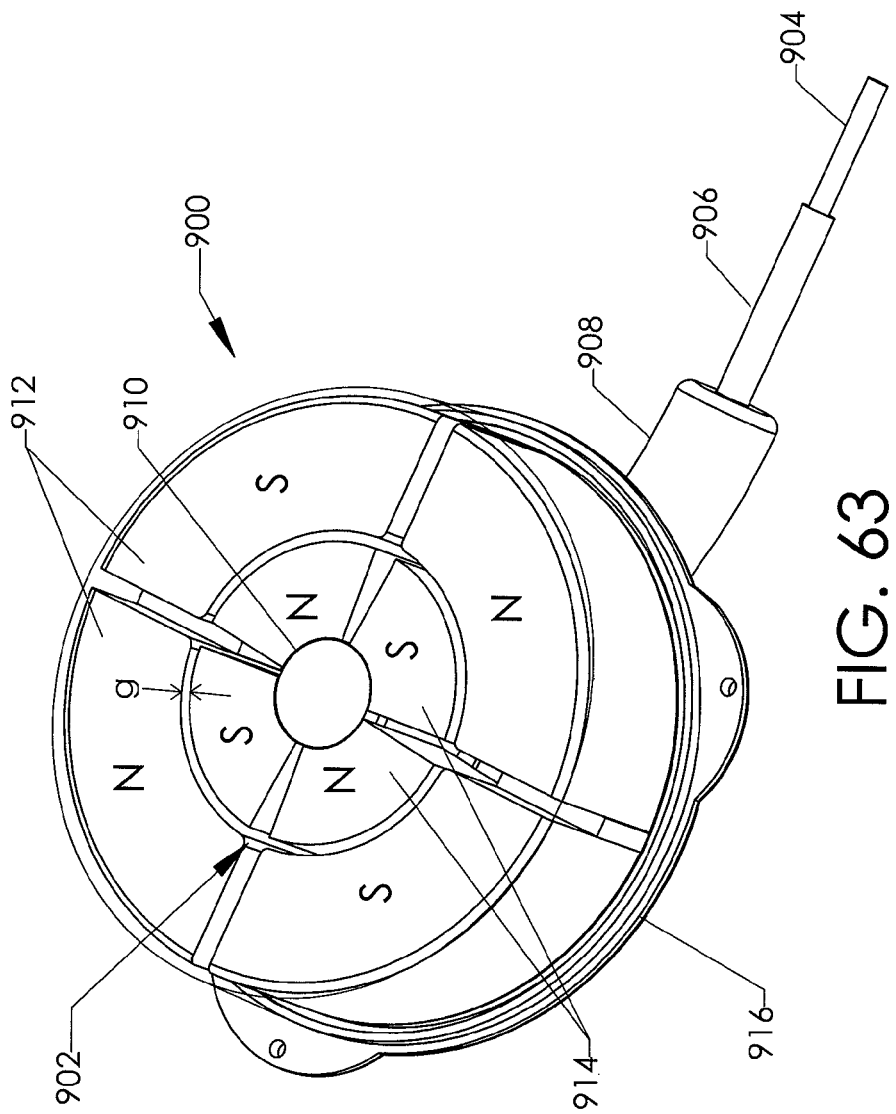
FIG. 63 illustrates a magnetic slip clutch for use with an implantable interface according to one embodiment.

FIG. 63 illustrates a magnetic slip clutch 902 for use with an implantable interface 900. Drive shaft 904 is coupled to hub 910. Four clutch magnets 914 are coupled to hub 910 so that hub 910, clutch magnets 914, and drive shaft 904 rotate in unison. Sheath 906 and flexible strain relief 908 are non-rotationally coupled to housing 916 of implantable interface 900. Driven magnets 912 rotate together based on magnetic coupling between the drive magnets or electromagnets of an external device. The only coupling between the driven magnets 912 and the drive shaft 904 is via the magnetic coupling of each individual clutch magnet 914 to each individual driven magnet 912. Gap (g) is chosen so that at a maximum desired torque, the torque overcomes the magnetic attraction and the driven magnets 912 slip in relation to the clutch magnets. Slippage protects against over-torqueing, which could cause failure of the components of the device. For example the drive shaft 904.

Figure 64:
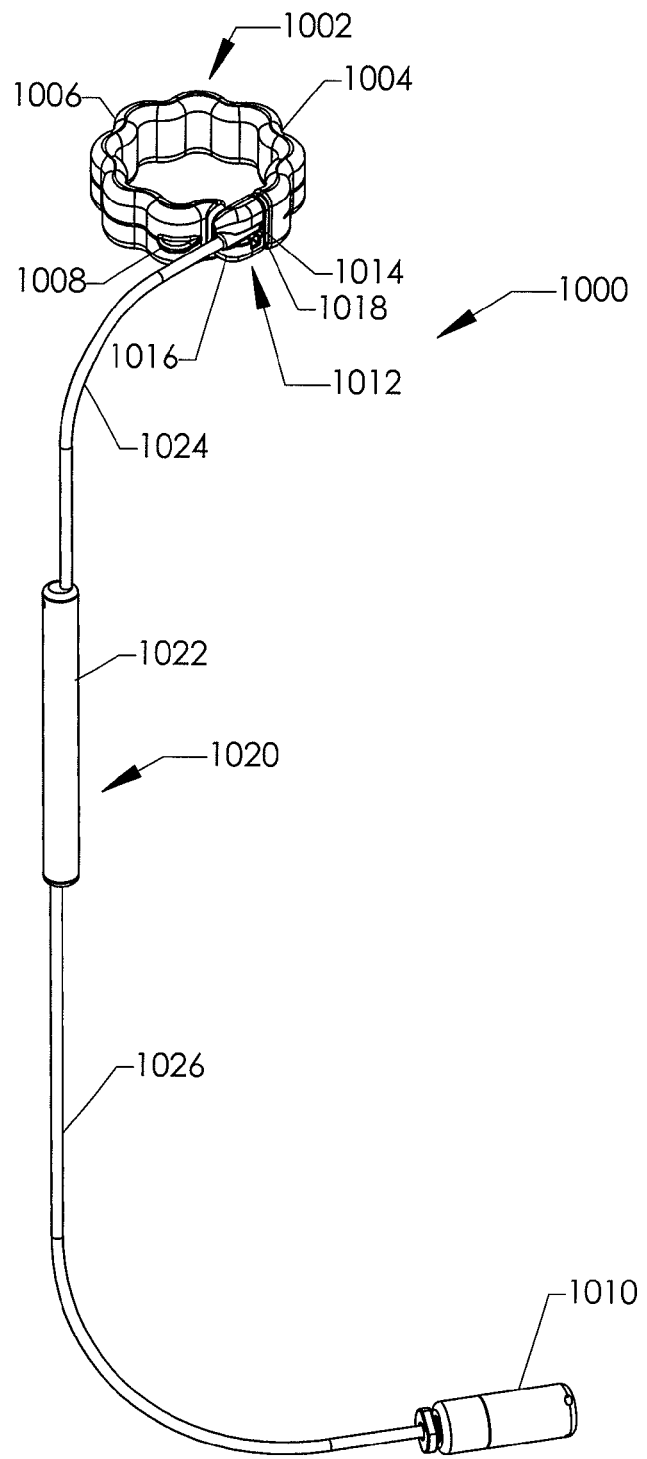
FIG. 64 illustrates a perspective view of an implantable obesity control system according to another embodiment.

FIG. 64 illustrates an implantable obesity control system 1000 according to another embodiment of the invention. The implantable obesity control system 1000 includes a restriction device 1002, an implantable interface 1010, and a drive transmission 1020. The restriction device 1002 includes an adjustable body portion 1004 that changes the size and/or shape in response to the driving action of the implantable interface 1010 and coupled drive transmission 1020 (explained in detail below). The adjustable body portion 1004 may include a flexible jacket 1006 that is shaped in an undulating or wavy-shape as illustrated in FIG. 64. The flexible jacket 1006 may be formed from a biocompatible polymer such as, for instance, polyurethane silicone or a silicone-urethane copolymer, such as ELAST-EON. An optional tab 1008 or the like may be secured to an exterior portion of the flexible jacket 1006 and used to hold or manipulate the restriction device 1002 during, for instance, placement and/or adjustment of the restriction device 1002.

Still referring to FIG. 64, the restriction device 1002 includes a connector 1012 that is used to secure the flexible jacket 1006 in the circular or looped configuration as illustrated in FIG. 64. The connector 1012 includes a proximal portion 1014 that links the flexible jacket 1006 to the proximal aspects of the system 1000. As used herein, the proximal direction refers to a direction or location that is disposed toward or closer to the implantable interface 1010. Conversely, the distal direction refers to a direction or location that is disposed away from the implantable interface 1010. The connector 1012 further includes a distal portion 1016 secured to a distal end of the flexible jacket 1006 that is configured to engage with the proximal portion 1014 of the connector 1012. In one aspect, the distal portion 1016 of the connector 1012 includes a groove or recess 1018 that is dimensioned to receive the proximal portion 1014 of the connector 1012. Preferably, the proximal portion 1014 can be locked or fixedly secured with respect to the distal portion 1016 through the use of one or more tabs, detents, locking members and the like (described in more detail below). In one aspect, as described in more detail below, the proximal portion 1014 and the distal portion 1016 of the connector 1012 may be unlocked to thereby open the flexible jacket 1006 from the circular or looped configuration as illustrated in FIG. 64

Still referring to FIG. 64, the system 1000 includes a drive transmission 1020 that, in one aspect of the invention, is used to translate rotational movement of a magnetic element (not shown in FIG. 64) contained in an implantable interface 1010 into linear movement of an actuator (not shown in FIG. 64) that adjusts the dimensions or configuration of an internal opening formed in the restriction device 1002. FIG. 64 illustrates a housing portion 1022 that includes an interior aspect that contains the mechanical transmission elements for effectuating the translation of rotational movement into linear movement. The housing portion 1022 is connected to an distal sheath or cover 1024. The sheath 1024 includes a lumen therein (not seen in FIG. 64) for holding the linear driven actuator that is used to alter the dimensions and shape of the internal opening formed in the restriction device 1002. The sheath 1024 may be formed from a spiral-wound wire (e.g., NITINOL) that is coated or covered on the exterior with a polymer tube or flexible coating (e.g., polyurethane). The interior may also be optionally coated with a lubricious polymer coating (e.g., PTFE) to reduce frictional engagement with the moving components of the drive transmission 1020. As seen in FIG. 64, a proximally located sheath or cover 1026 couples the housing portion 1022 to the implantable interface 1010. The proximally located sheath 1026 also includes a lumen therein configured for receiving a rotational drive member such as drive cable or the like. The proximally located sheath 1026 may be made of the same construction as described above with respect to the distal sheath 1024. Preferably, the proximal and distal sheaths/covers 1026, 1024 substantially prevent bodily fluids or the like from entering the housing portion 1022, implantable interface 1010, and the mechanical transmission elements contained in the sheaths/covers 1024, 1026.

Figure 65:
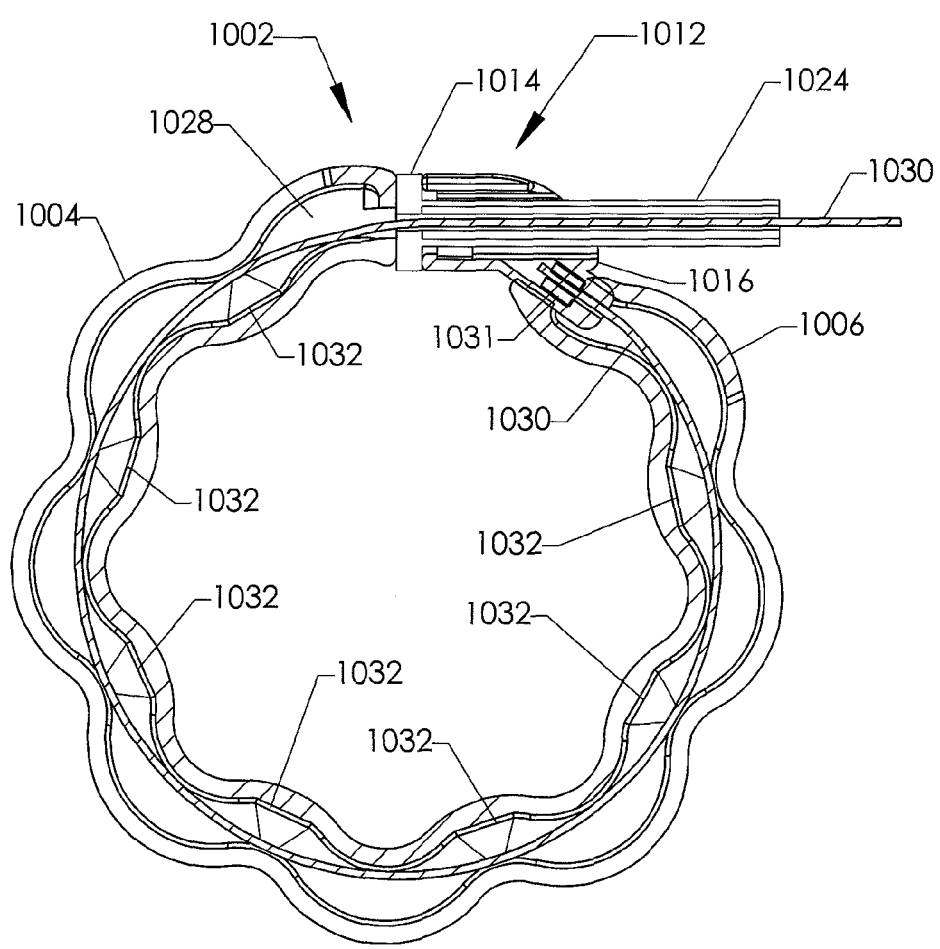
FIG. 65 illustrates a cross-sectional view of the distal end portion of the obesity control system illustrated in FIG. 64.

FIG. 65 illustrates a cross-sectional view of the restriction device 1002. As seen in FIG. 65, the flexible jacket 1006 contains an inner lumen or recess 1028. An actuating member 1030 is located within this lumen or recess 1028 and is fixedly secured at one end to the distal portion 1016 of the connector 1012. The actuating member 1030 may include a filament, wire, tape, or other elongate structure. For example, in one aspect of the invention, the actuating member 1030 may include NITINOL wire having an outer diameter of around 0.0012 inches. The actuating member 1030 may be secured to the distal portion 1016 of the connector 1012 using an adhesive, crimp or friction fit, weld, or anchor. For example, in FIG. 65, a stainless steel lug 1031 is bonded to the distal end of the NITINOL actuating member which is used to anchor the distal end of the actuating member in place.

Still referring to FIG. 65, a series of ribs 1032 are located within the jacket recess 1028. The ribs 1032 are preferably spaced periodically about the recess 1028 with substantially constant spacing between at least some of the ribs 1032. In addition, the location of the ribs 1032 are located in the radially inward portions of the undulating or wavy flexible jacket 1006. The ribs 1032 advantageously assist the adjustable body 1004 to change its shape in a substantially uniform manner without any kinking or buckling of the material forming the flexible jacket 1006. As seen in FIG. 65, the actuating member 1030 passes over an outer portion of each rib 1032. Optionally, a groove, hole, or the like located in each rib 1032 (not shown) may be used to properly orient and maintain contact between the actuating member 1030 and each rib 1032. As partially seen in FIG. 65, the actuating member 1030 is secured at one end to the distal portion 1016 of the connector 1012. The actuating member 1030 then passes through the flexible jacket 1006 and out the proximal portion 1014 of the connector 1012. The actuating member 1030 continues onward in the proximal direction until it reaches the housing 1022 (shown in FIG. 64). Alternatively, the actuating member 1030 may be serially attached to an extension spring or analogous mechanism, that allows the constriction of the restriction device 1002 to open a limited amount during an acute event, such as violent vomiting, thus serving as a safety feature to protect the tissue of the patient's stomach or esophagus. For example, the actuating member 1030 may be attached at one of its two ends via a spring whose spring constant is chosen to coincide with the pressure seen during significantly violent vomiting, for example greater than 200 mm Hg. Because this pressure is higher than the upper pressure commonly seen in normal gastrointestinal tract mechanics (120 mm Hg), a mechanism of this nature will not inadvertently allow patients to easily gorge on food. The length of the spring can be chosen to correspond to the total amount of diametrical relief that is desired during an acute violent vomiting event.

Figure 66:
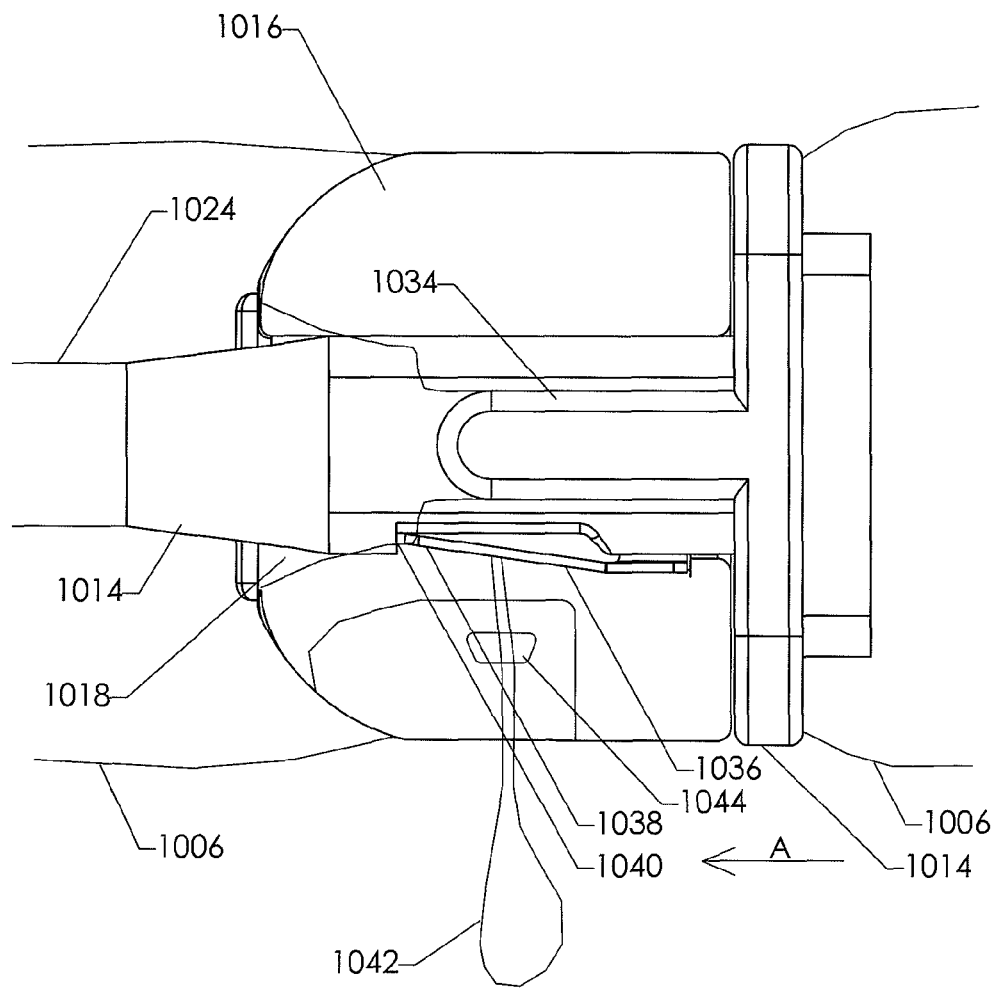
FIG. 66 is a plan view illustrating a connector used to connect or couple two ends or portions of a restriction device according to one embodiment.

FIG. 66 illustrates a top down view of the connector 1012 with the proximal portion 1014 of the connector 1012 being in a locked configuration with respect to the distal portion 1016 of the connector 1012. As seen in FIG. 66, the distal portion 1016 of the connector 1012 includes a recess 1018 dimensioned to receive the proximal portion 1014 of the connector 1012. The recess 1018 and/or proximal portion 1014 may be configured in a keyed arrangement such that the proximal connector portion 1014 may only be inserted into the distal portion 1016 of the connector 1012 in a correct orientation. FIG. 66, for example, illustrates a keyed portion 1034 in the form of a raised surface that enables the correct orientation between the distal and proximal connector portions 1014, 1016.

Still referring to FIG. 66, the distal connector portion 1016 includes a biased locking member 1036 that is affixed at one end to a surface of the recess 1018 of the distal connector portion 1016. The biased locking member 1036 includes a free end 1038 that is used as a locking surface to retain the proximal and distal connector portions 1014, 1016 in a locked configuration. The biased locking member 1036 may be made of a material (e.g., biocompatible polymer, metal, etc.) that naturally is biased to position the free end 1038 away from the surface of the recess 1018. In order to achieve the locking arrangement, the proximal connector portion 1014 includes an indent or groove that has an engagement surface 1040 that contacts the biased free end 1038 of the locking member 1036. For example, if the distal connector portion 1016 were moved in the direction of arrow A, the free end 1038 of the biased locking member 1036 would contact the engagement surface 1040 and thus prevent the unlocking of the proximal and distal connectors 1014, 1016.

Still referring to FIG. 66, a filament 1042 is secured to the biased locking member and terminates outside the connector 1012 via a passageway 1044 located in the distal connector portion 1016. The passageway 1044 may include a hole or groove through which the filament 1042 can pass. The filament 1042 may be made from, for example, suture filament or other biocompatible material. The filament 1042 may be looped as is shown in FIG. 66 or it may be have one or more strands. An exemplary material for the filament 1042 is monofilament polypropylene.

In one aspect, the filament 1042 may be made sufficiently long to pass along all or a portion of the length of the restriction device 1002, 1102 to terminate at or near the implantable interface 1010, 1104. For example, a separate lumen (not shown) may be used to hold the filament 1042 along the length of the restriction device 1002, 1102 and terminate at a location that is subcutaneous. If there is an emergency situation, the restriction device 1002, 1102 can be detached from the gastrointestinal tract (e.g., stomach) without completely removing the device 1002, 1102 which can be done at a later time if need be. In this aspect of the invention, with a simple incision, the end of the filament 1042 is exposed and can be pulled proximally so as to detach the restriction device 1002, 1102 from the site of interest. One the emergency situation ends, the incision is closed with suture, and a determination can be made later whether the entire device 1002, 1102 needs to be removed via surgery, or if it can later be salvaged and laparoscopically reattached.

Figure 67:
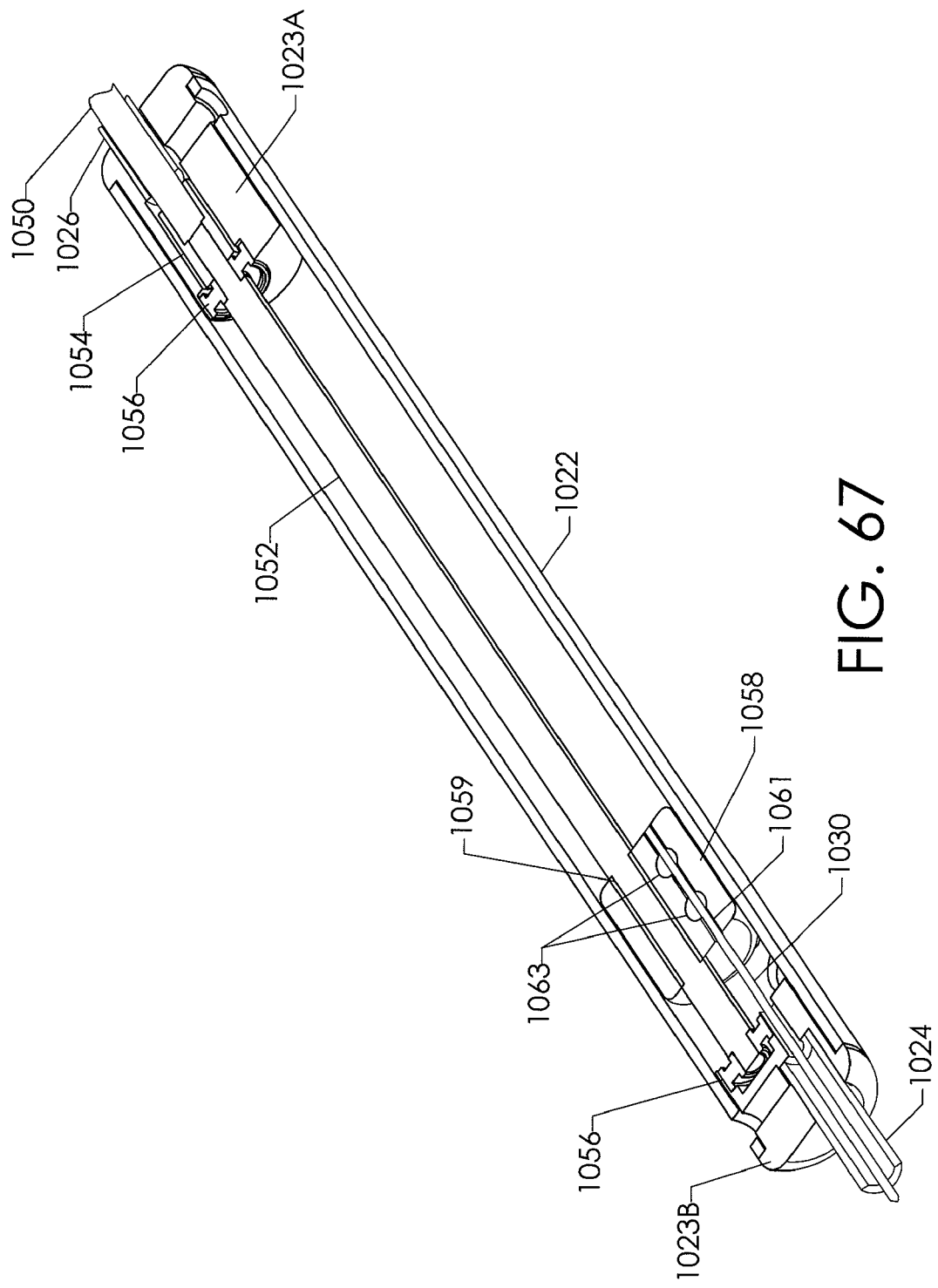
FIG. 67 illustrates a perspective cross-sectional view of the housing portion of the drive transmission and proximal/distal covers encapsulating or sealing the same according to one embodiment.

FIG. 67 illustrates a perspective cross-sectional view of the housing portion 1022 and proximal/distal covers 1026, 1024. The housing portion 1022 includes end caps 1023A, 1023B that seal the internal portions of the housing from the external environment. As seen in FIG. 67, a drive cable 1050 is located within the central lumen of the proximal sheath 1026. The drive cable 1050 may be formed from, for example, the drive shaft 190 of FIG. 26 for improved torque response and kink resistance. For instance, NITINOL wire wound in a manner described in relation with FIG. 26, with the drive cable 1050 having an outer diameter of around 0.0057 inches may be used. Of course, other metallic wires such as stainless steel or ELGILOY may also be used. Still referring to FIG. 67, the drive cable 1050 is secured to a lead screw 1052 located in the housing portion 1022. The drive cable 1050 may be secured to the lead screw 1052 using coupler 1054 which may include a section of tubing having different ID for insertion of the lead screw 1052 and drive cable 1050. The section of tubing 1054 may be crimped or welded to the drive cable 1050 and lead screw 1052 to fixedly secure the drive cable 1050 and lead screw 1052 to one another.

Still referring to FIG. 67, the lead screw 1052 is rotationally held within the housing 1022 via two ball bearings 1056 mounted on opposing ends of the housing 1022. In this regard, the lead screw 1052 is rotational about the long axis of the housing 1022. Rotation of the drive cable 1050 thus results in rotation of the lead screw 1052. The lead screw 1052 may be formed from a 300 series stainless steel 0-80 (or 2-120) lead screw. A nut 1058 is rotationally mounted on the lead screw 1052 and is used to translate rotational movement into linear movement. The nut 1058 may be made from, for example, brass and include an offset threaded hole 1059 for receiving the lead screw 1052. Rotation of the lead screw 1052 about its rotation axis thus causes the nut 1058 to move axially within the housing 1022. The nut 1058 is bonded or otherwise affixed to the actuating member 1030. When the actuating member 1030 is NITINOL wire, the end of the NITINOL wire may pass through a hole or aperture 1061 formed in the nut 1058. A plurality (e.g. four) of set screws (not shown) may be threaded into holes or apertures 1063 to mechanically bind the actuating member 1030 to the nut 1058.

FIG. 68 illustrates a cross-sectional view of the implantable interface 1010 according to another aspect of the invention. The implantable interface 1010 includes a housing 1062 in which is mounted a permanent magnet 1064. The permanent magnet 1064 may be formed from, for example, a rare earth magnet such as Neodymium-Iron-Boron (NdFeB). The permanent magnet 1064 is rod or cylindrically-shaped and is diametrically magnetized (poles are perpendicular the long axis of the permanent magnet 1064). As seen in FIG. 68, aluminum plates or axles 1066 are bonded to either end of the permanent magnet 1064. The axles 1066 are dimensioned to fit within the inner races of ball bearings 1068 which are mounted at opposing ends of the housing 1062. In this regard, the permanent magnet 1064 is rotationally mounted within the housing 1062. The housing 1062 is formed from a non-magnetic material (e.g., plastic, polymer, titanium or aluminum) and is substantially sealed from the external environment so as to prevent bodily fluids and other materials from entering the interior space, for example, with a silicone dip-coating.

Still referring to FIG. 68, the proximal end of the drive cable sheath 1026 (which is omitted from FIG. 68 for sake of clarity) may have a quick disconnect feature so that the drive cable 1050 and/or implantable interface 1010 may be rapidly changed. In one aspect, the proximal end of the drive cable sheath 1026 includes a flanged end portion 1027 that is dimensioned to abut a sheath retaining nut 1046 that engages with mating threads 1048 located at one end of the housing 1062. The flanged end portion 1027 and the retaining nut 1046 are permanently secured to the drive cable sheath 1026. The retaining nut 1046 is preferably rotationally secured and the flanged end portion 1027 is sealingly secured. The flanged end portion 1027 is inserted through a seal 1065 such as a compressible o-ring, which is nested within the housing 1062. The o-ring 1065 substantially seals the interface between drive cable sheath 1026 and the housing 1062 of the implantable interface 1010.

Still referring to FIG. 68, one axle 1066 includes a recess 1070, for example, in the shape of a hexagon or the like (female connector) that receives a correspondingly shaped keyed end 1072 of the drive cable 1050 (male connector) as illustrated in FIG. 69. FIG. 69 illustrates the proximal end of the drive cable 1050 cable including the keyed portion 1072. With reference to FIGS. 68 and 69, the implantable interface 1010 is initially connected to the drive cable 1050 by inserting the keyed portion 1072 into the corresponding recess 1070 located in the axle 1066. The sheath retaining nut 1046 can then be threaded and tightened, allowing the seal 1065 and the flanged end portion 1027 to form a sealed engagement between the drive cable sheath 1026 and the implantable interface 1010. To de-couple the implantable interface 1010 a user unscrews the sheath retaining nut 1046 completely and withdraws the drive cable sheath 1026. In this regard, a new drive cable 1050 and/or implantable interface 1010 may be exchanged or changed as appropriate.

Figure 70:
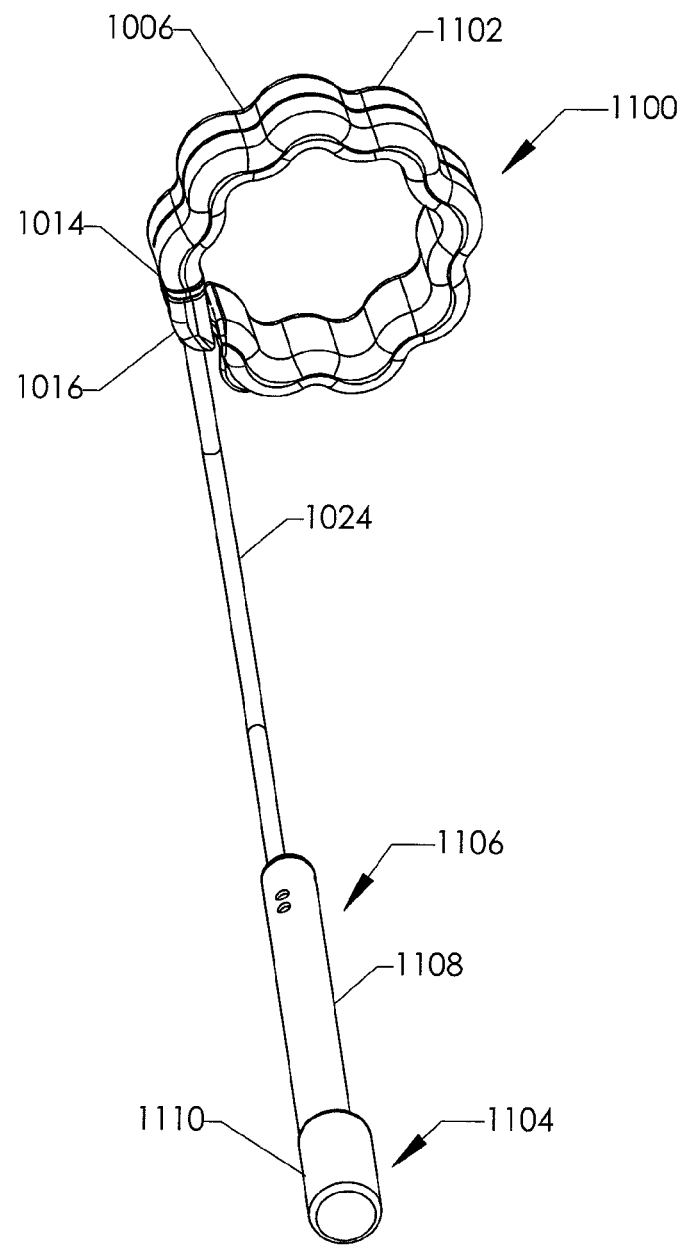
FIG. 70 illustrates a perspective view of an implantable obesity control system according to another embodiment.
Figure 71:
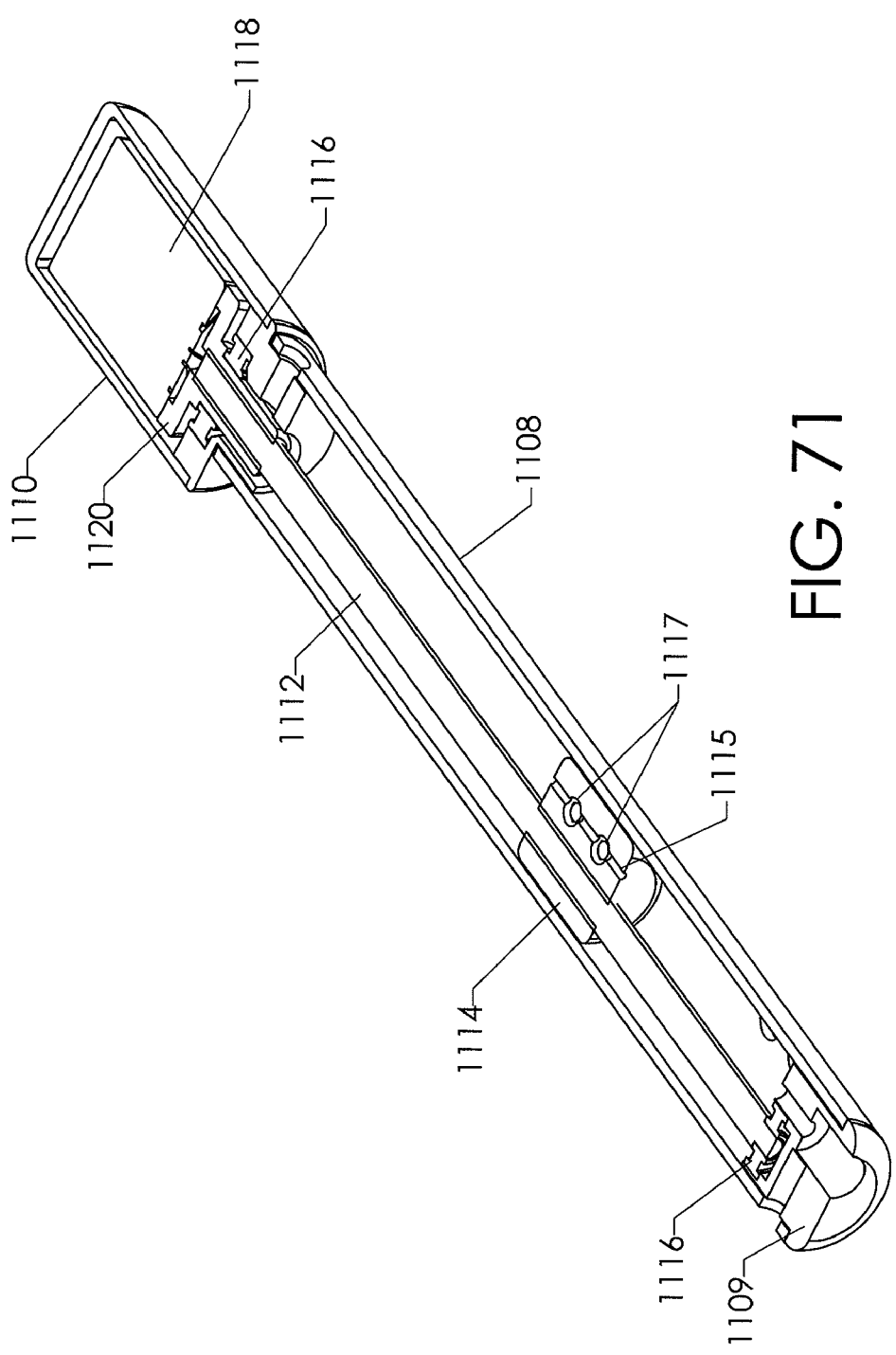
FIG. 71 illustrates a cross-sectional view of a proximal portion of the implantable obesity control system of FIG. 70.

FIG. 70 illustrates an implantable obesity control system 1100 according to another embodiment of the invention and includes a restriction device 1102, an implantable interface 1104, and a drive transmission 1106. The implantable obesity control system 1100 is similar to that illustrated in FIG. 64 with the exception that the drive cable 1050 has been omitted. This embodiment thus uses a direct connection between the lead screw 1112 and the permanent magnet 1118 (as shown in FIG. 71). There is no need for a separate drive cable 1050 or other transmission means between the permanent magnet and the lead screw 1052. This embodiment is advantageous because of the reduced number of components and the small, compact nature of the overall device.

FIG. 71 illustrates a cross-sectional view of the two housings 1108, 1110. Housing 1108 includes lead screw 1112, nut 1114, and ball bearings 1116 and may be sealed at the distal end via end cap 1109. The actuating member (not shown in FIG. 71) described above is secured to the nut 1114 in via a receiving lumen 1115. Set screws (not shown) may be used to mechanically engage the actuating member via a plurality of threaded apertures 1117. The remaining housing 1110 includes the permanent magnet 1118 in addition an aluminum axle or spindle 1120 that is mounted to one end of the magnet 1118. The proximal end of the lead screw 1112 may have a keyed portion (e.g., hexagonal-shaped tip or end) that fits within a correspondingly-shaped recess or the like (not shown) in the axle 1120 so that the implantable interface 1104 may be quickly changed. Alternatively, both housings 1108, 1110 could be replaced to exchange or change-out the implantable interface 1104. It should be noted that only a single bearing 1116 is needed to rotationally secure the magnet 1118 within the housing 1110. The amount of torque on the opposing end of the magnet 1118 is relatively low so there is no need for an additional bearing within the housing 1110.

In configurations in which there is a greater torque (i.e., moment) on the opposing end of the magnet 1118, a second bearing (not shown) can be used. The lead screw 1112 and magnet 1118 are arranged serially in this configuration, but alternatively they could be arranged in parallel, for example, wherein the magnet 1118 imparts rotation to the lead screw 1112 via a pair of spur gears. The parallel arrangement allows for a shorter overall length of the assembly in relation to the serial arrangement, however the serial arrangement allows for a thinner, narrower assembly. The appropriate arrangement can be chosen depending upon the desired clinical factors. For example, if the implantable interface is to be implanted in an area that undergoes a large amount of bending, the shorter, parallel arrangement may be preferred.

Figure 72:
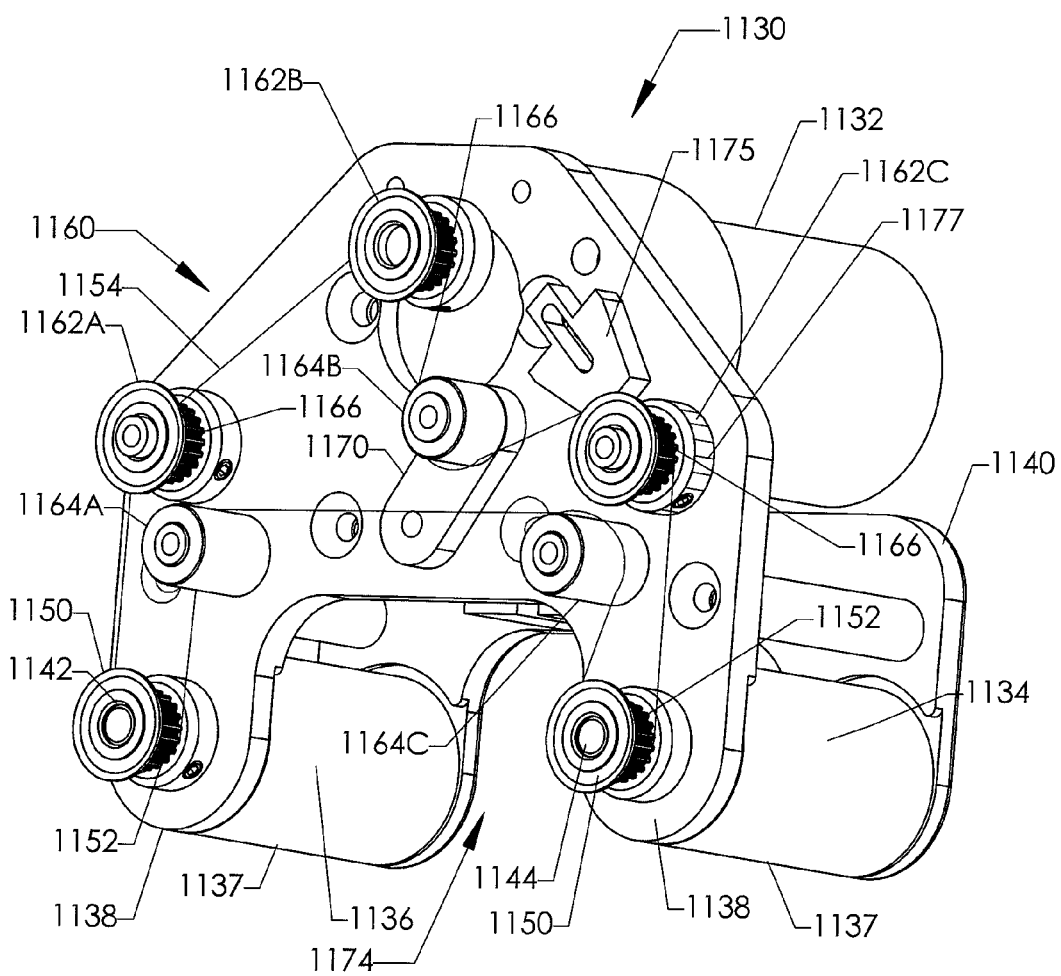
FIG. 72 illustrates a perspective view of an external magnetic driver according to one embodiment. The outer housing or cover is removed to illustrate the various aspects of the external magnetic driver.

FIG. 72 illustrates an external magnetic driver 1130 according to one aspect of the invention. The external magnetic driver 1130 may be used to externally impart rotational motion or "drive" a permanent magnet (e.g., magnets 1064, 1118) located within an implantable interface (e.g., interfaces 1010, 1104). The external magnetic driver 1130 includes a motor 1132 that is used to impart rotational movement to two permanent magnets 1134, 1136. The motor 1132 may include, for example, a DC powered motor or servo that is powered via one or more batteries (not shown) integrally contained within the external magnetic driver 1130. Alternatively, the motor 1132 may be powered via a power cord or the like to an external power source. For example, the external power source may include one or more batteries or even an alternating current source that is converted to DC.

Still referring to FIG. 72, the two permanent magnets 1134, 1136 are preferably cylindrically-shaped permanent magnets. The permanent magnets may be made from, for example, a rare earth magnet material such as Neodymium-Iron-Boron (NdFeB) although other rare earth magnets. For example, each magnet 1134, 1136 may have a length of around 1.5 inches and a diameter of around 1.0 to 3.5 inches. Both magnets 1134, 1136 are diametrically magnetized (poles are perpendicular the long axis of each permanent magnet 1134, 1136). The magnets 1134, 1136 may be contained within a non-magnetic cover or housing 1137. In this regard, the magnets 1134, 1136 are able to rotate within the stationary housing 1137 that separates the magnets 1134, 1136 from the external environment. Preferably, the housing 1137 is rigid and relatively thin walled at least at the portion directly covering the permanent magnets 1134, 1136, in order to minimize the gap between the permanent magnets 1134, 1136 and the internal magnet 1064.

As seen in FIG. 72, the permanent magnets 1134, 1136 are rotationally mounted between opposing bases members 1138, 1140. Each magnet 1134, 1136 may include axles or spindles 1142, 1144 mounted on opposing axial faces of each magnet 1134, 1136. The axles 1142, 1144 may be mounted in respective bearings (not shown) that are mounted in the base members 1138, 1140. As seen in FIG. 72, driven pulleys 1150 are mounted on one set of axles 1142 and 1144. The driven pulleys 1150 may optionally include grooves or teeth 1152 that are used to engage with corresponding grooves or teeth 1156 (partially illustrated in FIG. 73) contained within a drive belt (indicated by path 1154).

Figure 74:
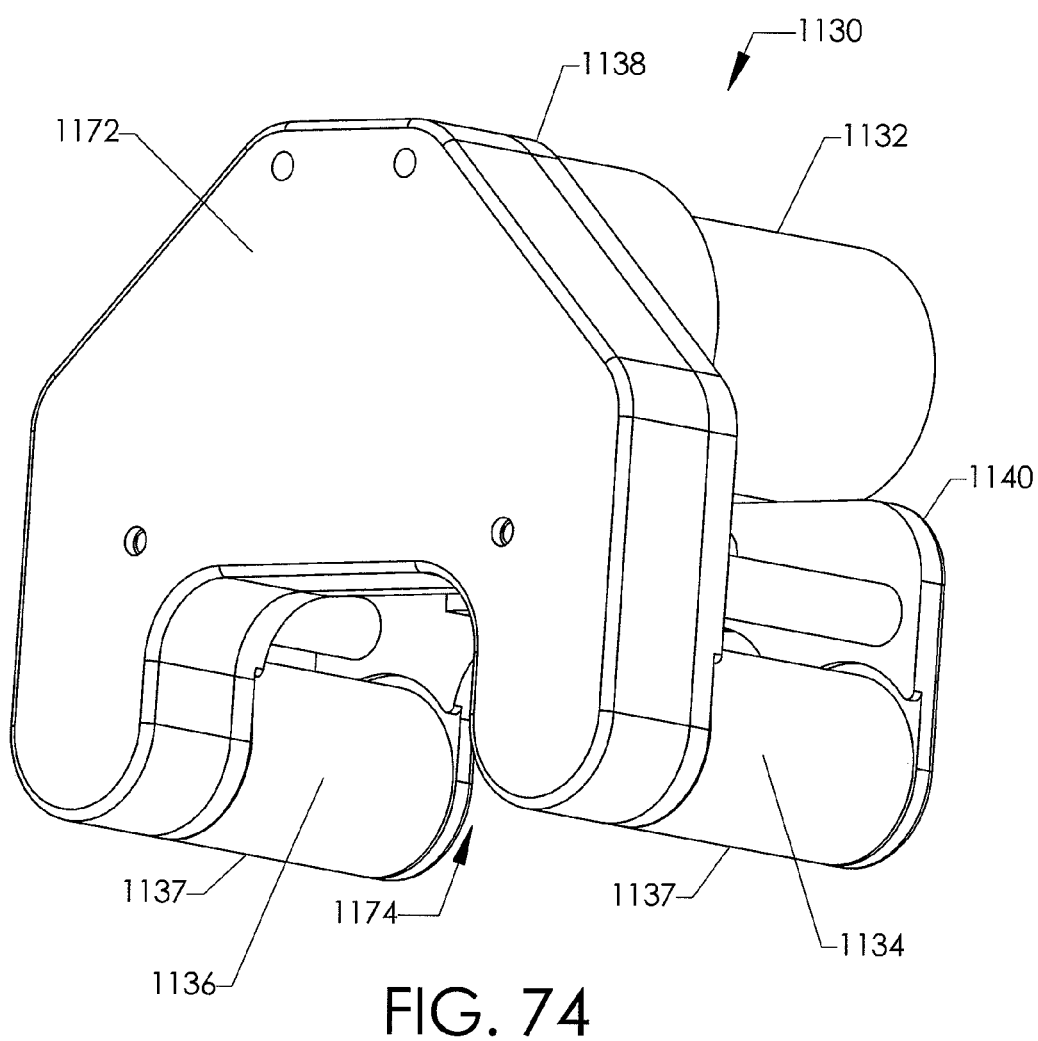
FIG. 74 illustrates a perspective view of an external magnetic driver of FIG. 72 with the outer housing or cover in place.

Still referring to FIG. 72, the external magnetic driver 1130 includes a drive transmission 1160 that includes the two driven pulleys 1150 along with a plurality of pulleys 1162a, 1162b, 1162c and rollers 1164a, 1164b, 1164c on which the drive belt 1154 is mounted. The pulleys 1162a, 1162b, 1162c may optionally include grooves or teeth 1166 used for gripping corresponding grooves or teeth 1156 of the drive belt 1154. Pulleys 1162a, 1162b, 1162c and rollers 1164a, 1164b, 1164c may be mounted on respective bearings (not shown). As seen in FIG. 72, pulley 1162b is mechanically coupled to the drive shaft (not shown) of the motor 1132. The pulley 1162b may be mounted directly to the drive shaft or, alternatively, may be coupled through appropriate gearing. One roller 1164b is mounted on a biased arm 1170 and thus provides tension to the belt 1154. The various pulleys 1150, 1162a, 1162b, 1162c and rollers 1164a, 1164b, 1164c along with the drive belt 1154 may be contained within a cover or housing 1172 that is mounted to the base 1138 (as seen in FIG. 74).

Figure 73:
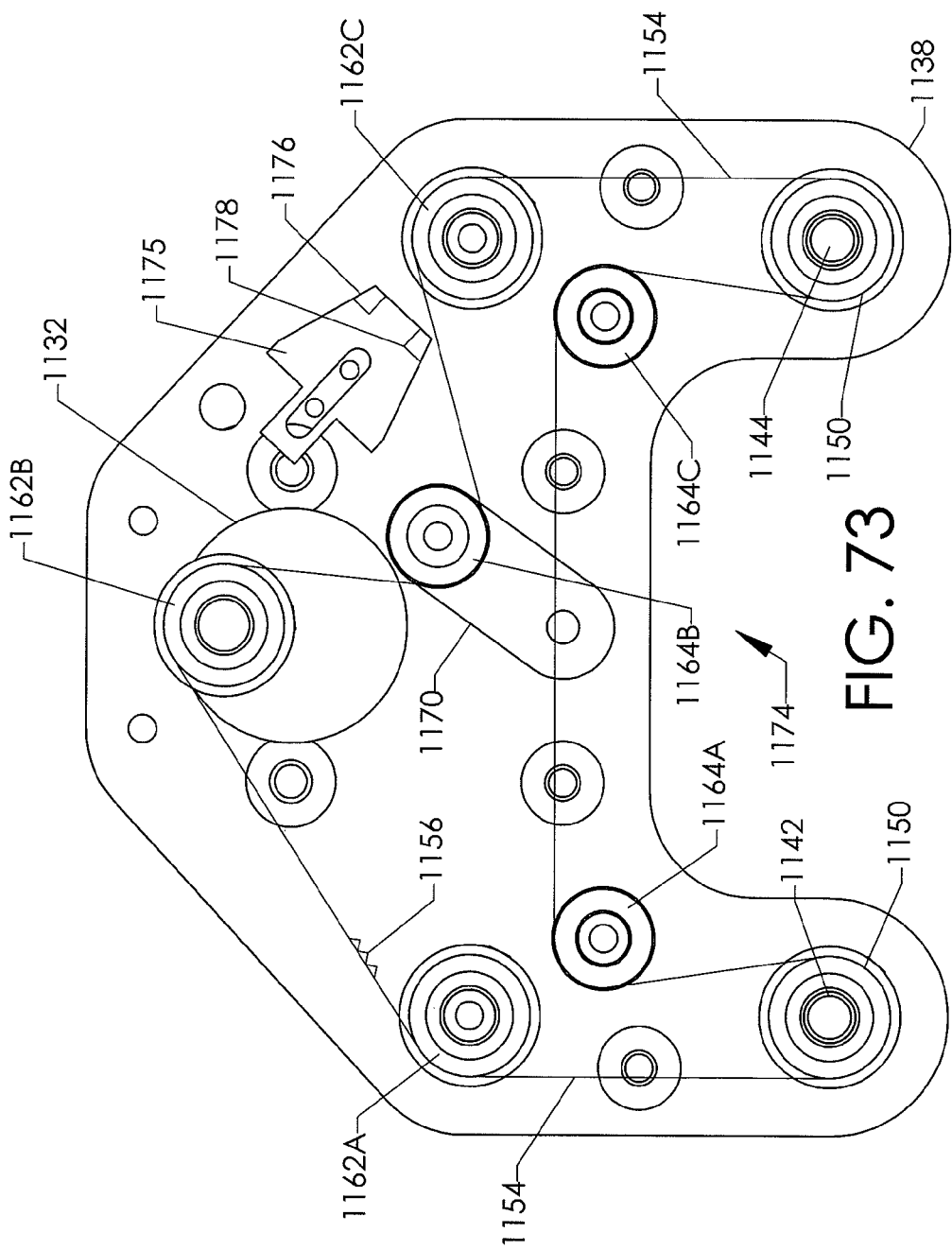
FIG. 73 illustrates a side or end view of the external magnetic driver of FIG. 72.

As seen in FIGS. 72 and 73, rotational movement of the pulley 1162b causes the drive belt 1154 to move around the various pulleys 1150, 1162a, 1162b, 1162c and rollers 1164a, 1164b, 1164c. In this regard, rotation movement of the motor 1132 is translated into rotational movement of the two permanent magnets 1134, 1136 via the drive transmission 1160. In one aspect of the invention, the base members 1138, 1140 are cut so as to form a recess 1174 that is located between the two magnets 1134, 1136. During use, the external magnetic driver 1130 is pressed against the skin of a patient, or against the clothing which covers the skin (e.g., the external driver 1130 may be used through clothing so the patient may not need to undress). The recess 1174 allows skin as well as the underlying tissue to gather or compress within the recessed region 1174. This advantageously reduces the overall distance between the external drive magnets 1134, 1136 and the magnet 1064, 1118 contained within the implantable interface 1010, 1104. By reducing the distance, this means that the externally located magnets 1134, 1136 and/or the internal magnet (e.g., 1064, 1118) may be made smaller.

Still referring to FIGS. 72 and 73, the external magnetic driver 1130 preferably includes an encoder 1175 that is used to accurately and precisely measure the degree of movement (e.g., rotational) of the external magnets 1134, 1136. In one embodiment, an encoder 1175 is mounted on the base member 1138 and includes a light source 1176 and a light receiver 1178. The light source 1176 may includes a LED which is pointed or directed toward pulley 1162c. Similarly, the light receiver 1178 may be directed toward the pulley 1162c. The pulley 1162c includes a number of reflective markers 1177 regularly spaced about the periphery of the pulley 1162c. Depending on the rotational orientation of the pulley 1162c, light is either reflected or not reflected back onto the light receiver 1178. The digital on/off signal generated by the light receiver 1178 can then be used to determine the rotational speed and displacement of the external magnets 1134, 1136.

FIGS. 75A, 75B, 75C, and 75D illustrate the progression of the external magnets 1134, 1136 and the internal magnet 1064 that is located within the implantable interface 1010 during use. Internal magnet 1064 is shown for illustration purposes. It should be understood that the internal magnet may also include, for example, internal magnet 1118 that is located within the implantable interface 1104 according to that alternative embodiment. FIGS. 75A, 75B, 75C, and 75D illustrate the external magnetic driver 1130 being disposed against the external surface of the patient's skin 1180. The external magnetic driver 1130 is placed against the skin 1180 in this manner to remotely rotate the internal magnet 1064. As explained herein, rotation of the internal magnet 1064 is translated into linear motion via the drive transmission 1020 to controllable adjust the stoma or opening in the restriction device 1002 mounted about a body lumen, such as, the patient's stomach.

As seen in FIGS. 75A, 75B, 75C, and 75D, the external magnetic driver 1130 may be pressed down on the patient's skin 1180 with some degree of force such that skin and other tissue such as the underlying layer of fat 1182 are pressed or forced into the recess 1174 of the external magnetic driver 1130. The implantable interface (e.g., 1010, 1104) which contains the internal magnet 1064 (which is contained in a housing 1062 not shown in FIGS. 75A, 75B, 75C, and 75D) is secured to the patient in an artificially created opening or passageway formed in or adjacent to the fascia layer 1184 separating the layer of fat 1182 from underlying abdominal muscle tissue 1186. Underneath the abdominal muscle tissue 1186 is the peritoneum 1188. Typically, as explained herein, the implantable interface 1104 is secured to the patient via a clamp, sutures, screws, retaining members, or the like. FIGS. 75A, 75B, 75C, and 75D omit these elements for sake of clarity to just show the magnetic orientation of the internal magnet 1064 as it undergoes a full rotation in response to movement of the permanent magnets 1134, 1136 of the external magnetic driver 1130.

Figure 75A:
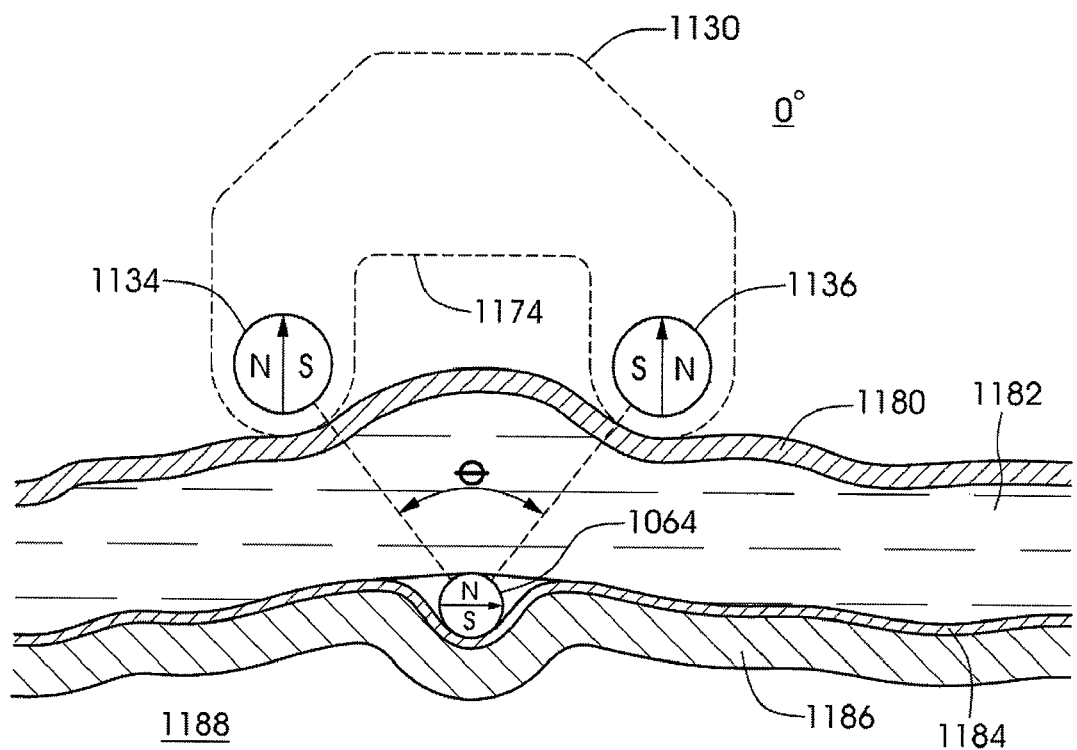
FIG. 75A illustrates a cross-sectional representation of the external magnetic driver being positioned on a patient's skin.

With reference to FIG. 75A, the internal magnet 1064 is shown being oriented with respect to the two permanent magnets 1134, 1136 via an angle θ. This angle θ may depend on a number of factors including, for instance, the separation distance between the two permanent magnets 1134, 1136, the location or depth of where the implantable interface 1104 is located, the degree of force at which the external magnetic driver 1130 is pushed against the patient's skin. Generally, the angle θ should be at or around 90° to achieve maximum drivability (e.g., torque).

FIG. 75A illustrates the initial position of the two permanent magnets 1134, 1136 and the internal magnet 1064. This represents the initial or starting location (e.g., 0° position as indicated). Of course, it should be understood that, during actual use, the particular orientation of the two permanent magnets 1134, 1136 and the internal magnet 1064 will vary and not likely will have the starting orientation as illustrated in FIG. 75A. In the starting location illustrated in FIG. 75A, the two permanent magnets 1134, 1136 are oriented with their poles in an N-S/S-N arrangement. The internal magnet 1064 is, however, oriented generally perpendicular to the poles of the two permanent magnets 1134, 1136.

Figure 75B:
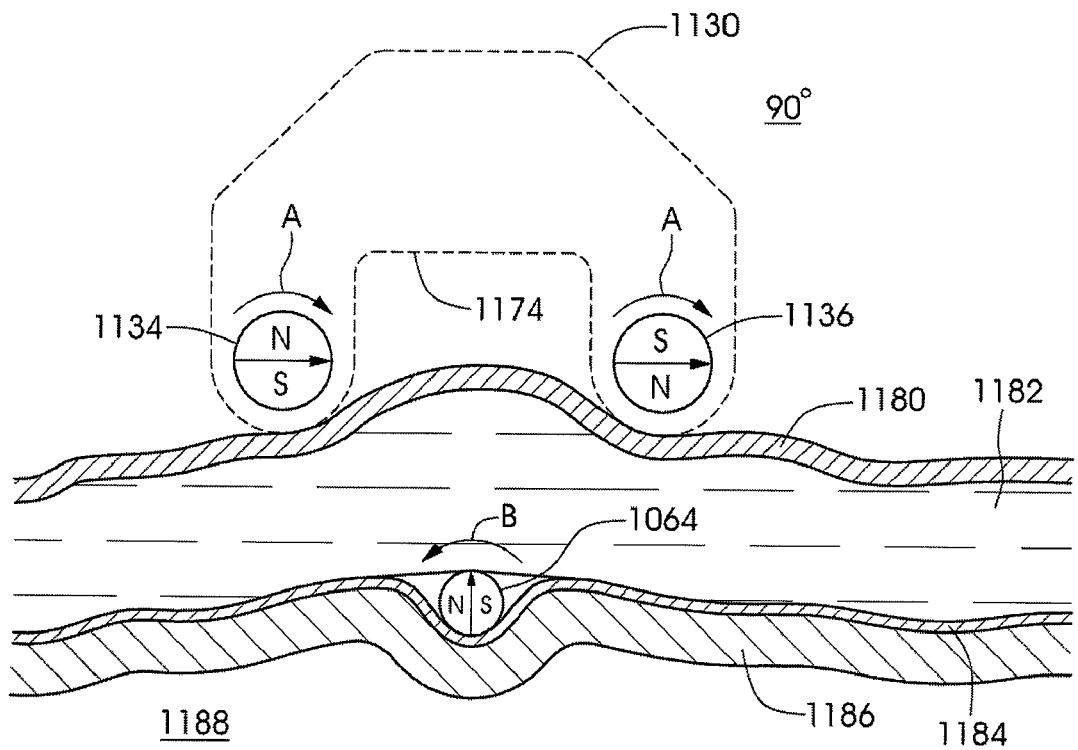
FIG. 75B illustrates a cross-sectional representation of the external magnetic driver being positioned on a patient's skin.
Figure 75C:
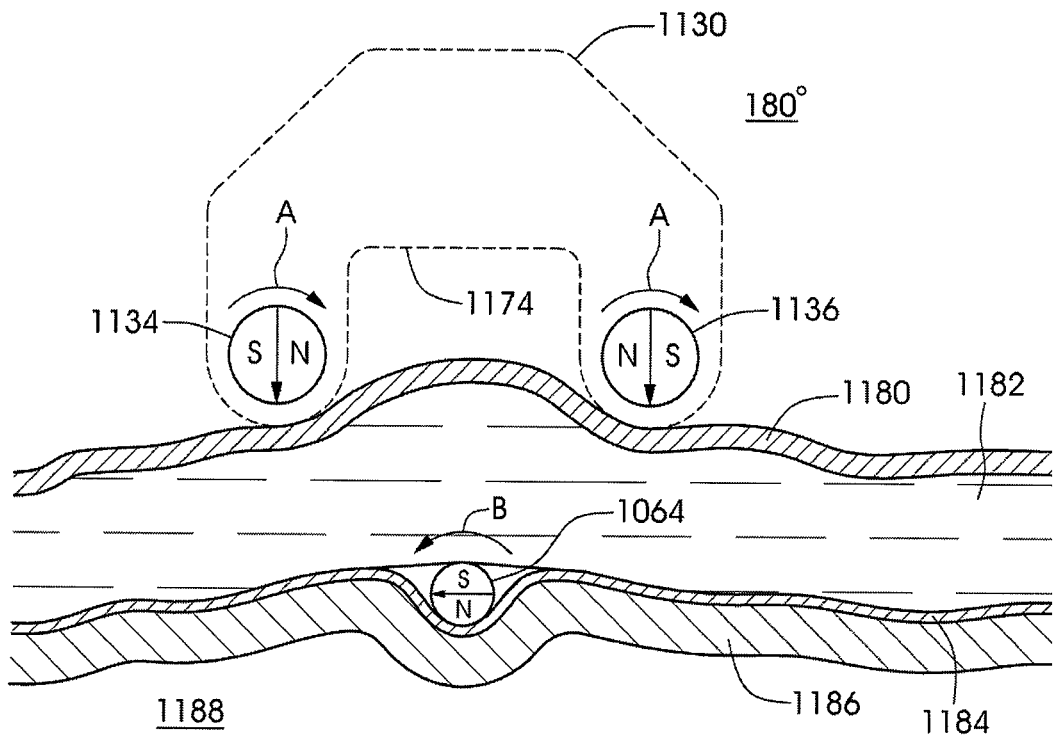
FIG. 75C illustrates a cross-sectional representation of the external magnetic driver being positioned on a patient's skin.
Figure 75D:
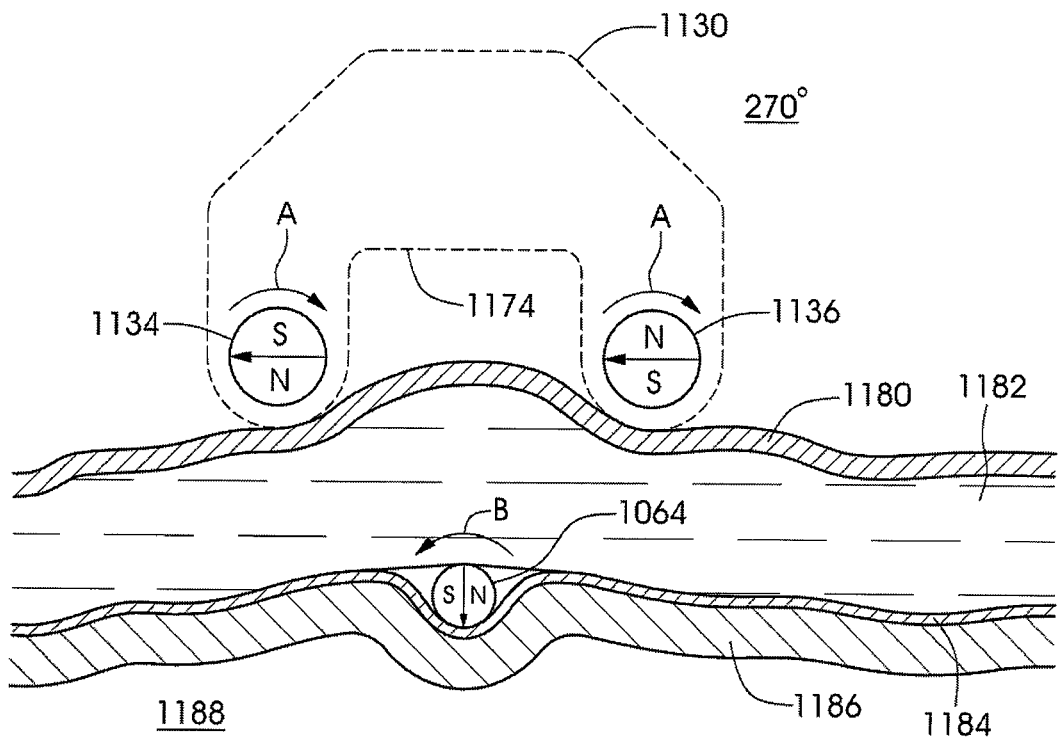
FIG. 75D illustrates a cross-sectional representation of the external magnetic driver being positioned on a patient's skin.

FIG. 75B illustrates the orientation of the two permanent magnets 1134, 1136 and the internal magnet 1064 after the two permanent magnets 1134, 1136 have rotated through 90°. The two permanent magnets 1134, 1136 rotate in the direction of arrow A (e.g., clockwise) while the internal magnet 1064 rotates in the opposite direction (e.g., counter clockwise) represented by arrow B. It should be understood that the two permanent magnets 1134, 1136 may rotate in the counter clockwise direction while the internal magnet 1064 may rotate in the clockwise direction. Rotation of the two permanent magnets 1134, 1136 and the internal magnet 1064 continues as represented by the 180° and 270° orientations as illustrated in FIGS. 75C and 75D. Rotation continues until the starting position (0°) is reached again.

During operation of the external magnetic driver 1130, the permanent magnets 1134, 1136 may be driven to rotate the internal magnet 1064 through one or more full rotations in either direction to tighten or loosen the restriction device 1002 as needed. Of course, the permanent magnets 1134, 1136 may be driven to rotate the internal magnet 1064 through a partial rotation as well (e.g., ¼, ⅛, 1/16, etc.). The use of two magnets 1134, 1136 is preferred over a single external magnet because the driven magnet (e.g., 1064, 1118) may not be oriented perfectly at the start of rotation, so one external magnet 1134, 1136 may not be able to deliver its maximum torque, which depends on the orientation of the internal driven magnet (e.g., 1064, 1118) to some degree. However, when two (2) external magnets (1134, 1136) are used, one of the two 1134 or 1136 will have an orientation relative to the internal driven magnet (e.g., 1064, 1118) that is better or more optimal than the other. In addition, the torques imparted by each external magnet 1134, 1136 are additive.

While the external magnetic driver 1130 and implantable interface 1010, 1104 have generally been described as functioning using rotational movement of driving elements (i.e., magnetic elements) it should be understood that non-rotational movement can also be used to drive or adjust the restriction device 1002, 1102. For example, linear or sliding motion back-and-forth may also be used to adjust the restriction device 1002, 1102. In this regard, a single magnet located internal to the patient that slides back-and-forth on a slide or other base can be used to adjust the restriction device 1002, 1102 using a ratchet-type device. The sliding, internal magnet may be driven via one or more externally-located permanent/electromagnets that slides or moves laterally (or moves the magnetic field) in a similar back-and-forth manner. Rotational movement of the externally-located magnetic element(s) may also be used to drive the internal magnet.

In still another alternative, permanent magnets may be located on a pivoting member that pivots back and forth (like a teeter-totter) about a pivot point. For example, a first permanent magnet having a North pole oriented in a first direction may be located at one end of the pivoting member while a permanent magnet having a South pole oriented in the first direction is located at the other end of the pivoting member. A ratchet-type device may be used to translate the pivoting movement into linear movement that can actuate or adjust the restriction device 1002, 1102. The first and second internally-located permanent magnets may be driven by one or more externally located magnetic elements (either permanent or electromagnets). External motion of the electric field by linear or even rotational movement may be used to the drive the pivoting member.

While certain embodiments of the gastric restriction systems discussed herein have been described as using a restriction device that is coupled to a separate implantable interface via a drive transmission, it should be understood that the various components could be integrated into a single device. For example, a single restriction device may include or be closely associated with the constituent components of the implantable interface and drive transmission. This, of course, would reduce the overall length of the device by integrating these components into a single device which may be placed around, for instance, the stomach of the patient.

Figure 76:
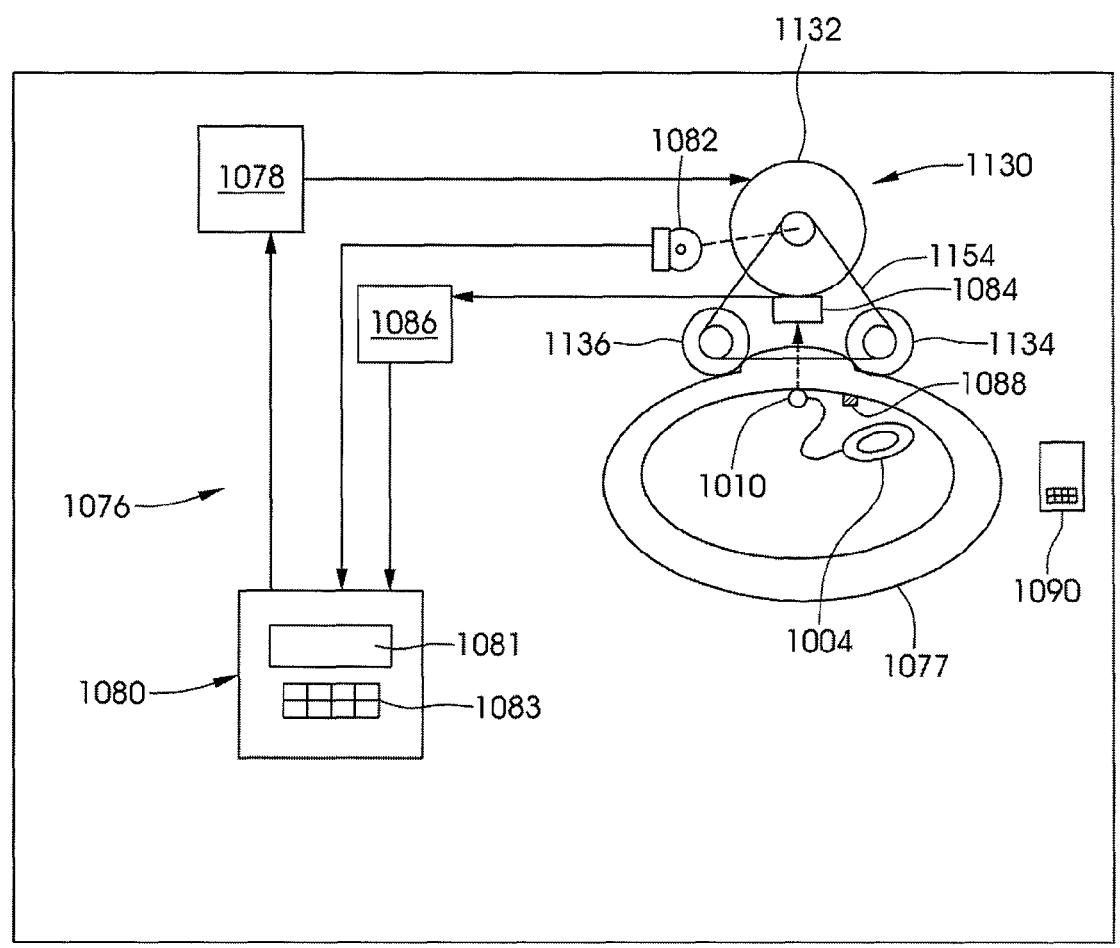
FIG. 76 schematically illustrates a system for driving the external magnetic driver according to one embodiment.

FIG. 76 illustrates a system 1076 according to one aspect of the invention for driving the external magnetic driver 1130. FIG. 76 illustrates the external magnetic driver 1130 pressed against the surface of a patient 1077 (torso shown in cross-section). The implantable interface 1010 located within the body cavity along with the adjustable body 1004 are illustrated. The permanent magnet (e.g., the driven magnet) that is located within the implantable interface 1010 located inside the patient 1077 is magnetically coupled through the patient's skin and other tissue to the two external magnets 1134, 1136 located in the external magnetic driver 1130. As explained herein, one rotation of the external magnets 1134, 1136 causes a corresponding single rotation of the driven magnet (e.g., magnets 1064 or 1118) located within the implantable interface (e.g., 1010, 1104). Turning the driven magnet 1064, 1118 in one direction causes the restriction device (e.g., 1002, 1102) to close while turning in the opposite direction causes the restriction device (e.g., 1002, 1102) to open. Changes to the opening or stoma in the restriction device 1002, 1102 are directly proportional to the number of turns of the driven magnet 1064, 1118.

The motor 1132 of the external magnetic driver 1130 is controlled via a motor control circuit 1078 operatively connected to a programmable logic controller (PLC) 1080. The PLC 1080 outputs an analog signal to the motor control circuit 1078 that is proportional to the desired speed of the motor 1132. The PLC 1080 may also select the rotational direction of the motor 1132 (i.e., forward or reverse). In one aspect, the PLC 1080 receives an input signal from a shaft encoder 1082 that is used to identify with high precision and accuracy the exact relative position of the external magnets 1134, 1136. For example, the shaft encoder 1082 may be an encoder 1175 as described above. In one embodiment, the signal is a pulsed, two channel quadrature signal that represents the angular position of the external magnets 1134, 1136. The PLC 1080 may include a built in screen or display 1081 that can display messages, warnings, and the like. The PLC 1080 may optionally include a keyboard 1083 or other input device for entering data. The PLC 1080 may be incorporated directly into the external magnetic driver 1130 or it may be a separate component that is electrically connected to the main external magnetic driver 1130.

In one aspect of the invention, a sensor 1084 is incorporated into the external magnetic driver 1130 that is able to sense or determine the rotational or angular position of the driven magnet 1064, 1118. The sensor 1084 may acquire positional information using, for example, sound waves, ultrasonic waves, light, radiation, or even changes or perturbations in the electromagnetic field between the driven magnet 1064, 1118 and the external magnets 1134, 1136. For example, the sensor 1084 may detect photons or light that is reflected from the driven magnet 1064, 1118 or a coupled structure (e.g., rotor) that is attached thereto. For example, light may be passed through the patient's skin and other tissue at wavelength(s) conducive for passage through tissue. Portions of the driven magnet 1064, 1118 or associated structure may include a reflective surface that reflects light back outside the patient as the driven magnet 1064, 1118 moves. The reflected light can then be detected by the sensor 1084 which may include, for example, a photodetector or the like.

In another aspect, the sensor 1084 may operate on the Hall effect, wherein two additional magnets are located within the implantable assembly. The additional magnets move axially in relation to each other as the driven assembly rotates and therefore as the restriction device constricts or loosens, allowing the determination of the current size of the restriction device.

In the embodiment of FIG. 76, the sensor 1084 is a microphone disposed on the external magnetic driver 1130. For instance, the microphone sensor 1084 may be disposed in the recessed portion 1174 of the external magnetic driver 1130. The output of the microphone sensor 1084 is directed to a signal processing circuit 1086 that amplifies and filters the detected acoustic signal. In this regard, the acoustic signal may include a "click" or other noise that is periodically generated by rotation of the driven magnet 1064, 1118. For example, the driven magnet 1064, 1118 may click every time a full rotation is made. The pitch of the click may different depending on the direction of rotation. For example, rotation in one direction (e.g., tightening) may produce a low pitch while rotation in the other direction (e.g., loosening) may produce a higher pitch signal (or vice versa). The amplified and filtered signal from the signal processing circuit 1086 can then pass to the PLC 1080.

During operation of the system 1076, each patient will have a number or indicia that corresponds to the current diameter or size of their restriction device 1002, 1102. For example, a fully open restriction device 1002, 1102 may have a diameter or size of around 2.90 cm while a fully closed device 1002, 1102 may have a diameter or size of around 1.20 cm. This number can be stored on a storage device 1088 (as shown in FIG. 76) that is carried by the patient (e.g., memory card, magnetic card, or the like) or is integrally formed with the implantable system (e.g., systems 1000, 1100). For example, a RFID tag 1088 implanted either as part of the system or separately may be disposed inside the patient (e.g., subcutaneously or as part of the device) and can be read and written via an antenna 1090 to update the current size of the restriction device 1002, 1102. In one aspect, the PLC 1080 has the ability to read the current number corresponding to the diameter or size of the restriction device 1002, 1102 from the storage device 1088. The PLC 1080 may also be able to write the adjusted or more updated current diameter or size of the restriction device 1002, 1102 to the storage device 1088. Of course, the current size may recorded manually in the patient's medical records (e.g., chart, card or electronic patient record) that is then viewed and altered, as appropriate, each time the patient visits his or her physician.

The patient, therefore, carries their medical record with them, and if, for example, they are in another country and need to be adjusted, the RFID tag 1088 has all of the information needed. Additionally, the RFID tag 1088 may be used as a security device. For example, the RFID tag 1088 may be used to allow only physicians to adjust the restriction device (1002, 1102) and not patients. Alternatively, the RFID tag 1088 may be used to allow only certain models or makes of restriction devices to be adjusted by a specific model or serial number of external magnetic driver 1130.

In one aspect, the current size or diameter of the restriction device 1002, 1102 is input into the PLC 1080. This may be done automatically or through manual input via, for instance, the keyboard 1083 that is associated with the PLC 1080. The PLC 1080 thus knows the patient's starting point. If the patient's records are lost, the PLC 1080 may be programmed to fully open the restriction device 1002, 1102 which is, of course, a known starting point. The number of turns required to meet the fully open position may be counted by the PLC 1080 and the restriction device 1002, 1102 can then be returned to the same restriction point.

The external magnetic driver 1130 is commanded to make an adjustment. This may be accomplished via a pre-set command entered into the PLC 1080 (e.g., reduce size of restriction device 1002, 1102 by 0.5 cm). The PLC 1080 configures the proper direction for the motor 1132 and starts rotation of the motor 1132. As the motor 1132 spins, the encoder 1082 is able to continuously monitor the shaft position of the motor directly, as is shown in FIG. 76, or through another shaft or surface that is mechanically coupled to the motor 1132. For example, the encoder 1082 may read the position of markings 1177 located on the exterior of a pulley 1162*c* like that disclosed in FIG. 72. Every rotation or partial rotation of the motor 1132 can then be counted and used to calculate the adjusted or new size of the restriction device 1002, 1102.

The sensor 1084, which may include a microphone sensor 1084, may be monitored continuously. For example, every rotation of the motor 1132 should generate the appropriate number and pitch of clicks generated by rotation of the permanent magnet inside the implant 1010 (or implant 1104). If the motor 1132 turns a full revolution but no clicks are sensed, the magnetic coupling may have been lost and an error message may be displayed to the operator on the display 1081 of the PLC 1080. Similarly, an error message may be displayed on the display 1081 if the sensor 1084 acquires the wrong pitch of the auditory signal (e.g., the sensor 1084 detects a loosening pitch but the external magnetic driver 1130 was configured to tighten).

Figure 77:
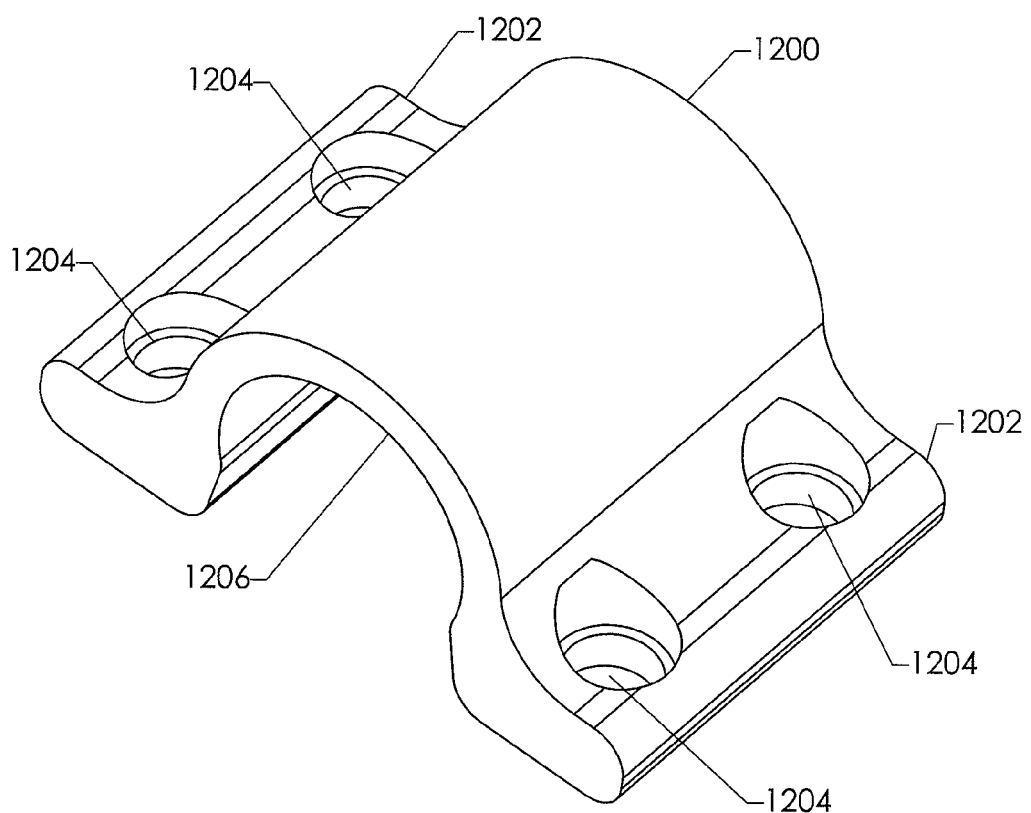
FIG. 77 illustrates a perspective view of a mount used to secure an implantable interface to a patient according to one embodiment.

FIG. 77 illustrates a mount 1200 according to one aspect of the invention that is used to secure the implantable interface 1010 (or implantable interface 1104) to the patient. The mount 1200 may be used to secure a variety of implantable apparatuses beyond the implantable interfaces discussed herein. This includes, for example, injection ports and other implantable interfaces usable with, for example, a gastric restriction device. The mount 1200 includes a base 1202 having a plurality of holes 1204 dimensioned for passage of fasteners 1210 (shown in FIGS. 78, 79A, 79B, 79D, 79E, 80, 81, 82). The mount 1200 also includes a receiving portion 1206 that is dimensioned to receive the implantable interface 1010. As seen in FIG. 77, the receiving portion 1206 is shaped in a hemi-cylindrical manner configured to receive the cylindrical shape of the implantable interface 1010. The receiving portion 1206 may be dimensioned such that the implantable interface 1010 forms a friction or snap-fit within the mount 1200. For example, in one aspect of the invention, prior to fastening the mount 1200 to the patient's tissue, the implantable interface 1010 is secured to the mount 1200. Of course, in an alternative aspect, the implantable interface 1010 may be inserted or slid into the receiving portion 1206 after the mount 1200 is secured to the patient. In another alternative configuration, the mount 1200 may be configured as the implantable interface itself (as shown in FIG. 82).

Figure 78:
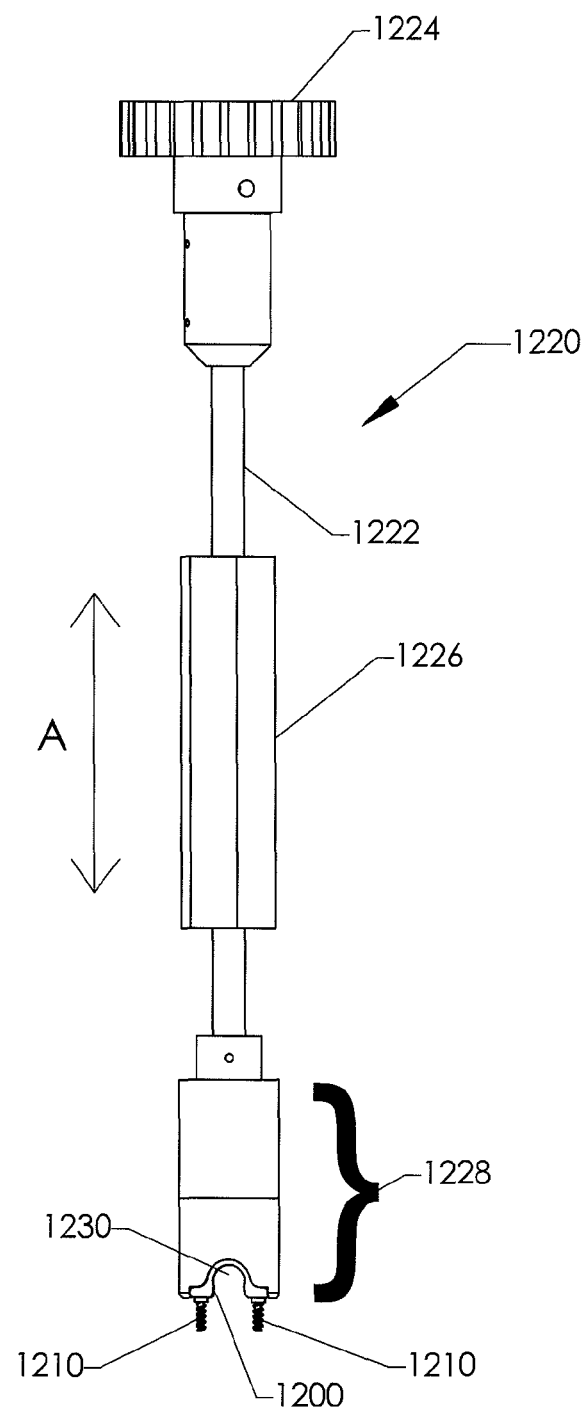
FIG. 78 illustrates a fastening tool used to secure a mount of the type illustrated in FIG. 77 to a patient according to one embodiment.

FIG. 78 illustrates a fastening tool or instrument 1220 that is used to rapidly and securely affix the mount 1200 to the patient's tissue. The fastening tool 1220 includes an elongate shaft 1222 with a proximally mounted knob 1224. A grip or handle 1226 is located on the elongate shaft 1222 and is used by the physician to grasp the fastening tool 1220 during the placement process. The distal end of the fastening tool 1220 includes a driving element 1228 that contains a recess or socket 1230 for holding the mount 1200. Fastening tool 1220 is used to drive a plurality of fasteners 1210 through respective holes 1204 in the base 1202 to fixedly secure the mount 1200 to the patient's tissue. As explained in more detail herein, rotational movement of the knob 1224 turns a central sun gear that, in turn, drives a series of outer gears within the fastening tool 1220 to rotate the individual fasteners 1210. Rotational movement of the knob 1224 also moves the driving element 1228 in the direction of arrow A to either extend or retract the driving element 1228 depending on direction of rotation of the knob 1224.

Figure 79C:
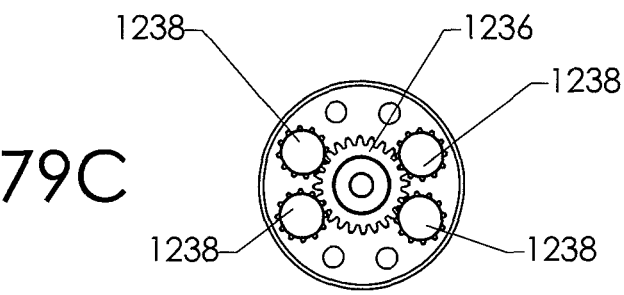
FIG. 79C an end view of the central gear and four outer gears as viewed along the line C-C' of FIG. 79A.
Figure 79A:
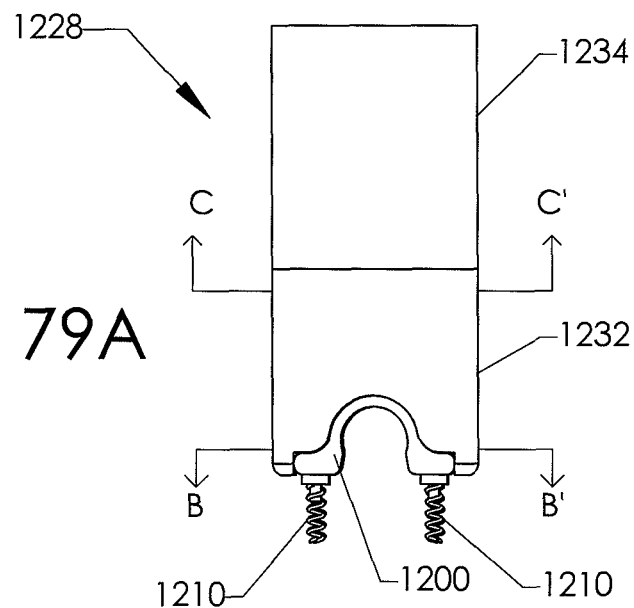
FIG. 79A illustrates a side view of a driving element portion of a fastening tool according to one embodiment.
Figure 79B:
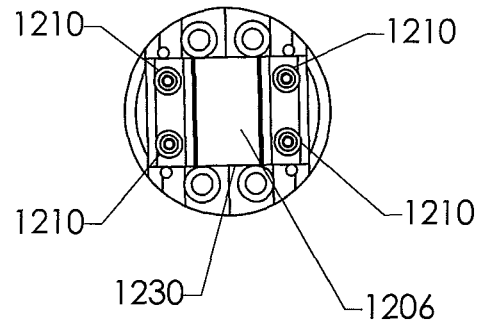
FIG. 79B illustrates an end view of a mount being loaded into a socket positioned in the base of the driving element. The view is taken along the line B-B' of FIG. 79A.

FIG. 79A illustrates a side view of the driving element 1228 holding the mount 1200 and illustrating the fasteners 1210 in the fully deployed (e.g., extended) position. FIG. 79B illustrates a cross-sectional view taken along the line B-B' of FIG. 79A. FIG. 79C illustrates a cross-sectional view taken along the line C-C' of FIG. 79A. The driving element 1228 generally includes a lower base or interface 1232 on which are mounted a central gear 1236 and a plurality of outer gears 1238 (four are illustrated in FIG. 79C. Rotation of the central gear 1236 thus causes each of the four outer gears 1238 to rotate as well.

Figure 79D:
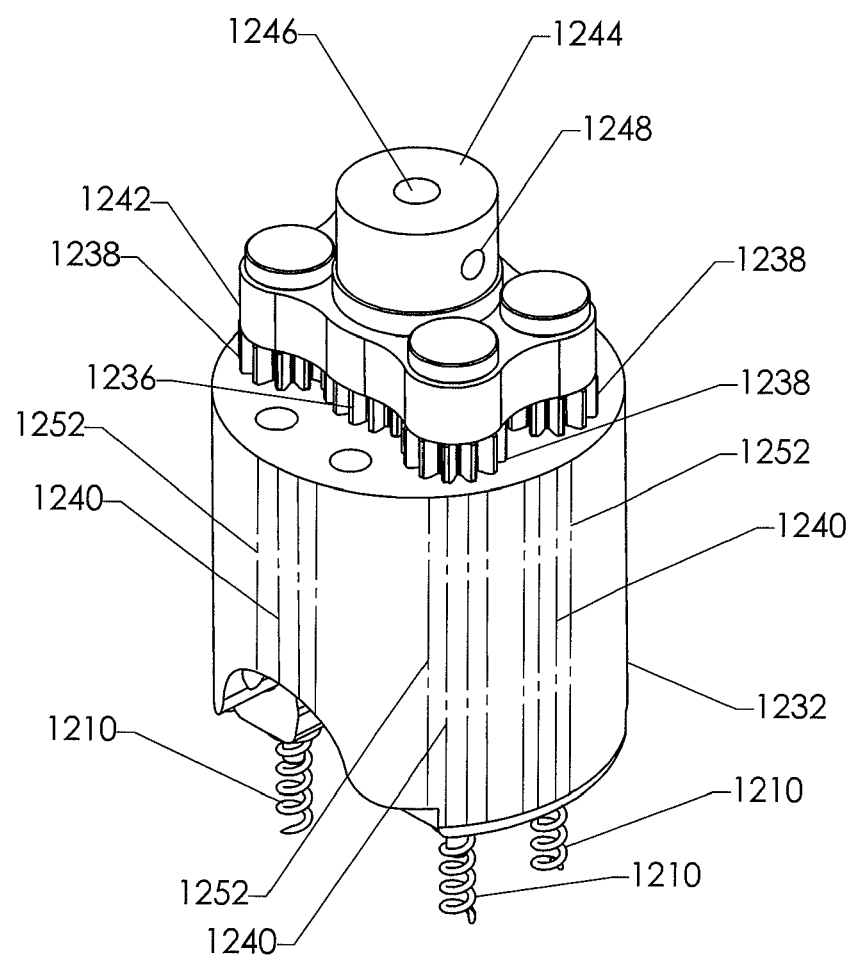
FIG. 79D illustrates a perspective view of the base portion of the driving element portion of the fastening tool.
Figure 80:
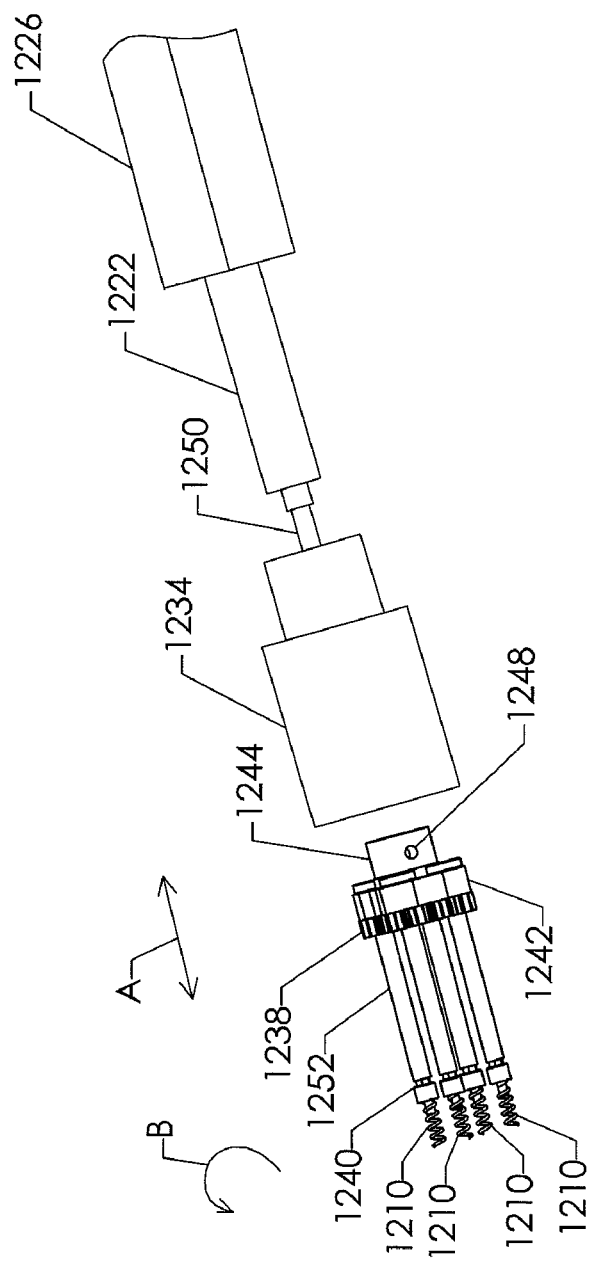
FIG. 80 illustrates an exploded perspective view of the distal end of the fastening tool according to one embodiment. The base portion is omitted for clarity purposes.

FIG. 79D illustrates a perspective view of the base 1232 portion of the driving element 1228. As seen in FIG. 79D each of the outer gears 1238 is coupled to a corresponding shaft or driver 1240 (shown in phantom) that has as distal end configured for engaging with the fasteners 1210. For example, the distal end of the driver 1240 may include a keyed portion (e.g., hexagonally-shaped end) that mates with a correspondingly-shaped recess (e.g., hex-shaped recess) in the fastener 1210. The drivers 1240 are thus rotationally mounted within the base 1232. Rotation of the central gear 1236 turns the outer gears 1238 which then turns the corresponding drivers 1240. Each driver 1240 is mounted within a barrel or tube 1252 (also shown in phantom) having a lumen therein dimensioned for passage of the driver 1240. The barrels or tubes 1252 may be machined, drilled, or molded within the base portion 1232 of the driving element 1228. FIG. 80 illustrates a partially exploded view showing the drivers 1240 disposed within respective barrels 1252.

Figure 79E:
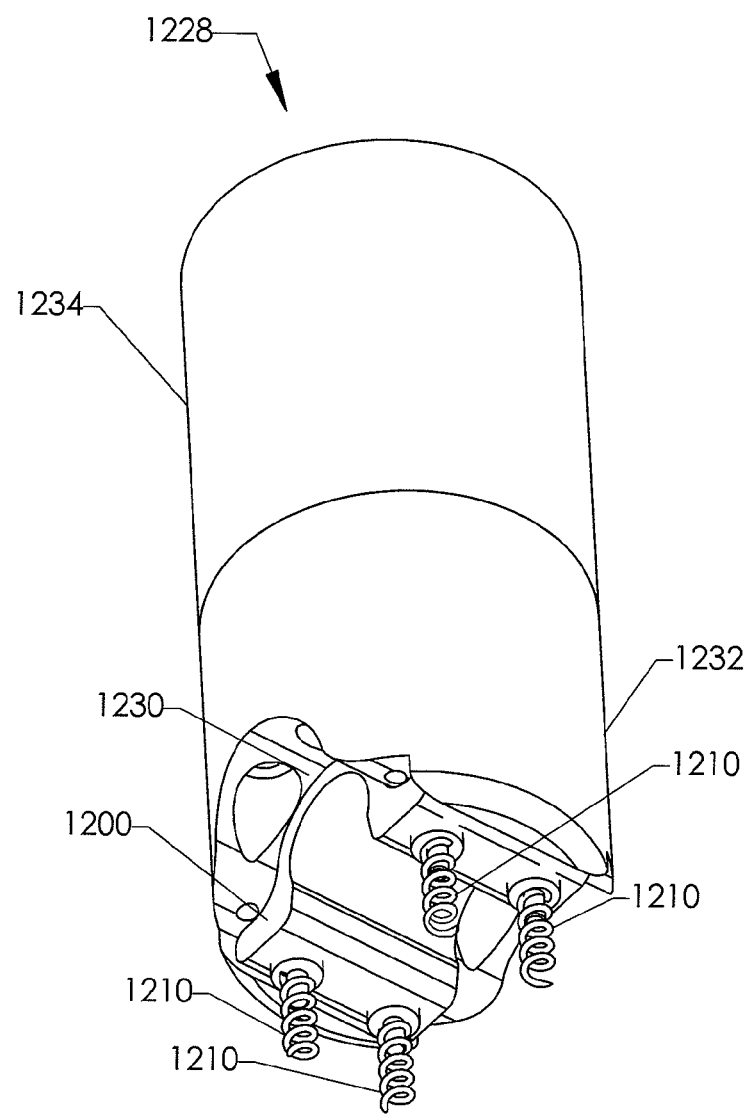
FIG. 79E illustrates a bottom perspective view of the driving element portion of the fastening tool.

Referring back to FIG. 79D, a plate 1242 is mounted above the central gear 1236 and outer gears 1238 and is used as a bearing surface that is used to move the base 1232 up or down as the knob 1224 is turned. A hub 1244 is located above the plate 1242 and is coupled to the central gear 1236. Rotation of the hub 1244 thus results in rotation of the central gear 1236. The hub 1244 includes a hole or recess 1246 for receiving a drive shaft 1250 (as seen in FIG. 80). The drive shaft 1250 may be fixedly secured to the hub 1244 using a set screw (not shown) that is inserted into the hub 1244 via aperture 1248. As seen in FIG. 79E, the driving element 1230 includes an upper housing 1234 that provides clearance for the base 1232 to move axially as the knob 1224 is turned. This allows for controlled delivery into the fascia.

As an alternative to the central gear 1236 which turns the outer gears 1238, the central gear 1236 may be omitted and an outer ring gear (not shown) having internal teeth may be used to engage and rotate the outer gears 1238. The advantage of this embodiment is that, as the physician turns the knob 1224 clockwise, the fasteners 1210 turn clockwise. With the central sun gear 1236, the fasteners 1210 have to be made left-hand wound and they turn counter-clockwise when the physician tightens the knob 1224 in the clockwise direction. The advantage of the central gear 1236 is that it requires less torque for the physician to turn the knob 1224.

FIG. 80 illustrates a partially exploded view of the distal end of the fastening tool 1220. In the assembled configuration, the drive shaft 1250 rotates in response to rotational movement of the proximally located knob 1224. In addition, the drive shaft 1250 moves axially within the length of the shaft 1222 in response to rotation of the knob 1224. Each fastener 1210 is thus moveable axially in the direction of arrow A and rotationally in the direction of arrow B. FIG. 80 illustrates four fasteners 1210 mounted at the end of each driver 1240. The four fasteners 1210 would pass through respective holes 1204 in the mount 1200 (as shown in FIG. 77). It should be noted that in one alternative embodiment the fasteners 1210 may be permanently, rotationally secured in the mount 1200.

Figure 81:
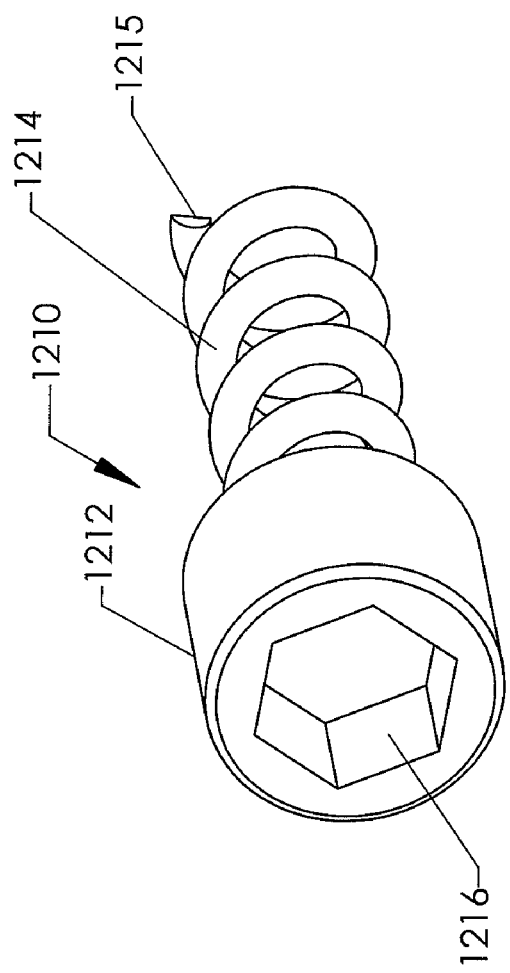
FIG. 81 illustrates a perspective view of a fastener according to one embodiment.
Figure 82:
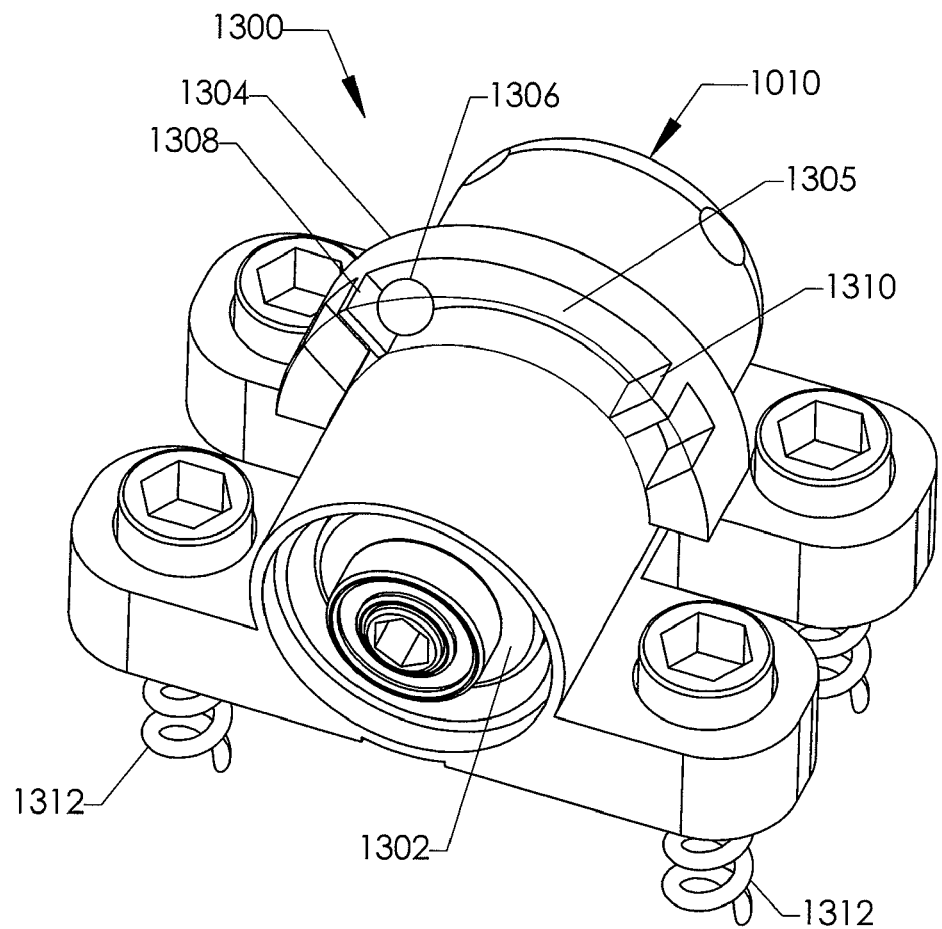
FIG. 82 illustrates a perspective view of a mount and associated acoustic or sonic indicator housing that contains a magnetic ball.

FIG. 81 illustrates a perspective view of a fastener 1210. The fastener 1210 may include a head 1212 portion along with a coil portion 1214. The head 1212 may be formed separately and bonded to the coil 1214 or the head 1212 and coil 1214 may be formed in an integrated manner. The head 1212 and coil 1214 may be formed from a biocompatible metallic material such as stainless steel, NITINOL, or the like. It may be preferred that a non-magnetic material like NITINOL or Titanium is used for all of the portions of the fastener 1210, so that there is no effect by any of the magnets, for example, during the adjustment procedure. While FIG. 81 illustrates a single coil 1214 originating from the head 1212, in other embodiments, there may be multiple, nested coils 1214 with different pitches affixed or otherwise mounted to a single head 1212. The additional coils 1214 may impart added anchoring ability. During securing, the coil 1214 may turn in the clockwise direction as illustrated in FIG. 81 or, alternatively, the coil 1214 may turn in the counter-clockwise direction. The coil 1214 may include a sharpened tip or end 1215 to aid in penetrating the tissue. A simple beveled tip is ideal. If the tip is too sharp, it can cause the patient more pain. The head 1212 preferably includes a recess 1216 that is dimensioned to interface with the distal end of the drivers 1240. For example, as illustrated in FIG. 81, the recess 1216 is hexagonally-shaped which can then receive the hexagonally-shaped distal end of the drivers 1240. The fastener 1210 may have a coil length of 4 mm or less. In addition, the wire forming the coil 1214 may have a diameter of around 0.20 inches and the coil 1214 may have an OD of around 0.100 inches and ID of around 0.060 inches. The diameter of the head 1212 is around 150 inches.

In one aspect of the invention, the fasteners 1210 are pre-loaded into the fastening tool 1220 prior to use. In addition, the mount 1200 may also be pre-loaded into the fastening tool 1220. In an alternate aspect, however, the mount 1200 may be loaded manually by the physician or surgeon prior to use. The fasteners 1210 may include a number retention means so that the fasteners 1210 do not prematurely fall out of the fastening tool 1220. For example, the ends of the drivers 1240 may include a bump, detent, or tab that locks into the recess 1216 of the fastener head 1212. Alternatively, an adhesive or the like may be used temporarily secure the fastener 1210 to the end of the drivers 1240. In still another alternative, an elastomeric membrane, ring or washer may be interposed between the fastener head 1212 and the barrel 1252 to provide a friction fit between the two to prevent premature release. It should be noted that the mount 1200 may be affixed to the internal or external wall of the patient's abdomen as described in more detail below.

FIG. 82 illustrates a perspective view of a mount 1300 that is used to hold or otherwise secure a cylindrically-shaped permanent magnet 1302. The permanent magnet 1302 is the "driven" magnet that is rotationally housed within the implantable interface (e.g., implantable interfaces 1010 and 1104). The mount 1300 includes an acoustic or sonic indicator housing 1304 that contains a magnetic ball 1306. The interior of the housing 1304 includes a groove or track 1305 dimensioned to permit movement of the magnetic ball 1306 (e.g., rolling motion). It is also contemplated that other magnetic structures capable of movement within the housing 1304 may also be used. For example, a roller or cylinder may be used in place of the magnetic ball 1306. Still referring to FIG. 82, first and second impact surfaces 1308, 1310 are disposed on opposing ends of the track 1305. The first and second impact surfaces 1308, 1310 may include a plate, tine(s), or other projection that prohibits or stops movement of the magnetic ball 1306. In one aspect, the mount 1300 is secured to the fascia by one or more helical fasteners 1312. Of course, sutures or other fasteners may also be used to fixedly secure the mount 1300 to the patient.

The mount 1300 may also include a resonance chamber for amplifying the sound created by the magnetic ball 1306 and the first and second impact surfaces 1308, 1310. For example, the sonic indicator housing 1304 itself may made from an appropriate material and/or have an appropriate wall thickness or chamber size, so that it acts as the resonance chamber itself. Another manner of creating a resonance chamber is by securing the mount 1300 to a more resonant portion of the body, for example a bony structure such as the sternum. The mount 1300 may be secured to the fascia covering the sternum via the subcutaneous securement method, or it may be attached to the intra-abdominal wall, behind the sternum, or it may be attached to the sternum directly via bone screws or the like. Alternatively, the mount 1200 depicted in FIG. 77 may be configured to act as a resonant structure.

FIGS. 83 through 98 schematically illustrate the acoustic indicator housing 1304 and driven magnet 1302 as the driven magnet 1302 is rotated in both the clockwise directions (arrow A) and counter-clockwise directions (arrow B). The mount 1300 is used to create an acoustic signal (e.g., a click) that can be used to count rotational movement of the driven magnet 1302 and also determine its rotational direction. An acoustic signal (i.e., sound) is generated when the magnetic ball 1306 strikes either the first impact surface 1308 or the second impact surface 1310. FIGS. 83-90 illustrate rotation of the driven magnet 1302 in the clockwise direction (arrow A) while FIGS. 91-98 illustrate rotation of the driven magnet 1302 in the counter-clockwise direction (arrow B). When the driven magnet 1302 is rotated in the clockwise direction, the magnetic ball 1306 strikes the first impact surface 1308 two times (2x) per full rotation, with the first impact surface 1308 producing sound with a first amplitude and/or frequency. When the driven magnet 1302 is rotated in the counter-clockwise direction, the magnetic ball 1306 strikes the second impact surface 1310 two times (2x) per full rotation, with the second impact surface 1310 producing sound with a second amplitude and/or frequency.

As illustrated in FIGS. 83-98, the first impact surface 1308 is thinner than the second impact surface 1310, and thus, the first impact surface 1308 is configured to resonate at a higher frequency than the second impact surface 13 10. Alternatively, the difference in frequency can be achieved by making the first impact surface 1308 from a different material than the second impact surface 1310. Alternatively, the amplitude of acoustic signal generated by the magnetic ball 1306 hitting the first and second impact surfaces 1308, 1310 may be used to discriminate rotational direction. For example, clockwise rotation may produce a relatively loud click while counter-clockwise rotation may produce a relatively quiet click.

Figure 83:
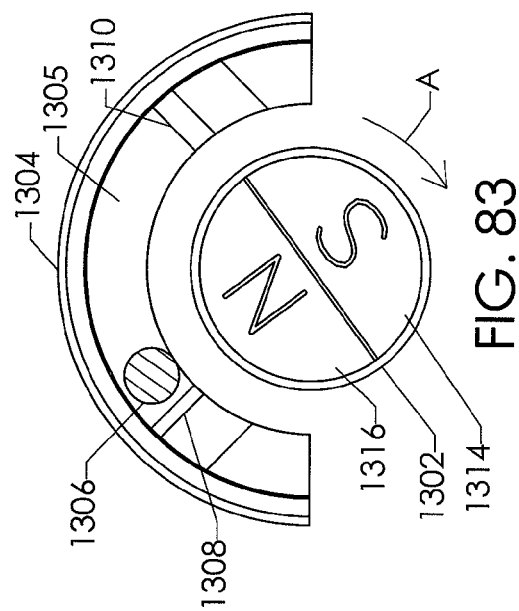
FIGS. 83-90 illustrate cross-sectional views of the driven magnet along with the acoustic or sonic indicator housing illustrating the rotational orientation of the magnet and the magnetic ball. Various states are illustrated as the magnet rotates in the clockwise direction.
Figure 84:
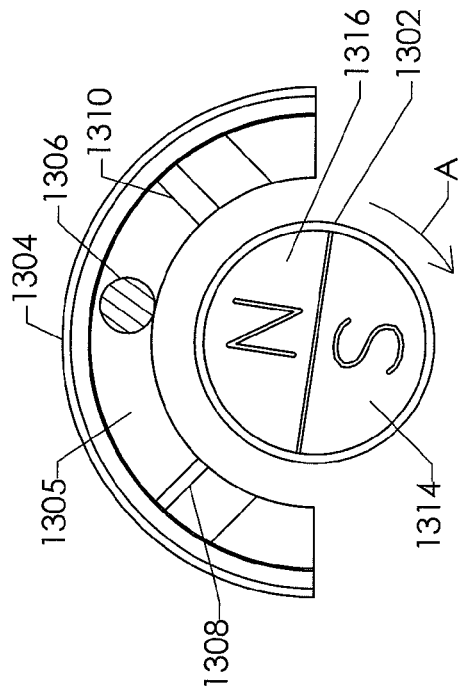
Figure 85:
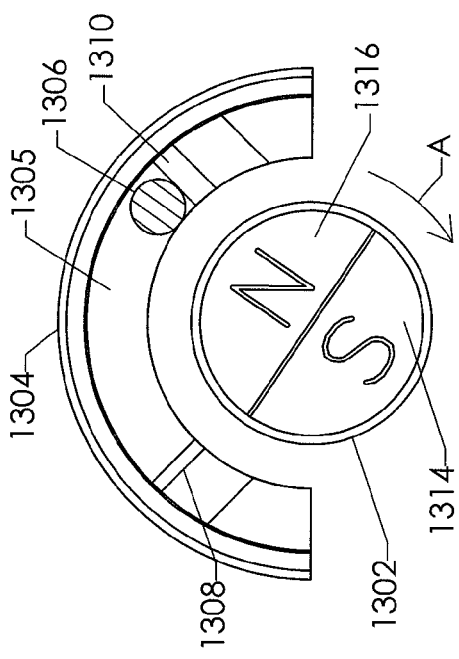
Figure 86:
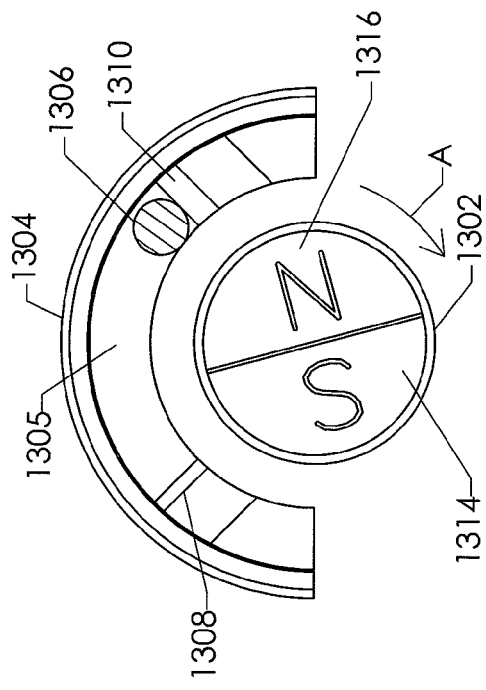
Figure 87:
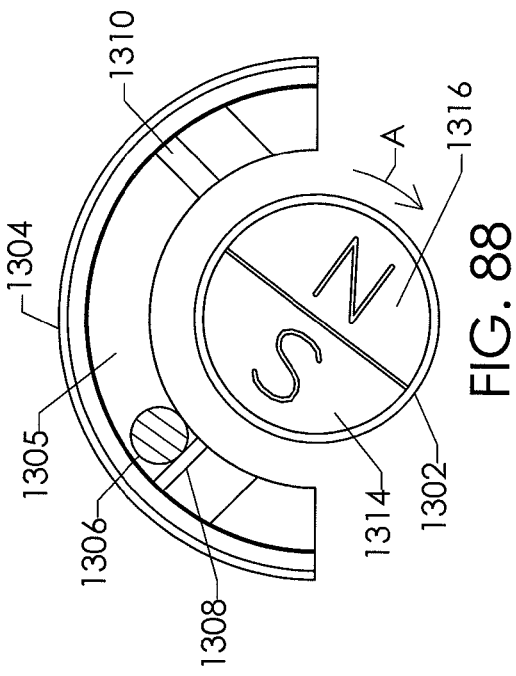
Figure 88:
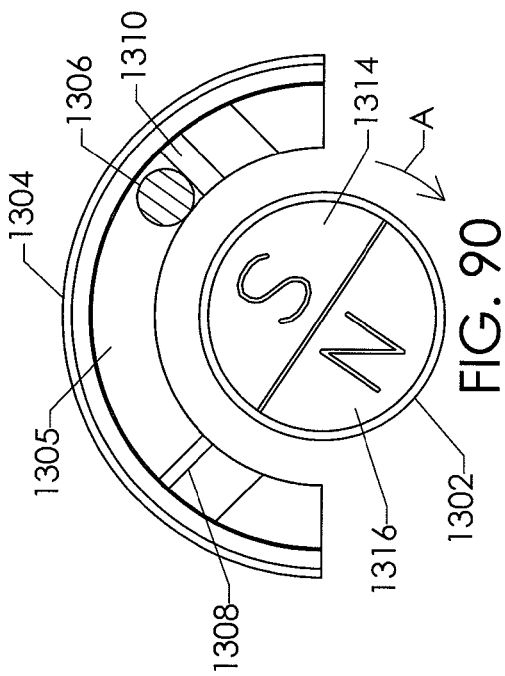
Figure 89:
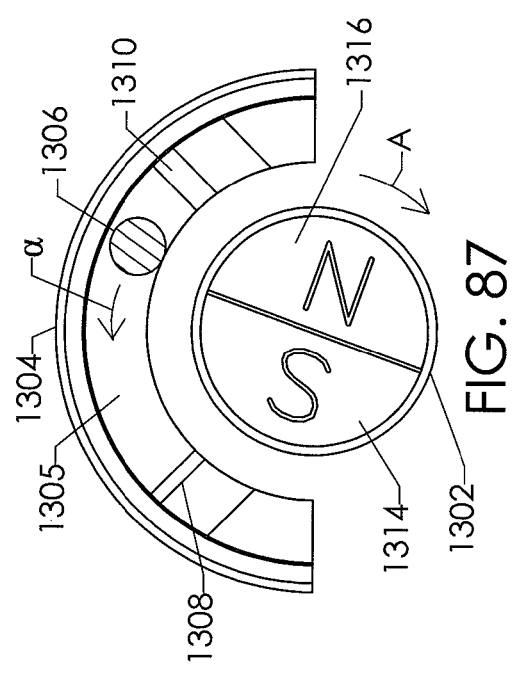
Figure 90:
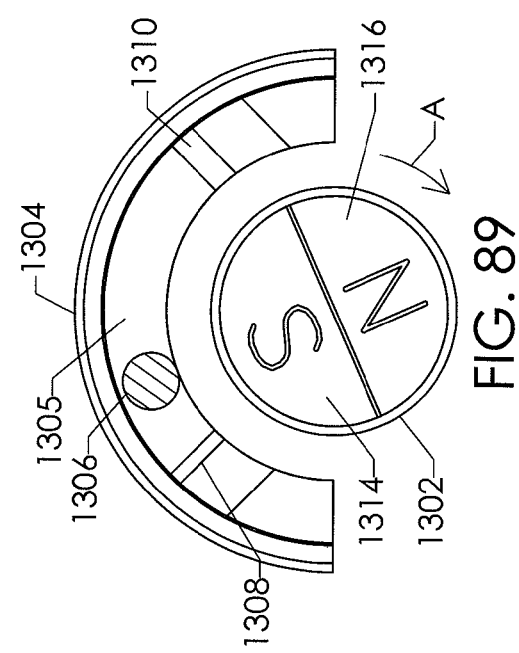

The magnetic ball 1306 is made from a magnetic material, for example 400 series stainless steel. The magnetic ball 1306 is attracted to both the south pole 1314 of the driven magnet 1302 and the north pole 1316 of the driven magnet 1302. As seen in FIG. 83, the driven magnet 1302 begins to rotate in the clockwise direction (arrow A). As pictured, the starting point of the magnetic ball 1306 is adjacent to the north pole 1316 of the magnet 1302. As seen in FIG. 84, as the magnet 1302 rotates, the magnetic ball 1306 follows the north pole 1316. This continues until, as shown in FIG. 85, the magnetic ball 1306 is stopped by the second impact surface 1310. Now, as seen in FIG. 86, the magnetic ball 1306 is trapped against the second impact surface 1310, while the driven magnet 1302 continues to rotate. The magnetic ball 1306 may roll at this point, but it is forced against the second impact surface 1310 by its attraction to the north pole 1316 of the magnet 1302, until the south pole 1314 becomes substantially closer to the magnetic ball 1306 as shown in FIG. 87, at which point the magnetic ball 1306 accelerates towards the first impact surface 1308 in the direction of arrow a, thereby hitting it (as seen in FIG. 88) and creating an acoustic signal or sound having a greater intensity than when the magnetic ball 1306 was stopped by the second impact surface 1310. Now, as the driven magnet 1302 continues to turn, the magnetic ball 1306 follows the south pole 1314 of the driven magnet 1302 as seen in FIG. 89, and continues to follow the south pole 1314 until the magnetic ball 1306 is stopped by the second impact surface 1310 as seen in FIG. 90.

Figure 95:
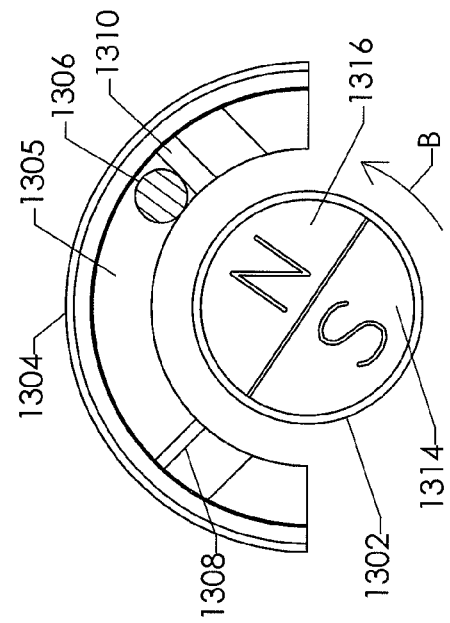
Figure 96:
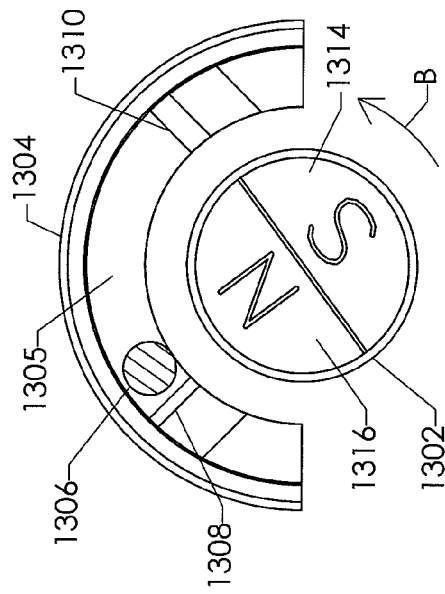
Figure 97:
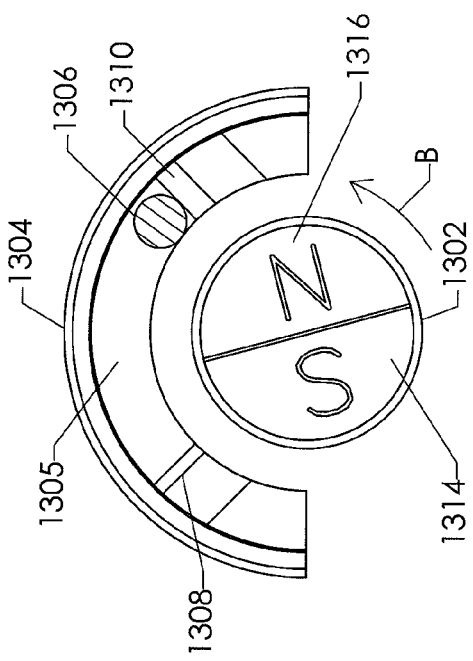
Figure 98:
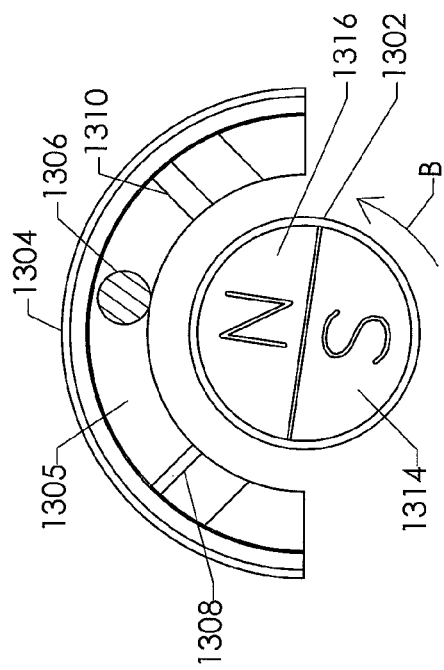

FIGS. 91-98 illustrate the acoustic mechanism being activated by counter-clockwise rotation of the driven magnet 1302. In this process, the first impact surface 1308 serves to stop the magnetic ball 1306, and the magnetic ball 1306 accelerates and impacts the second impact surface 1310, creating a different acoustic signal. For example, the different acoustic signal may include a louder signal or a signal with a different frequency (e.g., pitch). In FIG. 91, the driven magnet 1302 begins to rotate in the counter-clockwise direction (arrow B). As illustrated, the starting point of the magnetic ball 1306 is adjacent the south pole 1314 of the magnet 1302. As seen in FIG. 92, as the magnet 1302 rotates, the magnetic ball 1306 follows the south pole 1314. This continues until, as shown in FIG. 93, the magnetic ball 1306 is stopped by the first impact surface 1308. As seen in FIG. 93, the magnetic ball 1306 is trapped against the first impact surface 1308, while the driven magnet 1302 continues to rotate. The magnetic ball 1306 may roll at this point, but it is forced against the first impact surface 1308 by its attraction to the south pole 1314 of the magnet 1302, until the north pole 1316 becomes closer to the magnetic ball 1306 as shown in FIG. 94, at which point the magnetic ball 1306 accelerates towards the second impact plate 1310 in the direction of arrow β, thereby hitting it (as seen in FIG. 95) and creating an acoustic signal or sound having a greater intensity than when the magnetic ball 1306 was stopped by the first impact surface 1308. Now, as the magnet 1302 continues to turn, the magnetic ball 1306 follows the north pole 1316 of the magnet 1302 as seen in FIG. 97, and continues to follow the north pole 1316 until the magnetic ball 1306 is stopped by the first impact surface 1308 as illustrated in FIG. 98.

It can be appreciated that each turn of the magnet 1302 creates two (2) relatively loud strikes, which can be detected by a non-invasive, external device comprising a sonic sensor, for example, a microphone (e.g., sensor 1084 in FIG. 76). If, for example, the magnet 1302 is turning a 0-80 lead screw (e.g., 1052, 1112) to tighten the restriction device (1002, 1102), then each turn represents ⅛₀ of an inch in the change of circumference, and thus each half turn represents ¹⁄₁₆₀ of an inch, or 0.00625". By dividing by PI this represents 0.002" diametrical change of the restriction device (1002, 1102) per half turn, or 0.05 mm. This is even less than the expected precision needed for operation, which is believed to be around 0.2 mm.

It can also be appreciated that the acoustic signal or sound made by the strike due to the acceleration of the magnetic ball 1306 against the first impact surface 1308 during clockwise rotation of the magnet 1302 will contain a different frequency spectrum than the acoustic signal or sound made by the strike due to the acceleration of the magnetic ball 1306 against the second impact surface 1310 during counter-clockwise rotation of the magnet 1302. The mount 1300 thus provides a relatively simple, low-cost device in which the direction of the rotation (i.e., increasing diameter vs. decreasing diameter) can be automatically identified. Further, the mount 1300 is able to determine the exact number of half rotations in each direction.

The mount 1300 may be operatively integrated with a programmable logic controller (PLC) such as the PLC 1080 described herein. In this regard, the exact diameter of the restriction device 1002, 1102 can be determined. The PLC 1080 is be able to identify the direction of rotation via the frequency of sound, and then change the direction of rotation if this is not the desired direction. The PLC 1080 is also able to count the number of half rotations until amount of restriction is achieved. If there is any slip between the magnets 1134, 1136 of the external device 1130 and the driven magnet 1302, the PLC 1080 will not detect the acoustic signal and thus will not count these as rotations.

When the mount 1300 is implanted in a patient, the physician may be unaware of its orientation. Because of this, it is not known by the physician which direction of rotation of the external device magnets will cause tightening and which will cause loosening. The PLC 1080, however, will be able to immediately identify the correct direction of rotation by the detected frequency.

Figure 99:
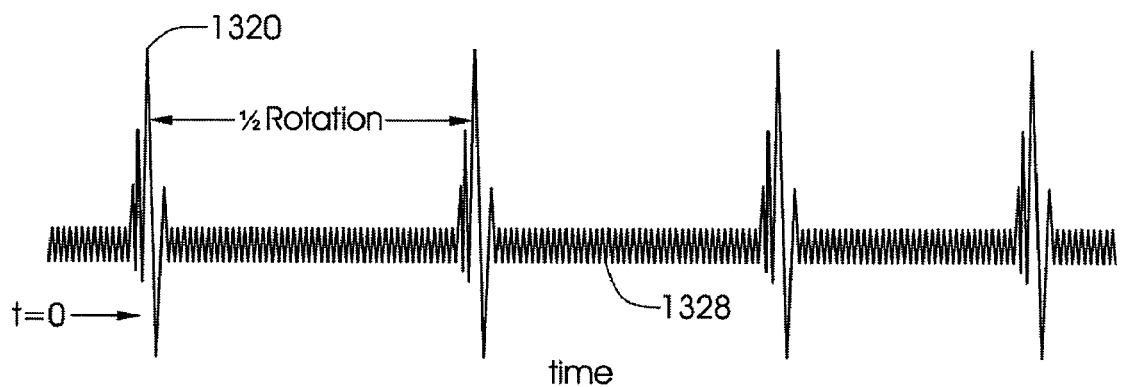
FIG. 99 illustrates the acoustic signal as a function of time of a coupler having an acoustic or sonic housing that contains a magnetic ball. Peaks are seen every ½ rotation of the driven magnet in the counter-clockwise direction.
Figure 100:
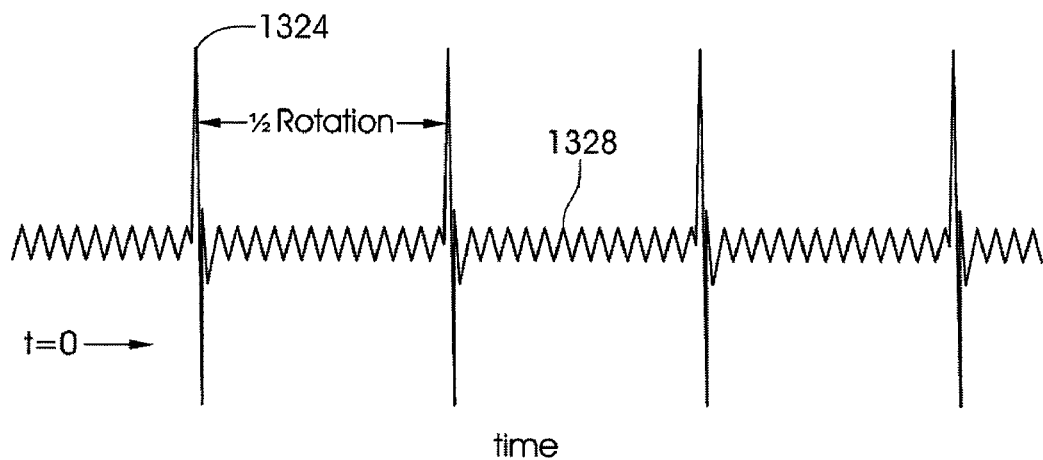
FIG. 100 illustrates the acoustic signal as a function of time of a coupler having an acoustic or sonic housing that contains a magnetic ball. Peaks are seen every ½ rotation of the driven magnet in the clockwise direction.
Figure 101:
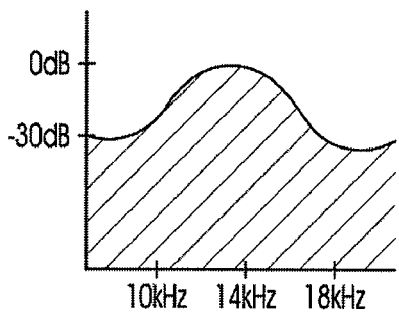
FIG. 101 illustrates the frequency response of the coupler of the type illustrated in FIG. 82 during counter-clockwise rotation of the driven magnet.
Figure 102:
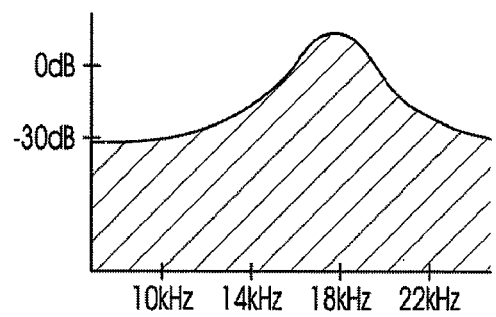
FIG. 102 illustrates the frequency response of the coupler of the type illustrated in FIG. 82 during clockwise rotation of the driven magnet.

For example, FIG. 99 illustrates the sound 1320 detected from counter-clockwise rotation of the magnet 1302 and FIG. 100 illustrates the sound 1324 detected from clockwise rotation. There may be additional background acoustic signals or noise 1328 created by, for example, the sound of the motor 1132 of the external device 1130. In both rotation directions, the acoustic "clicks" 1320 and 1324 look very similar to each other. However, by analyzing the frequency spectrum of the clicks, one is able to discern differences between clockwise and counter-clockwise rotation of the magnet 1302. As seen in FIG. 101, the frequency spectrum for the counter-clockwise rotation is centered at about 14 kHz, while the spectrum for clockwise rotation (FIG. 102) is centered at about 18 kHz. This shift or change in center frequency can be used as a basis for determining the absolute rotational direction of the magnet 1302.

Gastric restriction-based devices for obesity control are all currently placed with their interface portion located subcutaneously. Hydraulic-based gastric restriction devices have injection ports that are relatively large, and the method of placing these devices is usually one of the two following methods. The first method involves placing the entire device, with the exception of the port, through a 15 mm trocar into the insufflated abdominal cavity. The second method involves placing and then removing a 12 mm trocar and then placing the restriction device (without the port) into the abdominal cavity through the remaining tract in the tissue. In this second method, the 12 mm trocar is then replaced in order to maintain insufflation pressure. In both of these methods, however, an incision must be made in the skin near the trocar site in order to make a large enough passage through the skin for passage of the port. The fat is then separated from the fascia for a large enough area to allow the port to be secured to the fascia, usually with suture. The skin is then sutured to close the site. The various trocar sizes discussed herein refer to the commercial sizes of trocars used by physicians and surgeons. For example, a 12 mm trocar may have an OD that is greater than 12 mm but the trocar is still referred to as a "12 mm trocar."

In contrast to existing systems, the present obesity control system has a comparatively small overall cross-sectional diameter throughout its entire length, and the device has the option of being placed with the implantable interface located either in a subcutaneous position, or the entire device can be placed completely intra-abdominally. In either configuration, the relatively large incision heretofore required for the injection ports is not necessary. Because the entire device can fit down a 12 mm trocar, this incision is not required. The reason for the smaller overall cross-section diameter is multifold. First, the restriction device is non-inflatable, and thus it is does not require the space in the cross-section for the annular inflation lumen, nor the thick walls of the inflatable area necessary for resisting the stress due to the inflation pressure. In addition, the size of the magnet required to impart the necessary torque is significantly smaller than the inflation ports that are used with the hydraulic restriction device designs.

Figure 103:
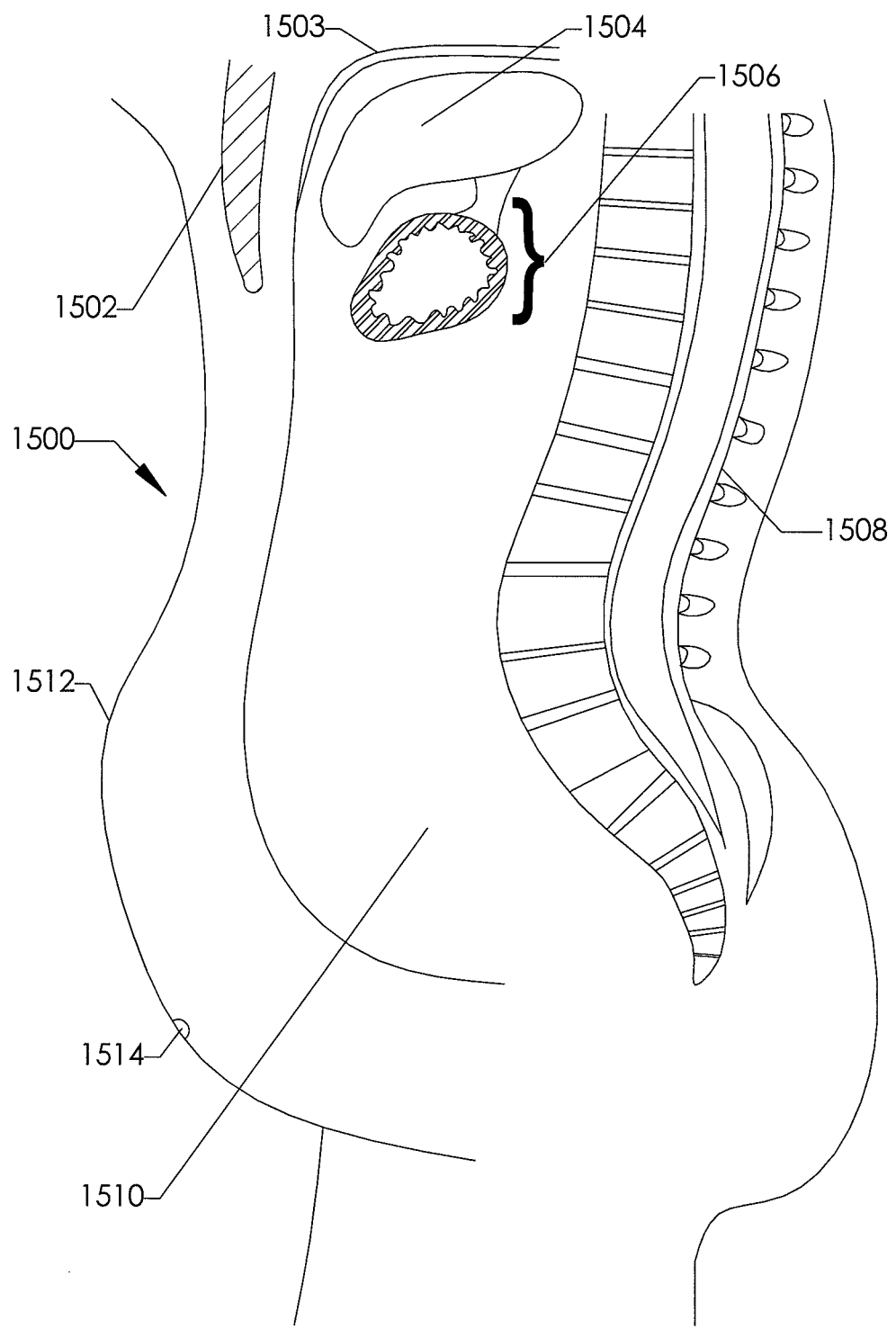
FIGS. 103-122 illustrate sagittal (i.e., lateral) sectional views of an obese patient illustrating various embodiments of laparoscopic implantation of an obesity control system.

FIG. 103 illustrates a sagittal (i.e., lateral) section of an obese patient 1500 prior to laparoscopic implantation of the inventive obesity control system. The abdominal cavity 1510 is located between the abdominal wall 1512 and the spine 1508. It should be noted that many of the major organs are not depicted for clarity sake. The stomach 1506 can be seen beneath the liver 1504. The sternum 1502 and diaphragm 1503 are also depicted, as is the naval 1514.

Figure 104:
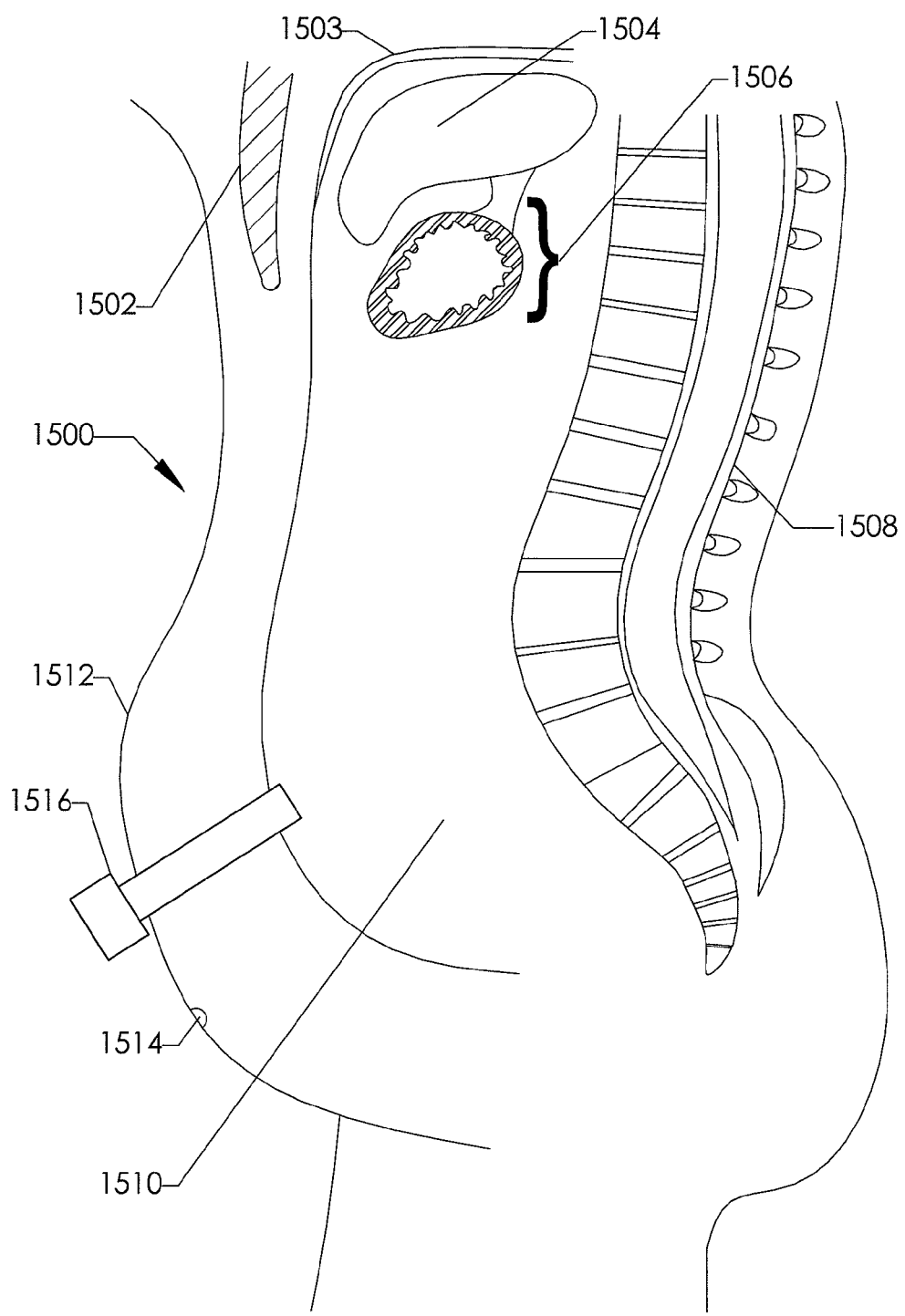
Figure 105:
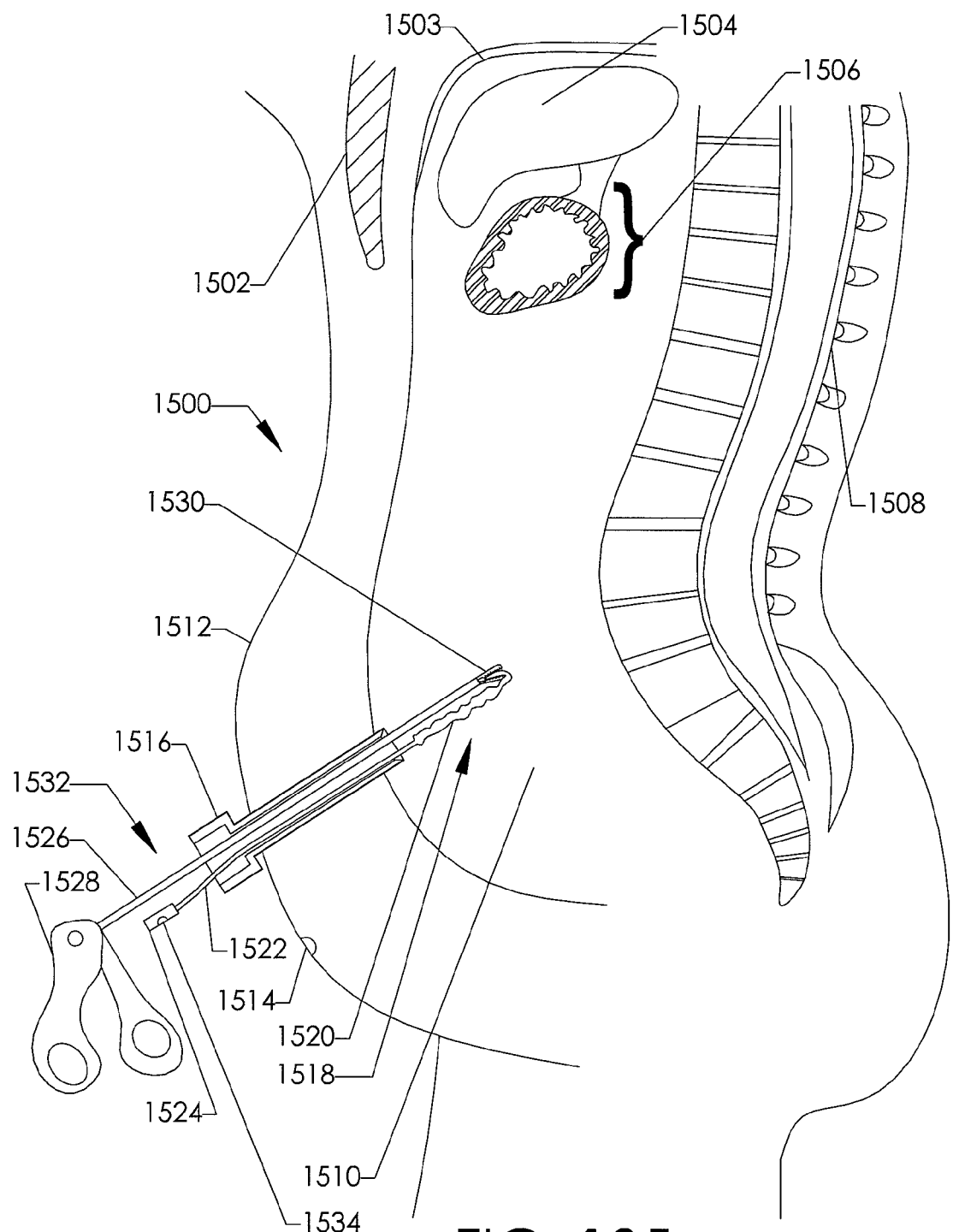

In FIG. 104 a 12 mm trocar 1516 is placed through the abdominal wall 1512, for example above the navel 1514, so that the tip of the trocar 1516 extends into the abdominal cavity 1510. Insufflation is then created, for example by injecting $CO_2$ through a Luer connection in the trocar 1516 at a pressure of 15 mm Hg. Insufflation of the body cavity allows for enough separation, such that other trocars may be safely placed and organs can be better identified. As seen in FIG. 105, the inventive obesity control system 1518, including restriction device 1520, implantable interface 1524 and drive transmission 1522 can be completely placed through the 12 mm trocar 1516 with the use of a 5 mm grasper 1532, which comprises a grasping tip 1530, a shaft 1526 and a handle 1528. The restriction device 1520 is grasped by the grasping tip 1530 of the 5 mm grasper 1532 and the obesity control system is placed into the abdominal cavity 1510.

Because of the small dimensions of the restriction device 1520 and drive transmission 1522, the shaft 1526 of the 5 mm grasper 1532 can be placed in parallel with the restriction device 1520 and drive transmission 1522, until the restriction device 1520 is located completely within the abdominal cavity 1510. The 5 mm grasper 1532 is then manipulated at the handle 1528 so that the grasping tip 1530 releases the restriction device 1520. The 5 mm grasper 1532 is then removed, and can be used to help push the implantable interface 1524 completely through the 12 mm trocar 1516. The implantable interface 1524 is depicted with foldable wings 1534 through which suture or other fasteners (such as helical coils) may be placed. The foldable nature of the wings 1534 allow the implantable interface 1524 to be placed completely through the trocar 1516. Alternatively, the implantable interface 1524 does not have foldable wings 1534, and instead has a separate bracket or mount which is configured for securing the implantable interface to the patient 1500.

Figure 106:
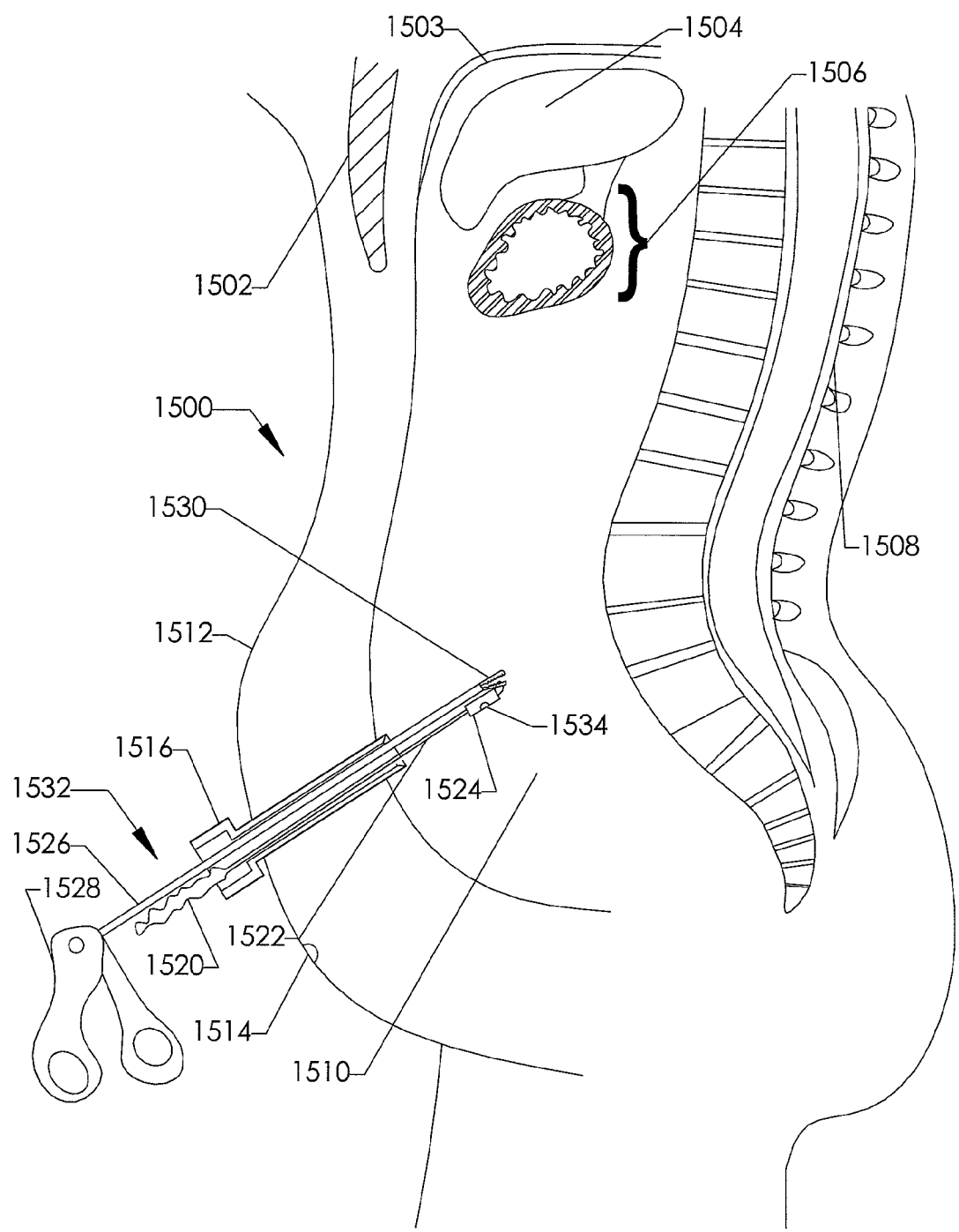

FIG. 106 depicts an alternative method of placing the obesity control system into the abdominal cavity. In this embodiment, the implantable interface 1524 is placed first, for example by pushing it through the 12 mm trocar 1516 with the 5 mm grasper 1532. The 5 mm grasper 1532 is then used to place the obesity control system into the abdominal cavity 1510 by manipulation of the drive transmission 1522 through the 12 mm trocar 1516. Once the obesity control system is placed in the abdominal cavity, the restriction device 1520 is placed around the stomach at the junction of the stomach and esophagus, and one or more gastrogastric sutures are placed to secure the stomach around the restriction device 1520.

Figure 107:
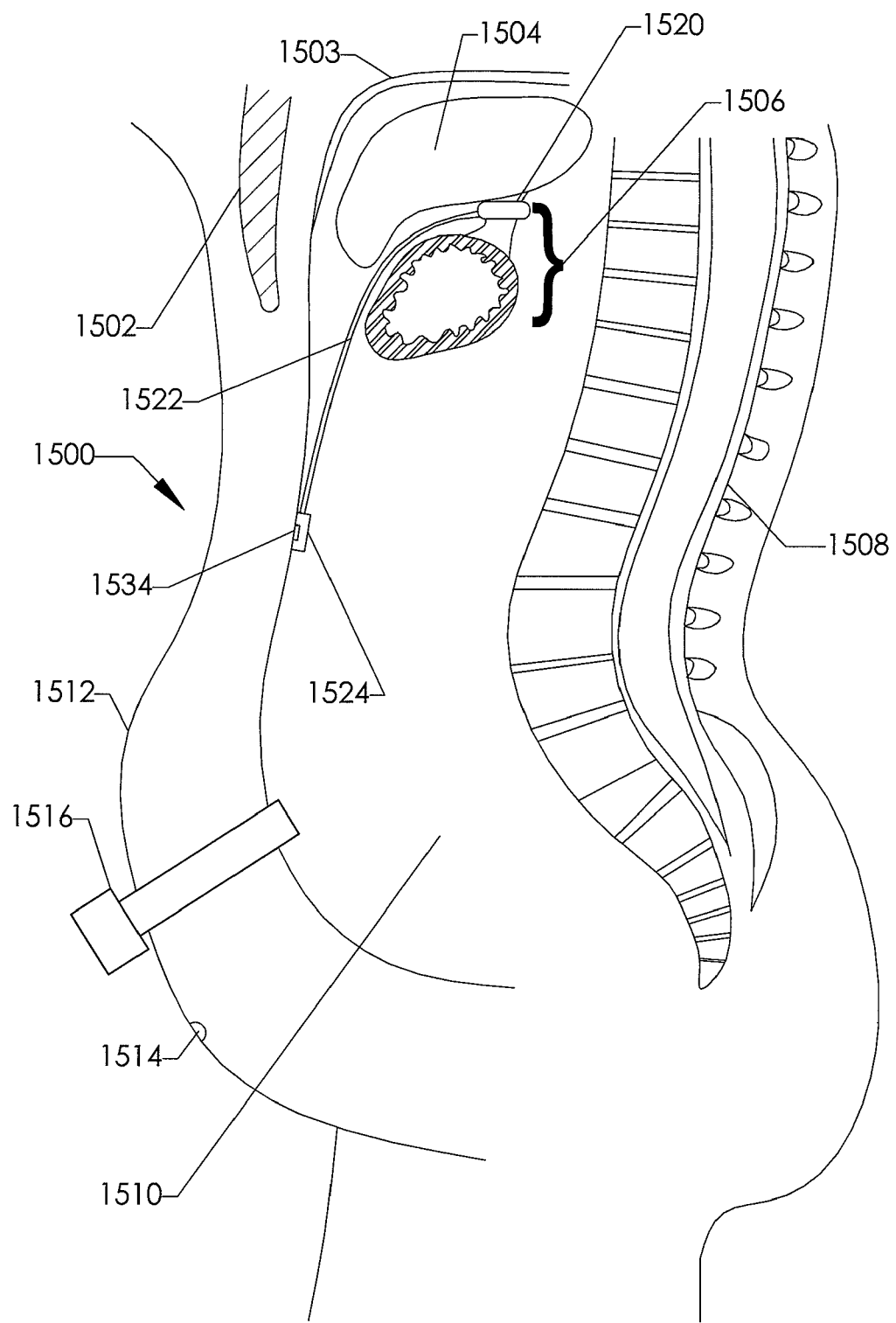
Figure 108:
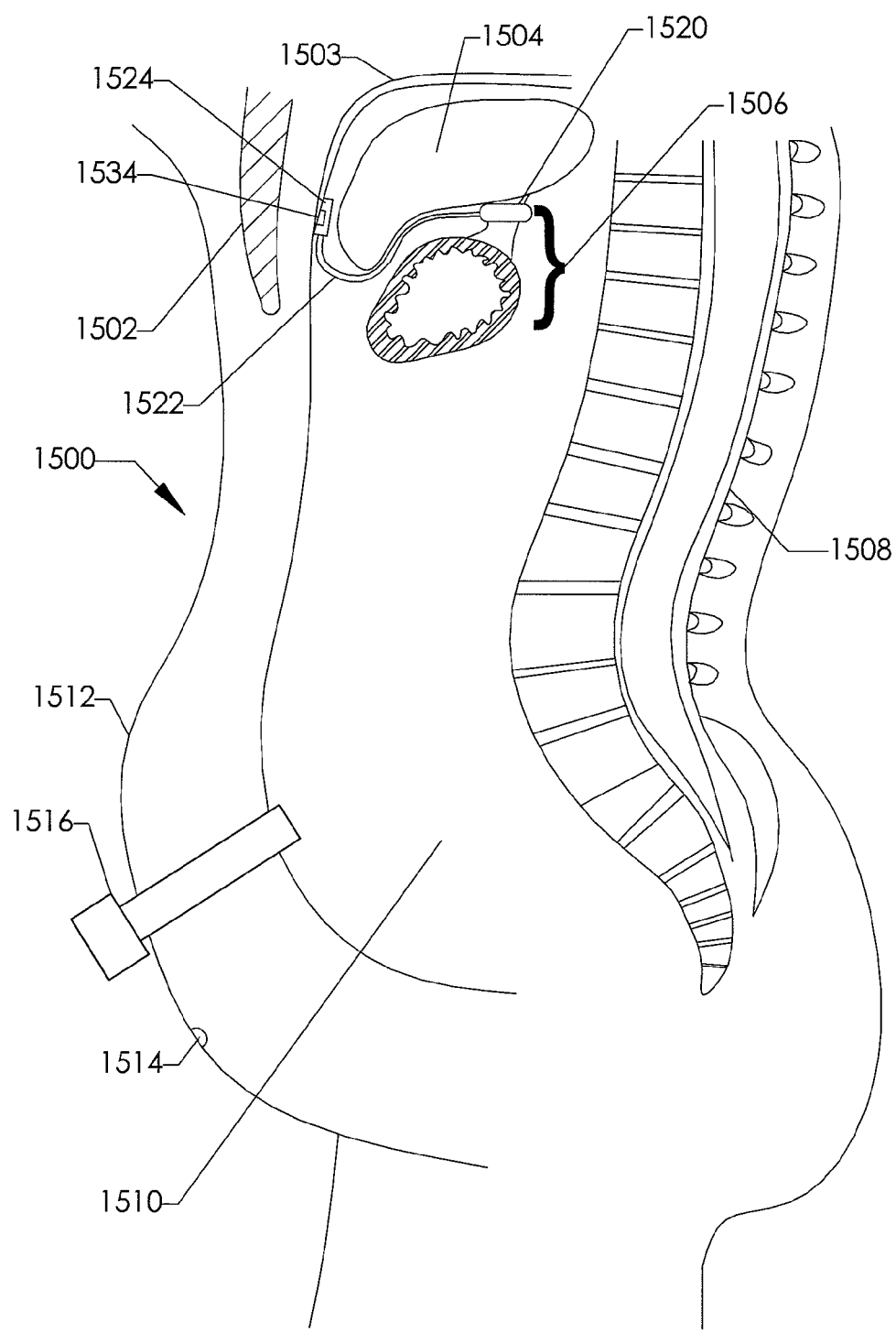

FIG. 107 depicts the obesity control system in position to be placed completely intra-abdominally in the patient 1500, with the implantable interface located in the lower abdominal area. FIG. 108 also depicts the obesity control system in position to be placed completely intra-abdominally, behind the lower portion of the sternum, and area known as xiphoid. Intra-abdominal placement has many advantages.

First, the patient will not be able to feel or be bothered by the implantable interface 1524, as they sometimes are in subcutaneous placements. Second, by securing the entire device intra-abdominally there is less time wasted manipulating the skin, fat, and fascia at the entry site and thus, a lower risk of infection. Third, it is possible to place the device with little or no incision at the skin because, as explained below, the attachment of the implantable interface 1524 intra-abdominally does not require a large surface area for manipulation from the outside.

Figure 109:
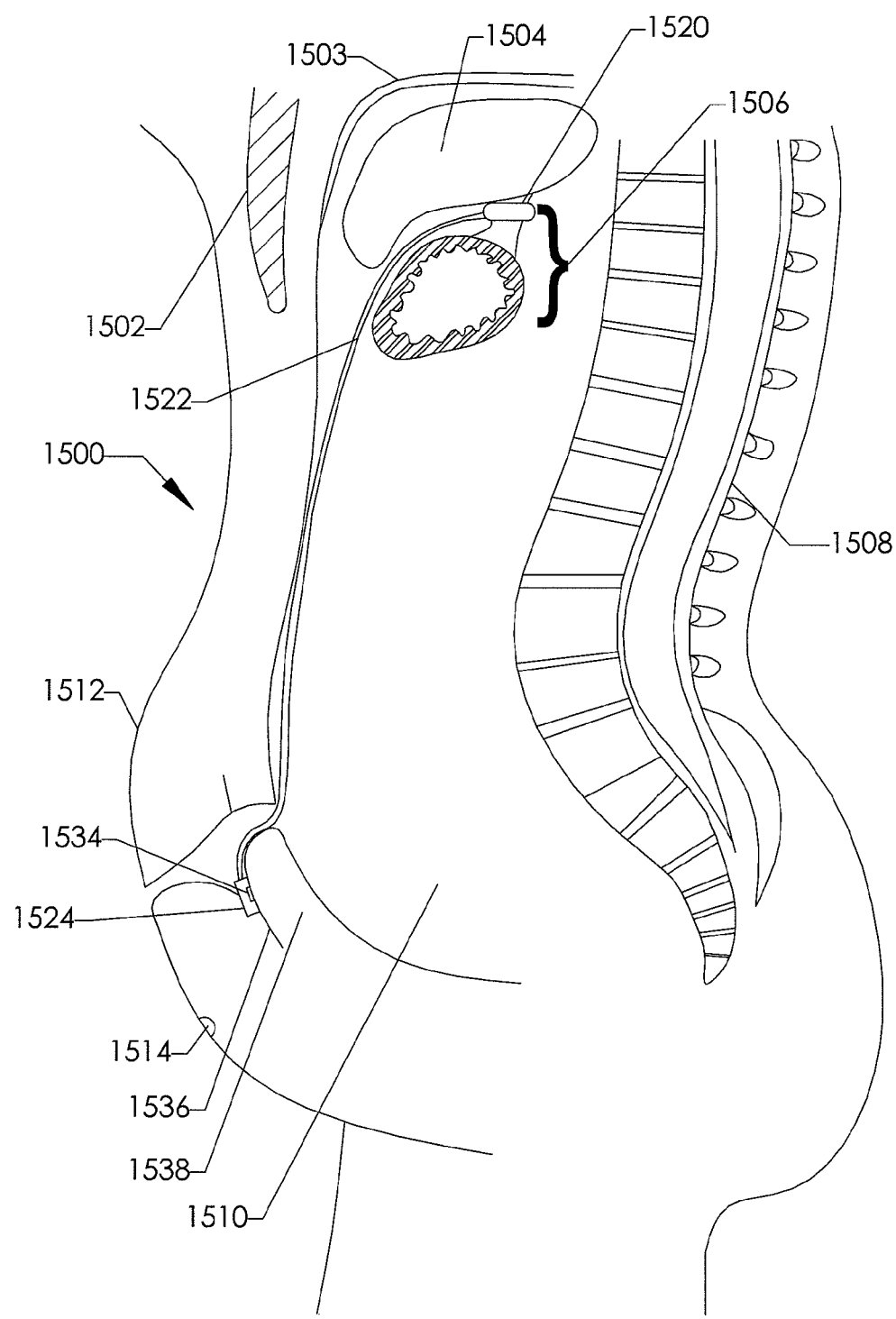
Figure 110:
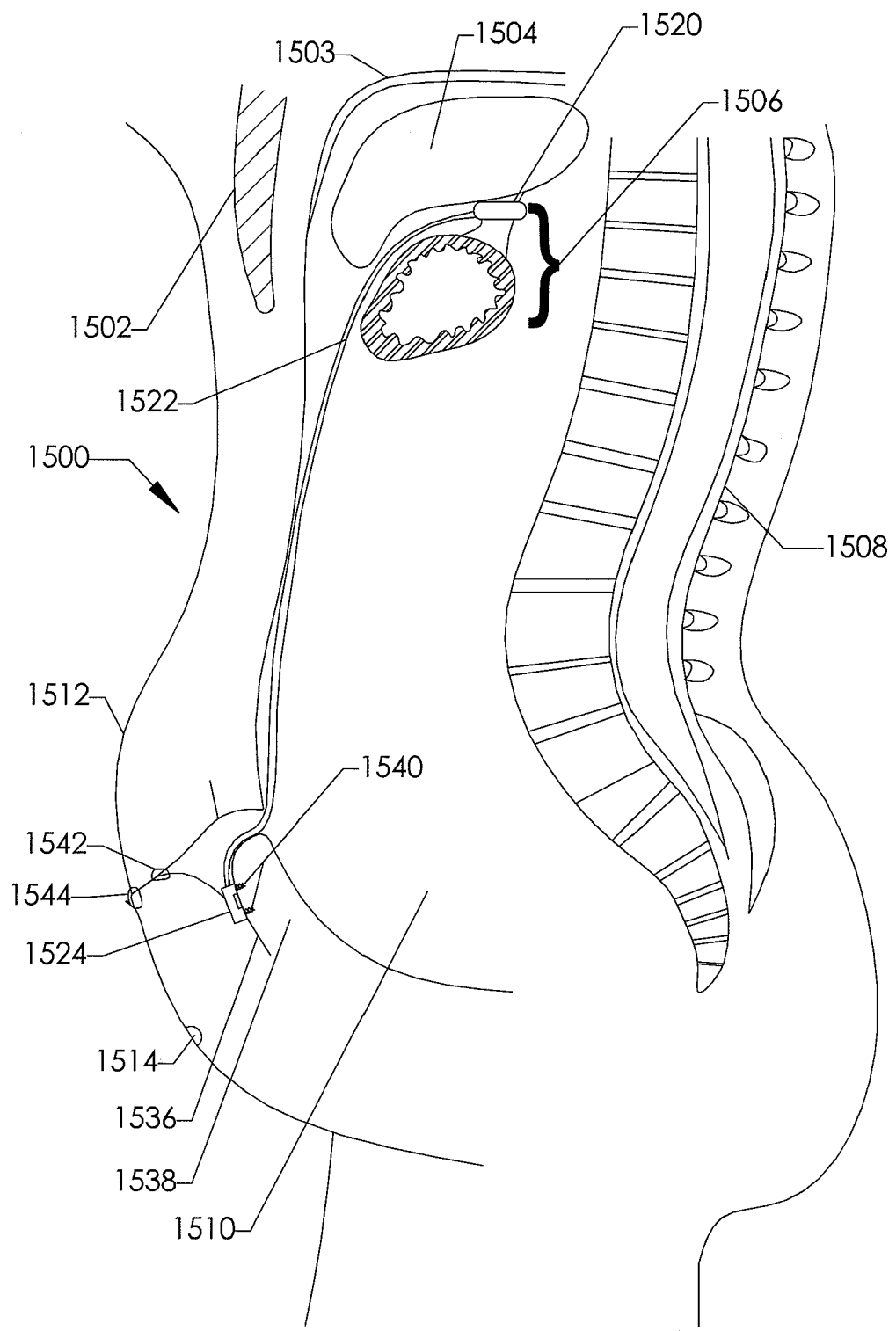

FIG. 109 demonstrates the configuration of an obesity control system that is placed when using the subcutaneous attachment of the implantable interface 1524. A tunnel is made in order to expose the fascia 1536 which covers the muscle 1538, and to which the implantable interface 1524 is attached. FIG. 110 depicts the obesity control system after it has been completely secured in the subcutaneous method. First and second sutures 1542, 1544 close the skin over the implantable interface 1524. In FIG. 110, the implantable interface 1524 has been attached to the fascia 1536 with helical screws 1540.

Figure 111:
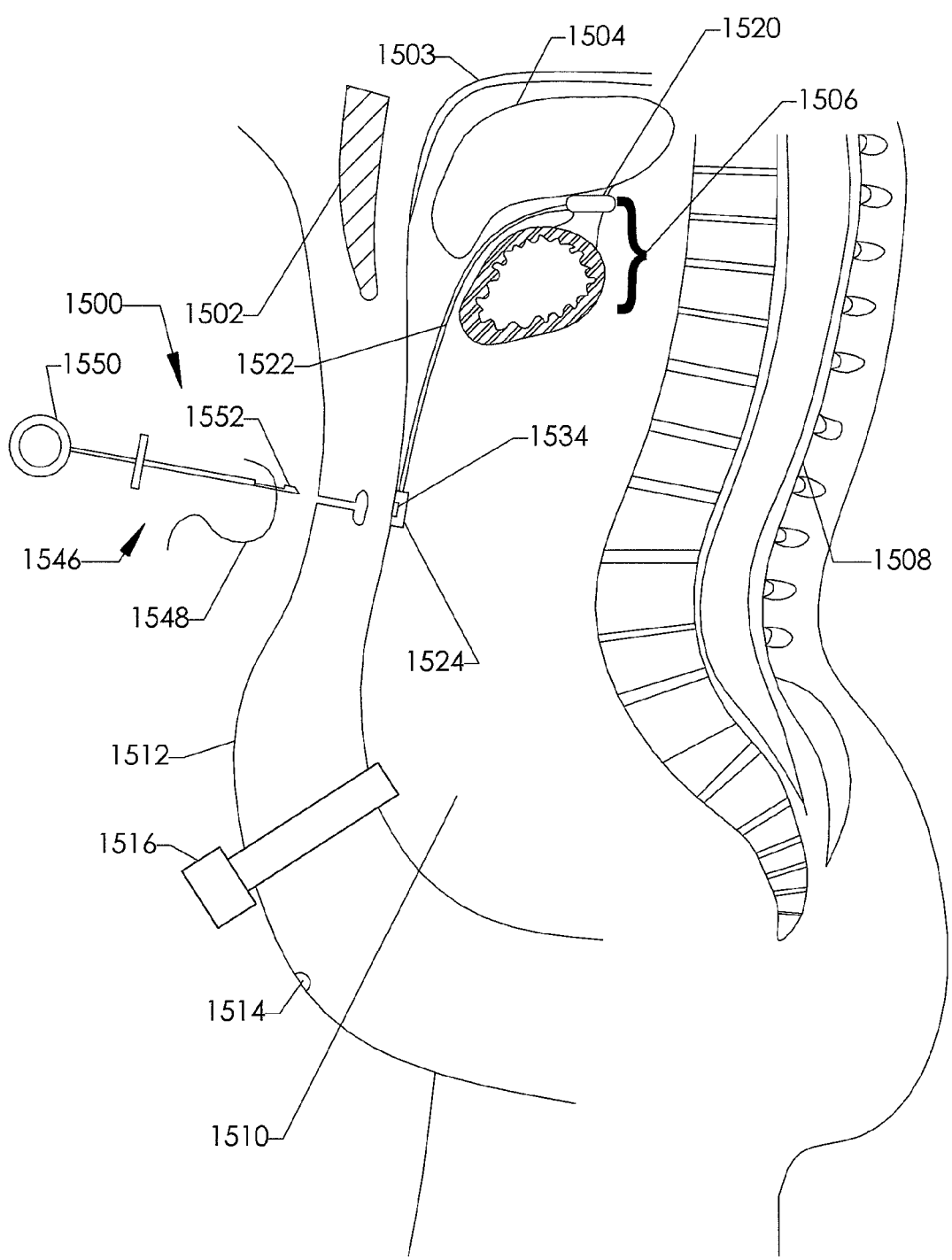
Figure 112:
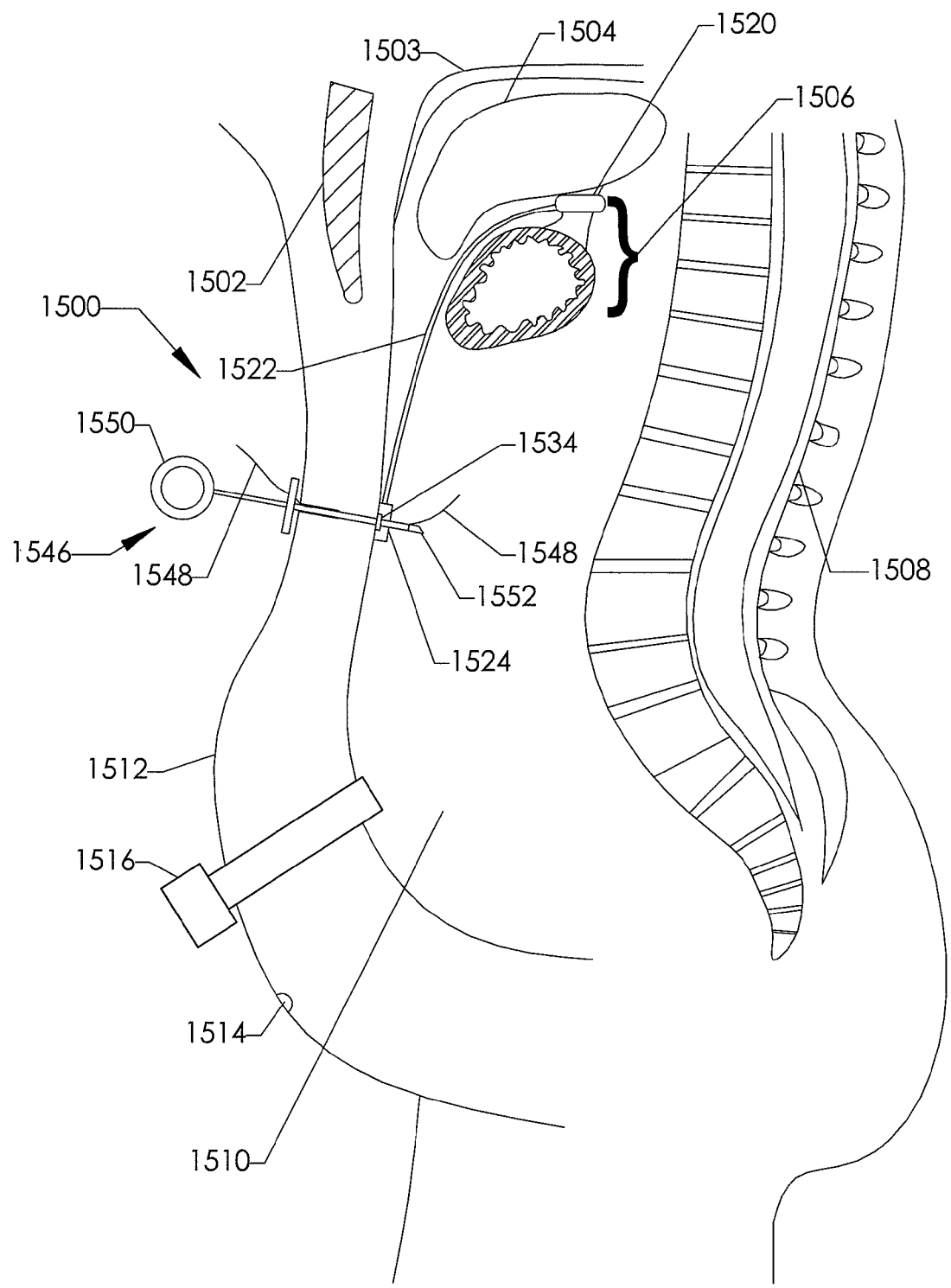

Returning to the embodiment that utilizes a completely intra-abdominal placement of the obesity control system, FIG. 111 depicts the use of a suture passer 1546 having an actuator handle 1550 and a grasping tip 1552 configured for securing suture 1548. The suture 1548 is grasped by the grasping tip 1552 via manipulation of the actuator handle 1550. The suture 1548 is then passed through a small opening in the skin (e.g., a trocar hole), and the sharp grasping tip 1552 of the suture passer 1546 is forced through the remaining abdominal wall and through a hole in the foldable wing 1534 of the implantable interface 1524 (as seen in FIG. 112).

Figure 113:
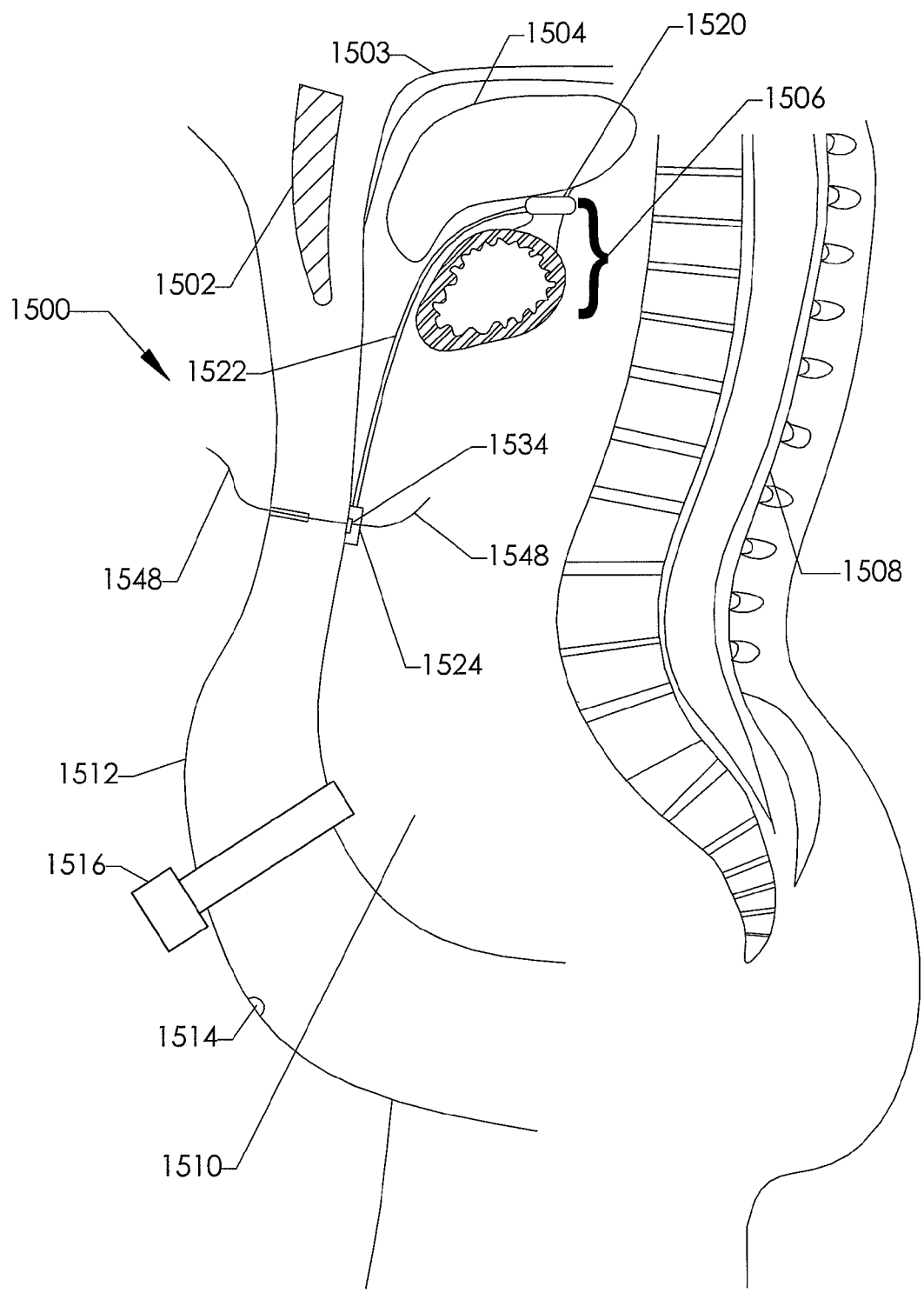
Figure 114:
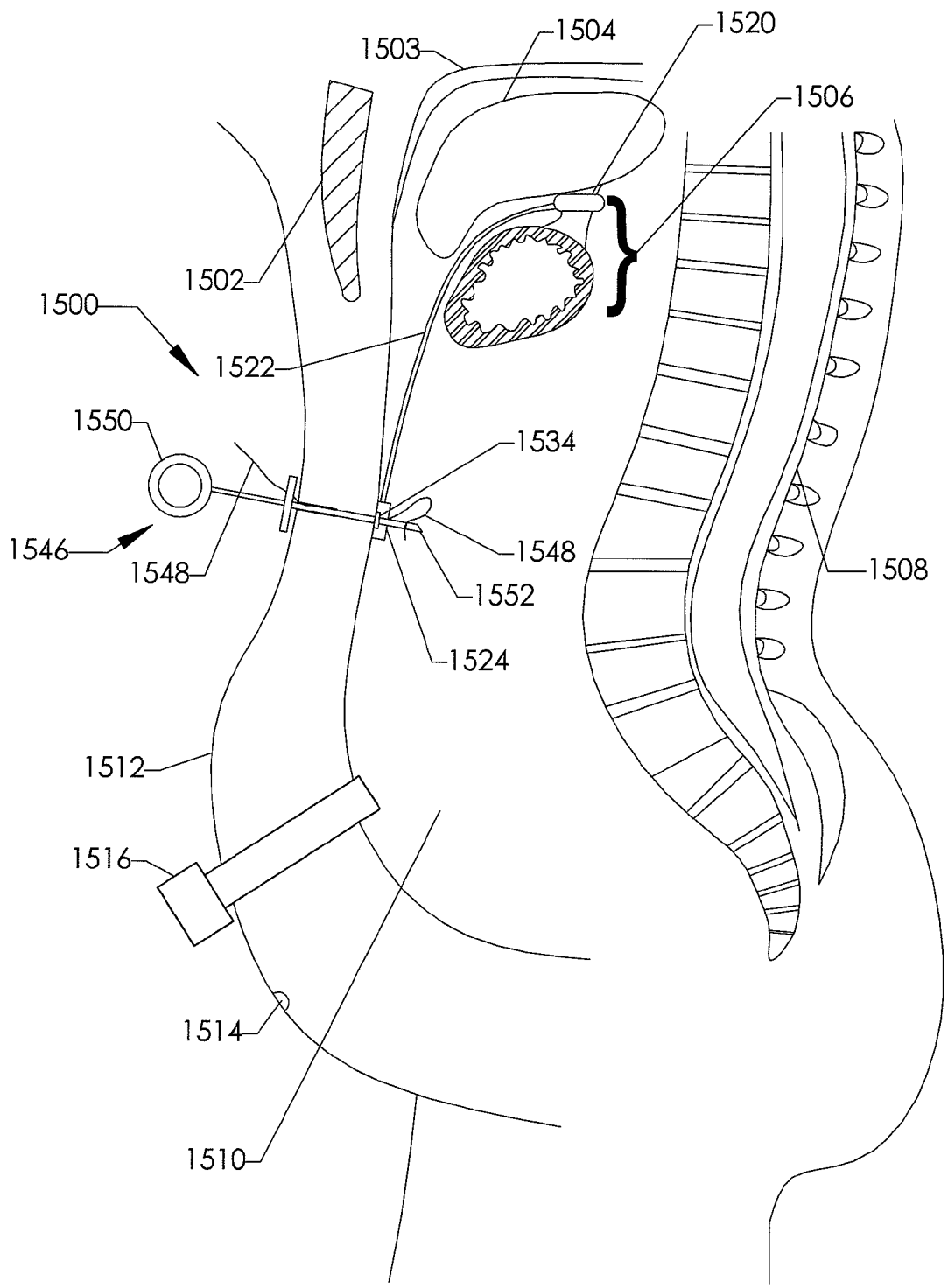
Figure 115:
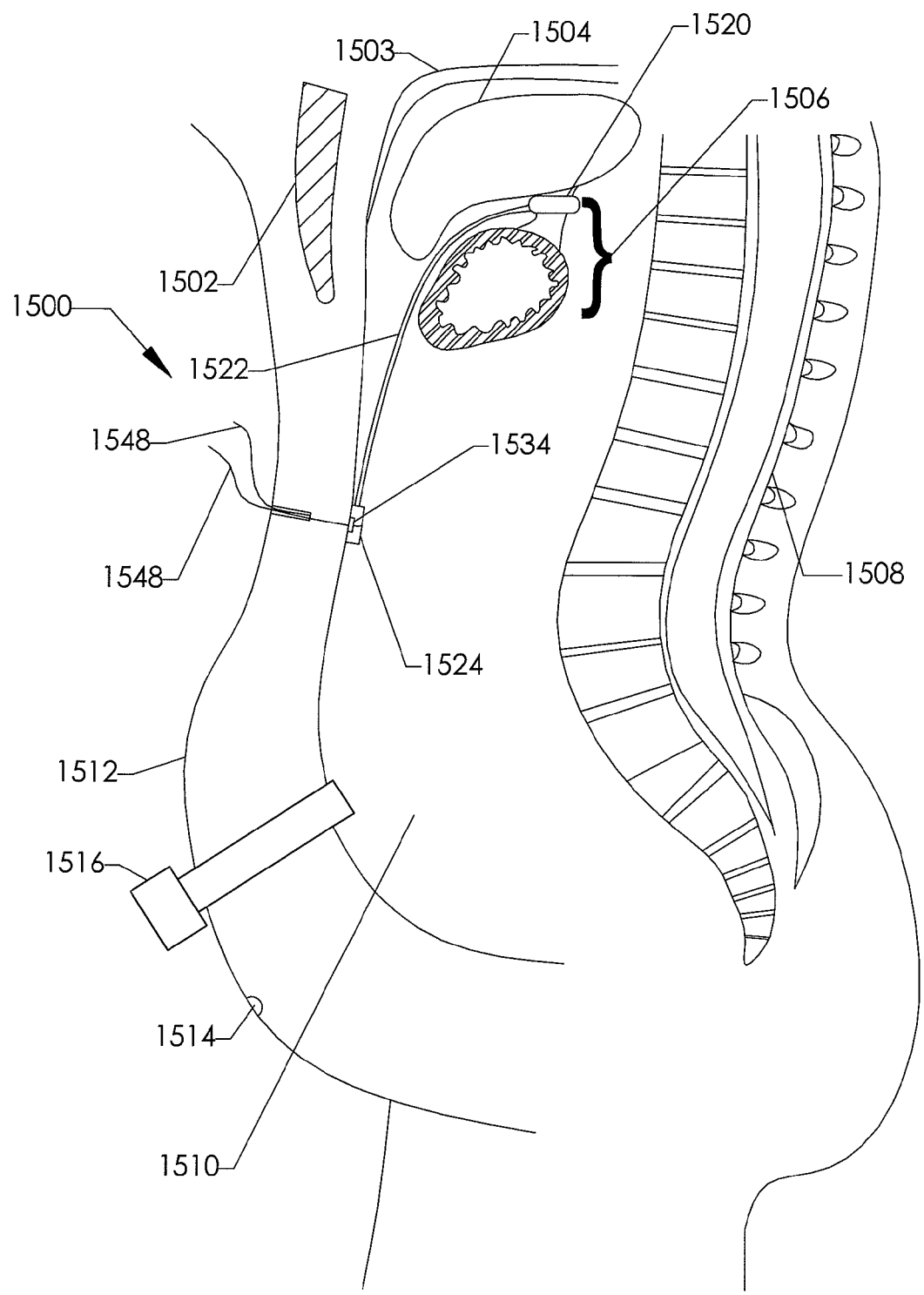
Figure 116:
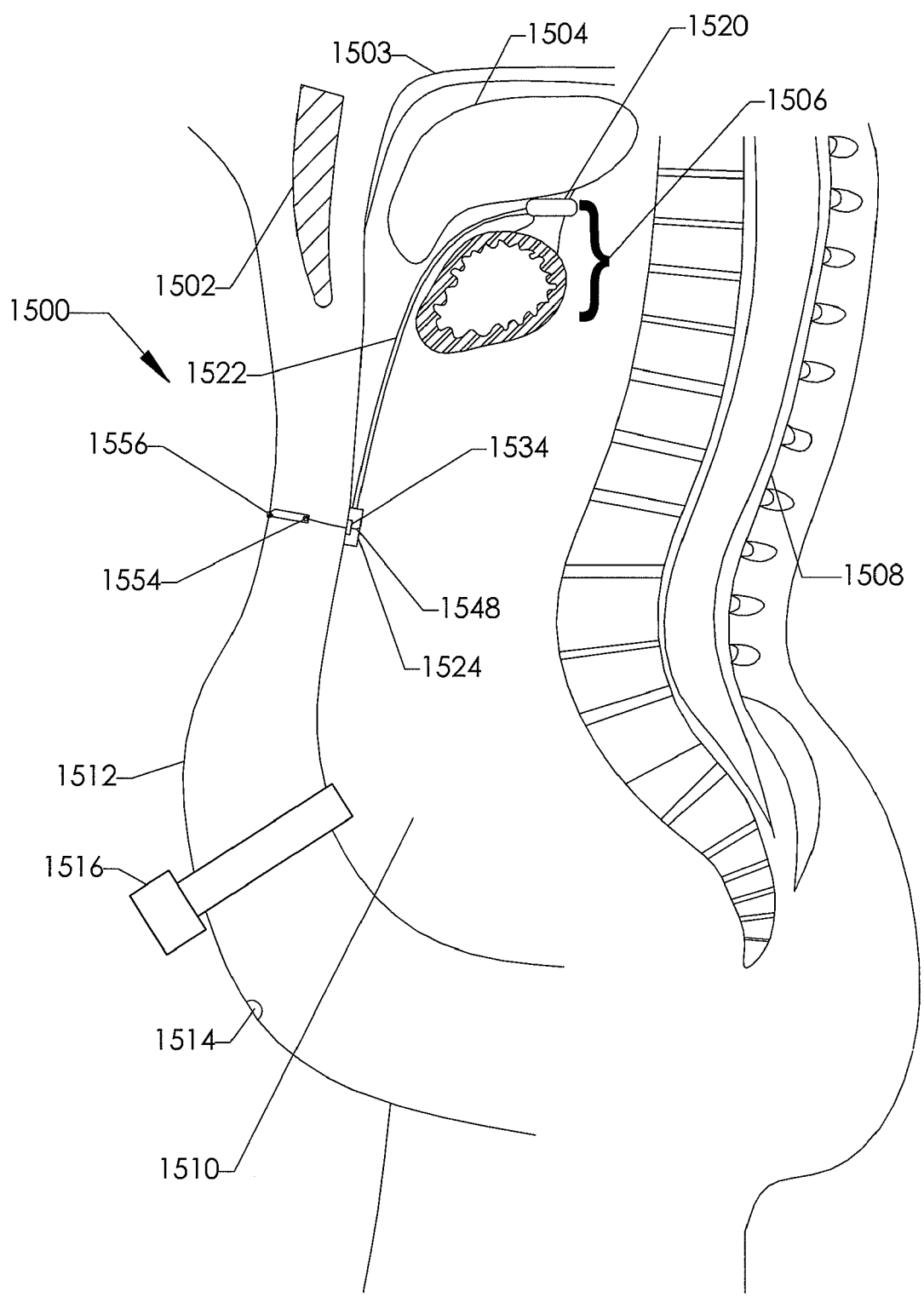

The implantable interface 1524 can be held stationary by using a separate grasper (not pictured). The suture 1548 is released, once it has passed through the hole in the foldable wing 1534 and into the abdominal cavity 1510. The suture passer 1546 is then removed and the suture is left in place as seen in FIG. 113. The suture passer 1546 is then inserted through the abdominal wall at another site and through another hole of a second foldable wing 1534. The suture 1548 is now grasped in the inside by the grasping tip 1552, as depicted in FIG. 114. This newly grasped end of the suture is then pulled back through the hole in the second foldable wing 1534 and then pulled out through the abdominal wall. The suture passes 1546 is now released from the suture 1548 via manipulation of the actuator handle 1550. The suture 1548 now loops into and out of the abdominal cavity and secures the implantable interface 1524 through two foldable wings 1534, as seen in FIG. 115. This may be repeated with other pieces of suture, for example if the implantable interface 1524 has four foldable wings 1534 instead of two. As shown in FIG. 116, the suture 1548 is then tied off in a knot 1554, to secure the implantable interface 1524 within the abdominal cavity, and the skin is closed with more suture 1556.

Figure 117:
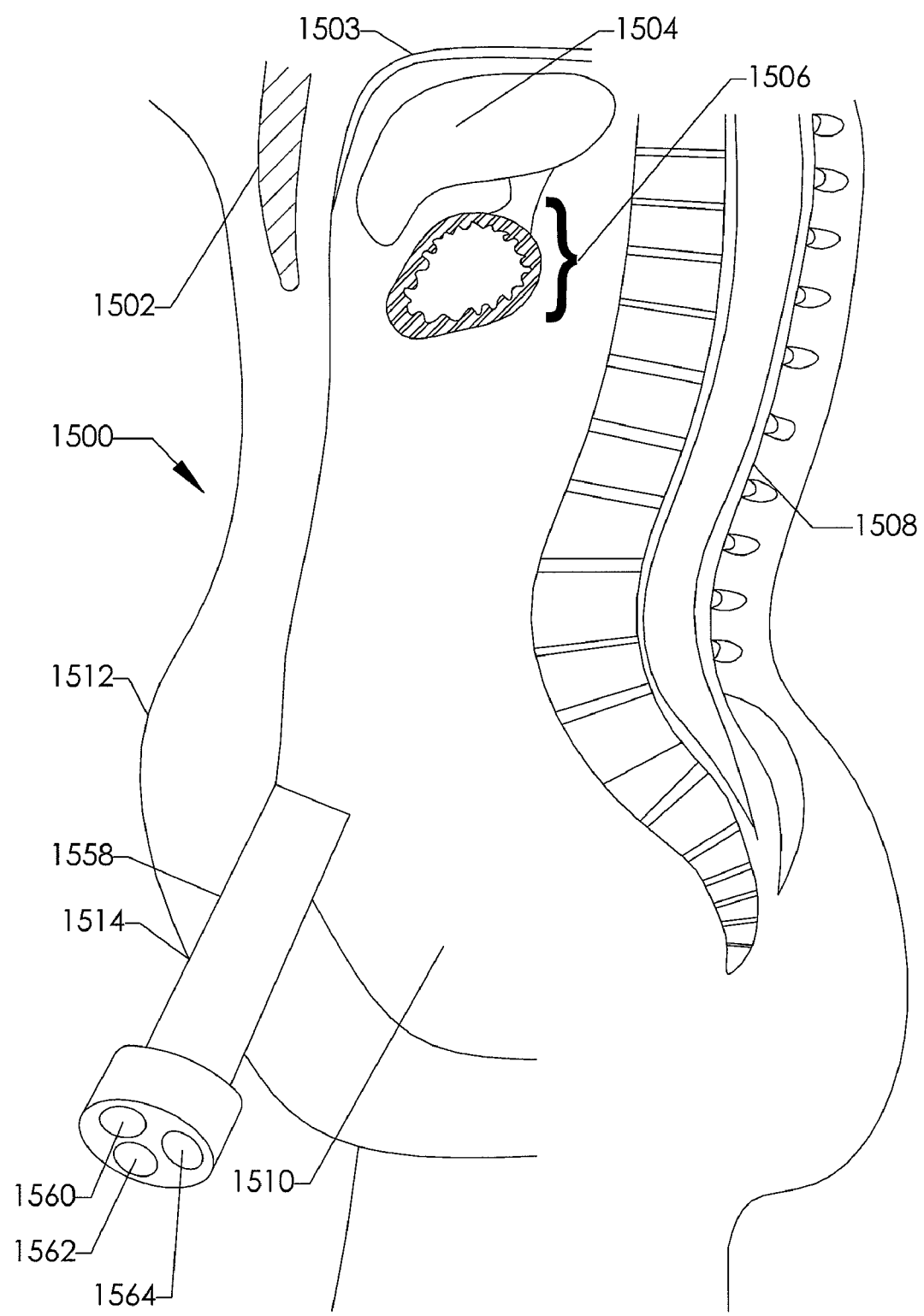

In the above-described subcutaneous and intra-abdominal methods for implanting and securing an obesity control system, it is common for there to be several 5 mm trocars in addition to the one 12 mm trocar depicted. For example, a 5 mm trocar for placing a liver retractor, and two or more other 5 mm trocars through which various surgical tools are placed (e.g., graspers, cutters, and cautery tools). FIG. 117 describes an alternative method of performing implantation and securement of an obesity control system, using a single trocar 1558. Trocars, unfortunately, can leave scars on the skin and can also cause port-surgical pain. Having a single trocar and thus single site or access passageway through the skin, will cause less scarring and less post-surgical pain. In additional, while this site may be located anywhere on the skin of the body (e.g., the abdominal wall), it may also be placed in the naval 1514 area, so that the scar is not noticeable. In addition, the single site may be chosen within the rectum or vagina, so that the scar does not show. These two sites allow access into the abdominal cavity, as does an additional site through the mouth and stomach. FIG. 117 depicts the single site as having been chosen through the naval 1514 general area although, as explained above, other site locations may also be used.

Figure 118:
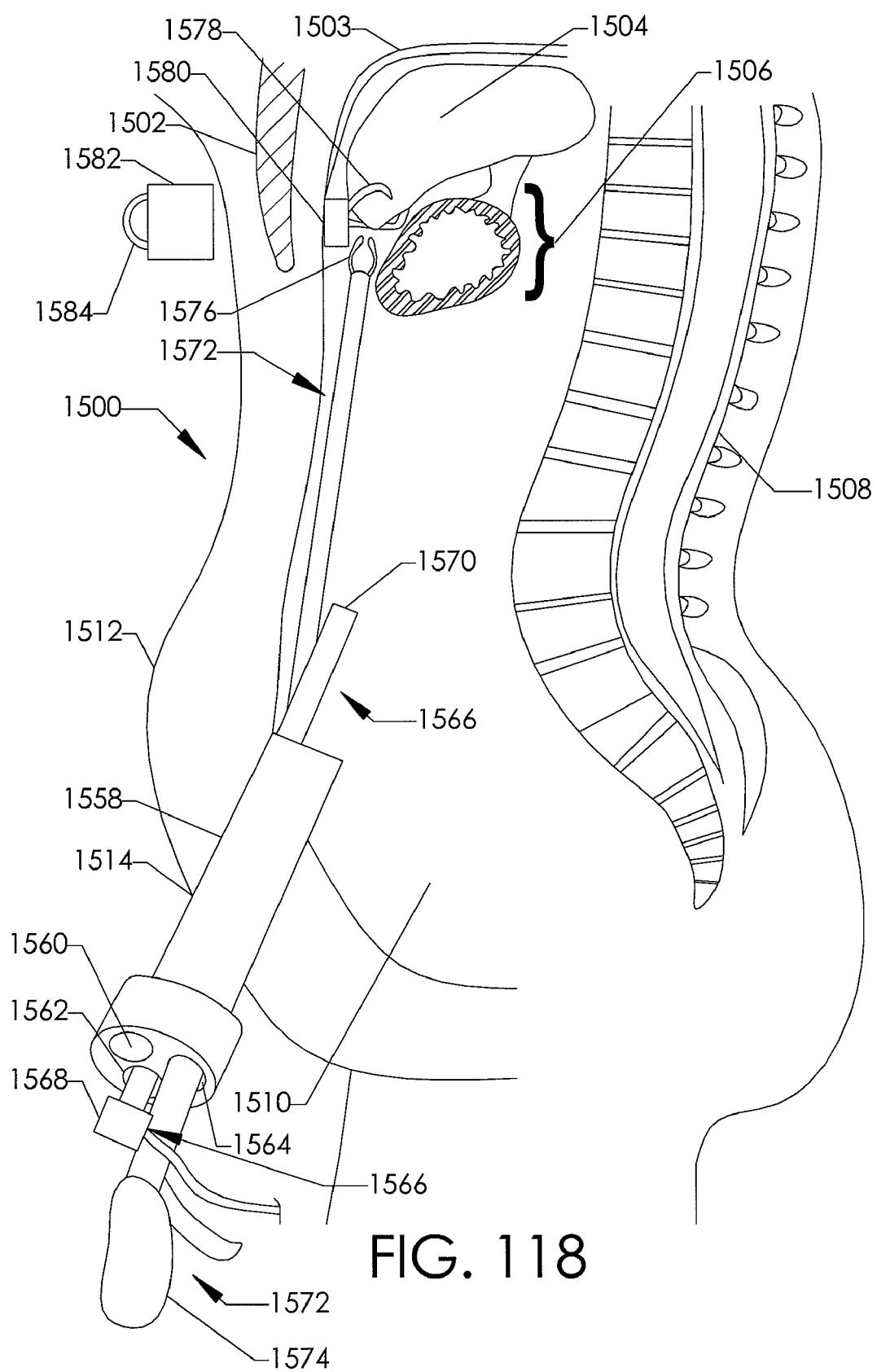

The single trocar 1558 has three (3) 5 mm lumens 1560, 1562, 1564. Turning to FIG. 118, a 5 mm laparoscope 1566 is placed through lumen 1562. The laparoscope 1566 comprises a distal end 1570 and a proximal end 1568, including a camera. A 5 mm grasper 1572 having a grasping tip 1576 and a manipulating handle 1574 is placed through lumen 1564 and into abdominal cavity 1510. The grasping tip 1576 of the 5 mm grasper 1572 carries a liver retraction magnet 1580 having clamp 1578 secured thereto. The 5 mm grasper 1572 is configured to grasp the clamp 1578 in a manner so that when the clamp 1578 and magnet 1580 are delivered to the liver 1504, the clamp 1578 is open.

Figure 119:
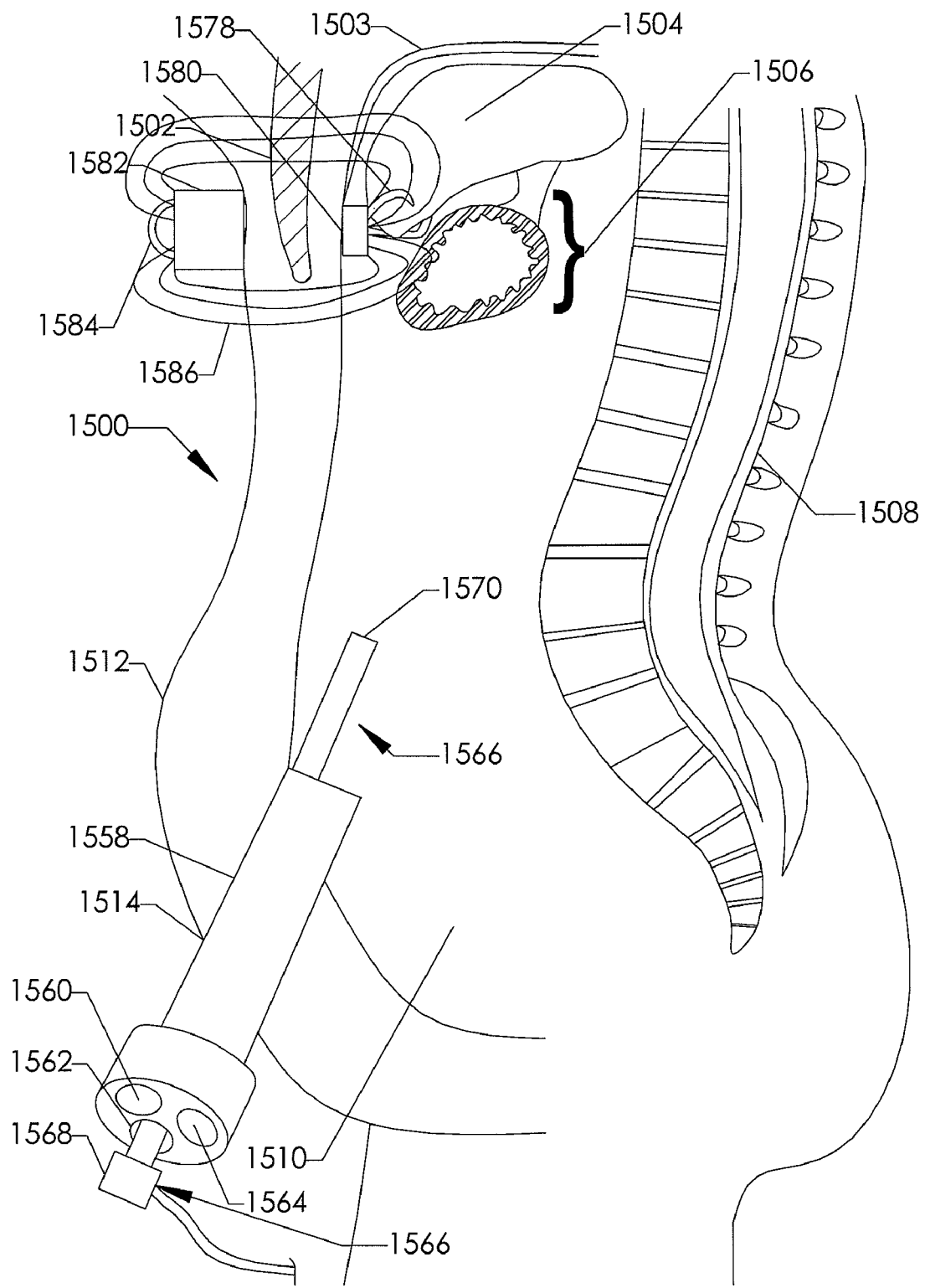

While viewing on laparoscopy, the clamp 1578 is released by the 5 mm grasper 1572, causing it to engage the liver 1504, securing the magnet 1580 to the liver 1504. The 5 mm grasper 1572 may also be used to retract the liver 1504 so that it is out-of-the-way from the surgical procedure in the area of the upper stomach. An external magnet 1582 having a handle 1584 is placed on the outside of the upper abdomen and an attraction force, shown be field 1586 in FIG. 119, maintains the external magnet 1582 and the magnet 1580 together. The liver 1504 is now retracted and the 5 mm grasper 1572 can be removed completely, or used for other purposes.

Figure 120:
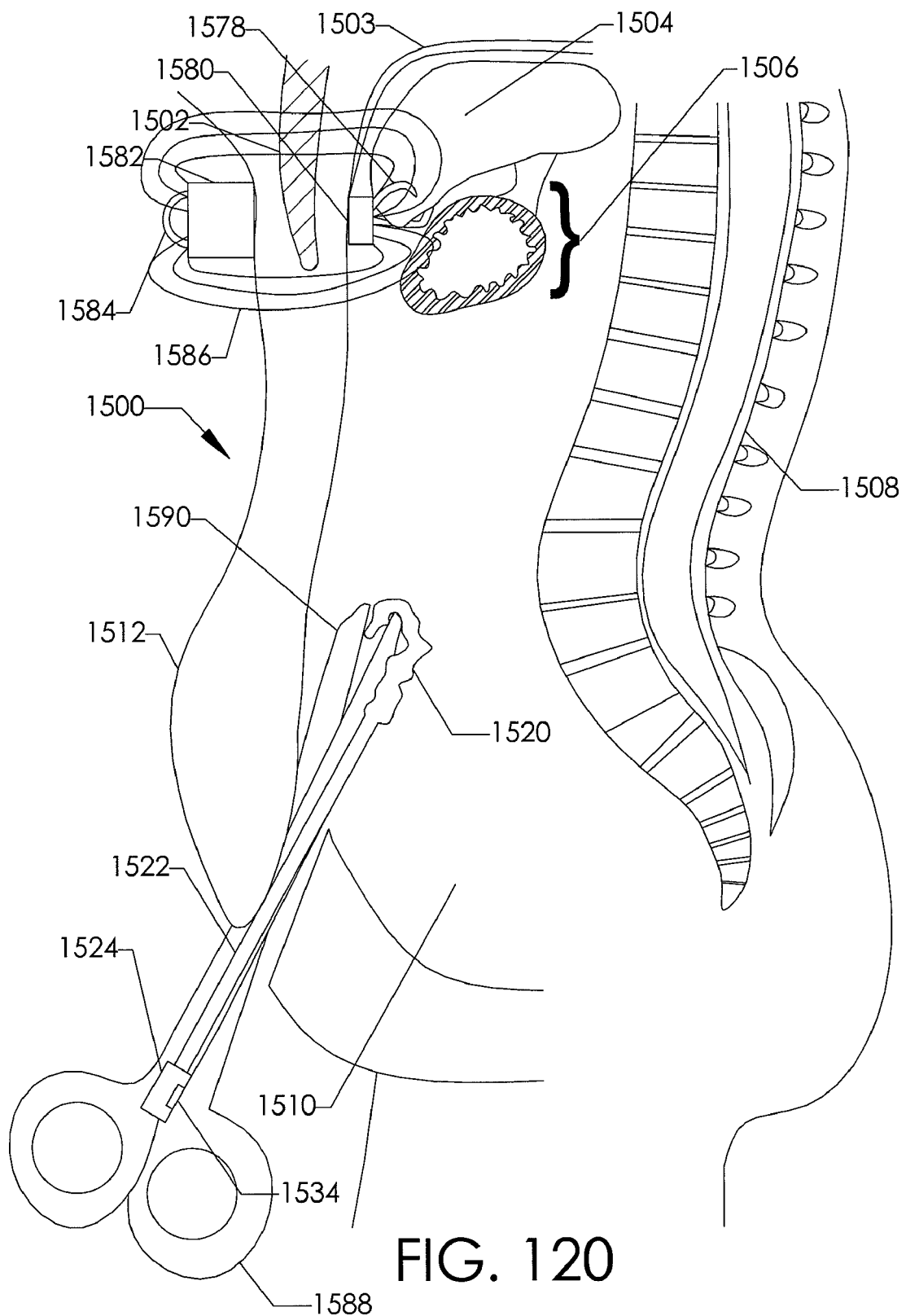
Figure 121:
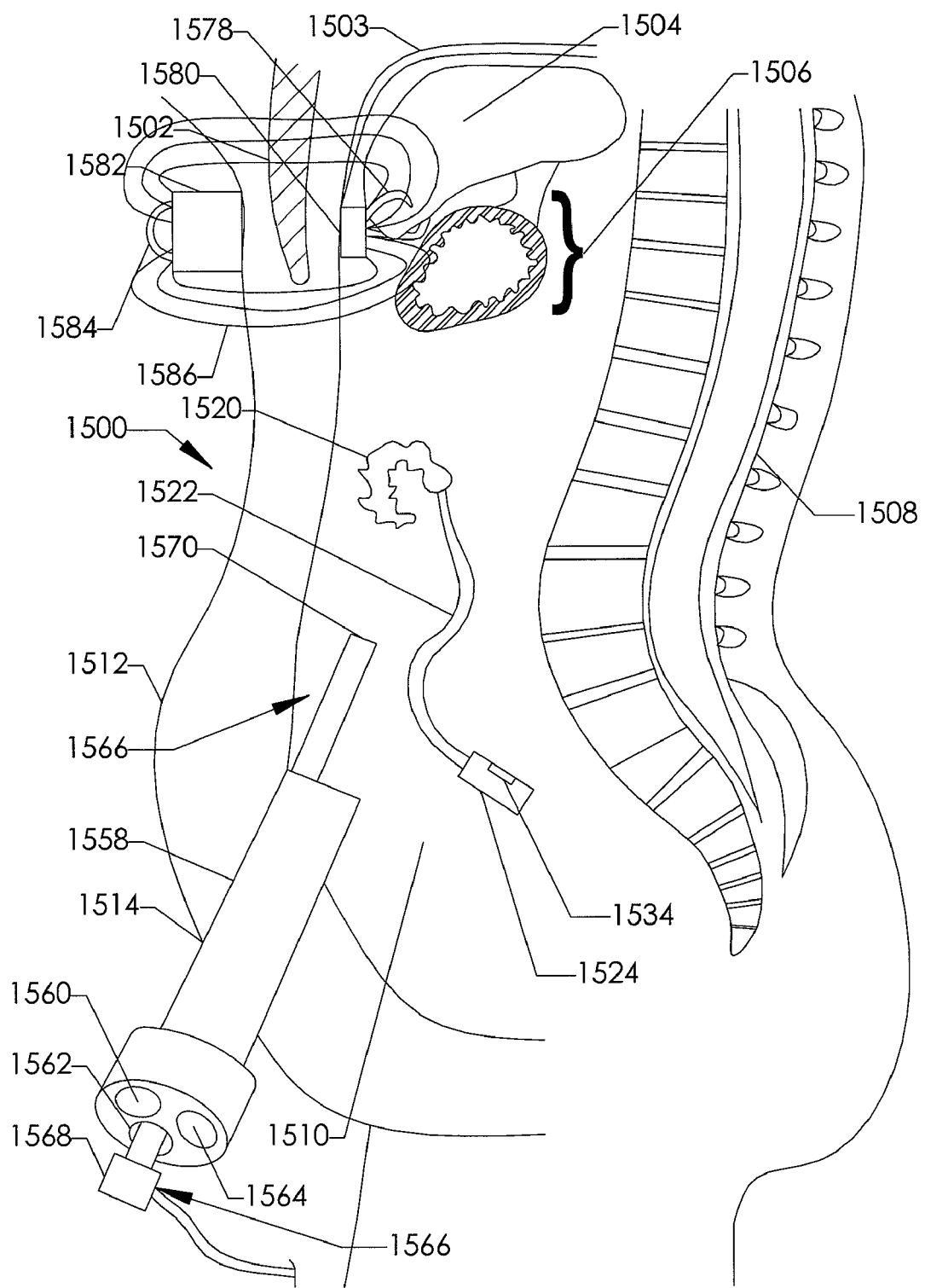

Turning now to FIG. 120, the single trocar 1558 is removed and the obesity control system is inserted through the tract made by the trocar 1558. The jaws 1590 of a forceps 1588 are used to grip the obesity control system as it is inserted into the abdominal cavity 1510. Once the obesity control system is placed completely within the abdominal cavity 1510, the trocar 1558 is replaced and the remaining portion of the implant procedure can be viewed through the laparoscope 1566 as seen in FIG. 121, while ports 1560 and 1564 are used for the placement of various instruments. The creation of a tunnel, for example in the pars flaccida method, can be performed with an articulating dissection tool. The creation of gastrogastric attachment, typically made using suture in most gastric restriction device procedures, presents a challenge in this single trocar method, because of the absence of good separation between, for example, two graspers being used to suture the stomach wall in two places, around the restriction device.

Figure 122:
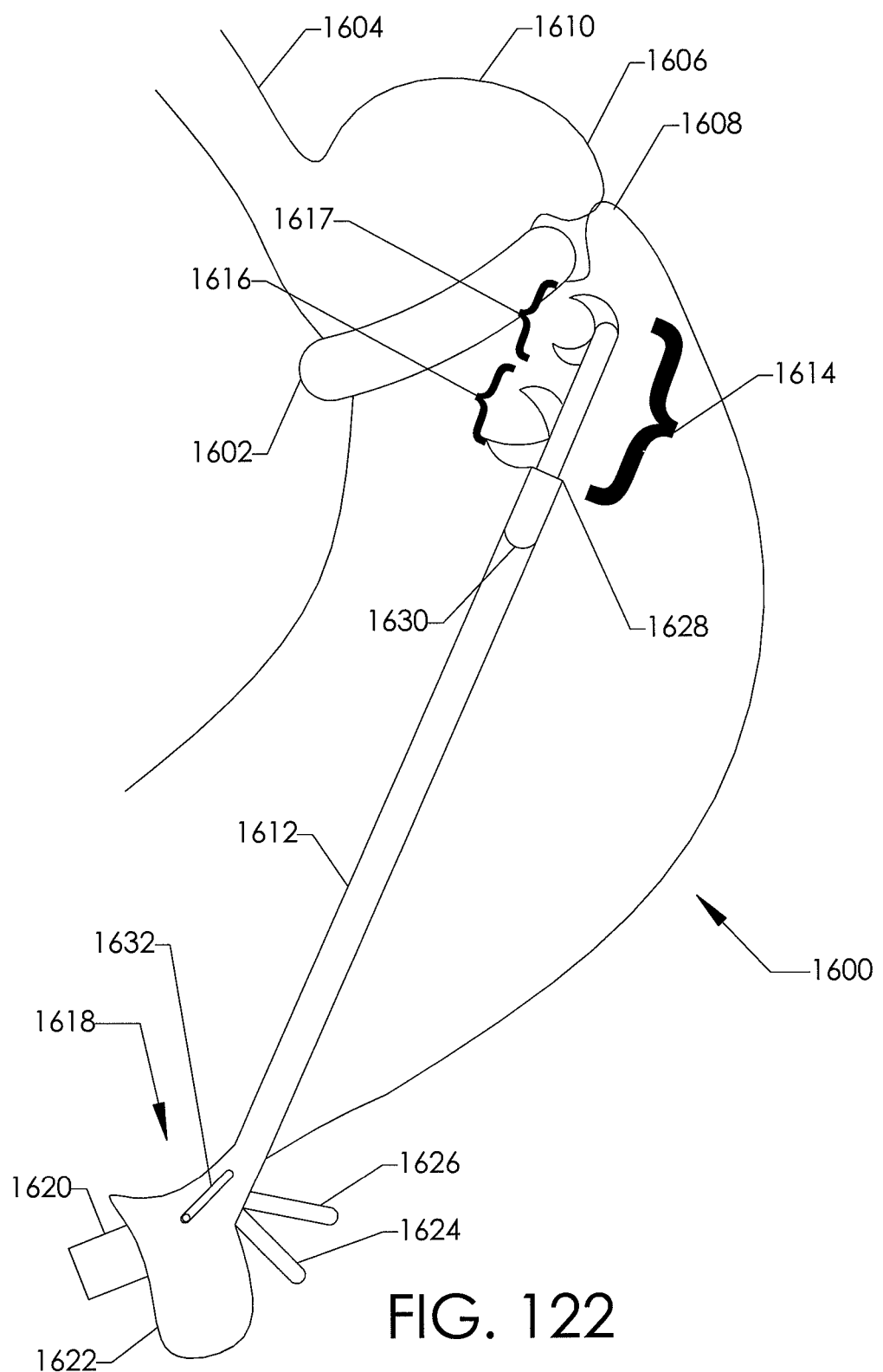

An alternative apparatus is shown in FIG. 122, and is configured to be placed through one of the ports of the trocar 1558. The gastric restriction device 1602 is shown in-place around the stomach 1600, creating a small pouch 1610 just below esophagus 1604. The wall of an upper portion 1606 and a lower portion 1608 adjacent the gastric restriction device 1602 are to be secured to each other. Instead of suturing the upper portion 1606 and the lower portion 1608 together, a tool 1618 having a shaft 1612 and a handle 1622 grips a releasable clip 1614. The tool 1618 is inserted through a port of the trocar 1558 and the releasable clip 1614 is advanced to close proximity of the upper portion 1606 and lower portion 1608. Proximal grip 1616 is secured to the lower portion 1608 by manipulating first trigger 1624. The lower portion 1608 is then manipulated close to the upper portion 1606 and then distal grip 1617 is secured to upper portion 1606 by manipulating second trigger 1626. The releasable clip 1614 is released at separation point 1628 by pressing release button 1620. The tool 1618 can be torqued as needed, and also, an articulation 1630 can be controlled by slide 1632 on the handle 1622. This allows the desired orientation to be achieved at each step. A second releasable clip may be attached to the tool 1618 (or a different tool) and a parallel attachment can be made.

It should be understood that in case of emergency, the entire gastric restriction device may be withdrawn from the patient via the trocar 1516, 1558. This includes a 12 mm trocar such as trocar 1516 in addition to a multi-lumen trocar 1558.

While embodiments of the present invention have been shown and described, various modifications may be made without departing from the scope of the present invention. The invention, therefore, should not be limited, except to the following claims, and their equivalents.

What is claimed is:

1. A gastrointestinal implant, comprising:
   a flexible adjustable body comprising a contact surface configured for at least partially engaging a surface of a gastrointestinal tract of a mammal, the contact surface having a first perimeter;
   an opposing surface, radially opposed to the contact surface, the opposing surface having a second perimeter, the contact surface having undulating increases and decreases in radius along the first perimeter and the opposing surface having substantially matched increases and decreases in radius along the second perimeter;
   an actuator configured to change the configurations of the contact surface and the opposing surface in response to rotational movement of an implantable interface operatively coupled to the actuator via a drive transmission, the actuator comprising a tensile member having a proximal end and distal end, the tensile member coupled to the flexible adjustable body;
   an external adjustment device configured to non-invasively couple to the implantable interface from a location external to the mammal;
   wherein movement of at least a portion of the implantable interface results in a change in the dimension or configuration of the contact surface;
   wherein the actuator is disposed at least partially within the flexible adjustable body about a plurality of ribs contained therein, wherein the ribs include holes; and
   wherein the actuator passes through at least a plurality of the holes.

2. The gastrointestinal implant of claim 1, wherein a rotatable lead screw is operatively coupled to a magnetic element contained in the implantable interface.

3. The gastrointestinal implant of claim 2, wherein the magnetic element comprises a permanent magnet.

4. The gastrointestinal implant of claim 1, wherein the tensile member comprises a filament or tape.

5. The gastrointestinal implant of claim 1, wherein the tensile member comprises NITINOL wire.

6. The gastrointestinal implant of claim 1, wherein the tensile member is slidably disposed within a protective sheath.

7. The gastrointestinal implant of claim 1, wherein the change in the configuration of the contact surface is adapted to change the effective internal dimension of the gastrointestinal tract.

8. The gastrointestinal implant of claim 1, wherein the flexible adjustable body is configured to change shape in a substantially uniform manner.

9. The gastrointestinal implant of claim 1, wherein the tensile member is coupled to a spring, the spring configured for allowing an increase in the effective length of the actuator in response to an acute event within the gastrointestinal tract.

10. The gastrointestinal implant of claim 9, wherein the acute event comprises a pressure in excess of 200 mm Hg.

11. The gastrointestinal implant of claim 1, wherein the flexible adjustable body contains a recess.

12. The gastrointestinal implant of claim 1, wherein the flexible adjustable body comprises silicone.

* * * * *